United States Patent
Brooks et al.

(10) Patent No.: US 12,215,320 B2
(45) Date of Patent: Feb. 4, 2025

(54) COMPOSITIONS AND METHODS FOR GENE EDITING BY TARGETING TRANSFERRIN

(71) Applicants: CRISPR Therapeutics AG, Zug (CH); BAYER HEALTHCARE LLC, Whippany, NJ (US)

(72) Inventors: Alan Richard Brooks, Cambridge, MA (US); Karen Vo, Cambridge, MA (US)

(73) Assignees: CRISPR Therapeutics AG, Zung (CH); BAYER HEALTHCARE LLC, Whippany, NJ (US)

( * ) Notice: Subject to any disclaimer, the term of this patent is extended or adjusted under 35 U.S.C. 154(b) by 1166 days.

(21) Appl. No.: 16/961,314

(22) PCT Filed: Jan. 11, 2019

(86) PCT No.: PCT/US2019/013384
§ 371 (c)(1),
(2) Date: Jul. 10, 2020

(87) PCT Pub. No.: WO2019/140330
PCT Pub. Date: Jul. 18, 2019

(65) Prior Publication Data
US 2021/0254057 A1    Aug. 19, 2021

Related U.S. Application Data

(60) Provisional application No. 62/617,044, filed on Jan. 12, 2018.

(51) Int. Cl.
| | | |
|---|---|---|
| *C12N 15/113* | (2010.01) | |
| *A61K 35/407* | (2015.01) | |
| *C12N 9/22* | (2006.01) | |
| *C12N 15/86* | (2006.01) | |

(52) U.S. Cl.
CPC .......... *C12N 15/113* (2013.01); *A61K 35/407* (2013.01); *C12N 9/22* (2013.01); *C12N 15/86* (2013.01); *C12N 2510/00* (2013.01); *C12N 2750/14143* (2013.01); *C12N 2830/42* (2013.01); *C12N 2830/50* (2013.01)

(58) Field of Classification Search
None
See application file for complete search history.

(56) References Cited

U.S. PATENT DOCUMENTS

2015/0353917 A1* 12/2015 Miller ................. C12N 15/102
435/441

FOREIGN PATENT DOCUMENTS

| WO | WO 2015/089077 A2 | 6/2015 |
|---|---|---|
| WO | WO 2017/074526 A1 | 5/2017 |
| WO | WO 2017/077386 A1 | 5/2017 |
| WO | WO 2017/093804 A2 | 6/2017 |

OTHER PUBLICATIONS

O'Mahony, Brian. (2009). Rare diseases treated by plasma proteins. Pharmaceuticals Policy and Law. 11. 245-257. 10.3233/PPL-2009-0229. (Year: 2009).*
Auer et al., Highly efficient CRISPR/Cas9-mediated knock-in in zebrafish by homology-independent DNA repair. Genome Res. Jan. 2014;24(1):142-53. Epub Oct. 31, 2013.
He et al., Knock-in of large reporter genes in human cells via CRISPR/Cas9-induced homology-dependent and independent DNA repair. Nucleic Acids Res. May 19, 2016;44(9):e85. Epub Feb. 2016.
Sharma et al., In vivo genome editing of the albumin locus as a platform for protein replacement therapy. Blood. Oct. 8, 2015;126(15):1777-84. doi: 10.1182/blood-2014-12-615492. Epub Aug. 21, 2015.

* cited by examiner

*Primary Examiner* — Allison M Fox
*Assistant Examiner* — Alyssa G Weston
(74) *Attorney, Agent, or Firm* — Casimir Jones, S.C.; J. Mitchell Jones

(57) ABSTRACT

Provided include compositions, methods, and systems for modulating the expression, function, and/or activity of a target gene, for example a blood-clotting protein such as Factor VIII (FVIII), in a cell by genome editing. Also provided include compositions, methods, and systems for treating a subject having or suspected of having a disorder or health condition, e.g., Hemophilia A, employing ex vivo and/or in vivo genome editing.

15 Claims, 7 Drawing Sheets

Specification includes a Sequence Listing.

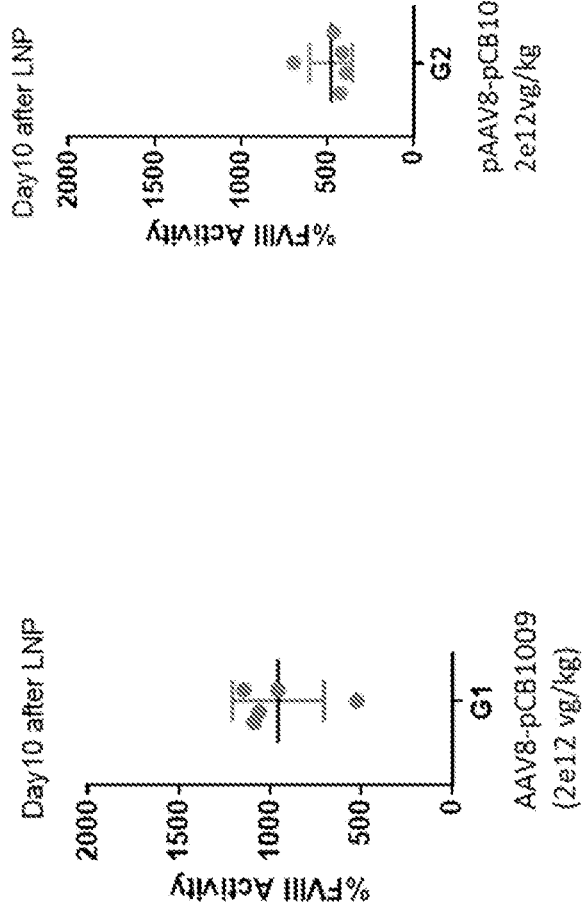
FIG. 4
FIG. 5
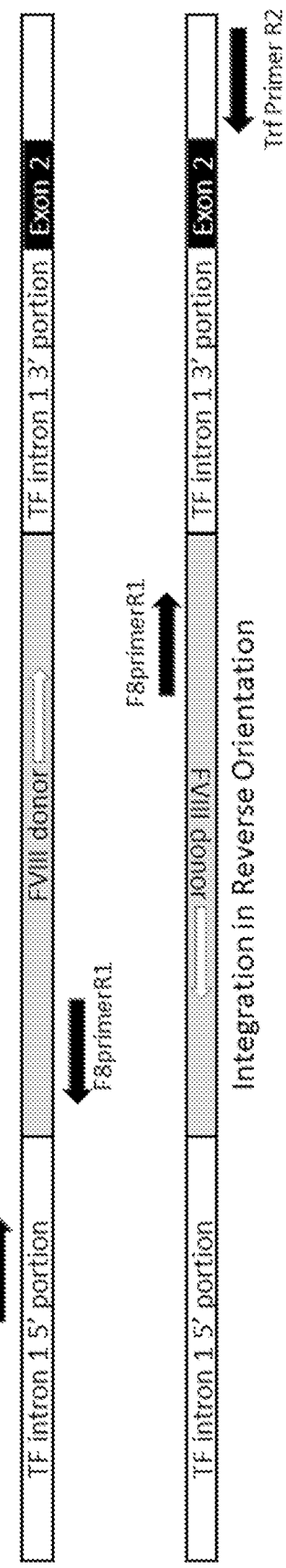
FIG. 6

COMPOSITIONS AND METHODS FOR GENE EDITING BY TARGETING TRANSFERRIN

CROSS-REFERENCE TO RELATED APPLICATIONS

This application is a national stage filing under 35 U.S.C. § 371 of international application number PCT/US2019/013384, filed on Jan. 11, 2019, which claims the benefit of priority to U.S. Provisional Application No. 62/617,044, filed Jan. 12, 2018, the disclosures of each of which are incorporated by reference herein in their entities.

STATEMENT REGARDING SEQUENCE LISTING

The text of the computer readable sequence listing filed Jul. 10, 2020, titled "662922-SeqList.txt", created Jul. 10, 2020, having a file size of 91,000 bytes, is hereby incorporated by reference in its entirety.

FIELD

The disclosures provided herewith relate generally to molecular biology and medicine. More particularly, the present disclosures provide compositions, methods, and systems for targeted delivery of nucleic acids, including DNA and RNA, to a target cell, such as, e.g., a human cell. Some embodiments of the disclosure relate to compositions, methods, and systems for modulating the expression, function, and/or activity of a target gene in a cell by genome editing.

BACKGROUND

Advances in genome sequencing techniques and analytical methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications.

Gene editing using site-specific nucleases has emerged as a technology for both basic biomedical research and therapeutic development. Various platforms based on four major types of endonucleases have been developed for gene editing, namely meganucleases and their derivatives, zinc finger nucleases (ZFNs), transcription activator-like effector nucleases (TALENs), and clustered regularly interspaced short palindromic repeat (CRISPR) associated endonuclease 9 (cas9). Each of nuclease type is capable of inducing a DNA double-stranded break (DSB) at specific DNA loci, thus triggering two DNA repair pathways. The non-homologous end joining (NHEJ) pathway generates random insertion/deletion (indel) mutations at the DSB, whereas the homology-directed repair (HDR) pathway repairs the DSB with the genetic information carried on a donor template. Therefore, these gene editing platforms are useful for manipulating genes at specific genomic loci in multiple ways, such as disrupting gene function, repairing a mutant gene to a wild type, and inserting new DNA sequences.

Although these genome-editing techniques have been developed for producing targeted genome modifications, there remains a need for new genome gene editing platforms that are capable of manipulating genes at specific genomic loci in multiple ways, such as disrupting gene function, repairing a mutant gene to produce a wild type product, and/or inserting heterologous DNA material at specific loci within the genome of a target cell, for example, for use in the treatment of diseases, such as monogenic diseases (e.g., hemophilia A).

Hemophilia A (HemA) is caused by a genetic defect in the Factor VIII (FVIII) gene that results in low or undetectable levels of FVIII protein in the blood. This results in ineffective clot formation at sites of tissue injury leading to uncontrolled bleeding that can be fatal if not treated. Replacement of the missing FVIII protein is the current standard of care. However, protein replacement therapy requires frequent intravenous injection or infusion of FVIII protein, which is inconvenient in adults, problematic in children, cost prohibitive (>$200,000/year), and can result in breakthrough bleeding events if the treatment regimen is not closely followed.

The FVIII gene (also referred to as F8) is expressed primarily in sinusoidal endothelial cells that are present in the liver as well as other sites in the body. Gene delivery methods have been developed that target the hepatocytes and these methods have been used to deliver a FVIII gene as a treatment for HemA both in animal models and in patients in clinical trials.

Despite progress with gene therapy, which is exclusively virus-based using Adeno Associated Virus (AAV), the methods have a number of disadvantages. For example, reported AAV-based gene therapy uses a FVIII gene driven by a liver specific promoter that is encapsulated inside an AAV virus capsid (for example, using the serotypes AAV5, AAV8, AAV3b or AAV9 or AAVhu37). In general, AAV viruses used for gene therapy deliver the packaged gene cassette into the nucleus of the transduced cells where the gene cassette remains almost exclusively extra-chromosomal and it is the extra-chromosomal copies of the therapeutic gene that give rise to the therapeutic protein. AAV does not have a mechanism to integrate the encapsulated DNA into the genome of the host cells. Instead because the therapeutic gene is maintained largely as an extra-chromosomal episome, the therapeutic gene is not replicated when the host cell divides. Furthermore, the therapeutic DNA can be subject to degradation over time. It has been demonstrated that when liver cells containing AAV episomes are induced to divide, the AAV genome is not replicated but is instead diluted (Grimm et al. 206, J Virol 80, 426-439; Colella et al. 2018, Mol Ther Methods Clin Dev 8, 87-104). As a result, AAV based gene therapy is not expected to be effective when used to treat children whose livers have not yet achieved adult size. In addition, it is currently unknown how long an AAV based gene therapy will persist when given to adult humans. Therefore, there is a critical need for developing new effective and permeant treatments for HemA.

SUMMARY

In one aspect, provided herein is a system comprising: a deoxyribonucleic acid (DNA) endonuclease or nucleic acid encoding the DNA endonuclease; a guide RNA (gRNA) comprising a spacer sequence that is complementary to a genomic sequence within or near an endogenous transferrin locus in a cell, or nucleic acid encoding the gRNA; and a donor template comprising a nucleic acid sequence encoding a protein-of-interest (POI) or a functional derivative thereof. In some embodiments, the gRNA comprises a spacer sequence that is complementary to a sequence within intron 1 of an endogenous transferrin gene in the cell.

In some embodiments, according to any of the systems described above, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

In some embodiments, according to any of the systems described above, the POI is selected from the group consisting of Factor VIII (FVIII), Factor IX, alpha-1-antitrypsin, FXIII, FVII, Factor X, a C1 esterase inhibitor, iduronate sulfatase, α-L-iduronidase, and Protein C. In some embodiments, the POI is FVIII.

In some embodiments, according to any of the systems described above, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional derivative thereof. In some embodiments, the DNA endonuclease is Cas9.

In some embodiments, according to any of the systems described above, the nucleic acid encoding the DNA endonuclease is codon-optimized for expression in a host cell.

In some embodiments, according to any of the systems described above, the nucleic acid sequence encoding a POI or a functional derivative thereof is codon-optimized for expression in a host cell.

In some embodiments, according to any of the systems described above, the nucleic acid sequence encoding a POI or a functional derivative thereof comprises a reduced content of CpG di-nucleotides than a nucleic acid sequence encoding the wild-type POI.

In some embodiments, according to any of the systems described above, the nucleic acid sequence encoding a POI or a functional derivative thereof comprises about or less than 20 CpG di-nucleotides. In some embodiments, the nucleic acid sequence encoding a POI or a functional derivative thereof comprises about or less than 10 CpG di-nucleotides. In some embodiments, the nucleic acid sequence encoding a POI or a functional derivative thereof comprises about or less than 5 CpG di-nucleotides. In some embodiments, the nucleic acid sequence encoding a POI or a functional derivative thereof does not comprise CpG di-nucleotides.

In some embodiments, according to any of the systems described above, the nucleic acid encoding the DNA endonuclease is a deoxyribonucleic acid (DNA).

In some embodiments, according to any of the systems described above, the nucleic acid encoding the DNA endonuclease is a ribonucleic acid (RNA). In some embodiments, the RNA encoding the DNA endonuclease is an mRNA.

In some embodiments, according to any of the systems described above, the donor template is encoded in an Adeno Associated Virus (AAV) vector.

In some embodiments, according to any of the systems described above, the donor template comprises a donor cassette comprising the nucleic acid sequence encoding a POI or a functional derivative thereof, and the donor cassette is flanked on one or both sides by a gRNA target site. In some embodiments, the donor cassette is flanked on both sides by a gRNA target site. In some embodiments, the gRNA target site is a target site for a gRNA in the system. In some embodiments, the gRNA target site of the donor template is the reverse complement of a genomic gRNA target site for a gRNA in the system.

In some embodiments, according to any of the systems described above, the DNA endonuclease or nucleic acid encoding the DNA endonuclease is formulated in a liposome or lipid nanoparticle. In some embodiments, the liposome or lipid nanoparticle also comprises the gRNA.

In some embodiments, according to any of the systems described above, the system comprises the DNA endonuclease precomplexed with the gRNA, forming a Ribonucleoprotein (RNP) complex.

In another aspect, provided herein is a method of editing a genome in a cell, the method comprising providing the following to the cell: (a) a gRNA comprising a spacer sequence that is complementary to a genomic sequence within or near an endogenous transferrin locus in the cell, or nucleic acid encoding the gRNA; (b) a DNA endonuclease or nucleic acid encoding the DNA endonuclease; and (c) a donor template comprising a nucleic acid sequence encoding a POI or a functional derivative thereof. In some embodiments, the gRNA comprises a spacer sequence that is complementary to a sequence within intron 1 of an endogenous transferrin gene in the cell.

In some embodiments, according to any of the methods described above, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

In some embodiments, according to any of the methods described above, the POI is selected from the group consisting of FVIII, Factor IX, alpha-1-antitrypsin, FXIII, FVII, Factor X, a C1 esterase inhibitor, iduronate sulfatase, α-L-iduronidase, and Protein C. In some embodiments, the POI is FVIII.

In some embodiments, according to any of the methods described above, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; or a functional derivative thereof. In some embodiments, the DNA endonuclease is Cas9.

In some embodiments, according to any of the methods described above, the nucleic acid encoding the DNA endonuclease is codon-optimized for expression in the cell.

In some embodiments, according to any of the methods described above, the nucleic acid sequence encoding a POI or a functional derivative thereof is codon-optimized for expression in the cell.

In some embodiments, according to any of the methods described above, the nucleic acid sequence encoding a POI or a functional derivative thereof comprises a reduced content of CpG di-nucleotides than a nucleic acid sequence encoding the wild-type POI.

In some embodiments, according to any of the methods described above, the nucleic acid sequence encoding a POI or a functional derivative thereof comprises about or less than 20 CpG di-nucleotides. In some embodiments, the nucleic acid sequence encoding a POI or a functional derivative thereof comprises about or less than 10 CpG di-nucleotides. In some embodiments, the nucleic acid sequence encoding a POI or a functional derivative thereof comprises about or less than 5 CpG di-nucleotides. In some embodiments, the nucleic acid sequence encoding a POI or a functional derivative thereof does not comprise CpG di-nucleotides.

In some embodiments, according to any of the methods described above, the nucleic acid encoding the DNA endonuclease is a deoxyribonucleic acid (DNA).

In some embodiments, according to any of the methods described above, the nucleic acid encoding the DNA endonuclease is a ribonucleic acid (RNA). In some embodiments, the RNA encoding the DNA endonuclease is an mRNA.

In some embodiments, according to any of the methods described above, the donor template is encoded in an Adeno Associated Virus (AAV) vector.

In some embodiments, according to any of the methods described above, the donor template comprises a donor cassette comprising the nucleic acid sequence encoding a POI or a functional derivative thereof, and the donor cassette is flanked on one or both sides by a gRNA target site. In some embodiments, the donor cassette is flanked on both sides by a gRNA target site. In some embodiments, the gRNA target site is a target site for the gRNA of (a). In some embodiments, the gRNA target site of the donor template is the reverse complement of a gRNA target site in the cell genome for the gRNA of (a).

In some embodiments, according to any of the methods described above, the DNA endonuclease or nucleic acid encoding the DNA endonuclease is formulated in a liposome or lipid nanoparticle. In some embodiments, the liposome or lipid nanoparticle also comprises the gRNA.

In some embodiments, according to any of the methods described above, the method comprises providing to the cell the DNA endonuclease precomplexed with the gRNA, forming a Ribonucleoprotein (RNP) complex.

In some embodiments, according to any of the methods described above, the gRNA of (a) and the DNA endonuclease or nucleic acid encoding the DNA endonuclease of (b) are provided to the cell more than 4 days after the donor template of (c) is provided to the cell. In some embodiments, according to any of the methods described above, the gRNA of (a) and the DNA endonuclease or nucleic acid encoding the DNA endonuclease of (b) are provided to the cell at least 14 days after (c) is provided to the cell. In some embodiments, one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b). In some embodiments, one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b) until a target level of targeted integration of the nucleic acid sequence encoding a POI or functional derivative and/or a target level of expression of the nucleic acid sequence encoding a POI or functional derivative is achieved.

In some embodiments, according to any of the methods described above, the nucleic acid sequence encoding a POI or functional derivative is expressed under the control of the endogenous transferrin promoter.

In some embodiments, according to any of the methods described above, the cell is a hepatocyte.

In another aspect, provided herein is a genetically modified cell in which the genome of the cell is edited by a method according to any of the embodiments described above. In some embodiments, the nucleic acid sequence encoding a POI or functional derivative is expressed under the control of the endogenous transferrin promoter. In some embodiments, the nucleic acid sequence encoding a POI or a functional derivative thereof is codon-optimized for expression in the cell.

In some embodiments, according to any of the genetically modified cells described above, the cell is a hepatocyte.

In another aspect, provided herein is a method of treating a disease or condition associated with a POI in a subject, comprising providing the following to a cell in the subject: (a) a gRNA comprising a spacer sequence that is complementary to a genomic sequence within or near an endogenous transferrin locus in the cell, or nucleic acid encoding the gRNA; (b) a DNA endonuclease or nucleic acid encoding the DNA endonuclease; and (c) a donor template comprising a nucleic acid sequence encoding the POI or a functional derivative thereof. In some embodiments, the gRNA comprises a spacer sequence that is complementary to a sequence within intron 1 of an endogenous transferrin gene in the cell.

In some embodiments, according to any of the methods described above, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

In some embodiments, according to any of the methods described above, the POI is i) FVIII and the disease or condition is Hemophilia A; ii) Factor IX and the disease or condition is Hemophilia B; iii) alpha-1-antitrypsin and the disease or condition is alpha-1-antitrypsin deficiency; iv) FXIII and the disease or condition is Factor XIII deficiency; v) FVII and the disease or condition is Factor VII deficiency; vi) Factor X and the disease or condition is Factor X deficiency; vii) a C1 esterase inhibitor, and the disease or condition is Hereditary Angioedema (HAE); viii) iduronate sulfatase, and the disease or condition is Hunter syndrome; ix) α-L-iduronidase, and the disease or condition is mucopolysaccharidosis type 1 (MPS 1); or x) Protein C and the disease or condition is Protein C deficiency. In some embodiments, the POI is FVIII and the disease or condition is Hemophilia A.

In some embodiments, according to any of the methods described above, the subject is a patient having or suspected of having the disease or condition.

In some embodiments, according to any of the methods described above, the subject is diagnosed with a risk of the disease or condition.

In some embodiments, according to any of the methods described above, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; or a functional derivative thereof. In some embodiments, the DNA endonuclease is Cas9.

In some embodiments, according to any of the methods described above, the nucleic acid encoding the DNA endonuclease is codon-optimized for expression in the cell.

In some embodiments, according to any of the methods described above, the nucleic acid sequence encoding a POI or a functional derivative thereof is codon-optimized for expression in the cell.

In some embodiments, according to any of the methods described above, the nucleic acid sequence encoding a POI or a functional derivative thereof comprises a reduced content of CpG di-nucleotides than a nucleic acid sequence encoding the wild-type POI. In some embodiments, the nucleic acid sequence encoding a POI or a functional derivative thereof comprises about or less than 20 CpG di-nucleotides. In some embodiments, the nucleic acid sequence encoding a POI or a functional derivative thereof comprises about or less than 10 CpG di-nucleotides. In some embodiments, the nucleic acid sequence encoding a POI or a functional derivative thereof comprises about or less than 5 CpG di-nucleotides. In some embodiments, the nucleic acid sequence encoding a POI or a functional derivative thereof does not comprise CpG di-nucleotides.

In some embodiments, according to any of the methods described above, the nucleic acid encoding the DNA endonuclease is a deoxyribonucleic acid (DNA).

In some embodiments, according to any of the methods described above, the nucleic acid encoding the DNA endonuclease is a ribonucleic acid (RNA). In some embodiments, the RNA encoding the DNA endonuclease is an mRNA.

In some embodiments, according to any of the methods described above, one or more of the gRNA of (a), the DNA endonuclease or nucleic acid encoding the DNA endonuclease of (b), and the donor template of (c) are formulated in a liposome or lipid nanoparticle.

In some embodiments, according to any of the methods described above, the donor template is encoded in an Adeno Associated Virus (AAV) vector.

In some embodiments, according to any of the methods described above, the donor template comprises a donor cassette comprising the nucleic acid sequence encoding a POI or a functional derivative thereof, and the donor cassette is flanked on one or both sides by a gRNA target site. In some embodiments, the donor cassette is flanked on both sides by a gRNA target site. In some embodiments, the gRNA target site is a target site for the gRNA of (a). In some embodiments, the gRNA target site of the donor template is the reverse complement of the gRNA target site in the cell genome for the gRNA of (a).

In some embodiments, according to any of the methods described above, providing the donor template to the cell comprises administering the donor template to the subject. In some embodiments, the administration is via intravenous route.

In some embodiments, according to any of the methods described above, the DNA endonuclease or nucleic acid encoding the DNA endonuclease is formulated in a liposome or lipid nanoparticle. In some embodiments, the liposome or lipid nanoparticle also comprises the gRNA. In some embodiments, providing the gRNA and the DNA endonuclease or nucleic acid encoding the DNA endonuclease to the cell comprises administering the liposome or lipid nanoparticle to the subject. In some embodiments, the administration is via intravenous route.

In some embodiments, according to any of the methods described above, the method comprises providing to the cell the DNA endonuclease pre-complexed with the gRNA, forming a Ribonucleoprotein (RNP) complex.

In some embodiments, according to any of the methods described above, the gRNA of (a) and the DNA endonuclease or nucleic acid encoding the DNA endonuclease of (b) are provided to the cell more than 4 days after the donor template of (c) is provided to the cell. In some embodiments, according to any of the methods described above, the gRNA of (a) and the DNA endonuclease or nucleic acid encoding the DNA endonuclease of (b) are provided to the cell at least 14 days after the donor template of (c) is provided to the cell. In some embodiments, one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b). In some embodiments, one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b) until a target level of targeted integration of the nucleic acid sequence encoding a POI or functional derivative and/or a target level of expression of the nucleic acid sequence encoding a POI or functional derivative is achieved. In some embodiments, providing the gRNA of (a) and the DNA endonuclease or nucleic acid encoding the DNA endonuclease of (b) to the cell comprises administering to the subject a lipid nanoparticle comprising nucleic acid encoding the DNA endonuclease and the gRNA. In some embodiments, providing the donor template of (c) to the cell comprises administering to the subject the donor template encoded in an AAV vector.

In some embodiments, according to any of the methods described above, the nucleic acid sequence encoding a POI or functional derivative is expressed under the control of the endogenous transferrin promoter.

In some embodiments, according to any of the methods described above, the cell is a hepatocyte.

In some embodiments, according to any of the methods described above, the nucleic acid sequence encoding a POI or functional derivative is expressed in the liver of the subject.

In another aspect, provided herein is a method of treating a disease or condition associated with a POI in a subject comprising administering a genetically modified cell according to any of the embodiments described above to the subject. In some embodiments, the genetically modified cell is autologous to the subject. In some embodiments, the method further comprises obtaining a biological sample from the subject, wherein the biological sample comprises a hepatocyte cell, and wherein the genetically modified cell is prepared from the hepatocyte.

In another aspect, provided herein is a kit comprising one or more elements of a system according to any of the embodiments described above, and further comprising instructions for use.

In another aspect, provided herein is a gRNA comprising a spacer sequence that is complementary to a genomic sequence within or near an endogenous transferrin locus in a cell. In some embodiments, the gRNA comprises a spacer sequence that is complementary to a sequence within intron 1 of an endogenous transferrin gene in the cell.

In some embodiments, according to any of the gRNAs described above, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

In another aspect, provided herein is a donor template comprising a nucleotide sequence encoding a protein-of-interest (POI) or a functional derivative thereof for targeted integration into intron 1 of a transferrin gene, wherein the donor template comprises, from 5' to 3', i) a first gRNA target site; ii) a splice acceptor; iii) the nucleotide sequence encoding a POI or a functional derivative thereof; and iv) a polyadenylation signal. In some embodiments, the donor template further comprises a second gRNA target site downstream of the iv) polyadenylation signal. In some embodiments, the first gRNA target site and the second gRNA target site are the same. In some embodiments, the donor template further comprises a sequence encoding the terminal portion of the transferrin signal peptide encoded on exon 2 of the transferrin gene or a variant thereof that retains at least some of the activity of the endogenous sequence between the ii) splice acceptor and iii) nucleotide sequence encoding a POI or a functional derivative thereof. In some embodiments, the donor template further comprises a polynucleotide spacer between the i) first gRNA target site and the ii) splice acceptor. In some embodiments, the polynucleotide spacer is 18 nucleotides in length. In some embodiments, the donor template is flanked on one side by a first AAV ITR and/or flanked on the other side by a second AAV ITR. In some embodiments, the first AAV ITR is an AAV2 ITR and/or the second AAV ITR is an AAV2 ITR.

In some embodiments, according to any of the donor templates described above, the POI is selected from the group consisting of Factor VIII (FVIII), Factor IX, alpha-1-antitrypsin, FXIII, FVII, Factor X, a C1 esterase inhibitor, iduronate sulfatase, α-L-iduronidase, and Protein C. In some embodiments, the POI is FVIII. In some embodiments, the iii) nucleotide sequence encoding a POI or a functional derivative thereof encodes a mature human B-domain deleted FVIII.

BRIEF DESCRIPTION OF THE DRAWINGS

An understanding of certain features and advantages of the present disclosure will be obtained by reference to the following detailed description that sets forth illustrative embodiments, in which the principles of the disclosure are utilized, and the accompanying drawings of which:

FIG. 4 shows FVIII activity in the blood of Hemophilia A mice 10 days after dosing with an LNP encapsulating spCas9 and mTF-T2 gRNA in mice that were previously injected with AAV8-pCB1009.

FIG. 5 shows FVIII activity in the blood of NSG mice 10 days after dosing with an LNP encapsulating spCas9 and mTF-T2 gRNA in mice that were previously injected with AAV8-pCB1009.

FIG. 6 shows a diagram depicting the location of binding sites for PCR primers used to detect targeted integration of the FVIII donor from pAAV8-pCB1009 into mouse transferrin intron 1.

DETAILED DESCRIPTION

Figure 1:
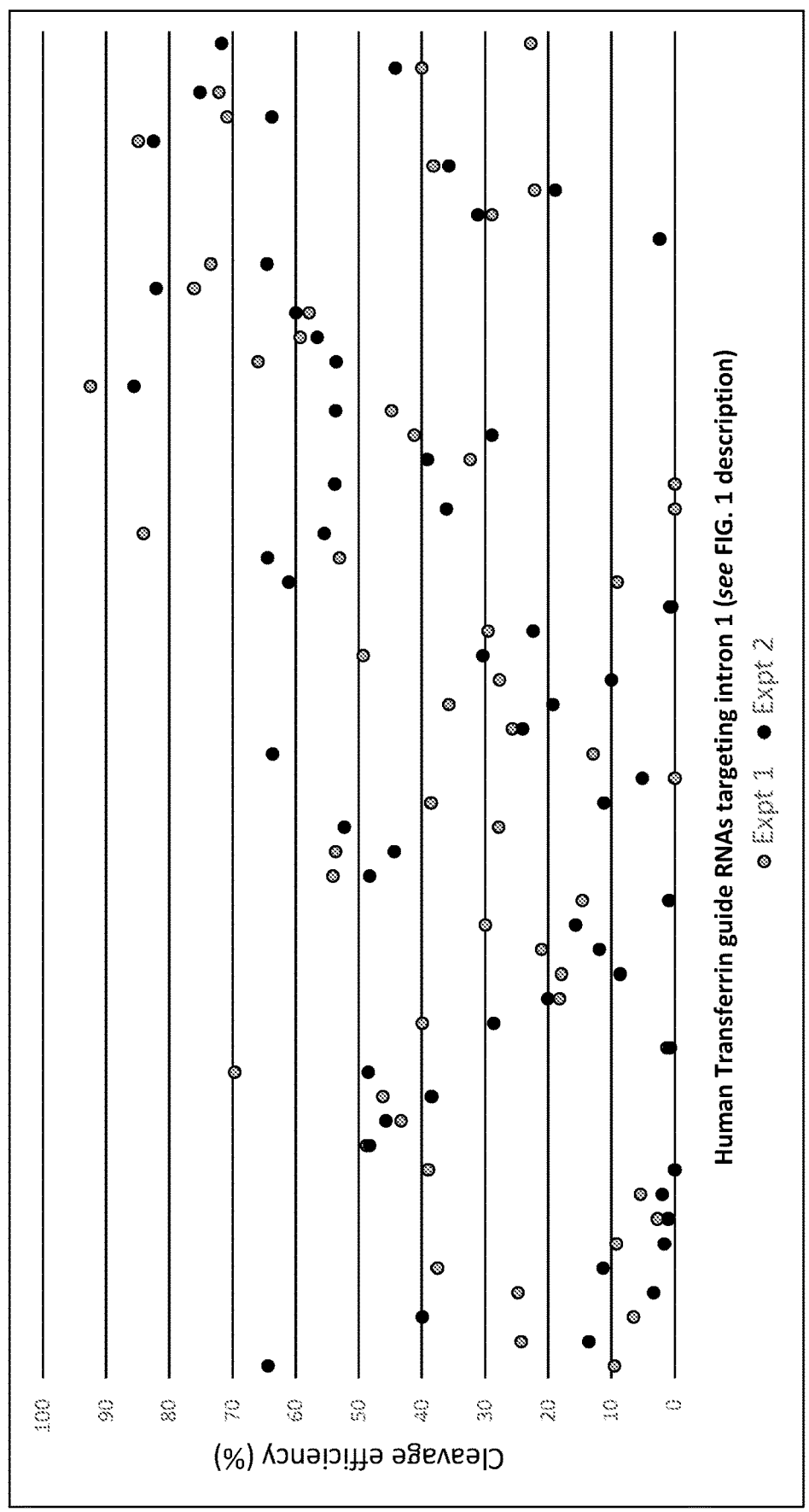
FIG. 1 shows the results for cleavage efficiency of human transferrin guide RNAs with 100% match to non-human primate plotted from left to right according to their relative position from 5' to 3' within human transferrin intron 1. The transferrin guide RNAs represented in the plot, from left to right, are T8, T31, T25, T11, T54, T82, T93, T37, T140, T73, T58, T2, T22, T1, T147, T173, T56, T88, T165, T122, T91, T186, T164, T124, T109, T64, T94, T65, T52, T159, T86, T33, T18, T40, T132, T5, T157, T71, T67, T158, T85, T107, T66, T156, T154, T59, T57, T100, T117, T167, T110, and T63, respectively.

The disclosures provide, inter alia, compositions, methods, and systems for targeted delivery of nucleic acids, including DNA and RNA, to a target cell such as, for example, a mammalian cell, e.g., a human cell. Some embodiments of the disclosure relate to compositions, methods, and systems for modulating the expression, function, and/or activity of a target gene in a cell by genome editing. Some embodiments relate to compositions and methods for genome editing to modulate the expression, function, and/or activity of a blood-clotting protein such as Factor VIII (FVIII) in a cell by genome editing. The disclosures also provide, inter alia, compositions, methods, and systems for treating a subject having or suspected of having a disorder or health condition, e.g., Hemophilia A, employing ex vivo and/or in vivo genome editing.

Furthermore, Applicants have discovered that a transferrin gene can be used for targeted integration and expression of a heterologous nucleic acid. Accordingly, Applicants have developed a series of novel CRISPR/Cas systems for targeted integration of a heterologous nucleic acid sequence encoding a protein-of-interest (POI) into intron 1 of a transferrin gene in a cell genome, where the POI is to be secreted from the cell, taking advantage of the endogenous transferrin promoter and portion of the signal peptide encoded on exon 1. Guide RNAs (gRNAs) with spacer sequences identified by in silico analysis for gRNA target sites with an NGG protospacer adjacent motif (PAM) in intron 1 of the human transferrin gene were screened in two different human liver cell lines, yielding gRNAs that were able to direct highly efficient Cas9-mediated cleavage, ranging up to cutting efficiencies exceeding 90%. At least one of the gRNAs had a highly favorable on/off-target cleavage profile, with only two off-target sites that were detected at 0.09% and 0.05% of the on-target read count as determined by GUIDE-seq. Importantly, when mice with Factor VIII (FVIII) gene inactivation were edited using a gRNA targeting mouse transferrin intron 1 in combination with a donor cassette designed to allow for splicing of transferrin exon 1 to a FVIII coding sequence contained in the integrated donor cassette, allowing for expression of the FVIII coding sequence to be regulated by the endogenous transferrin promoter, FVIII activity in the edited mice averaged 954% (+/−251%) of normal human FVIII levels. This was a surprising result in that, compared to mice edited similarly, but for targeted integration of the FVIII donor cassette into albumin intron 1, integration of the FVIII cassette into transferrin intron 1 resulted in approximately 40-fold higher levels of FVIII expression than integration of the FVIII cassette into albumin intron 1 when normalized for integration frequency. These findings indicate that the CRISPR/Cas systems described herein are useful for treating diseases, for example, diseases in which it is desirable to introduce a heterologous gene to be expressed, e.g., for treating Hemophilia A by using the disclosed system(s) to introduce a donor cassette for expression of FVIII.

Definitions

Unless defined otherwise, all technical and scientific terms used herein have the same meaning as is commonly understood by one of skill in the art to which the claimed subject matter belongs. It is to be understood that the detailed descriptions are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the disclosures may be described in the context of a single embodiment, the features may also be provided separately or in any suitable combination. Conversely, although the disclosures may be described herein in the context of separate embodiments for clarity, the disclosures may also be implemented in a single embodiment. Any published patent applications and any other published references, documents, manuscripts, and scientific literature cited herein are incorporated herein by reference for any purpose. In the case of conflict, the present specification, including definitions, will control. In addition, the materials, methods, and examples are illustrative only and not intended to be limiting.

As used herein, ranges and amounts can be expressed as "about" a particular value or range. "About" also includes the exact amount. Hence "about 5 μL" means "about 5 μL"

and also "5 µL." Generally, the term "about" includes an amount that would be expected to be within experimental error such as ±10%.

When a range of numerical values is presented herein, it is contemplated that each intervening value between the lower and upper limit of the range, the values that are the upper and lower limits of the range, and all stated values with the range are encompassed within the disclosure. All the possible sub-ranges within the lower and upper limits of the range are also contemplated by the disclosure.

The terms "polypeptide," "polypeptide sequence," "peptide," "peptide sequence," "protein," "protein sequence" and "amino acid sequence" are used interchangeably herein to designate a linear series of amino acid residues connected one to the other by peptide bonds, which series may include proteins, polypeptides, oligopeptides, peptides, and fragments thereof. The protein may be made up of naturally occurring amino acids and/or synthetic (e.g., modified or non-naturally occurring) amino acids. Thus "amino acid", or "peptide residue", as used herein means both naturally occurring and synthetic amino acids. The terms "polypeptide", "peptide", and "protein" includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, and the like. Furthermore, a dash at the beginning or end of an amino acid sequence indicates either a peptide bond to a further sequence of one or more amino acid residues or a covalent bond to a carboxyl or hydroxyl end group. However, the absence of a dash should not be taken to mean that such peptide bond or covalent bond to a carboxyl or hydroxyl end group is not present, as it is conventional in representation of amino acid sequences to omit such.

The term "polynucleotide," "polynucleotide sequence," "oligonucleotide," "oligonucleotide sequence," "oligomer," "oligo," "nucleic acid sequence" or "nucleotide sequence" used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer having purine and pyrimidine bases or other natural, chemically or biochemically modified, non-natural, or derivatized nucleotide bases.

The terms "derivative" and "variant" refer without limitation to any compound such as nucleic acid or protein that has a structure or sequence derived from the compounds disclosed herein and whose structure or sequence is sufficiently similar to those disclosed herein such that it has the same or similar activities and utilities or, based upon such similarity, would be expected by one skilled in the art to exhibit the same or similar activities and utilities as the referenced compounds, thereby also interchangeably referred to "functionally equivalent" or as "functional equivalents." Modifications to obtain "derivatives" or "variants" may include, for example, addition, deletion and/or substitution of one or more of the nucleic acids or amino acid residues.

The functional equivalent or fragment of the functional equivalent, in the context of a protein, may have one or more conservative amino acid substitutions. The term "conservative amino acid substitution" refers to substitution of an amino acid for another amino acid that has similar properties as the original amino acid. The groups of conservative amino acids are as follows:

| Group | Name of the amino acids |
|---|---|
| Aliphatic | Gly, Ala, Val, Leu, Ile |
| Hydroxyl or Sulfhydryl/Selenium-containing | Ser, Cys, Thr, Met |
| Cyclic | Pro |
| Aromatic | Phe, Tyr, Trp |
| Basic | His, Lys, Arg |
| Acidic and their Amide | Asp, Glu, Asn, Gln |

Conservative substitutions may be introduced in any position of a predetermined peptide or fragment thereof. It may however also be desirable to introduce non-conservative substitutions, particularly, but not limited to, a non-conservative substitution in any one or more positions. A non-conservative substitution leading to the formation of a functionally equivalent fragment of the peptide would for example differ substantially in polarity, in electric charge, and/or in steric bulk while maintaining the functionality of the derivative or variant fragment.

"Percentage of sequence identity" is determined by comparing two optimally aligned sequences over a comparison window, wherein the portion of the polynucleotide or polypeptide sequence in the comparison window may have additions or deletions (i.e., gaps) as compared to the reference sequence (which does not have additions or deletions) for optimal alignment of the two sequences. In some cases, the percentage can be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity" in the context of two or more nucleic acid or polypeptide sequences, refer to two or more sequences or subsequences that are the same or have a specified percentage of amino acid residues or nucleotides that are the same (e.g., 60%, 65%, 70%, 75%, 80%, 85%, 90%, 95%, 98%, or 99% identity over a specified region, e.g., the entire polypeptide sequences or individual domains of the polypeptides), when compared and aligned for maximum correspondence over a comparison window or designated region as measured using one of the following sequence comparison algorithms or by manual alignment and visual inspection. Such sequences are then said to be "substantially identical." This definition also refers to the complement of a test sequence.

The term "complementary" or "substantially complementary," interchangeably used herein, means that a nucleic acid (e.g. DNA or RNA) has a sequence of nucleotides that enables it to non-covalently bind, i.e., form Watson-Crick base pairs and/or G/U base pairs, to another nucleic acid in a sequence-specific, antiparallel, manner (i.e., a nucleic acid specifically binds to a complementary nucleic acid). As is known in the art, standard Watson-Crick base-pairing includes: adenine (A) pairing with thymidine (T), adenine (A) pairing with uracil (U), and guanine (G) pairing with cytosine (C).

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g., tRNA, rRNA, or a guide RNA; also referred to herein as "non-coding" RNA or "ncRNA"). A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences.

As used herein, "codon" refers to a sequence of three nucleotides that together form a unit of genetic code in a DNA or RNA molecule. As used herein the term "codon degeneracy" refers to the nature in the genetic code permitting variation of the nucleotide sequence without affecting the amino acid sequence of an encoded polypeptide.

The term "codon-optimized" or "codon optimization" refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism. Codon usage tables are readily available, for example, at the "Codon Usage Database" available at www.kazusa.or.jp/codon/(visited Mar. 20, 2008). By utilizing the knowledge on codon usage or codon preference in each organism, one of ordinary skill in the art can apply the frequencies to any given polypeptide sequence and produce a nucleic acid fragment of a codon-optimized coding region which encodes the polypeptide, but which uses codons optimal for a given species. Codon-optimized coding regions can be designed by various methods known to those skilled in the art.

The term "recombinant" or "engineered" when used with reference, for example, to a cell, a nucleic acid, a protein, or a vector, indicates that the cell, nucleic acid, protein or vector has been modified by or is the result of laboratory methods. Thus, for example, recombinant or engineered proteins include proteins produced by laboratory methods. Recombinant or engineered proteins can include amino acid residues not found within the native (non-recombinant or wild-type) form of the protein or can be include amino acid residues that have been modified, e.g., labeled. The term can include any modifications to the peptide, protein, or nucleic acid sequence. Such modifications may include the following: any chemical modifications of the peptide, protein or nucleic acid sequence, including of one or more amino acids, deoxyribonucleotides, or ribonucleotides; addition, deletion, and/or substitution of one or more amino acids in the peptide or protein; and addition, deletion, and/or substitution of one or more nucleic acids in the nucleic acid sequence.

The term "genomic DNA" or "genomic sequence" refers to the DNA of a genome of an organism including, but not limited to, the DNA of the genome of a bacterium, fungus, archaeon, plant, or animal.

As used herein, "transgene," "exogenous gene" or "exogenous sequence," in the context of nucleic acid, refers to a nucleic acid sequence or gene that was not present in the genome of a cell but artificially introduced into the genome, e.g., via genome-edition.

As used herein, "endogenous gene" or "endogenous sequence," in the context of nucleic acid, refers to a nucleic acid sequence or gene that is naturally present in the genome of a cell, without being introduced via any artificial means.

The term "vector" or "expression vector" means a replicon, such as plasmid, phage, virus, or cosmid, to which another DNA segment, i.e., an "insert", may be attached so as to bring about the replication of the attached segment in a cell.

The term "expression cassette" refers to a vector having a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression. The terms "recombinant expression vector," or "DNA construct" are used interchangeably herein to refer to a DNA molecule having a vector and at least one insert. Recombinant expression vectors are usually generated for the purpose of expressing and/or propagating the insert(s), or for the construction of other recombinant nucleotide sequences. The nucleic acid(s) may or may not be operably linked to a promoter sequence and may or may not be operably linked to DNA regulatory sequences.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

A cell has been "genetically modified" or "transformed" or "transfected" by exogenous DNA, e.g., a recombinant expression vector, when such DNA has been introduced inside the cell. The presence of the exogenous DNA results in permanent or transient genetic change. The transforming DNA may or may not be integrated (covalently linked) into the genome of the cell. The genetically modified (or transformed or transfected) cells that have therapeutic activity, e.g., treating Hemophilia A, can be used and referred to as therapeutic cells.

The term "concentration" used in the context of a molecule such as peptide fragment refers to an amount of molecule, e.g., the number of moles of the molecule, present in a given volume of solution.

The terms "individual," "subject" and "host" are used interchangeably herein and refer to any subject for whom diagnosis, treatment or therapy is desired. In some aspects, the subject is a mammal. In some aspects, the subject is a human being. In some aspects, the subject is a human patient. In some aspects, the subject can have or is suspected of having a disorder or health condition associated with a protein-of-interest (POI). In some aspects, the subject is a human who is diagnosed with a risk of disorder or health condition associated with a POI at the time of diagnosis or later. In some cases, the diagnosis with a risk of disorder or health condition associated with a POI can be determined based on the presence of one or more mutations in an endogenous gene encoding the POI or nearby genomic sequence that may affect the expression of the POI. For example, in some aspects the POI is Factor VIII (FVIII), and the subject can have or is suspected of having Hemophilia A and/or has one or more symptoms of Hemophilia A. In some aspects, the subject is a human who is diagnosed with a risk of Hemophilia A at the time of diagnosis or later. In some cases, the diagnosis with a risk of Hemophilia A can be determined based on the presence of one or more mutations in an endogenous FVIII gene or genomic sequence near the FVIII gene in the genome that may affect the expression of the FVIII gene.

The term "treatment" used referring to a disease or condition means that at least an amelioration of the symptoms associated with the condition afflicting an individual is achieved, where amelioration is used in a broad sense to refer to at least a reduction in the magnitude of a parameter, e.g., a symptom, associated with the condition (e.g., Hemophilia A) being treated. As such, treatment also includes situations where the pathological condition, or at least symptoms associated therewith, are completely inhibited, e.g., prevented from happening, or eliminated entirely such that the host no longer suffers from the condition, or at least the symptoms that characterize the condition. Thus, treatment includes: (i) prevention, that is, reducing the risk of development of clinical symptoms, including causing the clinical symptoms not to develop, e.g., preventing disease progression; (ii) inhibition, that is, arresting the development or further development of clinical symptoms, e.g., mitigating or completely inhibiting an active disease.

The terms "effective amount," "pharmaceutically effective amount," or "therapeutically effective amount" as used herein mean a sufficient amount of the composition to provide the desired utility when administered to a subject having a particular condition. In the context of ex vivo treatment of Hemophilia A, the term "effective amount" refers to the amount of a population of therapeutic cells or their progeny needed to prevent or alleviate at least one or more signs or symptoms of Hemophilia A, and relates to a sufficient amount of a composition having the therapeutic cells or their progeny to provide the desired effect, e.g., to treat symptoms of Hemophilia A of a subject. The term "therapeutically effective amount" therefore refers to a number of therapeutic cells or a composition having therapeutic cells that is sufficient to promote a particular effect when administered to a subject in need of treatment, such as one who has or is at risk for Hemophilia A. An effective amount would also include an amount sufficient to prevent or delay the development of a symptom of the disease, alter the course of a symptom of the disease (for example but not limited to, slow the progression of a symptom of the disease), or reverse a symptom of the disease. In the context of in vivo treatment of Hemophilia A in a subject (e.g., a patient) or genome edition done in a cell cultured in vitro, an effective amount refers to an amount of components used for genome edition such as gRNA, donor template and/or a site-directed polypeptide (e.g. DNA endonuclease) needed to edit the genome of the cell in the subject or the cell cultured in vitro. It is understood that for any given case, an appropriate "effective amount" can be determined by one of ordinary skill in the art using routine experimentation.

The term "pharmaceutically acceptable excipient" as used herein refers to any suitable substance that provides a pharmaceutically acceptable carrier, additive or diluent for administration of a compound(s) of interest to a subject. "Pharmaceutically acceptable excipient" can encompass substances referred to as pharmaceutically acceptable diluents, pharmaceutically acceptable additives, and pharmaceutically acceptable carriers.

Nucleic Acids

Genome-Targeting Nucleic Acid or Guide RNA

The present disclosure provides a genome-targeting nucleic acid that can direct the activities of an associated polypeptide (e.g., a site-directed polypeptide or DNA endonuclease) to a specific target sequence within a target nucleic acid. In some embodiments, the genome-targeting nucleic acid is an RNA. A genome-targeting RNA is referred to as a "guide RNA" or "gRNA" herein. A guide RNA has at least a spacer sequence that hybridizes to a target nucleic acid sequence of interest and a CRISPR repeat sequence. In Type II systems, the gRNA also has a second RNA referred to as a tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex binds a site-directed polypeptide such that the guide RNA and site-direct polypeptide form a complex. The genome-targeting nucleic acid provides target specificity to the complex by virtue of its association with the site-directed polypeptide. The genome-targeting nucleic acid thus directs the activity of the site-directed polypeptide.

In some embodiments, the genome-targeting nucleic acid is a double-molecule guide RNA. In some embodiments, the genome-targeting nucleic acid is a single-molecule guide RNA. A double-molecule guide RNA has two strands of RNA. The first strand has in the 5' to 3' direction, an optional spacer extension sequence, a spacer sequence and a minimum CRISPR repeat sequence. The second strand has a minimum tracrRNA sequence (complementary to the minimum CRISPR repeat sequence), a 3' tracrRNA sequence and an optional tracrRNA extension sequence. A single-molecule guide RNA (sgRNA) in a Type II system has, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may have elements that contribute additional functionality (e.g., stability) to the guide RNA. The single-molecule guide linker links the minimum CRISPR repeat and the minimum tracrRNA sequence to form a hairpin structure. The optional tracrRNA extension has one or more hairpins. A single-molecule guide RNA (sgRNA) in a Type V system has, in the 5' to 3' direction, a minimum CRISPR repeat sequence and a spacer sequence.

By way of illustration, guide RNAs used in the CRISPR/Cas/Cpf1 system, or other smaller RNAs can be readily synthesized by chemical means as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In some embodiments, provided herein is a guide RNA (gRNA) comprising a spacer sequence that is complementary to a genomic sequence within or near an endogenous transferrin locus in a cell. In some embodiments, the gRNA comprises a spacer sequence that is complementary to a sequence within intron 1 of an endogenous transferrin gene in the cell. In some embodiments, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

Spacer Extension Sequence

In some embodiments of genome-targeting nucleic acids, a spacer extension sequence can modify activity, provide stability and/or provide a location for modifications of a genome-targeting nucleic acid. A spacer extension sequence can modify on-or off-target activity or specificity. In some embodiments, a spacer extension sequence is provided. A spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of about 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. In some embodiments, a spacer extension sequence is less than 10 nucleotides in length. In some embodiments, a spacer extension sequence is between 10-30 nucleotides in length. In some embodiments, a spacer extension sequence is between 30-70 nucleotides in length.

In some embodiments, the spacer extension sequence has another moiety (e.g., a stability control sequence, an endoribonuclease binding sequence, a ribozyme). In some embodiments, the moiety decreases or increases the stability of a nucleic acid targeting nucleic acid. In some embodiments, the moiety is a transcriptional terminator segment (i.e., a transcription termination sequence). In some embodiments, the moiety functions in a eukaryotic cell. In some embodiments, the moiety functions in a prokaryotic cell. In some embodiments, the moiety functions in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid interacts with a target nucleic acid in a sequence-specific manner via hybridization (i.e., base pairing). The nucleotide sequence of the spacer thus varies depending on the sequence of the target nucleic acid of interest.

In a CRISPR/Cas system herein, the spacer sequence is designed to hybridize to a target nucleic acid that is located 5' of a PAM of the Cas9 enzyme used in the system. The spacer can perfectly match the target sequence or can have mismatches. Each Cas9 enzyme has a particular PAM sequence that it recognizes in a target DNA. For example, S. pyogenes recognizes in a target nucleic acid a PAM that has the sequence 5'-NRG-3', where R has either A or G, where N is any nucleotide and N is immediately 3' of the target nucleic acid sequence targeted by the spacer sequence.

In some embodiments, the target nucleic acid sequence has 20 nucleotides. In some embodiments, the target nucleic acid has less than 20 nucleotides. In some embodiments, the target nucleic acid has more than 20 nucleotides. In some embodiments, the target nucleic acid has at least: 5, 10, 15, 16, 17, 18, 19, 20, 21, 22, 23, 24, 25, 30 or more nucleotides. In some embodiments, the target nucleic acid has at most: 5, 10, 15, 16, 17, 18, 19, 20, 21, 22, 23, 24, 25, 30 or more nucleotides. In some embodiments, the target nucleic acid sequence has 20 bases immediately 5' of the first nucleotide of the PAM. For example, in a sequence having 5'-NNNNNNNNNNNNNNNNNNNNNRG-3' (SEQ ID NO: 191), the target nucleic acid has the sequence that corresponds to the Ns, wherein N is any nucleotide, and the underlined NRG sequence (R is G or A) is the Streptococcus pyogenes Cas9 PAM. In some embodiments, the PAM sequence used in the compositions and methods of the present disclosure as a sequence recognized by S.p. Cas9 is NGG.

In some embodiments, the spacer sequence that hybridizes to the target nucleic acid has a length of at least about 6 nucleotides (nt). The spacer sequence can be at least about 6 nt, about 10 nt, about 15 nt, about 18 nt, about 19 nt, about 20 nt, about 25 nt, about 30 nt, about 35 nt or about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some embodiments, the spacer sequence has 20 nucleotides. In some embodiments, the spacer has 19 nucleotides. In some embodiments, the spacer has 18 nucleotides. In some embodiments, the spacer has 17 nucleotides. In some embodiments, the spacer has 16 nucleotides. In some embodiments, the spacer has 15 nucleotides.

In some embodiments, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some embodiments, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some embodiments, the percent complementarity between the spacer sequence and the target nucleic acid is 100% over the six contiguous 5'-most nucleotides of the target sequence of the complementary strand of the target nucleic acid. In some embodiments, the percent complementarity between the spacer sequence and the target nucleic acid is at least 60% over about 20 contiguous nucleotides. In some embodiments, the length of the spacer sequence and the target nucleic acid can differ by 1 to 6 nucleotides, which can be thought of as a bulge or bulges.

In some embodiments, the spacer sequence is designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

In some embodiments, a minimum CRISPR repeat sequence is a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from *S. pyogenes*).

In some embodiments, a minimum CRISPR repeat sequence has nucleotides that can hybridize to a minimum tracrRNA sequence in a cell. The minimum CRISPR repeat sequence and a minimum tracrRNA sequence form a duplex, i.e., a base-paired double-stranded structure. Together, the minimum CRISPR repeat sequence and the minimum tracrRNA sequence bind to the site-directed polypeptide. At least a part of the minimum CRISPR repeat sequence hybridizes to the minimum tracrRNA sequence. In some embodiments, at least a part of the minimum CRISPR repeat sequence has at least about 30%, about 40%, about 50%, about 60%, about 65%, about 70%, about 75%, about 80%, about 85%, about 90%, about 95%, or 100% complementary to the minimum tracrRNA sequence. In some embodiments, at least a part of the minimum CRISPR repeat sequence has at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the minimum CRISPR repeat sequence is approximately 9 nucleotides in length. In some embodiments, the minimum CRISPR repeat sequence is approximately 12 nucleotides in length.

In some embodiments, the minimum CRISPR repeat sequence is at least about 60% identical to a reference minimum CRISPR repeat sequence (e.g., wild-type crRNA from *S. pyogenes*) over a stretch of at least 6, 7, or 8 contiguous nucleotides. For example, the minimum CRISPR repeat sequence is at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

In some embodiments, a minimum tracrRNA sequence is a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

In some embodiments, a minimum tracrRNA sequence has nucleotides that hybridize to a minimum CRISPR repeat sequence in a cell. A minimum tracrRNA sequence and a minimum CRISPR repeat sequence form a duplex, i.e., a base-paired double-stranded structure. Together, the minimum tracrRNA sequence and the minimum CRISPR repeat bind to a site-directed polypeptide. At least a part of the minimum tracrRNA sequence can hybridize to the minimum CRISPR repeat sequence. In some embodiments, the minimum tracrRNA sequence is at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. In some embodiments, the minimum tracrRNA sequence is approximately 9 nucleotides in length. In some embodiments, the minimum tracrRNA sequence is approximately 12 nucleotides. In some embodiments, the minimum tracrRNA consists of tracrRNA nt 23-48 described in Jinek et al. *Science,* 337 (6096): 816-821 (2012).

In some embodiments, the minimum tracrRNA sequence is at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence is at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

In some embodiments, the duplex between the minimum CRISPR RNA and the minimum tracrRNA has a double helix. In some embodiments, the duplex between the minimum CRISPR RNA and the minimum tracrRNA has at least about 1, 2, 3, 4, 5, 6, 7, 8, 9, or 10 or more nucleotides. In some embodiments, the duplex between the minimum CRISPR RNA and the minimum tracrRNA has at most about 1, 2, 3, 4, 5, 6, 7, 8, 9, or 10 or more nucleotides.

In some embodiments, the duplex has a mismatch (i.e., the two strands of the duplex are not 100% complementary). In some embodiments, the duplex has at least about 1, 2, 3, 4, or 5 or mismatches. In some embodiments, the duplex has at most about 1, 2, 3, 4, or 5 or mismatches. In some embodiments, the duplex has no more than 2 mismatches.

Bulges

In some embodiments, there is a "bulge" in the duplex between the minimum CRISPR RNA and the minimum tracrRNA. The bulge is an unpaired region of nucleotides within the duplex. In some embodiments, the bulge contributes to the binding of the duplex to the site-directed polypeptide. A bulge has, on one side of the duplex, an unpaired 5'-XXXY-3' where X is any purine and Y has a nucleotide that can form a wobble pair with a nucleotide on the opposite strand, and an unpaired nucleotide region on the other side of the duplex. The number of unpaired nucleotides on the two sides of the duplex can be different.

In one example, the bulge has an unpaired purine (e.g., adenine) on the minimum CRISPR repeat strand of the bulge. In some embodiments, a bulge has an unpaired 5'-AAGY-3' of the minimum tracrRNA sequence strand of the bulge, where Y has a nucleotide that can form a wobble pairing with a nucleotide on the minimum CRISPR repeat strand.

In some embodiments, a bulge on the minimum CRISPR repeat side of the duplex has at least 1, 2, 3, 4, or 5 or more unpaired nucleotides. In some embodiments, a bulge on the minimum CRISPR repeat side of the duplex has at most 1, 2, 3, 4, or 5 or more unpaired nucleotides. In some embodiments, a bulge on the minimum CRISPR repeat side of the duplex has 1 unpaired nucleotide.

In some embodiments, a bulge on the minimum tracrRNA sequence side of the duplex has at least 1, 2, 3, 4, 5, 6, 7, 8, 9, or 10 or more unpaired nucleotides. In some embodiments, a bulge on the minimum tracrRNA sequence side of the duplex has at most 1, 2, 3, 4, 5, 6, 7, 8, 9, or 10 or more unpaired nucleotides. In some embodiments, a bulge on a second side of the duplex (e.g., the minimum tracrRNA sequence side of the duplex) has 4 unpaired nucleotides.

In some embodiments, a bulge has at least one wobble pairing. In some embodiments, a bulge has at most one wobble pairing. In some embodiments, a bulge has at least one purine nucleotide. In some embodiments, a bulge has at least 3 purine nucleotides. In some embodiments, a bulge sequence has at least 5 purine nucleotides. In some embodiments, a bulge sequence has at least one guanine nucleotide. In some embodiments, a bulge sequence has at least one adenine nucleotide.

Hairpins

In various embodiments, one or more hairpins are located 3' to the minimum tracrRNA in the 3' tracrRNA sequence.

In some embodiments, the hairpin starts at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. In some embodiments, the hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

In some embodiments, a hairpin has at least about 1, 2, 3, 4, 5, 6, 7, 8, 9, 10, 15, or 20 or more consecutive nucleotides. In some embodiments, a hairpin has at most about 1, 2, 3, 4, 5, 6, 7, 8, 9, 10, 15, or more consecutive nucleotides.

In some embodiments, a hairpin has a CC di-nucleotide (i.e., two consecutive cytosine nucleotides).

In some embodiments, a hairpin has duplexed nucleotides (e.g., nucleotides in a hairpin, hybridized together). For example, a hairpin has a CC di-nucleotide that is hybridized to a GG di-nucleotide in a hairpin duplex of the 3' tracrRNA sequence.

One or more of the hairpins can interact with guide RNA-interacting regions of a site-directed polypeptide.

In some embodiments there are two or more hairpins, and in some embodiments there are three or more hairpins.

3' tracrRNA Sequence

In some embodiments, a 3' tracrRNA sequence has a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

In some embodiments, the 3' tracrRNA sequence has a length from about 6 nucleotides to about 100 nucleotides. For example, the 3' tracrRNA sequence can have a length from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the 3' tracrRNA sequence has a length of approximately 14 nucleotides.

In some embodiments, the 3' tracrRNA sequence is at least about 60% identical to a reference 3' tracrRNA sequence (e.g., wild type 3' tracrRNA sequence from *S. pyogenes*) over a stretch of at least 6, 7, or 8 contiguous nucleotides. For example, the 3' tracrRNA sequence is at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from *S. pyogenes*) over a stretch of at least 6, 7, or 8 contiguous nucleotides.

In some embodiments, a 3' tracrRNA sequence has more than one duplexed region (e.g., hairpin, hybridized region). In some embodiments, a 3' tracrRNA sequence has two duplexed regions.

In some embodiments, the 3' tracrRNA sequence has a stem loop structure. In some embodiments, a stem loop structure in the 3' tracrRNA has at least 1, 2, 3, 4, 5, 6, 7, 8, 9, 10, 15 or 20 or more nucleotides. In some embodiments, the stem loop structure in the 3' tracrRNA has at most 1, 2, 3, 4, 5, 6, 7, 8, 9 or 10 or more nucleotides. In some embodiments, the stem loop structure has a functional moiety. For example, the stem loop structure can have an aptamer, a ribozyme, a protein-interacting hairpin, a CRISPR array, an intron, or an exon. In some embodiments, the stem loop structure has at least about 1, 2, 3, 4, or 5 or more functional moieties. In some embodiments, the stem loop structure has at most about 1, 2, 3, 4, or 5 or more functional moieties.

In some embodiments, the hairpin in the 3' tracrRNA sequence has a P-domain. In some embodiments, the P-domain has a double-stranded region in the hairpin.

tracrRNA Extension Sequence

In some embodiments, a tracrRNA extension sequence can be provided whether the tracrRNA is in the context of single-molecule guides or double-molecule guides. In some embodiments, a tracrRNA extension sequence has a length from about 1 nucleotide to about 400 nucleotides. In some embodiments, a tracrRNA extension sequence has a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. In some embodiments, a tracrRNA extension sequence has a length from about 20 to about 5000 or more nucleotides. In some embodiments, a tracrRNA extension sequence has a length of more than 1000 nucleotides. In some embodiments, a tracrRNA extension sequence has a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. In some embodiments, a tracrRNA extension sequence can have a length of less than 1000 nucleotides. In some embodiments, a tracrRNA extension sequence has less than 10 nucleotides in length. In some embodiments, a tracrRNA extension sequence is 10-30 nucleotides in length. In some embodiments, tracrRNA extension sequence is 30-70 nucleotides in length.

In some embodiments, the tracrRNA extension sequence has a functional moiety (e.g., a stability control sequence, ribozyme, endoribonuclease binding sequence). In some embodiments, the functional moiety has a transcriptional terminator segment (i.e., a transcription termination sequence). In some embodiments, the functional moiety has a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. In some embodiments, the functional moiety functions in a eukaryotic cell. In some embodiments, the functional moiety functions in a prokaryotic cell. In some embodiments, the functional moiety functions in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). In some embodiments, a tracrRNA extension sequence has a primer binding site or a molecular index (e.g., barcode sequence). In some embodiments, the tracrRNA extension sequence has one or more affinity tags.

Single-Molecule Guide Linker Sequence

In some embodiments, the linker sequence of a single-molecule guide nucleic acid has a length from about 3 nucleotides to about 100 nucleotides. In Jinek et al., supra, for example, a simple 4 nucleotide "tetraloop" (-GAAA-) was used, Science, 337 (6096): 816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single-molecule guide nucleic acid is between 4 and 40 nucleotides. In some embodiments, a linker is at least about 100, 500, 1000, 1500, 2000, 2500, 3000, 3500, 4000, 4500, 5000, 5500, 6000, 6500, or 7000 or more nucleotides. In some embodiments, a linker is at most about 100, 500, 1000, 1500, 2000, 2500, 3000, 3500, 4000, 4500, 5000, 5500, 6000, 6500, or 7000 or more nucleotides.

Linkers can have any of a variety of sequences, although in some embodiments, the linker will not have sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337 (6096): 816-821 (2012), but numerous other sequences, including longer sequences can likewise be used.

In some embodiments, the linker sequence has a functional moiety. For example, the linker sequence can have one or more features, including an aptamer, a ribozyme, a protein-interacting hairpin, a protein binding site, a CRISPR array, an intron, or an exon. In some embodiments, the linker sequence has at least about 1, 2, 3, 4, or 5 or more functional moieties. In some embodiments, the linker sequence has at most about 1, 2, 3, 4, or 5 or more functional moieties.

In some embodiments, a genomic location targeted by gRNAs in accordance with the preset disclosure can be at, within or near the endogenous transferrin locus in a genome, e.g., a human genome. Exemplary guide RNAs targeting such locations include the spacer sequences listed in Table 2 (e.g., spacer sequences from SEQ ID NOs: 1-188). For example, a gRNA including a spacer sequence from SEQ ID NO: 1 can have a spacer sequence including i) the sequence of SEQ ID NO: 1, ii) the sequence from position 2 to position 20 of SEQ ID NO: 1, iii) the sequence from position 3 to position 20 of SEQ ID NO: 1, iv) the sequence from position 4 to position 20 of SEQ ID NO: 1, and so forth. As is understood by the person of ordinary skill in the art, each guide RNA is designed to include a spacer sequence complementary to its genomic target sequence. For example, each of the spacer sequences listed in Table 2 can be put into a single RNA chimera or a crRNA (along with a corresponding tracrRNA). See Jinek et al., Science, 337, 816-821 (2012) and Deltcheva et al., Nature, 471, 602-607 (2011).

Donor DNA or Donor Template

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair (HDR) or non-homologous end joining or alternative non-homologous end joining (A-NHEJ) or microhomology-mediated end joining (MMEJ). NHEJ can repair cleaved target nucleic acid without the need for a homologous template. This can sometimes result in small deletions or insertions (indels) in the target nucleic acid at the site of cleavage, and can lead to disruption or alteration of gene expression. HDR, which is also known as homologous recombination (HR) can occur when a homologous repair template, or donor, is available.

The homologous donor template has sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide, double-stranded oligonucleotide, or viral nucleic acid. With exogenous donor templates, it is common to introduce an additional nucleic acid sequence (such as a transgene) or modification (such as a single or multiple base change or a deletion) between the flanking regions of homology so that the additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few base pairs flanking the cleavage site to drive a favored end-joining DNA repair outcome. In some instances, it can be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor polynucleotide (or donor or donor sequence or polynucleotide donor template) herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, i.e., a sequence that does not naturally occur at the target nucleic acid cleavage site.

When an exogenous DNA molecule is supplied in sufficient concentration inside the nucleus of a cell in which the double-strand break occurs, the exogenous DNA can be inserted at the double-strand break during the NHEJ repair process and thus become a permanent addition to the genome. These exogenous DNA molecules are referred to as donor templates in some embodiments. If the donor template contains a coding sequence for a gene of interest such as a FVIII gene optionally together with relevant regulatory sequences such as promoters, enhancers, polyA sequences and/or splice acceptor sequences (also referred to herein as a "donor cassette"), the gene of interest can be expressed from the integrated copy in the genome resulting in permanent expression for the life of the cell. Moreover, the integrated copy of the donor DNA template can be transmitted to the daughter cells when the cell divides.

In the presence of sufficient concentrations of a donor DNA template that contains flanking DNA sequences with homology to the DNA sequence either side of the double-strand break (referred to as homology arms), the donor DNA template can be integrated via the HDR pathway. The homology arms act as substrates for homologous recombination between the donor template and the sequences either side of the double-strand break. This can result in an error free insertion of the donor template in which the sequences either side of the double-strand break are not altered from that in the unmodified genome.

Supplied donors for editing by HDR vary markedly but generally contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors can be used. These oligonucleotides range in size from less than 100 nt to over many kb, though longer ssDNA can also be generated and used. Double-stranded donors are often used, including PCR amplicons, plasmids, and mini-circles. In general, it has been found that an AAV vector is a very effective means of delivery of a donor template, though the packaging limits for individual donors is <5 kb. Active transcription of the donor increased HDR three-fold, indicating the inclusion of promoter can increase conversion. Conversely, CpG methylation of the donor can decrease gene expression and HDR.

In some embodiments, the donor DNA can be supplied with the nuclease or independently by a variety of different methods, for example by transfection, nano-particle, micro-injection, or viral transduction. A range of tethering options can be used to increase the availability of the donors for HDR in some embodiments. Examples include attaching the donor to the nuclease, attaching to DNA binding proteins that bind nearby, or attaching to proteins that are involved in DNA end binding or repair.

In addition to genome editing by NHEJ or HDR, site-specific gene insertions can be conducted that use both the NHEJ pathway and HR. A combination approach can be applicable in certain settings, possibly including intron/exon borders. NHEJ can prove effective for ligation in the intron, while the error-free HDR can be better suited in the coding region.

In some embodiments, an exogenous sequence that is intended to be inserted into a genome is a nucleotide sequence encoding a protein-of-interest (POI) or a functional derivative thereof, e.g., Factor VIII (FVIII) or a functional derivative thereof. The functional derivative of a POI can include a derivative of the POI that has a substantial activity of a wild-type POI, such as the wild-type human POI, e.g., at least about 30%, about 40%, about 50%, about 60%, about 70%, about 80%, about 90%, about 95% or about 100% of the activity that the wild-type POI exhibits. In some embodiments, the functional derivative of a POI can have at least about 30%, about 40%, about 50%, about 60%, about 70%, about 80%, about 85%, about 90%, about 95%, about 96%, about 97%, about 98% or about 99% amino acid sequence identity to the POI, e.g., the wild-type POI. In some embodiments, one having ordinary skill in the art can use a number of methods known in the field to test the functionality or activity of a compound, e.g., a peptide or protein. The functional derivative of the POI can also include any fragment of the wild-type POI or fragment of a modified POI that has conservative modification on one or more of amino acid residues in the full length, wild-type POI. Thus, in some embodiments, a nucleic acid sequence encoding a functional derivative of a POI can have at least about 30%, about 40%, about 50%, about 60%, about 70%, about 80%, about 85%, about 90%, about 95%, about 96%, about 97%, about 98% or about 99% nucleic acid sequence identity to a nucleic acid sequence encoding the POI, e.g., the wild-type POI. In some embodiments, the POI is FVIII.

In some embodiments where the insertion of a nucleic acid encoding a POI (e.g., FVIII) or a functional derivative thereof is concerned, a cDNA of the POI gene or a functional derivative thereof can be inserted into a genome of a subject having a defective POI gene or its regulatory sequences. In such a case, a donor DNA or donor template can be an expression cassette or vector construct having a sequence encoding the POI or a functional derivative thereof, e.g., a cDNA sequence. In some embodiments, the expression vector contains a sequence encoding a modified POI, such as FVIII-BDD, which is described elsewhere in the disclosures. In some embodiments, the POI is FVIII.

In some embodiments, according to any of the donor templates described herein comprising a donor cassette, the donor cassette is flanked on one or both sides by a gRNA target site. For example, such a donor template may comprise a donor cassette with a gRNA target site 5' of the donor cassette and/or a gRNA target site 3' of the donor cassette. In some embodiments, the donor template comprises a donor cassette with a gRNA target site 5' of the donor cassette. In some embodiments, the donor template comprises a donor cassette with a gRNA target site 3' of the donor cassette. In some embodiments, the donor template comprises a donor cassette with a gRNA target site 5' of the donor cassette and a gRNA target site 3' of the donor cassette. In some embodiments, the donor template comprises a donor cassette with a gRNA target site 5' of the donor cassette and a gRNA target site 3' of the donor cassette, and the two gRNA target sites comprise the same sequence. In some embodiments, the donor template comprises at least one gRNA target site, and the at least one gRNA target site in the donor template comprises the same sequence as a gRNA target site in a target locus into which the donor cassette of the donor template is to be integrated. In some embodiments, the donor template comprises at least one gRNA target site, and the at least one gRNA target site in the donor template comprises the reverse complement of a gRNA target site in a target locus into which the donor cassette of the donor template is to be integrated. In some embodiments, the donor template comprises a donor cassette with a gRNA target site 5' of the donor cassette and a gRNA target site 3' of the donor cassette, and the two gRNA target sites in the donor template comprises the same sequence as a gRNA target site in a target locus into which the donor cassette of the donor template is to be integrated. In some embodiments, the donor template comprises a donor cassette with a gRNA target site 5' of the donor cassette and a gRNA target site 3' of the donor cassette, and the two gRNA target sites in the donor template comprises the reverse complement of a gRNA target site in a target locus into which the donor cassette of the donor template is to be integrated.

In some embodiments, provided herein is a donor template comprising a nucleotide sequence encoding a protein-of-interest (POI) or a functional derivative thereof for targeted integration into intron 1 of a transferrin gene, wherein the donor template comprises, from 5' to 3', i) a first gRNA target site; ii) a splice acceptor; iii) the nucleotide sequence encoding a POI or a functional derivative thereof; and iv) a polyadenylation signal. In some embodiments, the donor template further comprises a second gRNA target site downstream of the iv) polyadenylation signal. In some embodiments, the first gRNA target site and the second gRNA target site are the same. In some embodiments, the donor template further comprises a sequence encoding the terminal portion of the transferrin signal peptide encoded on exon 2 of the transferrin gene or a variant thereof that retains at least some of the activity of the endogenous sequence between the ii) splice acceptor and iii) nucleotide sequence encoding a POI or a functional derivative thereof. In some embodiments, the donor template further comprises a polynucleotide spacer between the i) first gRNA target site and the ii) splice acceptor. In some embodiments, the polynucleotide spacer is 18 nucleotides in length. In some embodiments, the donor template is flanked on one side by a first AAV ITR and/or flanked on the other side by a second AAV ITR. In some embodiments, the first AAV ITR is an AAV2 ITR and/or the second AAV ITR is an AAV2 ITR. In some embodiments, the POI is selected from the group consisting of Factor VIII (FVIII), Factor IX, alpha-1-antitrypsin, FXIII, FVII, Factor X, a C1 esterase inhibitor, iduronate sulfatase, α-L-iduronidase, and Protein C. In some embodiments, the POI is FVIII. In some embodiments, the iii) nucleotide sequence encoding a POI or a functional derivative thereof encodes a mature human B-domain deleted FVIII. Exemplary sequences for the donor template components can be found in the donor template sequences of SEQ ID NO: 224 and/or 251.

Nucleic Acid Encoding a Site-Directed Polypeptide or DNA Endonuclease

In some embodiments, the methods of genome edition and compositions therefore can use a nucleic acid sequence (or oligonucleotide) encoding a site-directed polypeptide or DNA endonuclease. The nucleic acid sequence encoding the site-directed polypeptide can be DNA or RNA. If the nucleic acid sequence encoding the site-directed polypeptide is RNA, it can be covalently linked to a gRNA sequence or exist as a separate sequence. In some embodiments, a peptide sequence of the site-directed polypeptide or DNA endonuclease can be used instead of the nucleic acid sequence thereof.

Vectors

In another aspect, the present disclosure provides a nucleic acid having a nucleotide sequence encoding a genome-targeting nucleic acid of the disclosure, a site-directed polypeptide of the disclosure, and/or any nucleic acid or proteinaceous molecule necessary to carry out the embodiments of the methods of the disclosure. In some embodiments, such a nucleic acid is a vector (e.g., a recombinant expression vector).

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some embodiments, a vector has one or more transcription and/or translation control elements. Depending on the host/vector system utilized, any of a number of suitable transcription and translation control elements, including constitutive and inducible promoters, transcription enhancer elements, transcription terminators, etc., can be used in the expression vector. In some embodiments, the vector is a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct having the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., *Molecular Therapy—Nucleic Acids* 3, e161 (2014) doi: 10.1038/mtna.2014.12.

The expression vector can also contain a ribosome binding site for translation initiation and a transcription terminator. The expression vector can also include appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

In some embodiments, a promoter is an inducible promoter (e.g., a heat shock promoter, tetracycline-regulated promoter, steroid-regulated promoter, metal-regulated promoter, estrogen receptor-regulated promoter, etc.). In some embodiments, a promoter is a constitutive promoter (e.g., CMV promoter, UBC promoter). In some embodiments, the promoter is a spatially restricted and/or temporally restricted promoter (e.g., a tissue specific promoter, a cell type specific promoter, etc.). In some embodiments, a vector does not have a promoter for at least one gene to be expressed in a host cell if the gene is going to be expressed, after it is inserted into a genome, under an endogenous promoter present in the genome.

Site-Directed Polypeptide or DNA Endonuclease

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The process of integrating non-native nucleic acid into genomic DNA is an example of genome editing.

A site-directed polypeptide is a nuclease used in genome editing to cleave DNA. The site-directed polypeptide can be administered to a cell or a subject as either: one or more polypeptides, or one or more mRNAs encoding the polypeptide.

In the context of a CRISPR/Cas or CRISPR/Cpf1 system, the site-directed polypeptide can bind to a guide RNA that, in turn, specifies the site in the target DNA to which the polypeptide is directed. In embodiments of CRISPR/Cas or CRISPR/Cpf1 systems herein, the site-directed polypeptide is an endonuclease, such as a DNA endonuclease.

In some embodiments, a site-directed polypeptide has a plurality of nucleic acid-cleaving (i.e., nuclease) domains. Two or more nucleic acid-cleaving domains can be linked together via a linker. In some embodiments, the linker has a flexible linker. Linkers can have 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes have two nuclease domains, a HNH nuclease domain and a RuvC domain. Herein, the "Cas9" refers to both naturally-occurring and recombinant Cas9s. Cas9 enzymes contemplated herein have a HNH or HNH-like nuclease domain, and/or a RuvC or RuvC-like nuclease domain.

HNH or HNH-like domains have a McrA-like fold. HNH or HNH-like domains has two antiparallel β-strands and an α-helix. HNH or HNH-like domains has a metal binding site (e.g., a divalent cation binding site). HNH or HNH-like domains can cleave one strand of a target nucleic acid (e.g., the complementary strand of the crRNA targeted strand).

RuvC or RuvC-like domains have an RNaseH or RNaseH-like fold. RuvC/RNaseH domains are involved in a diverse set of nucleic acid-based functions including acting on both RNA and DNA. The RNaseH domain has 5 β-strands surrounded by a plurality of α-helices. RuvC/RNaseH or RuvC/RNaseH-like domains have a metal binding site (e.g., a divalent cation binding site). RuvC/RNaseH or RuvC/RNaseH-like domains can cleave one strand of a target nucleic acid (e.g., the non-complementary strand of a double-stranded target DNA).

In some embodiments, the site-directed polypeptide has an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from *S. pyogenes*, US2014/0068797 Sequence ID No. 8 or Sapranauskas et al., *Nucleic Acids Res*, 39 (21): 9275-9282 (2011)], and various other site-directed polypeptides).

In some embodiments, the site-directed polypeptide has an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to the nuclease domain of a wild-type exemplary site-directed polypeptide (e.g., Cas9 from *S. pyogenes*, supra).

In some embodiments, a site-directed polypeptide has at least 70, 75, 80, 85, 90, 95, 97, 99, or 100% identity to a wild-type site-directed polypeptide (e.g., Cas9 from *S. pyogenes*, supra) over 10 contiguous amino acids. In some embodiments, a site-directed polypeptide has at most: 70, 75, 80, 85, 90, 95, 97, 99, or 100% identity to a wild-type site-directed polypeptide (e.g., Cas9 from *S. pyogenes*, supra) over 10 contiguous amino acids. In some embodiments, a site-directed polypeptide has at least: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. In some embodiments, a site-directed polypeptide has at most: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. In some embodiments, a site-directed polypeptide has at least: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide. In some embodiments, a site-directed polypeptide has at most: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide.

In some embodiments, the site-directed polypeptide has a modified form of a wild-type exemplary site-directed polypeptide. The modified form of the wild-type exemplary site-directed polypeptide has a mutation that reduces the nucleic acid-cleaving activity of the site-directed polypeptide. In some embodiments, the modified form of the wild-type exemplary site-directed polypeptide has less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from *S. pyogenes*, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

In some embodiments, the modified form of the site-directed polypeptide has a mutation such that it can induce a single-strand break (SSB) on a target nucleic acid (e.g., by cutting only one of the sugar-phosphate backbones of a double-strand target nucleic acid). In some embodiments, the mutation results in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra). In some embodiments, the mutation results in one or more of the plurality of nucleic acid-cleaving domains retaining the ability to cleave the complementary strand of the target nucleic acid, but reducing its ability to cleave the non-complementary strand of the target nucleic acid. In some embodiments, the mutation results in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854 and Asn856, are mutated to inactivate one or more of the plurality of nucleic acid-cleaving domains (e.g., nuclease domains). In some embodiments, the residues to be mutated correspond to residues Asp10, His840, Asn854 and Asn856 in the wild-type exemplary *S. pyogenes* Cas9 polypeptide (e.g., as determined by sequence and/or structural alignment). Non-limiting examples of mutations include D10A, H840A, N854A or N856A. One skilled in the art will recognize that mutations other than alanine substitutions are suitable.

In some embodiments, a D10A mutation is combined with one or more of H840A, N854A, or N856A mutations to produce a site-directed polypeptide substantially lacking DNA cleavage activity. In some embodiments, a H840A mutation is combined with one or more of D10A, N854A, or N856A mutations to produce a site-directed polypeptide substantially lacking DNA cleavage activity. In some embodiments, a N854A mutation is combined with one or more of H840A, D10A, or N856A mutations to produce a site-directed polypeptide substantially lacking DNA cleavage activity. In some embodiments, a N856A mutation is combined with one or more of H840A, N854A, or D10A mutations to produce a site-directed polypeptide substantially lacking DNA cleavage activity. Site-directed polypeptides that have one substantially inactive nuclease domain are referred to as "nickases".

In some embodiments, variants of RNA-guided endonucleases, for example Cas9, can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes. Descriptions of various CRISPR/Cas systems for use in gene editing can be found, e.g., in international patent application publication number WO2013/176772, and in *Nature Biotechnology* 32, 347-355 (2014), and references cited therein.

In some embodiments, the site-directed polypeptide (e.g., variant, mutated, enzymatically inactive and/or conditionally enzymatically inactive site-directed polypeptide) targets nucleic acid. In some embodiments, the site-directed polypeptide (e.g., variant, mutated, enzymatically inactive and/or conditionally enzymatically inactive endoribonuclease) targets DNA. In some embodiments, the site-directed polypeptide (e.g., variant, mutated, enzymatically inactive and/or conditionally enzymatically inactive endoribonuclease) targets RNA.

In some embodiments, the site-directed polypeptide has one or more non-native sequences (e.g., the site-directed polypeptide is a fusion protein).

In some embodiments, the site-directed polypeptide has an amino acid sequence having at least 15% amino acid identity to a Cas9 from a bacterium (e.g., *S. pyogenes*), a nucleic acid binding domain, and two nucleic acid cleaving domains (i.e., a HNH domain and a RuvC domain).

In some embodiments, the site-directed polypeptide has an amino acid sequence having at least 15% amino acid identity to a Cas9 from a bacterium (e.g., *S. pyogenes*), and two nucleic acid cleaving domains (i.e., a HNH domain and a RuvC domain).

In some embodiments, the site-directed polypeptide has an amino acid sequence having at least 15% amino acid identity to a Cas9 from a bacterium (e.g., *S. pyogenes*), and two nucleic acid cleaving domains, wherein one or both of the nucleic acid cleaving domains have at least 50% amino acid identity to a nuclease domain from Cas9 from a bacterium (e.g., *S. pyogenes*).

In some embodiments, the site-directed polypeptide has an amino acid sequence having at least 15% amino acid identity to a Cas9 from a bacterium (e.g., *S. pyogenes*), two nucleic acid cleaving domains (i.e., a HNH domain and a RuvC domain), and non-native sequence (for example, a nuclear localization signal) or a linker linking the site-directed polypeptide to a non-native sequence.

In some embodiments, the site-directed polypeptide has an amino acid sequence having at least 15% amino acid identity to a Cas9 from a bacterium (e.g., *S. pyogenes*), two nucleic acid cleaving domains (i.e., a HNH domain and a RuvC domain), wherein the site-directed polypeptide has a mutation in one or both of the nucleic acid cleaving domains that reduces the cleaving activity of the nuclease domains by at least 50%.

In some embodiments, the site-directed polypeptide has an amino acid sequence having at least 15% amino acid identity to a Cas9 from a bacterium (e.g., *S. pyogenes*), and two nucleic acid cleaving domains (i.e., a HNH domain and a RuvC domain), wherein one of the nuclease domains has mutation of aspartic acid 10, and/or wherein one of the nuclease domains has mutation of histidine 840, and wherein the mutation reduces the cleaving activity of the nuclease domain(s) by at least 50%.

In some embodiments, the one or more site-directed polypeptides, e.g. DNA endonucleases, include two nickases that together effect one double-strand break at a specific locus in the genome, or four nickases that together effect two double-strand breaks at specific loci in the genome. Alternatively, one site-directed polypeptide, e.g. DNA endonuclease, affects one double-strand break at a specific locus in the genome.

In some embodiments, a polynucleotide encoding a site-directed polypeptide can be used to edit genome. In some of such embodiments, the polynucleotide encoding a site-directed polypeptide is codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

The following provides some examples of site-directed polypeptides that can be used in various embodiments of the disclosures.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary hairpin structures (e.g., hairpins) and/or have unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA has a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also has polynucleotide sequences encoding CRISPR Associated (Cas) genes. Cas genes encode endonucleases involved in the biogenesis and the interference stages of crRNA function in prokaryotes. Some Cas genes have homologous secondary and/or tertiary structures.

Type II CRISPR Systems crRNA biogenesis in a Type II CRISPR system in nature requires a trans-activating CRISPR RNA (tracrRNA). The tracrRNA is modified by endogenous RNaseIII, and then hybridizes to a crRNA repeat in the pre-crRNA array. Endogenous RNaseIII is recruited to cleave the pre-crRNA. Cleaved crRNAs are subjected to exoribonuclease trimming to produce the mature crRNA form (e.g., 5' trimming). The tracrRNA remains hybridized to the crRNA, and the tracrRNA and the crRNA associate with a site-directed polypeptide (e.g., Cas9). The crRNA of the crRNA-tracrRNA-Cas9 complex guides the complex to a target nucleic acid to which the crRNA can hybridize. Hybridization of the crRNA to the target nucleic acid activates Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science*, 337 (6096): 816-821 (2012) showed that the CRISPR/Cas9 system is useful for RNA-programmable genome editing, and international patent application publication number WO 2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays are processed into mature crRNAS without the requirement of an additional trans-activating tracrRNA. The Type V CRISPR array is processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems start with 20-24 nucleotides of spacer sequence followed by about 22 nucleotides of direct repeat. Also, Cpf1 utilizes a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Exemplary CRISPR/Cas polypeptides include the Cas9 polypeptides in FIG. 1 of Fonfara et al., *Nucleic Acids Research*, 42:2577-2590 (2014). The CRISPR/Cas gene naming system has undergone extensive rewriting since the Cas genes were discovered. FIG. 5 of Fonfara, supra, provides PAM sequences for the Cas9 polypeptides from various species.

Complexes of a Genome-Targeting Nucleic acid and a Site-Directed Polypeptide

A Genome-Targeting Nucleic Acid Interacts with a Site-Directed Polypeptide (e.g., a nucleic acid-guided nuclease such as Cas9), thereby forming a complex. The genome-targeting nucleic acid (e.g., gRNA) guides the site-directed polypeptide to a target nucleic acid.

As stated previously, in some embodiments the site-directed polypeptide and genome-targeting nucleic acid can each be administered separately to a cell or a subject. On the other hand, in some other embodiments the site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

Systems for Genome Editing

Provided herein are systems for genome editing in a cell to modulate the expression, function, and/or activity of a protein-of-interest (POI), such as by targeted integration of a nucleic acid encoding the POI or a functional derivative thereof into the genome of the cell. In some embodiments, the POI is a polypeptide selected from the group consisting of a therapeutic polypeptide and a prophylactic polypeptide. In some embodiments, the POI is a protein selected from the group consisting of Factor VIII (FVIII), Factor IX, alpha-1-antitrypsin, FXIII, FVII, Factor X, a C1 esterase inhibitor, iduronate sulfatase, α-L-iduronidase, Protein C, and any functional derivatives thereof. The disclosures also provide, inter alia, systems for treating a subject having or suspected of having a disorder or health condition associated with one or more of the foregoing proteins, employing ex vivo and/or in vivo genome editing. In some embodiments, the subject has or is suspected of having a disorder or health condition selected from the group consisting of Factor VIII deficiency (Hemophilia A), Factor IX deficiency (Hemophilia B), Hunters syndrome (MPS II), mucopolysaccharidosis type 1 (MPS 1), alpha-1-antitrypsin deficiency, Factor XIII deficiency, Factor VII deficiency, Factor X deficiency, Protein C deficiency, and Hereditary Angioedema (HAE). In some embodiments, the subject has or is suspected of having Hemophilia A.

In some embodiments, provided herein is a system comprising (a) a deoxyribonucleic acid (DNA) endonuclease or nucleic acid encoding said DNA endonuclease; (b) a guide RNA (gRNA) targeting the transferrin locus in the genome of a cell; and (c) a donor template comprising a nucleic acid sequence encoding a POI or a functional derivative thereof (e.g., FVIII or a functional derivative thereof). In some embodiments, the gRNA targets intron 1 of the transferrin gene. In some embodiments, the gRNA comprises a spacer sequence from any one of SEQ ID NOs: 1-190.

In some embodiments, according to any of the systems described herein, the POI is a protein selected from the group consisting of a Factor VIII protein, Factor IX, alpha-1-antitrypsin, FXIII, FVII, Factor X, a C1 esterase inhibitor, iduronate sulfatase, α-L-iduronidase, and Protein C. In some embodiments, the POI is a Factor VIII protein. In some embodiments, the cell is isolated from a subject that has or is suspected of having a disorder or health condition selected from the group consisting of Factor VIII deficiency (Hemophilia A), Factor IX deficiency (Hemophilia B), Hunters syndrome (MPS II), mucopolysaccharidosis type 1 (MPS 1), alpha-1-antitrypsin deficiency, Factor XIII deficiency, Factor VII deficiency, Factor X deficiency, Protein C deficiency, and Hereditary Angioedema (HAE). In some embodiments, the subject has or is suspected of having Hemophilia A.

In some embodiments, provided herein is a system comprising (a) a deoxyribonucleic acid (DNA) endonuclease or nucleic acid encoding said DNA endonuclease; (b) a guide RNA (gRNA) comprising a spacer sequence that is complementary to a genomic sequence within or near an endogenous transferrin locus in a cell; and (c) a donor template comprising a nucleic acid sequence encoding a POI or a functional derivative thereof (e.g., FVIII or a functional derivative thereof). In some embodiments, the gRNA comprises a spacer sequence that is complementary to a sequence within intron 1 of an endogenous transferrin gene in the cell. In some embodiments, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

In some embodiments, according to any of the systems described herein, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from SEQ ID NO: 96 or a variant thereof having no more than 3 mismatches. In some embodiments, the gRNA comprises a spacer sequence from SEQ ID NO: 5 or a variant thereof having no more than 3 mismatches. In some embodiments, the gRNA comprises a spacer sequence from SEQ ID NO: 6 or a variant thereof having no more than 3 mismatches. In some embodiments, the gRNA comprises a spacer sequence from SEQ ID NO: 9 or a variant thereof having no more than 3 mismatches. In some embodiments, the gRNA comprises a spacer sequence from SEQ ID NO: 8 or a variant thereof having no more than 3 mismatches. In some embodiments, the gRNA comprises a spacer sequence from SEQ ID NO: 11 or a variant thereof having no more than 3 mismatches. In some embodiments, the gRNA comprises a spacer sequence from SEQ ID NO: 15 or a variant thereof having no more than 3 mismatches. In some embodiments, the gRNA comprises a spacer sequence from SEQ ID NO: 16 or a variant thereof having no more than 3 mismatches. In some embodiments, the gRNA comprises a spacer sequence from SEQ ID NO: 12 or a variant thereof having no more than 3 mismatches. In some embodiments, the gRNA comprises a spacer sequence from SEQ ID NO: 7 or a variant thereof having no more than 3 mismatches. In some embodiments, the gRNA comprises a spacer sequence from SEQ ID NO: 10 or a variant thereof having no more than 3 mismatches. In some embodiments, the gRNA comprises a spacer sequence from SEQ ID NO: 17 or a variant thereof having no more than 3 mismatches. In some embodiments, the gRNA comprises a spacer sequence from SEQ ID NO: 18 or a variant thereof having no more than 3 mismatches. In some embodiments, the gRNA comprises a spacer sequence from SEQ ID NO: 29 or a variant thereof having no more than 3 mismatches. In some embodiments, the gRNA comprises a spacer sequence from SEQ ID NO: 76 or a variant thereof having no more than 3 mismatches. In some embodiments, the gRNA comprises a spacer sequence from SEQ ID NO: 50 or a variant thereof having no more than 3 mismatches. In some embodiments, the gRNA comprises a spacer sequence from SEQ ID NO: 54 or a variant thereof having no more than 3 mismatches. In some embodiments, the gRNA comprises a spacer sequence from SEQ ID NO: 81 or a variant thereof having no more than 3 mismatches. In some embodiments, the gRNA comprises a spacer sequence from SEQ ID NO: 64 or a variant thereof having no more than 3 mismatches. In some embodiments, the gRNA comprises a spacer sequence from SEQ ID NO: 51 or a variant thereof having no more than 3 mismatches.

In some embodiments, according to any of the systems described herein, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional derivative thereof. In some embodiments, the DNA endonuclease is Cas9. In some embodiments, the Cas9 is from *Streptococcus pyogenes* (spCas9). In some embodiments, the Cas9 is from *Staphylococcus lugdunensis* (SluCas9).

In some embodiments, according to any of the systems described herein, the nucleic acid sequence encoding a POI or a functional derivative thereof (e.g., FVIII or a functional derivative thereof) is codon-optimized for expression in a host cell. In some embodiments, the nucleic acid sequence encoding the POI or a functional derivative thereof is codon-optimized for expression in a human cell.

In some embodiments, according to any of the systems described herein, the system comprises a nucleic acid encoding the DNA endonuclease. In some embodiments, the nucleic acid encoding the DNA endonuclease is codon-optimized for expression in a host cell. In some embodiments, the nucleic acid encoding the DNA endonuclease is codon-optimized for expression in a human cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the systems described herein, the donor template is encoded in an Adeno Associated Virus (AAV) vector. In some embodiments, the donor template comprises a donor cassette comprising the nucleic acid sequence encoding a POI or a functional derivative thereof (e.g., FVIII or a functional derivative thereof), and the donor cassette is flanked on one or both sides by a gRNA target site. In some embodiments, the donor cassette is flanked on both sides by a gRNA target site. In some embodiments, the gRNA target site is a target site for a gRNA in the system. In some embodiments, the gRNA target site of the donor template is the reverse complement of a cell genome gRNA target site for a gRNA in the system.

In some embodiments, according to any of the systems described herein, the donor template comprises a nucleic acid sequence encoding a POI or a functional derivative thereof (e.g., FVIII or a functional derivative thereof) for targeted integration into intron 1 of a transferrin gene, wherein the donor template comprises, from 5' to 3', i) a first gRNA target site; ii) a splice acceptor; iii) the nucleotide sequence encoding a POI or a functional derivative thereof; and iv) a polyadenylation signal. In some embodiments, the donor template further comprises a second gRNA target site downstream of the iv) polyadenylation signal. In some embodiments, the first gRNA target site and the second gRNA target site are the same. In some embodiments, the donor template further comprises a sequence encoding the terminal portion of the transferrin signal peptide encoded on exon 2 of the transferrin gene or a variant thereof that retains at least some of the activity of the endogenous sequence between the ii) splice acceptor and iii) nucleotide sequence encoding a POI or a functional derivative thereof. In some embodiments, the donor template further comprises a polynucleotide spacer between the i) first gRNA target site and the ii) splice acceptor. In some embodiments, the polynucleotide spacer is 18 nucleotides in length. In some embodiments, the donor template is flanked on one side by a first AAV ITR and/or flanked on the other side by a second AAV ITR. In some embodiments, the first AAV ITR is an AAV2 ITR and/or the second AAV ITR is an AAV2 ITR. In some embodiments, the POI is selected from the group consisting of Factor VIII (FVIII), Factor IX, alpha-1-antitrypsin, FXIII, FVII, Factor X, a C1 esterase inhibitor, iduronate sulfatase, α-L-iduronidase, and Protein C. In some embodiments, the POI is FVIII. In some embodiments, the iii) nucleotide sequence encoding a POI or a functional derivative thereof encodes a mature human B-domain deleted FVIII. Exemplary sequences for the donor template components can be found in the donor template sequences of SEQ ID NO: 224 and/or 251.

In some embodiments, according to any of the systems described herein, the DNA endonuclease or nucleic acid encoding the DNA endonuclease is formulated in a liposome or lipid nanoparticle. In some embodiments, the liposome or lipid nanoparticle also comprises the gRNA. In some embodiments, the liposome or lipid nanoparticle is a lipid nanoparticle. In some embodiments, the system comprises a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the systems described herein, the DNA endonuclease is complexed with the gRNA, forming a ribonucleoprotein (RNP) complex.

Method of Editing Genome

One approach to express a protein-of-interest (POI), such as a therapeutic protein (e.g., FVIII), in an organism in need thereof is to using genome editing to target the integration of a copy of a gene encoding the therapeutic protein into a gene that is highly expressed in a relevant cell type in such a way that expression of the integrated gene is driven by the endogenous promoter of the highly expressed gene. In embodiments, in the case of therapeutic proteins that are active in the circulating blood, the targeted gene in the genome can be one that expresses a secreted protein that is present at high levels in the blood stream. In addition, in embodiments it is desirable that the expression of the endogenous gene be specific to the targeted cell type or tissue in order to avoid expression in non-relevant cell types.

In some embodiments, a factor to consider regarding the selection of a genomic target gene is that the expression of the target gene is regulated in a way that is suited to the required expression of the therapeutic protein. For example, if constant levels of the therapeutic protein are desirable then the endogenous gene that is not altered by physiologic stimuli such as inflammation, infection and the like can be used to control the expression of the therapeutic gene. Alternatively, it may be desirable if the therapeutic gene is regulated by certain physiologic stimuli.

In some embodiments, provided herein is a method of genome editing in a cell to modulate the expression, function, and/or activity of a protein-of-interest (POI), such as by targeted integration of a nucleic acid encoding the POI or a functional derivative thereof into the genome of the cell. In some embodiments, the POI is a polypeptide selected from the group consisting of a therapeutic polypeptide and a prophylactic polypeptide. In some embodiments, the POI is a protein selected from the group consisting of Factor VIII (FVIII), Factor IX, alpha-1-antitrypsin, FXIII, FVII, Factor X, a C1 esterase inhibitor, iduronate sulfatase, α-L-iduronidase, Protein C, and any functional derivatives thereof. This method can be used for treating a subject having or suspected of having a disorder or health condition associated with one or more of the foregoing proteins, employing ex vivo and/or in vivo genome editing. In some embodiments, the subject has or is suspected of having a disorder or health condition selected from the group consisting of Factor VIII deficiency (Hemophilia A), Factor IX deficiency (Hemophilia B), Hunters syndrome (MPS II), mucopolysaccharidosis type 1 (MPS 1), alpha-1-antitrypsin deficiency, Factor XIII deficiency, Factor VII deficiency, Factor X deficiency, Protein C deficiency, and Hereditary Angioedema (HAE). In some embodiments, the subject has or is suspected of having Hemophilia A. In some embodiments, the cell is not in an animal, e.g., not in a human. In some embodiments, a cell is isolated from the subject or a separate donor. Then, the chromosomal DNA of the cell is edited using the materials and methods described herein.

In some embodiments, a knock-in strategy involves knocking-in a sequence encoding a POI (e.g., FVIII), such as a wild-type POI gene (e.g., a wild-type human POI gene), a POI cDNA, a minigene (having natural or synthetic enhancer and promoter, one or more exons, and natural or synthetic introns, and natural or synthetic 3'UTR and polyadenylation signal) or a modified POI gene, into a genomic sequence. In some embodiments, the genomic sequence where the POI-encoding sequence is inserted is at, within or near the transferrin locus.

In some embodiments, provided herein are methods to knock-in a sequence encoding a POI (e.g., FVIII) or a functional derivative thereof into a genome. In one aspect, the present disclosure provides insertion of a nucleic acid sequence of a POI gene, i.e., a nucleic acid sequence encoding the POI or a functional derivative thereof, into a genome of a cell. In some embodiments, the POI gene can encode a wild-type POI. The functional derivative of a POI can include a derivative of the POI that has a substantial activity of a wild-type POI, such as the wild-type human POI, e.g., at least about 30%, about 40%, about 50%, about 60%, about 70%, about 80%, about 90%, about 95% or about 100% of the activity that the wild-type POI exhibits. In some embodiments, the functional derivative of a POI can have at least about 30%, about 40%, about 50%, about 60%, about 70%, about 80%, about 85%, about 90%, about 95%, about 96%, about 97%, about 98% or about 99% amino acid sequence identity to the POI, e.g., the wild-type POI. In some embodiments, the POI is encoded by a nucleotide sequence that lacks introns. In some embodiments, one having ordinary skill in the art can use methods known in the art to test the functionality or activity of a compound, e.g., a peptide or protein. The functional derivative of the POI can also include any fragment of the wild-type POI or fragment of a modified POI that has conservative modification on one or more of amino acid residues in the full length, wild-type POI. Thus, in some embodiments, a nucleic acid sequence encoding a functional derivative of a POI can have at least about 30%, about 40%, about 50%, about 60%, about 70%, about 80%, about 85%, about 90%, about 95%, about 96%, about 97%, about 98% or about 99% nucleic acid sequence identity to a nucleic acid sequence encoding the POI, e.g., the wild-type POI. In some embodiments, the POI is a FVIII.

In some embodiments, a sequence encoding a POI (e.g., FVIII) or a functional derivative thereof is inserted into a genomic sequence in a cell. In some embodiments, the insertion site is at, or within the transferrin locus in the genome of the cell. The insertion method uses one or more gRNAs targeting the first intron (or intron 1 which is 1928 bp in size) of the transferrin gene. In some embodiments, the donor DNA is single- or double-stranded DNA having a POI gene or a functional derivative thereof.

In some embodiments, the genome editing methods utilize a DNA endonuclease such as a CRISPR/Cas system to genetically introduce (knock-in) a sequence encoding a POI (e.g., FVIII) or a functional derivative thereof. In some embodiments, the DNA endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, a homolog thereof, recombination of the naturally occurring molecule, codon-optimized, or modified version thereof, and combinations of any of the foregoing. In some embodiments, the DNA endonuclease is Cas9. In some embodiments, the Cas9 is from *Streptococcus pyogenes* (spCas9). In some embodiments, the Cas9 is from *Staphylococcus lugdunensis* (SluCas9).

In some embodiments, the cell subject to the genome-edition has one or more mutation(s) in the genome which results in reduction of the expression of an endogenous POI (e.g., FVIII) gene as compared to the expression in a normal cell that does not have such mutation(s). The normal cell can be a healthy or control cell that is originated (or isolated) from a different subject who does not have POI gene defects. In some embodiments, the cell subject to the genome-edition can be originated (or isolated) from a subject who is in need of treatment of POI gene related condition or disorder, e.g. Hemophilia A. Therefore, in some embodiments the expression of an endogenous POI gene in such cell is about 10%, about 20%, about 30%, about 40%, about 50%, about 60%, about 70%, about 80%, about 90% or about 100% reduced as compared to the expression of an endogenous POI gene in the normal cell.

In some embodiments, the genome editing method employs targeted integration at a non-coding region of the genome of a functional POI (e.g., FVIII) gene, e.g., a POI coding sequence that is operably linked to a supplied promoter so as to stably generate the POI in vivo. In some embodiments, the targeted integration of a POI coding sequence occurs in an intron of the transferrin gene that is highly expressed in the cell type of interest, e.g., hepatocytes. In some embodiments, the POI coding sequence to be inserted can be a wild-type POI coding sequence, e.g., a wild-type human POI coding sequence. In some embodiments, the POI coding sequence can be a functional derivative of a wild-type POI coding sequence such as the wild-type human POI coding sequence.

In embodiments, a therapeutic gene, e.g., a POI (e.g., FVIII) coding sequence, contains a splice acceptor sequence at the 5' end and is inserted into the first intron of the genomic target gene such that splicing occurs between the endogenous gene (e.g., exon 1 of the endogenous gene) and the splice acceptor of the integrated therapeutic gene. Genes encoding secreted proteins are composed of a signal peptide at the 5' end of the coding sequence that directs the protein into the secretory pathway whereby the signal peptide is cleaved off leaving the mature protein. Signal peptides are typically 15 to 20 amino acids in length and are typically encoded by exon 1 or exon 1 and part of exon 2. In embodiments, it is desirable that the therapeutic protein produced by the above described strategy contain only the exact residues of the native mature protein in order to avoid potential loss of function and/or acquired immunogenicity. For example, in a situation where exon 1 of the genomic target gene encodes the signal peptide together with additional residues of the mature protein these additional residues of the mature protein will be appended to the N-terminus of the therapeutic protein after secretion and cleavage of the signal peptide. In a situation where exon 1 of the genomic target gene encodes only the signal peptide without additional residues of the mature protein the therapeutic protein will contain an authentic N-terminus after secretion and cleavage of the signal peptide. In another example, in a situation where the signal peptide of the genomic target gene is encoded by exon 1 and part of exon 2 the therapeutic gene can be designed to be inserted into intron 1 and contain the additional residues of the endogenous signal peptide from exon 2 encoded at its 5' end. In this way the therapeutic protein is predicted to contain an authentic N-terminus after secretion and cleavage of the signal peptide.

In one aspect, the present disclosure proposes insertion of a nucleic acid sequence encoding a POI (e.g., FVIII) or a functional derivative thereof into a genome of a cell. In embodiments, the POI coding sequence to be inserted is a modified POI coding sequence. In some embodiments, the POI is FVIII, and in the modified FVIII coding sequence the B-domain of the wild-type FVIII coding sequence is deleted and replaced with a linker peptide referred to herein as "SQ link" (amino acid sequence SFSQNPPVLKRHQR, SEQ ID NO: 192). This B-domain deleted FVIII (FVIII-BDD) is well known in the art and has equivalent biological activity as full length FVIII. In some embodiments, a B-domain deleted FVIII is preferable over a full length FVIII because of its smaller size (4371 bp vs 7053 bp). In some embodiments, the POI coding sequence lacks a signal peptide and contains a splice acceptor sequence at its 5' end (N-Terminus of the POI coding sequence), and is integrated specifically into intron 1 of the transferrin gene in the hepatocytes of mammals, including humans. The transcription of this modified POI coding sequence from the transferrin promoter can result in a pre-mRNA that contains exon 1 of transferrin, part of intron 1 and the integrated POI gene sequence. When this pre-mRNA undergoes the natural splicing process to remove the introns, the splicing machinery can join the splice donor at the 3' side of transferrin exon 1 to the next available splice acceptor which will be the splice acceptor at the 5' end of the POI coding sequence of the inserted DNA donor. This can result in a mature mRNA containing transferrin exon 1 fused to the mature coding sequence for the POI.

In some embodiments, a DNA sequence encoding a POI (e.g., FVIII, such as FVIII-BDD) in which the codon usage has been optimized (also referred to herein as "codon-optimized" or "codon optimization") can be used so as to improve the expression in mammalian cells. Computer algorithms are also available in the art for performing codon optimization and these generate distinct DNA sequences. Examples of commercially available codon optimization algorithms are those employed by companies ATUM and GeneArt (part of Thermo Fisher Scientific). Codon optimization of the FVIII coding sequence was demonstrated to significantly improve the expression of FVIII after gene based delivery to mice (Nathwani A C, Gray J T, Ng C Y, et al. Blood. 2006; 107 (7): 2653-2661; Ward N J, Buckley S M, Waddington S N, et al. Blood. 2011; 117 (3): 798-807; Radcliffe P A, Sion C J, Wilkes F J, et al. Gene Ther. 2008; 15 (4): 289-297).

In some embodiments, the sequence homology or identity between a POI (e.g., FVIII, such as FVIII-BDD) coding sequence that was codon-optimized by different algorithms and the native POI sequence (as present in the human genome) can range from about 30%, about 40%, about 50%, about 60%, about 65%, about 70%, about 75%, about 80%, about 85%, about 90%, about 95%, or 100%. In some embodiments, the codon-optimized POI coding sequence has between about 75% to about 79% of sequence homology or identity to the native POI sequence. In some embodiments, the codon-optimized POI coding sequence has about 70%, about 71%, about 72%, about 73%, about 74%, about 75%, about 76%, about 77%, about 78%, about 79% or about 80% of sequence homology or identity to the native POI sequence.

In some embodiments, a donor template or donor construct is prepared to contain a DNA sequence encoding a POI (e.g., FVIII, such as FVIII-BDD). In some embodiments, a DNA donor template is designed to contain a codon-optimized human POI coding sequence. In some embodiments, the codon-optimization is done in such a way that the sequence at the 5' end encoding the signal peptide of the POI has been deleted and replaced with a splice acceptor sequence, and in addition a polyadenylation signal is added to the 3' end after the POI stop codon. The splice acceptor sequence can be selected from among known splice acceptor sequences from known genes or a consensus splice acceptor sequence can be used that is derived from an alignment of many splice acceptor sequences known in the field. In some embodiments, a splice acceptor sequence from highly expressed genes is used since such sequences are thought to provide optimal splicing efficiency. In some embodiments, the consensus splicing acceptor sequence is composed of a branch site with the consensus sequence yUnAy (where the A is the branch point) followed by a polypyrimidine tract (C or T) that spans 4 to 24 downstream of the branch point (Gao et al. 2008, Nucleic Acids Research, 2008, Vol. 36, 2257-2267) followed by AG>G/A in which the > is the location of the intron/exon boundary. In one embodiment, a synthetic splice acceptor sequence (CTGACCTCTTCTCTTCCTCC-CACAG, SEQ ID NO: 193) is used. In another embodiment, the native splice acceptor sequence from the transferrin gene intron 1/exon 2 boundary of human is used (ggagtgggcccttc-cacctetggcctctctcccccag, SEQ ID NO: 194). Alternatively splice acceptor sequences derived from other highly expressed genes such as serum albumin may be used.

In some embodiments, the nucleic acid sequence encoding a POI or a functional derivative thereof (e.g., FVIII or a functional derivative thereof) contains a reduced content of CpG di-nucleotides than a nucleic acid sequence encoding the wild-type POI. In some embodiments, the nucleic acid sequence encoding the POI or a functional derivative thereof comprises about or less than 20 CpG di-nucleotides. In some embodiments, the nucleic acid sequence encoding the POI or a functional derivative thereof comprises about or less than 10 CpG di-nucleotides. In some embodiments, the nucleic acid sequence encoding the POI or a functional derivative thereof comprises about or less than 5 CpG di-nucleotides. In some embodiments, the nucleic acid sequence encoding the POI or a functional derivative thereof does not comprises CpG di-nucleotides.

The polyadenylation signal sequence provides a signal for the cell to add a polyA tail which is essential for the stability of the mRNA within the cell. In some embodiments in which the DNA-donor template is to be packaged into AAV particles, the size of the packaged DNA is generally within the packaging limits for AAV; for example, less than about 5 Kb and in some embodiments, not greater than about 4.7 Kb. Thus, in some embodiments it is desirable to use as short a polyA signal sequence as possible, e.g., about 10-mer, about 20-mer, about 30-mer, about 40-mer, about 50-mer or about 60-mer or any intervening number of nucleotides of the foregoing. In mammals, an exemplary polyadenylation signal is composed of the sequence AAUAAA (SEQ ID NO: 195) followed within 10 to 30 nucleotides by the cleavage and polyadenylation site and a GU-rich sequence referred to as the DSE (Colgan et al. 1997, Genes Dev. 11:2755-2766). A consensus synthetic poly A signal sequence has been described in the literature (Levitt N, et al. (1989) Genes Dev 3 (7): 1019-1025) with the sequence AATAAAAGATCTT-TATTTTCATTAGATCTGTGTGTTGGTTTTTTGTGTG (SEQ ID NO: 196) and has been used in expression vectors. Additional examples of polyadenylation signals that are useful include a bovine growth hormone polyA signal sequence (CTGTGCCTTCTAGTTGCCAGC-CATCTGTTGTTTGCCCCTCCCCCGTGCCTTCC TTGACCCTGGAAGGTGCCACTCC-CACTGTCCTTTCCTAATAAAATGAGGAAAT TGCATCGCATTGTCTGAGTAGGTGTCATTCTAT-TCTGGGGGGTGGGGTGGGGC AGGACAGCAAGGGGGAGGATTGGGAA-GACAATAGCAGGCATGCTGGGGATG CGGTGGGCTCTATGG, SEQ ID NO: 197) or an SV40 polyadenylation signal sequence (TAAGATACATTGAT-GAGTTTGGACAAACCACAACTAGAATGCAGT-GAAAAA AATGCTTTATTTGTGAAATTTGTGATGCT-ATTGCTTTATTTGTAACCATTATAA GCTGCAATAAACAAGTT, SEQ ID NO: 198).

In some embodiments, additional sequence elements can be added to the DNA donor template to improve the integration frequency. One such element is homology arms, which are sequences identical to the DNA sequence on either side of the double-strand break in the genome at which integration is targeted to enable integration by HDR. A sequence from the left side of the double-strand break (LHA) is appended to the 5' (N-terminal to the POI (e.g., FVIII) coding sequence) end of the DNA donor template and a sequence from the right side of the double-strand break (RHA) is appended to the 3' (C-terminal of the POI coding sequence) end of the DNA donor template.

An alternative DNA donor template design that is provided in some embodiments has a sequence complementary to the recognition sequence for the sgRNA that isused to cleave the genomic site. By including the sgRNA recognition site the DNA donor template is cleaved by the sgRNA/Cas9 complex inside the nucleus of the cell to which the DNA donor template and the sgRNA/Cas9 have been delivered. Cleavage of the donor DNA template into linear fragments can increase the frequency of integration at a double-strand break by the non-homologous end joining mechanism or by the HDR mechanism. This can be particularly beneficial in the case of delivery of donor DNA templates packaged in AAV because after delivery to the nucleus the AAV genomes are known to concatemerize to form larger circular double-stranded DNA molecules (Nakai et al. JVirol 2001, 75:6969-6976). Therefore, in some cases the circular concatemers can be less efficient donors for integration at double-strand breaks, particularly by the NHEJ mechanism. It was previously reported that the efficiency of targeted integration using circular plasmid DNA donor templates could be increased by including zinc finger nuclease cut sites in the plasmid (Cristea et al. Biotechnol Bioeng 2013; 110:871-880). More recently this approach was also applied using the CRISPR/Cas9 nuclease (Suzuki et al. 2017, Nature 540, 144-149). While a sgRNA recognition sequence is active when present on either strand of a double-stranded DNA donor template, use of the reverse complement of the sgRNA recognition sequence that is present in the genome is predicted to favor stable integration because integration in the reverse orientation re-creates the sgRNA recognition sequence which can be recut thereby releasing the inserted donor DNA template. Integration of such a donor DNA template in the genome in the forward orientation by NHEJ is predicted to not re-create the sgRNA recognition sequence such that the integrated donor DNA template cannot be excised out of the genome. The benefit of including sgRNA recognition sequences in the donor with or without homology arms upon the efficiency of integration of POI (e.g., FVIII) donor DNA template can be tested and determined, e.g., in mice using AAV for delivery of the donor and LNP for delivery of the CRISPR-Cas9 components.

In some embodiments, the donor DNA template comprises the sequence encoding the POI (e.g., FVIII) or a functional derivative thereof in a donor cassette according to any of the embodiments described herein flanked on one or both sides by a gRNA target site. In some embodiments, the donor template comprises a gRNA target site 5' of the donor cassette and/or a gRNA target site 3' of the donor cassette. In some embodiments, the donor template comprises two flanking gRNA target sites, and the two gRNA target sites comprise the same sequence. In some embodiments, the donor template comprises at least one gRNA target site, and the at least one gRNA target site in the donor template is a target site for at least one of the one or more gRNAs targeting the first intron of the transferrin gene. In some embodiments, the donor template comprises at least one gRNA target site, and the at least one gRNA target site in the donor template is the reverse complement of a target site for at least one of the one or more gRNAs in the first intron of the transferrin gene. In some embodiments, the donor template comprises a gRNA target site 5' of the donor cassette and a gRNA target site 3' of the donor cassette, and the two gRNA target sites in the donor template are targeted by the one or more gRNAs targeting the first intron of the transferrin gene. In some embodiments, the donor template comprises a gRNA target site 5' of the donor cassette and a gRNA target site 3' of the donor cassette, and the two gRNA target sites in the donor template are the reverse complement of a target site for at least one of the one or more gRNAs in the first intron of the transferrin gene.

Insertion of a POI (e.g., FVIII)-encoding gene into a target site, e.g., a genomic location where the POI-encoding gene is to be inserted, can be in the endogenous transferrin gene locus or neighboring sequences thereof. In some embodiments, the POI-encoding gene is inserted in a manner that the expression of the inserted gene is controlled by the endogenous promoter of the transferrin gene. In some embodiments, the POI-encoding gene is inserted in one of introns of the transferrin gene. In some embodiments, the POI-encoding gene is inserted in one of exons of the transferrin gene. In some embodiments, the POI-encoding gene is inserted at a junction of intron: exon (or vice versa). In some embodiments, the insertion of the POI-encoding gene is in the first intron (or intron 1) of the transferrin locus. In some embodiments, the insertion of the POI-encoding gene does not significantly affect, e.g., upregulate or downregulate, the expression of the transferrin gene.

In embodiments, the target site for the insertion of a POI (e.g., FVIII)-encoding gene is at, within, or near the endogenous transferrin gene. In some embodiments, the target site is in an intergenic region that is upstream of the promoter of the transferrin gene locus in the genome. In some embodiments, the target site is within the transferrin gene locus. In some embodiments, the target site in one of the introns of the transferrin gene locus. In some embodiments, the target site in one of the exons of the transferrin gene locus. In some embodiments, the target site is in one of the junctions between an intron and exon (or vice versa) of the transferrin gene locus. In some embodiments, the target site is in the first intron (or intron 1) of the transferrin gene locus. In certain embodiments, the target site is at least, about or at most 0, 1, 5, 10, 20, 30, 40, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, or 1928 bp, or any intervening length, of the nucleic acids downstream of the first exon (i.e., from the last nucleic acid or 3' end of the first exon) of the transferrin gene. In some embodiments, the target site is at least, about or at most 0.1 kb, about 0.2 kb, about 0.3 kb, about 0.4 kb, about 0.5 kb, about 1 kb, about 1.5 kb, about 2 kb or any intervening length of the nucleic acids upstream of the second exon of the transferrin gene (i.e., from the first nucleic acid or 5' end of the second exon). In some embodiments, the target site is anywhere within about 0 bp to about 100 bp, about 101 bp to about 200 bp, about 201 bp to about 300 bp, about 301 bp to about 400 bp, about 401 bp to about 500 bp, about 501 bp to about 600 bp, about 601 bp to about 700 bp, about 701 bp to about 800 bp, about 801 bp to about 900 bp, about 901 bp to about 1000 bp, about 1001 bp to about 1500 bp, about 1501 bp to about 2000 bp upstream of the second exon of the transferrin gene (i.e., from the first nucleic acid or 5' end of the second exon).

In some embodiments, the target site for the insertion of a POI (e.g., FVIII)-encoding gene is at least 40 bp downstream of the end of the first exon of the human transferrin gene in the genome and at least 60 bp upstream of the start of the second exon of the human transferrin gene in the genome.

In some embodiments, the target site for the insertion of a POI (e.g., FVIII)-encoding gene is at least 42 bp downstream of the end of the first exon of the human transferrin gene in the genome and at least 65 bp upstream of the start of the second exon of the human transferrin gene in the genome.

In some embodiments, the target site for the insertion of a POI (e.g., FVIII)-encoding gene is at least 42 bp downstream of the end of the first exon of the human transferrin gene in the genome and at least 67 bp upstream of the start of the second exon of the human transferrin gene in the genome.

In some embodiments, the target site for the insertion of a POI (e.g., FVIII)-encoding gene is about 338 bp downstream of the end of the first exon of the human transferrin gene in the genome and about 67 bp upstream of the start of the second exon of the human transferrin gene in the genome.

In some embodiments, provided herein is a method of editing a genome in a cell, the method comprising providing the following to the cell: (a) a guide RNA (gRNA) targeting the transferrin locus in the cell genome; (b) a DNA endonuclease or nucleic acid encoding said DNA endonuclease; and (c) a donor template comprising a nucleic acid sequence encoding a POI or a functional derivative thereof (e.g., FVIII or a functional derivative thereof). In some embodiments, the gRNA targets intron 1 of the transferrin gene. In some embodiments, the gRNA comprises a spacer sequence from any one of SEQ ID NOs: 1-190.

In some embodiments, according to any of the methods described herein, the POI is a protein selected from the group consisting of a Factor VIII protein, Factor IX, alpha-1-antitrypsin, FXIII, FVII, Factor X, a C1 esterase inhibitor, iduronate sulfatase, α-L-iduronidase, and Protein C. In some embodiments, the POI is a Factor VIII protein.

In some embodiments, provided herein is a method of editing a genome in a cell, the method comprising providing the following to the cell: (a) a gRNA comprising a spacer sequence that is complementary to a genomic sequence within or near an endogenous transferrin locus in a cell; (b) a DNA endonuclease or nucleic acid encoding said DNA endonuclease; and (c) a donor template comprising a nucleic acid sequence encoding a POI or a functional derivative thereof (e.g., FVIII or a functional derivative thereof). In some embodiments, the gRNA comprises a spacer sequence that is complementary to a sequence within intron 1 of an endogenous transferrin gene in the cell. In some embodiments, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

In some embodiments, according to any of the methods of editing a genome in a cell described herein, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional derivative thereof. In some embodiments, the DNA endonuclease is Cas9. In some embodiments, the Cas9 is from *Streptococcus pyogenes* (spCas9). In some embodiments, the Cas9 is from *Staphylococcus lugdunensis* (SluCas9).

In some embodiments, according to any of the methods of editing a genome in a cell described herein, the nucleic acid sequence encoding a POI or a functional derivative thereof (e.g., FVIII or a functional derivative thereof) is codon-optimized for expression in the cell. In some embodiments, the cell is a human cell.

In some embodiments, according to any of the methods of editing a genome in a cell described herein, the method employs a nucleic acid encoding the DNA endonuclease. In some embodiments, the nucleic acid encoding the DNA endonuclease is codon-optimized for expression in the cell. In some embodiments, the cell is a human cell, e.g., a human hepatocyte cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the methods of editing a genome in a cell described herein, the donor template is encoded in an Adeno Associated Virus (AAV) vector. In some embodiments, the donor template comprises a donor cassette comprising the nucleic acid sequence encoding a POI or a functional derivative thereof (e.g., FVIII or a functional derivative thereof), and the donor cassette is flanked on one or both sides by a gRNA target site. In some embodiments, the donor cassette is flanked on both sides by a gRNA target site. In some embodiments, the gRNA target site is a target site for the gRNA of (a). In some embodiments, the gRNA target site of the donor template is the reverse complement of a cell genome gRNA target site for the gRNA of (a).

In some embodiments, according to any of the methods of editing a genome in a cell described herein, the DNA endonuclease or nucleic acid encoding the DNA endonuclease is formulated in a liposome or lipid nanoparticle. In some embodiments, the liposome or lipid nanoparticle also comprises the gRNA. In some embodiments, the liposome or lipid nanoparticle is a lipid nanoparticle. In some embodiments, the method employs a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the methods of editing a genome in a cell described herein, the DNA endonuclease is pre-complexed with the gRNA, forming a ribonucleoprotein (RNP) complex.

In some embodiments, according to any of the methods of editing a genome in a cell described herein, the gRNA of (a) and the DNA endonuclease or nucleic acid encoding the DNA endonuclease of (b) are provided to the cell after the donor template of (c) is provided to the cell. In some embodiments, the gRNA of (a) and the DNA endonuclease or nucleic acid encoding the DNA endonuclease of (b) are provided to the cell more than 4 days after the donor template of (c) is provided to the cell. In some embodiments, the gRNA of (a) and the DNA endonuclease or nucleic acid encoding the DNA endonuclease of (b) are provided to the cell at least 14 days after the donor template of (c) is provided to the cell. In some embodiments, the gRNA of (a) and the DNA endonuclease or nucleic acid encoding the DNA endonuclease of (b) are provided to the cell at least 17 days after the donor template of (c) is provided to the cell. In some embodiments, (a) and (b) are provided to the cell as a lipid nanoparticle comprising nucleic acid encoding the DNA endonuclease and the gRNA. In some embodiments, the nucleic acid encoding the DNA endonuclease is an mRNA encoding the DNA endonuclease. In some embodiments, (c) is provided to the cell as an AAV vector encoding the donor template.

In some embodiments, according to any of the methods of editing a genome in a cell described herein, one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b). In some embodiments, one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b) until a target level of targeted integration of the nucleic acid sequence encoding a POI or a functional derivative thereof (e.g., FVIII or a functional derivative thereof) and/or a target level of expression of the nucleic acid sequence encoding the POI or functional derivative is achieved.

In some embodiments, according to any of the methods of editing a genome in a cell described herein, the nucleic acid sequence encoding a POI or a functional derivative thereof (e.g., FVIII or a functional derivative thereof) is expressed under the control of the endogenous transferrin promoter.

In some embodiments, provided herein is a method of inserting a sequence encoding a POI (e.g., FVIII) or a functional derivative thereof into the transferrin locus of a cell genome, comprising introducing into the cell (a) a Cas DNA endonuclease (e.g., Cas9) or nucleic acid encoding the Cas DNA endonuclease, (b) a gRNA or nucleic acid encoding the gRNA, wherein the gRNA is capable of guiding the Cas DNA endonuclease to cleave a target polynucleotide sequence in the transferrin locus, and (c) a donor template according to any of the embodiments described herein comprising the POI gene or a functional derivative thereof. In some embodiments, the method comprises introducing into the cell an mRNA encoding the Cas DNA endonuclease. In some embodiments, the method comprises introducing into the cell an LNP according to any of the embodiments described herein comprising i) an mRNA encoding the Cas DNA endonuclease and ii) the gRNA. In some embodiments, the donor template is an AAV donor template. In some embodiments, the donor template comprises a donor cassette comprising the POI gene or a functional derivative thereof, wherein the donor cassette is flanked on one or both sides by a target site of the gRNA. In some embodiments, the gRNA target sites flanking the donor cassette are the reverse complement of the gRNA target site in the transferrin locus. In some embodiments, the Cas DNA endonuclease or nucleic acid encoding the Cas DNA endonuclease and the gRNA or nucleic acid encoding the gRNA are introduced into the cell following introduction of the donor template into the cell. In some embodiments, the Cas DNA endonuclease or nucleic acid encoding the Cas DNA endonuclease and the gRNA or nucleic acid encoding the gRNA are introduced into the cell a sufficient time following introduction of the donor template into the cell to allow for the donor template to enter the cell nucleus. In some embodiments, the Cas DNA endonuclease or nucleic acid encoding the Cas DNA endonuclease and the gRNA or nucleic acid encoding the gRNA are introduced into the cell a sufficient time following introduction of the donor template into the cell to allow for the donor template to be converted from a single-stranded AAV genome to a double-stranded DNA molecule in the cell nucleus. In some embodiments, the Cas DNA endonuclease is Cas9.

In some embodiments, according to any of the methods of inserting a sequence encoding a POI (e.g., FVIII) or a functional derivative thereof into the transferrin locus of a cell genome described herein, the target polynucleotide sequence is in intron 1 of the transferrin gene. In some embodiments, the gRNA comprises a spacer sequence listed in Table 2. In some embodiments, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

In some embodiments, provided herein is a method of inserting a sequence encoding a POI (e.g., FVIII) or a functional derivative thereof into the transferrin locus of a cell genome, comprising introducing into the cell (a) an LNP according to any of the embodiments described herein comprising i) an mRNA encoding a Cas9 DNA endonuclease and ii) a gRNA, wherein the gRNA is capable of guiding the Cas9 DNA endonuclease to cleave a target polynucleotide sequence in the transferrin locus, and (b) an AAV donor template according to any of the embodiments described herein comprising the POI gene or a functional derivative thereof. In some embodiments, the donor template comprises a donor cassette comprising the POI gene or a functional derivative thereof, wherein the donor cassette is flanked on one or both sides by a target site of the gRNA. In some embodiments, the gRNA target sites flanking the donor cassette are the reverse complement of the gRNA target site in the transferrin locus. In some embodiments, the LNP is introduced into the cell following introduction of the AAV donor template into the cell. In some embodiments, the LNP is introduced into the cell a sufficient time following introduction of the AAV donor template into the cell to allow for the donor template to enter the cell nucleus. In some embodiments, the LNP is introduced into the cell a sufficient time following introduction of the AAV donor template into the cell to allow for the donor template to be converted from a single-stranded AAV genome to a double-stranded DNA molecule in the cell nucleus. In some embodiments, one or more (such as 2, 3, 4, 5, or more) additional introductions of the LNP into the cell are performed following the first introduction of the LNP into the cell. In some embodiments, the gRNA comprises a spacer sequence that is complementary to a sequence within intron 1 of an endogenous transferrin gene in the cell. In some embodiments, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected.

In some embodiments, according to any of the methods of inserting a sequence encoding a POI (e.g., FVIII) or a functional derivative thereof into the transferrin locus of a cell genome described herein, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from SEQ ID NO: 96 or a variant thereof having no more than 3 mismatches. In some embodiments, the gRNA comprises a spacer sequence from SEQ ID NO: 5 or a variant thereof having no more than 3 mismatches. In some embodiments, the gRNA comprises a spacer sequence from SEQ ID NO: 6 or a variant thereof having no more than 3 mismatches. In some embodiments, the gRNA comprises a spacer sequence from SEQ ID NO: 9 or a variant thereof having no more than 3 mismatches. In some embodiments, the gRNA comprises a spacer sequence from SEQ ID NO: 8 or a variant thereof having no more than 3 mismatches. In some embodiments, the gRNA comprises a spacer sequence from SEQ ID NO: 11 or a variant thereof having no more than 3 mismatches. In some embodiments, the gRNA comprises a spacer sequence from SEQ ID NO: 15 or a variant thereof having no more than 3 mismatches. In some embodiments, the gRNA comprises a spacer sequence from SEQ ID NO: 16 or a variant thereof having no more than 3 mismatches. In some embodiments, the gRNA comprises a spacer sequence from SEQ ID NO: 12 or a variant thereof having no more than 3 mismatches. In some embodiments, the gRNA comprises a spacer sequence from SEQ ID NO: 7 or a variant thereof having no more than 3 mismatches. In some embodiments, the gRNA comprises a spacer sequence from SEQ ID NO: 10 or a variant thereof having no more than 3 mismatches. In some embodiments, the gRNA comprises a spacer sequence from SEQ ID NO: 17 or a variant thereof having no more than 3 mismatches. In some embodiments, the gRNA comprises a spacer sequence from SEQ ID NO: 18 or a variant thereof having no more than 3 mismatches. In some embodiments, the gRNA comprises a spacer sequence from SEQ ID NO: 29 or a variant thereof having no more than 3 mismatches. In some embodiments, the gRNA comprises a spacer sequence from SEQ ID NO: 76 or a variant thereof having no more than 3 mismatches. In some embodiments, the gRNA comprises a spacer sequence from SEQ ID NO: 50 or a variant thereof having no more than 3 mismatches. In some embodiments, the gRNA comprises a spacer sequence from SEQ ID NO: 54 or a variant thereof having no more than 3 mismatches. In some embodiments, the gRNA comprises a spacer sequence from SEQ ID NO: 81 or a variant thereof having no more than 3 mismatches. In some embodiments, the gRNA comprises a spacer sequence from SEQ ID NO: 64 or a variant thereof having no more than 3 mismatches. In some embodiments, the gRNA comprises a spacer sequence from SEQ ID NO: 51 or a variant thereof having no more than 3 mismatches.

Target Sequence Selection

In some embodiments, shifts in the location of the 5' boundary and/or the 3' boundary relative to particular reference loci are used to facilitate or enhance particular applications of gene editing, which depend in part on the endonuclease system selected for the editing, as further described and illustrated herein.

In a first, non-limiting aspect of such target sequence selection, many endonuclease systems have rules or criteria that guide the initial selection of potential target sites for cleavage, such as the requirement of a PAM sequence motif in a particular position adjacent to the DNA cleavage sites in the case of CRISPR Type II or Type V endonucleases.

In another, non-limiting aspect of target sequence selection or optimization, the frequency of "off-target" activity for a particular combination of target sequence and gene editing endonuclease (i.e., the frequency of DSBs occurring at sites other than the selected target sequence) is assessed relative to the frequency of on-target activity. In some cases, cells that have been correctly edited at the desired locus can have a selective advantage relative to other cells. Illustrative, but non-limiting, examples of a selective advantage include the acquisition of attributes such as enhanced rates of replication, persistence, resistance to certain conditions, enhanced rates of successful engraftment or persistence in vivo following introduction into a subject, and other attributes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the correction. In some embodiments, cells can be edited two or more times in order to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

In embodiments, whether any selective advantage is applicable or any directed selection is to be applied in a particular case, target sequence selection is also guided by consideration of off-target frequencies in order to enhance the effectiveness of the application and/or reduce the potential for undesired alterations at sites other than the desired target. As described further and illustrated herein and in the art, the occurrence of off-target activity is influenced by a number of factors including similarities and dissimilarities between the target site and various off-target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical inducers). Many such inducers cause DSBs to occur indiscriminately in the genome, and DSBs are regularly being induced and repaired in normal cells. During repair, the original sequence can be reconstructed with complete fidelity, however, in some cases, small insertions or deletions (referred to as "indels") are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can have as few as ten base pairs or less, can also be used to bring about desired deletions. For example, a single DSB is introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which can or cannot be desired given the particular circumstances.

The examples provided herein further illustrate the selection of various target regions for the creation of DSBs designed to insert a POI (e.g., FVIII)-encoding gene, as well as the selection of specific target sequences within such regions that are designed to minimize off-target events relative to on-target events.

Targeted Integration

In some embodiments, the method provided herein is to integrate a POI (e.g., FVIII) encoding gene or a functional POI gene at a specific location in the genome of the hepatocytes which is referred to as "targeted integration". In some embodiments, targeted integration is enabled by using a sequence-specific nuclease to generate a double-stranded break in the genomic DNA.

The CRISPR-Cas system used in some embodiments has the advantage that a large number of genomic targets can be rapidly screened to identify an optimal CRISPR-Cas design. The CRISPR-Cas system uses an RNA molecule referred to as a single guide RNA (sgRNA) that targets an associated Cas nuclease (for example the Cas9 nuclease) to a specific sequence in DNA. This targeting occurs by Watson-Crick based pairing between the sgRNA and the sequence of the genome within the approximately 20 bp targeting sequence of the sgRNA. Once bound at a target site the Cas nuclease cleaves both strands of the genomic DNA creating a double-strand break. The only requirement for designing a sgRNA to target a specific DNA sequence is that the target sequence must contain a protospacer adjacent motif (PAM) sequence at the 3' end of the sgRNA sequence that is complementary to the genomic sequence. In the case of the Cas9 nuclease the PAM sequence is NRG (where R is A or G and N is any base), or the more restricted PAM sequence NGG. Therefore, sgRNA molecules that target any region of the genome can be designed in silico by locating the 20 bp sequence adjacent to all PAM motifs. PAM motifs occur on average very 15 bp in the genome of eukaryotes. However, sgRNA designed by in silico methods will generate double-strand breaks in cells with differing efficiencies and it is not possible to predict the cutting efficiencies of a series of sgRNA molecule using in silico methods. Because sgRNA can be rapidly synthesized in vitro this enables the rapid screening of all potential sgRNA sequences in a given genomic region to identify the sgRNA that results in the most efficient cutting. Typically, when a series of sgRNAs within a given genomic region are tested in cells a range of cleavage efficiencies between 0 and 90% is observed. In silico algorithms as well as laboratory experiments can also be used to determine the off-target potential of any given sgRNA. While a perfect match to the 20 bp recognition sequence of a sgRNA will primarily occur only once in most eukaryotic genomes there will be a number of additional sites in the genome with 1 or more base pair mismatches to the sgRNA. These sites can be cleaved at variable frequencies which are often not predictable based on the number or location of the mismatches. Cleavage at additional off-target sites that were not identified by the in silico analysis can also occur. Thus, screening a number of sgRNA in a relevant cell type to identify sgRNA that have the most favorable off-target profile is a critical component of selecting an optimal sgRNA for therapeutic use. A favorable off-target profile takes into account not only the number of actual off-target sites and the frequency of cutting at these sites, but also the location in the genome of these sites. For example, off-target sites close to or within functionally important genes, particularly oncogenes or anti-oncogenes would be considered as less favorable than sites in intergenic regions with no known function. Thus, the identification of an optimal sgRNA cannot be predicted simply by in silico analysis of the genomic sequence of an organism but requires experimental testing. While in silico analysis can be helpful in narrowing down the number of guides to test it cannot predict guides that have high on-target cutting or predict guides with low desirable off-target cutting. Experimental data indicates that the cutting efficiency of sgRNA that each has a perfect match to the genome in a region of interest (such as the transferrin intron 1) varies from no cutting to >90% cutting and is not predictable by any known algorithm. The ability of a given sgRNA to promote cleavage by a Cas enzyme can relate to the accessibility of that specific site in the genomic DNA which can be determined by the chromatin structure in that region. While the majority of the genomic DNA in a quiescent differentiated cell, such as a hepatocyte, exists in highly condensed heterochromatin, regions that are actively transcribed exists in more open chromatin states that are known to be more accessible to large molecules such as proteins like the Cas protein. Even within actively transcribed genes some specific regions of the DNA are more accessible than others due to the presence or absence of bound transcription factors or other regulatory proteins. Predicting sites in the genome or within a specific genomic locus or region of a genomic locus such as an intron, and such as transferrin intron 1 is not possible and therefore would need to be determined experimentally in a relevant cell type. Once some sites are selected as potential sites for insertion, it can be possible to add some variations to such a site, e.g., by moving a few nucleotides upstream or downstream from the selected sites, with or without experimental tests.

In some embodiments, gRNAs that can be used in the methods disclosed herein comprise one or more spacers listed in Table 2 (e.g., spacer sequences from SEQ ID NOs: 1-188) or any derivatives thereof having at least about 85% nucleotide sequence identity to those listed in Table 2.

Nucleic Acid Modifications

In some embodiments, polynucleotides introduced into cells have one or more modifications that can be used individually or in combination, for example, to enhance activity, stability or specificity, alter delivery, reduce innate immune responses in host cells, or for other enhancements, as further described herein and known in the art.

In certain embodiments, modified polynucleotides are used in the CRISPR/Cas9/Cpf1 system, in which case the guide RNAs (either single-molecule guides or double-molecule guides) and/or a DNA or an RNA encoding a Cas or Cpf1 endonuclease introduced into a cell can be modified, as described and illustrated below. Such modified polynucleotides can be used in the CRISPR/Cas9/Cpf1 system to edit any one or more genomic loci.

Using the CRISPR/Cas9/Cpf1 system for purposes of non-limiting illustrations of such uses, modifications of guide RNAs can be used to enhance the formation or stability of the CRISPR/Cas9/Cpf1 genome editing complex having guide RNAs, which can be single-molecule guides or double-molecule, and a Cas or Cpf1 endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in embodiments in which a Cas or Cpf1 endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e., the endonuclease), and/or modifications that decrease the likelihood or degree to which the RNAs introduced into cells elicit innate immune responses.

Combinations of modifications, such as the foregoing and others, can likewise be used. In the case of CRISPR/Cas9/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modified RNAs of greater length is to produce two or more molecules that are ligated together. Much longer RNAs, such as those encoding a Cas9 endonuclease, are more readily generated enzymatically. While fewer types of modifications are generally available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can have one or more nucleotides modified at the 2' position of the sugar, in some embodiments a 2'-O-alkyl, 2'-O-alkyl-O-alkyl, or 2'-fluoro-modified nucleotide. In some embodiments, RNA modifications include 2'-fluoro, 2'-amino or 2' O-methyl modifications on the ribose of pyrimidines, abasic residues, or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those having modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone), $CH_2$—O—N($CH_3$)—$CH_2$, $CH_2$—N($CH_3$)—N ($CH_3$)—$CH_2$ and O—N($CH_3$)—$CH_2$—$CH_2$ backbones, wherein the native phosphodiester backbone is represented as O—P—O—CH); amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates having 3'alkylene phosphonates and chiral phosphonates, phosphinates, phosphoramidates having 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41 (14): 4503-4510 (2002); Genesis, Volume 30, Issue 3, (2001); Heasman, Dev. Biol., 243:209-214 (2002); Nasevicius et al., Nat. Genet., 26:216-220 (2000); Lacerra et al., Proc. Natl. Acad. Sci., 97:9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122:8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These have those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3$ $OCH_3$, $OCH_3$ $O(CH_2)_n$ $CH_3$, $O(CH_2)_n$ $NH_2$, or $O(CH_2)$ n $CH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some embodiments, a modification includes 2'-methoxyethoxy (2'-O—$CH_2CH_2OCH_3$, also known as 2'-O-(2-methoxyethyl)) (Martin et al., Helv Chim Acta, 1995, 78, 486). Other modifications include 2'-methoxy (2'-O—$CH_3$), 2'-propoxy (2'-$OCH_2$ $CH_2CH_3$) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds have, but are not limited to, U.S. Pat. Nos. 5,539,082; 5,714,331; and 5,719,262. Further teaching of PNA compounds can be found in Nielsen et al., Science, 254:1497-1500 (1991).

In some embodiments, guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino) adenine, 2-(imidazolylalkyl) adenine, 2-(aminoalklyamino) adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl) adenine, and 2,6-diaminopurine. Kornberg, A., DNA Replication, W. H. Freeman & Co., San Francisco, pp 75-77 (1980); Gebeyehu et al., Nucl Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are embodiments of base substitutions.

In some embodiments, modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases include those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the disclosure. These include 5-substituted pyrimidines, 6-azapyrimidines and N-2, N-6 and 0-6 substituted purines, having 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications,' CRC Press, Boca Raton, 1993, pp. 276-278) and are embodiments of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 2003/0158403.

In some embodiments, the guide RNAs and/or mRNA (or DNA) encoding an endonuclease are chemically linked to one or more moieties or conjugates that enhance the activity, cellular distribution, or cellular uptake of the oligonucleotide. Such moieties include, but are not limited to, lipid moieties such as a cholesterol moiety [Letsinger et al., Proc. Natl. Acad. Sci. USA, 86:6553-6556 (1989)]; cholic acid [Manoharan et al., Bioorg. Med. Chem. Let., 4:1053-1060 (1994)]; a thioether, e.g., hexyl-S-tritylthiol [Manoharan et al., Ann. N. Y. Acad. Sci., 660:306-309 (1992) and Manoharan et al., Bioorg. Med. Chem. Let., 3:2765-2770 (1993)]; a thiocholesterol [Oberhauser et al., Nucl. Acids Res., 20:533-538 (1992)]; an aliphatic chain, e.g., dodecandiol or undecyl residues [Kabanov et al., FEBS Lett., 259:327-330 (1990) and Svinarchuk et al., Biochimie, 75:49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36:3651-3654 (1995) and Shea et al., Nucl. Acids Res., 18:3777-3783 (1990)]; a polyamine or a polyethylene glycol chain [Mancharan et al., Nucleosides & Nucleotides, 14:969-973 (1995)]; adamantane acetic acid [Manoharan et al., Tetrahedron Lett., 36:3651-3654 (1995)]; a palmityl moiety [(Mishra et al., Biochim. Biophys. Acta, 1264:229-237 (1995)]; or an octadecylamine or hexylamino-carbonyl-t oxycholesterol moiety [Crooke et al., J. Pharmacol. Exp. Ther., 277:923-937 (1996)]. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, sugars and other moieties can be used to target proteins and complexes having nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21 (10): 1025-30 (2014). Other systems known in the art and regularly developed can be used to target biomolecules of use in the present case and/or complexes thereof to particular target cells of interest.

In some embodiments, these targeting moieties or conjugates can include conjugate groups covalently bound to functional groups, such as primary or secondary hydroxyl groups. Conjugate groups of the disclosure include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this disclosure, include groups that improve uptake, distribution, metabolism or excretion of the compounds of the present disclosure. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G (5') ppp (5') G (mCAP)), modified 5' or 3' untranslated regions (UTRs), use of modified bases such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7 (5): 618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G (5') ppp (5') G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6 (4): 440-468 (2013); Kanasty et al., Molecular Therapy 20 (3): 513-524 (2012); Burnett et al., Biotechnol J. 6 (9): 1130-46 (2011); Judge and MacLachlan, Hum Gene Ther 19 (2): 111-24 (2008); and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2:77-96 (2011); Gaglione and Messere, Mini Rev Med Chem, 10 (7): 578-95 (2010); Chernolovskaya et al., Curr Opin Mol Ther., 12 (2): 158-67 (2010); Deleavey et al., Curr Protoc Nucleic Acid Chem Chapter 16: Unit 16.3 (2009); Behlke, Oligonucleotides 18 (4): 305-19 (2008); Fucini et al., Nucleic Acid Ther 22 (3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and $N_6$-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013), and references cited therein.

Delivery

In some embodiments, any nucleic acid molecules used in the methods provided herein, e.g., a nucleic acid encoding a genome-targeting nucleic acid of the disclosure and/or a site-directed polypeptide, are packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

In embodiments, guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In some embodiments, the DNA endonuclease can be delivered as one or more polypeptides, either alone or pre-complexed with one or more guide RNAs, or one or more crRNA together with a tracrRNA.

In embodiments, polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18:1127-1133 (2011) (which focuses on non-viral delivery vehicles for siRNA that are also useful for delivery of other polynucleotides).

In embodiments, polynucleotides, such as guide RNA, sgRNA, and mRNA encoding an endonuclease, can be delivered to a cell or a subject by a lipid nanoparticle (LNP).

While several non-viral delivery methods for nucleic acids have been tested both in animal models and in humans the most well developed system is lipid nanoparticles. Lipid nanoparticles (LNP) are generally composed of an ionizable cationic lipid and 3 or more additional components, typically cholesterol, DOPE and a polyethylene glycol (PEG) containing lipid, see, e.g. Example 2. The cationic lipid can bind to the positively charged nucleic acid forming a dense complex that protects the nucleic from degradation. During passage through a micro fluidics system the components self-assemble to form particles in the size range of 50 to 150 nM in which the nucleic acid is encapsulated in the core complexed with the cationic lipid and surrounded by a lipid bilayer like structure. After injection into the circulation of a subject these particles can bind to apolipoprotein E (apoE). ApoE is a ligand for the LDL receptor and mediates uptake into the hepatocytes of the liver via receptor mediated endocytosis. LNP of this type have been shown to efficiently deliver mRNA and siRNA to the hepatocytes of the liver of rodents, primates and humans. After endocytosis, the LNP are present in endosomes. The encapsulated nucleic acid undergoes a process of endosomal escape mediate by the ionizable nature of the cationic lipid. This delivers the nucleic acid into the cytoplasm where mRNA can be translated into the encoded protein. Thus, in some embodiments encapsulation of gRNA and mRNA encoding Cas9 into an LNP is used to efficiently deliver both components to the hepatocytes after IV injection. After endosomal escape the Cas9 mRNA is translated into Cas9 protein and can form a complex with the gRNA. In some embodiments, inclusion of a nuclear localization signal into the Cas9 protein sequence promotes translocation of the Cas9 protein/gRNA complex to the nucleus. Alternatively, the small gRNA crosses the nuclear pore complex and form complexes with Cas9 protein in the nucleus. Once in the nucleus the gRNA/Cas9 complex scan the genome for homologous target sites and generate double-strand breaks preferentially at the desired target site in the genome. The half-life of RNA molecules in vivo is typically short, on the order of hours to days. Similarly, the half-life of proteins tends to be short, on the order of hours to days. Thus, in some embodiments, delivery of the gRNA and Cas9 mRNA using an LNP can result in only transient expression and activity of the gRNA/Cas9 complex. This can provide the advantage of reducing the frequency of off-target cleavage and thus minimize the risk of genotoxicity in some embodiments. LNP are generally less immunogenic than viral particles. While many humans have preexisting immunity to AAV there is no pre-existing immunity to LNP. In additional and adaptive immune response against LNP is unlikely to occur which enables repeat dosing of LNP.

Several different ionizable cationic lipids have been developed for use in LNP. These include C12-200 (Love et al. (2010), PNAS vol. 107, 1864-1869), MC3, LN16, MD1 among others. In one type of LNP a GalNac moiety is attached to the outside of the LNP and acts as a ligand for uptake into the liver via the asialyloglycoprotein receptor. Any of these cationic lipids are used to formulate LNP for delivery of gRNA and Cas9 mRNA to the liver.

In some embodiments, an LNP refers to any particle having a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses. LNPs can also have hydrophobic lipids, hydrophilic lipids, or both hydrophobic and hydrophilic lipids.

Any lipid or combination of lipids that are known in the art can be used to produce an LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

In embodiments, the lipids can be combined in any number of molar ratios to produce an LNP. In addition, the polynucleotide(s) can be combined with lipid(s) in a wide range of molar ratios to produce an LNP.

In embodiments, the site-directed polypeptide and genome-targeting nucleic acid can each be administered separately to a cell or a subject. On the other hand, the site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

RNA can form specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

In some embodiments, the endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be generally combined in a 1:1 molar ratio. Alternatively, the endonuclease, crRNA and tracrRNA can be generally combined in a 1:1:1 molar ratio. However, a wide range of molar ratios can be used to produce a RNP.

In some embodiments, a recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, international patent application publication number WO 01/83692. See Table 1.

TABLE 1

AAV serotype and Genbank Accession No. of some selected AAVs.

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

In some embodiments, a method of generating a packaging cell involves creating a cell line that stably expresses all of the necessary components for AAV particle production. For example, a plasmid (or multiple plasmids) having a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); Mclaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others. For example, the serotypes of AAV vectors suitable to liver tissue/cell type include, but not limited to, AAV3, AAV5, AAV8 and AAV9.

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirus, poxvirus, vaccinia virus, and herpes simplex virus.

In some embodiments, Cas9 mRNA, sgRNA targeting one or two loci in transferrin genes, and donor DNA are each separately formulated into lipid nanoparticles, or are all co-formulated into one lipid nanoparticle, or co-formulated into two or more lipid nanoparticles.

In some embodiments, Cas9 mRNA is formulated in a lipid nanoparticle, while sgRNA and donor DNA are delivered in an AAV vector. In some embodiments, Cas9 mRNA and sgRNA are co-formulated in a lipid nanoparticle, while donor DNA is delivered in an AAV vector.

Options are available to deliver the Cas9 nuclease as a DNA plasmid, as mRNA or as a protein. The guide RNA can be expressed from the same DNA, or can also be delivered as an RNA. The RNA can be chemically modified to alter or improve its half-life, or decrease the likelihood or degree of immune response. The endonuclease protein can be complexed with the gRNA prior to delivery. Viral vectors allow efficient delivery; split versions of Cas9 and smaller orthologs of Cas9 can be packaged in AAV, as can donors for HDR. A range of non-viral delivery methods also exist that can deliver each of these components, or non-viral and viral methods can be employed in tandem. For example, nanoparticles can be used to deliver the protein and guide RNA, while AAV can be used to deliver a donor DNA.

In some embodiments that are related to deliver genome-editing components for therapeutic treatments, at least two components are delivered into the nucleus of a cell to be transformed, e.g., hepatocytes; a sequence-specific nuclease and a DNA donor template. In some embodiments, the donor DNA template is packaged into an Adeno Associated Virus (AAV) with tropism for the liver. In some embodiments, the AAV is selected from the serotypes AAV8, AAV9, AAVrh10, AAV5, AAV6 or AAV-DJ. In some embodiments, the AAV packaged DNA donor template is administered to a subject, e.g., a patient, first by peripheral IV injection followed by the sequence-specific nuclease. The advantage of delivering an AAV packaged donor DNA template first is that the delivered donor DNA template will be stably maintained in the nucleus of the transduced hepatocytes which allows for the subsequent administration of the sequence-specific nuclease which will create a double-strand break in the genome with subsequent integration of the DNA donor by HDR or NHEJ. It is desirable in some embodiments that the sequence-specific nuclease remain active in the target cell only for the time required to promote targeted integration of the transgene at sufficient levels for the desired therapeutic effect. If the sequence-specific nuclease remains active in the cell for an extended duration this will result in an increased frequency of double-strand breaks at off-target sites. Specifically, the frequency of off-target cleavage is a function of the off-target cutting efficiency multiplied by the time over which the nuclease is active. Delivery of a sequence-specific nuclease in the form of a mRNA results in a short duration of nuclease activity in the range of hours to a few days because the mRNA and the translated protein are short lived in the cell. Thus, delivery of the sequence-specific nuclease into cells that already contain the donor template is expected to result in the highest possible ratio of targeted integration relative to off-target integration. In addition, AAV mediated delivery of a donor DNA template to the nucleus of hepatocytes after peripheral IV injection takes time, typically on the order of 1 to 14 days due to the requirement for the virus to infect the cell, escape the endosomes and then transit to the nucleus and conversion of the single-stranded AAV genome to a double-stranded DNA molecule by host components. Thus, it is preferable at least in some embodiments to allow the process of delivery of the donor DNA template to the nucleus to be completed before supplying the CRISPR-Cas9 components since these nuclease components will only be active for about 1 to 3 days.

In some embodiments, the sequence-specific nuclease is CRISPR-Cas9 which is composed of a sgRNA directed to a DNA sequence within intron 1 of the transferrin gene together with a Cas9 nuclease. In some embodiments, the Cas9 nuclease is delivered as a mRNA encoding the Cas9 protein operably fused to one or more nuclear localization signals (NLS). In some embodiments, the sgRNA and the Cas9 mRNA are delivered to the hepatocytes by packaging into a lipid nanoparticle. In some embodiments, the lipid nanoparticle contains the lipid C12-200 (Love et al. 2010, PNAS 107:1864-1869). In some embodiments, the ratio of the sgRNA to the Cas9 mRNA that is packaged in the LNP is 1:1 (mass ratio) to result in maximal DNA cleavage in vivo in mice. In alternative embodiments, different mass ratios of the sgRNA to the Cas9 mRNA that is packaged in the LNP can be used, for example, 10:1, 9:1, 8:1, 7:1, 6:1, 5:1, 4:1, 3:1 or 2:1 or reverse ratios. In some embodiments, the Cas9 mRNA and the sgRNA are packaged into separate LNP formulations and the Cas9 mRNA containing LNP is delivered to the subject about 1 to about 8 hours before the LNP containing the sgRNA to allow optimal time for the Cas9 mRNA to be translated prior to delivery of the sgRNA.

In some embodiments, an LNP formulation encapsulating a gRNA and a Cas9 mRNA ("the LNP-nuclease formulation") is administered to a subject, e.g., a patient, that previously was administered a DNA donor template packaged into an AAV. In some embodiments, the LNP-nuclease formulation is administered to the subject within 1 day to 28 days or within 7 days to 28 days or within 7 days to 14 days after administration of the AAV-donor DNA template. The optimal timing of delivery of the LNP-nuclease formulation relative to the AAV-donor DNA template can be determined using the techniques known in the art, e.g., studies done in animal models including mice and monkeys.

In some embodiments, a DNA-donor template is delivered to the hepatocytes of a subject, e.g., a patient, using a non-viral delivery method. While some subjects (typically 30%) have pre-existing neutralizing antibodies directed to most commonly used AAV serotypes that prevents the efficacious gene delivery by said AAV, all subjects will be treatable with a non-viral delivery method. Several non-viral delivery methodologies have been known in the field. In particular lipid nanoparticles (LNP) are known to efficiently deliver their encapsulated cargo to the cytoplasm of hepatocytes after intravenous injection in animals and humans. These LNP are actively taken up by the liver through a process of receptor mediated endocytosis resulting in preferential uptake into the liver.

In some embodiments, in order to promote nuclear localization of a donor template, DNA sequence that can promote nuclear localization of plasmids, e.g., a 366 bp region of the simian virus 40 (SV40) origin of replication and early promoter, can be added to the donor template. Other DNA sequences that bind to cellular proteins can also be used to improve nuclear entry of DNA.

In some embodiments, a level of expression or activity of introduced POI (e.g., FVIII) gene is measured in the blood of a subject, e.g., a patient, following the first administration of an LNP-nuclease formulation, e.g., containing gRNA and Cas9 nuclease or mRNA encoding Cas9 nuclease, after the AAV-donor DNA template. If the POI level is not sufficient to cure the disease as defined for example as POI levels of at least 5 to 50%, in particular 5 to 20% of normal levels, then a second or third administration of the LNP-nuclease formulation can be given to promote additional targeted integration into the transferrin intron 1 site. The feasibility of using multiple doses of the LNP-nuclease formulation to obtain the desired therapeutic levels of POI can be tested and optimized using the techniques known in the field, e.g., tests using animal models including the mouse and the monkey.

In some embodiments, according to any of the methods described herein comprising administration of i) an AAV-donor DNA template comprising a donor cassette and ii) an LNP-nuclease formulation to a subject, an initial dose of the LNP-nuclease formulation is administered to the subject within 1 day to 28 days after administration of the AAV-donor DNA template to the subject. In some embodiments, the initial dose of the LNP-nuclease formulation is administered to the subject after a sufficient time to allow delivery of the donor DNA template to the nucleus of a target cell. In some embodiments, the initial dose of the LNP-nuclease formulation is administered to the subject after a sufficient time to allow conversion of the single-stranded AAV genome to a double-stranded DNA molecule in the nucleus of a target cell. In some embodiments, one or more (such as 2, 3, 4, 5, or more) additional doses of the LNP-nuclease formulation are administered to the subject following administration of the initial dose. In some embodiments, one or more doses of the LNP-nuclease formulation are administered to the subject until a target level of targeted integration of the donor cassette and/or a target level of expression of the donor cassette is achieved. In some embodiments, the method further comprises measuring the level of targeted integration of the donor cassette and/or the level of expression of the donor cassette following each administration of the LNP-nuclease formulation, and administering an additional dose of the LNP-nuclease formulation if the target level of targeted integration of the donor cassette and/or the target level of expression of the donor cassette is not achieved. In some embodiments, the amount of at least one of the one or more additional doses of the LNP-nuclease formulation is the same as the initial dose. In some embodiments, the amount of at least one of the one or more additional doses of the LNP-nuclease formulation is less than the initial dose. In some embodiments, the amount of at least one of the one or more additional doses of the LNP-nuclease formulation is more than the initial dose.

Genetically Modified Cells and Cell Populations

In one aspect, the disclosures herewith provide a method of editing a genome in a cell, thereby creating a genetically modified cell. In some aspects, a population of genetically modified cells are provided. The genetically modified cell therefore refers to a cell that has at least one genetic modification introduced by genome editing (e.g., using the CRISPR/Cas9/Cpf1 system). In some embodiments, the genetically modified cell is a genetically modified hepatocyte cell. A genetically modified cell having an exogenous genome-targeting nucleic acid and/or an exogenous nucleic acid encoding a genome-targeting nucleic acid is contemplated herein.

In some embodiments, the genome of a cell can be edited by inserting a nucleic acid sequence encoding a POI (e.g., FVIII) or a functional derivative thereof into a genomic sequence of the cell. In some embodiments, the cell subject to the genome-edition has one or more mutation(s) in the genome which results in reduction of the expression of endogenous POI gene as compared to the expression in a normal that does not have such mutation(s). The normal cell can be a healthy or control cell that is originated (or isolated) from a different subject who does not have POI gene defects. In some embodiments, the cell subject to the genome-edition can be originated (or isolated) from a subject who is in need of treatment of POI gene related condition or disorder. Therefore, in some embodiments the expression of endogenous POI gene in such cell is about 10%, about 20%, about 30%, about 40%, about 50%, about 60%, about 70%, about 80%, about 90% or about 100% reduced as compared to the expression of endogenous POI gene expression in the normal cell.

Upon successful insertion of the transgene, e.g., a nucleic acid encoding a POI (e.g., FVIII) or a functional fragment thereof, the expression of the introduced nucleic acid encoding a POI or a functional derivative thereof in the cell can be at least about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1,000%, about 2,000%, about 3,000%, about 5,000%, about 10,000% or more as compared to the expression of endogenous POI gene of the cell. In some embodiments, the activity of introduced POI gene products including the functional fragment of POI in the genome-edited cell can be at least about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, about 1,000%, about 2,000%, about 3,000%, about 5,000%, about 10,000% or more as compared to the expression of endogenous POI gene of the cell. In some embodiments, the expression of the introduced POI gene or a functional derivative thereof in the cell is at least about 2 folds, about 3 folds, about 4 folds, about 5 folds, about 6 folds, about 7 folds, about 8 folds, about 9 folds, about 10 folds, about 15 folds, about 20 folds, about 30 folds, about 50 folds, about 100 folds, about 1000 folds or more of the expression of endogenous POI gene of the cell. Also, in some embodiments, the activity of introduced POI gene products including the functional fragment of POI in the genome-edited cell can be comparable to or more than the activity of POI gene products in a normal, healthy cell.

In embodiments where treating or ameliorating Hemophilia A is concerned, the principal targets for gene editing are human cells. For example, in the ex vivo methods and the in vivo methods, the human cells are hepatocytes. In some embodiments, by performing gene editing in autologous cells that are derived from and therefore already completely matched with the subject in need, it is possible to generate cells that can be safely re-introduced into the subject, and effectively give rise to a population of cells that will be effective in ameliorating one or more clinical conditions associated with the subject's disease. In some embodiments for such treatments, hepatocyte cells can be isolated according to any method known in the art and used to create genetically modified, therapeutically effective cells. In one embodiment liver stem cells are genetically modified ex vivo and then re-introduced into the subject where they will give rise to genetically modified hepatocytes or sinusoidal endothelial cells that express the inserted FVIII gene.

Therapeutic Approach

In one aspect, provided herein is a gene therapy approach for treating a subject having or suspected of having a disorder or health condition associated with a protein-of-interest (POI) by editing the genome of the subject. For example, in some embodiments, the POI is FVIII and the disorder or health condition is hemophilia A. In some embodiments, the gene therapy approach integrates a functional POI gene into the genome of a relevant cell type in subjects and this can provide a permanent cure for disorder of health condition. In some embodiments, a cell type subject to the gene therapy approach in which to integrate the POI gene is the hepatocyte because these cells efficiently express and secrete many proteins into the blood. In addition, this integration approach using hepatocytes can be considered for pediatric subjects whose livers are not fully grown because the integrated gene would be transmitted to the daughter cells as the hepatocytes divide.

In another aspect, provided herein are cellular, ex vivo and in vivo methods for using genome engineering tools to create permanent changes to the genome by knocking-in a POI (e.g., FVIII)-encoding gene or a functional derivative thereof into a gene locus into a genome and restoring POI activity. Such methods use endonucleases, such as CRISPR-associated (CRISPR/Cas9, Cpf1 and the like) nucleases, to permanently delete, insert, edit, correct, or replace any sequences from a genome or insert an exogenous sequence, e.g., a FVIII-encoding gene, in a genomic locus. In this way, the examples set forth in the present disclosure restore the activity of FVIII with a single treatment (rather than requiring the delivery of alternative therapies for the lifetime of the subject).

In some embodiments, an ex vivo cell-based therapy is done using a hepatocyte that is isolated from a subject. Next, the chromosomal DNA of these cells is edited using the materials and methods described herein. Finally, the edited cells are implanted into the subject.

One advantage of an ex vivo cell therapy approach is the ability to conduct a comprehensive analysis of the therapeutic prior to administration. All nuclease-based therapeutics have some level of off-target effects. Performing gene correction ex vivo allows one to fully characterize the corrected cell population prior to implantation. Aspects of the disclosure include sequencing the entire genome of the corrected cells to ensure that the off-target cuts, if any, are in genomic locations associated with minimal risk to the subject. Furthermore, populations of specific cells, including clonal populations, can be isolated prior to implantation.

Another embodiment of such method is an in vivo based therapy. In this method, the chromosomal DNA of the cells in the subject is corrected using the materials and methods described herein. In some embodiments, the cells are hepatocytes.

An advantage of in vivo gene therapy is the ease of therapeutic production and administration. The same therapeutic approach and therapy can be used to treat more than one subject, for example a number of subjects who share the same or similar genotype or allele. In contrast, ex vivo cell therapy typically uses a subject's own cells, which are isolated, manipulated and returned to the same subject.

In some embodiments, the subject who is in need of the treatment method accordance with the disclosures is a subject having symptoms of a disease or condition associated with a POI. For example, in some embodiments, the POI is FVIII and the subject has symptoms of Hemophilia A. In some embodiments, the subject can be a human suspected of having the disease or condition. Alternatively, the subject can be a human diagnosed with a risk of the disease or condition. In some embodiments, the subject who is in need of the treatment can have one or more genetic defects (e.g., deletion, insertion, and/or mutation) in the endogenous POI gene or its regulatory sequences such that the activity including the expression level or functionality of the POI is substantially reduced compared to a normal, healthy subject.

In some embodiments, provided herein is a method of treating a disease or condition associated with a POI (e.g., Hemophilia A where the POI is FVIII) in a subject, the method comprising providing the following to a cell in the subject: (a) a guide RNA (gRNA) targeting the transferrin locus in the cell genome; (b) a DNA endonuclease or nucleic acid encoding said DNA endonuclease; and (c) a donor template comprising a nucleic acid sequence encoding the POI or a functional derivative thereof (e.g., FVIII or a functional derivative thereof). In some embodiments, the gRNA targets intron 1 of the transferrin gene. In some embodiments, the gRNA comprises a spacer sequence from any one of SEQ ID NOs: 1-190.

In some embodiments, according to any of the methods of treating a disease or condition associated with a POI described herein, the POI is a protein selected from the group consisting of a Factor VIII protein, Factor IX, alpha-1-antitrypsin, FXIII, FVII, Factor X, a C1 esterase inhibitor, iduronate sulfatase, α-L-iduronidase, and Protein C. In some embodiments, the POI is a Factor VIII protein. In some embodiments, the subject has or is suspected of having a disorder or health condition selected from the group consisting of Factor VIII deficiency (Hemophilia A), Factor IX deficiency (Hemophilia B), Hunters syndrome (MPS II), mucopolysaccharidosis type 1 (MPS 1), alpha-1-antitrypsin deficiency, Factor XIII deficiency, Factor VII deficiency, Factor X deficiency, Protein C deficiency, and Hereditary Angioedema (HAE). In some embodiments, the subject has or is suspected of having Hemophilia A.

In some embodiments, provided herein is a method of treating a disease or condition associated with a POI (e.g., Hemophilia A where the POI is FVIII) in a subject, the method comprising providing the following to a cell in the subject: (a) a gRNA comprising a spacer sequence that is complementary to a genomic sequence within or near an endogenous transferrin locus in the cell; (b) a DNA endonuclease or nucleic acid encoding said DNA endonuclease; and (c) a donor template comprising a nucleic acid sequence encoding the POI or a functional derivative thereof (e.g., FVIII or a functional derivative thereof). In some embodiments, the gRNA comprises a spacer sequence that is complementary to a sequence within intron 1 of an endogenous transferrin gene in the cell. In some embodiments, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10. In some embodiments, the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51. In some embodiments, the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11. In some embodiments, the spacer sequence is 19 nucleotides in length and does not include the nucleotide at position 1 of the sequence from which it is selected. In some embodiments, the cell is a human cell, e.g., a human hepatocyte cell. In some embodiments, the POI is FVIII. In some embodiments, the subject is a patient having or suspected of having Hemophilia A. In some embodiments, the subject is diagnosed with a risk of Hemophilia A.

In some embodiments, according to any of the methods of treating a disease or condition associated with a POI (e.g., Hemophilia A where the POI is FVIII) in a subject, the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190. In some embodiments, the gRNA comprises a spacer sequence from SEQ ID NO: 96 or a variant thereof having no more than 3 mismatches. In some embodiments, the gRNA comprises a spacer sequence from SEQ ID NO: 5 or a variant thereof having no more than 3 mismatches. In some embodiments, the gRNA comprises a spacer sequence from SEQ ID NO: 6 or a variant thereof having no more than 3 mismatches. In some embodiments, the gRNA comprises a spacer sequence from SEQ ID NO: 9 or a variant thereof having no more than 3 mismatches. In some embodiments, the gRNA comprises a spacer sequence from SEQ ID NO: 8 or a variant thereof having no more than 3 mismatches. In some embodiments, the gRNA comprises a spacer sequence from SEQ ID NO: 11 or a variant thereof having no more than 3 mismatches. In some embodiments, the gRNA comprises a spacer sequence from SEQ ID NO: 15 or a variant thereof having no more than 3 mismatches. In some embodiments, the gRNA comprises a spacer sequence from SEQ ID NO: 16 or a variant thereof having no more than 3 mismatches. In some embodiments, the gRNA comprises a spacer sequence from SEQ ID NO: 12 or a variant thereof having no more than 3 mismatches. In some embodiments, the gRNA comprises a spacer sequence from SEQ ID NO: 7 or a variant thereof having no more than 3 mismatches. In some embodiments, the gRNA comprises a spacer sequence from SEQ ID NO: 10 or a variant thereof having no more than 3 mismatches. In some embodiments, the gRNA comprises a spacer sequence from SEQ ID NO: 17 or a variant thereof having no more than 3 mismatches. In some embodiments, the gRNA comprises a spacer sequence from SEQ ID NO: 18 or a variant thereof having no more than 3 mismatches. In some embodiments, the gRNA comprises a spacer sequence from SEQ ID NO: 29 or a variant thereof having no more than 3 mismatches. In some embodiments, the gRNA comprises a spacer sequence from SEQ ID NO: 76 or a variant thereof having no more than 3 mismatches. In some embodiments, the gRNA comprises a spacer sequence from SEQ ID NO: 50 or a variant thereof having no more than 3 mismatches. In some embodiments, the gRNA comprises a spacer sequence from SEQ ID NO:

54 or a variant thereof having no more than 3 mismatches. In some embodiments, the gRNA comprises a spacer sequence from SEQ ID NO: 81 or a variant thereof having no more than 3 mismatches. In some embodiments, the gRNA comprises a spacer sequence from SEQ ID NO: 64 or a variant thereof having no more than 3 mismatches. In some embodiments, the gRNA comprises a spacer sequence from SEQ ID NO: 51 or a variant thereof having no more than 3 mismatches.

In some embodiments, according to any of the methods of treating a disease or condition associated with a POI (e.g., Hemophilia A where the POI is FVIII) described herein, the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional derivative thereof. In some embodiments, the DNA endonuclease is Cas9. In some embodiments, the Cas9 is from *Streptococcus pyogenes* (spCas9). In some embodiments, the Cas9 is from *Staphylococcus lugdunensis* (SluCas9).

In some embodiments, according to any of the methods of treating a disease or condition associated with a POI (e.g., Hemophilia A where the POI is FVIII) described herein, the nucleic acid sequence encoding the POI or a functional derivative thereof (e.g., FVIII or a functional derivative thereof) is codon-optimized for expression in the cell. In some embodiments, the cell is a human cell.

In some embodiments, according to any of the methods of treating a disease or condition associated with a POI (e.g., Hemophilia A where the POI is FVIII) described herein, the method employs a nucleic acid encoding the DNA endonuclease. In some embodiments, the nucleic acid encoding the DNA endonuclease is codon-optimized for expression in the cell. In some embodiments, the cell is a human cell, e.g., a human hepatocyte cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the methods of treating a disease or condition associated with a POI (e.g., Hemophilia A where the POI is FVIII) described herein, the donor template is encoded in an Adeno Associated Virus (AAV) vector. In some embodiments, the donor template comprises a donor cassette comprising the nucleic acid sequence encoding the POI or a functional derivative thereof (e.g., FVIII or a functional derivative thereof), and the donor cassette is flanked on one or both sides by a gRNA target site. In some embodiments, the donor cassette is flanked on both sides by a gRNA target site. In some embodiments, the gRNA target site is a target site for the gRNA of (a). In some embodiments, the gRNA target site of the donor template is the reverse complement of a cell genome gRNA target site for the gRNA of (a). In some embodiments, providing the donor template to the cell comprises administering the donor template to the subject. In some embodiments, the administration is via intravenous route.

In some embodiments, according to any of the methods of treating a disease or condition associated with a POI (e.g., Hemophilia A where the POI is FVIII) described herein, the DNA endonuclease or nucleic acid encoding the DNA endonuclease is formulated in a liposome or lipid nanoparticle. In some embodiments, the liposome or lipid nanoparticle also comprises the gRNA. In some embodiments, providing the gRNA and the DNA endonuclease or nucleic acid encoding the DNA endonuclease to the cell comprises administering the liposome or lipid nanoparticle to the subject. In some embodiments, the administration is via intravenous route. In some embodiments, the liposome or lipid nanoparticle is a lipid nanoparticle. In some embodiments, the method employs a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the methods of treating a disease or condition associated with a POI (e.g., Hemophilia A where the POI is FVIII) described herein, the DNA endonuclease is pre-complexed with the gRNA, forming a ribonucleoprotein (RNP) complex.

In some embodiments, according to any of the methods of treating a disease or condition associated with a POI (e.g., Hemophilia A where the POI is FVIII) described herein, the gRNA of (a) and the DNA endonuclease or nucleic acid encoding the DNA endonuclease of (b) are provided to the cell after the donor template of (c) is provided to the cell. In some embodiments, the gRNA of (a) and the DNA endonuclease or nucleic acid encoding the DNA endonuclease of (b) are provided to the cell more than 4 days after the donor template of (c) is provided to the cell. In some embodiments, the gRNA of (a) and the DNA endonuclease or nucleic acid encoding the DNA endonuclease of (b) are provided to the cell at least 14 days after the donor template of (c) is provided to the cell. In some embodiments, the gRNA of (a) and the DNA endonuclease or nucleic acid encoding the DNA endonuclease of (b) are provided to the cell at least 17 days after the donor template of (c) is provided to the cell. In some embodiments, providing (a) and (b) to the cell comprises administering (such as by intravenous route) to the subject a lipid nanoparticle comprising nucleic acid encoding the DNA endonuclease and the gRNA. In some embodiments, the nucleic acid encoding the DNA endonuclease is an mRNA encoding the DNA endonuclease. In some embodiments, providing (c) to the cell comprises administering (such as by intravenous route) to the subject the donor template encoded in an AAV vector.

In some embodiments, according to any of the methods of treating a disease or condition associated with a POI (e.g., Hemophilia A where the POI is FVIII) described herein, one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b). In some embodiments, one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b) until a target level of targeted integration of the nucleic acid sequence encoding the POI or a functional derivative thereof (e.g., FVIII or a functional derivative thereof) and/or a target level of expression of the nucleic acid sequence encoding the POI or functional derivative is achieved. In some embodiments, providing (a) and (b) to the cell comprises administering (such as by intravenous route) to the subject a lipid nanoparticle comprising nucleic acid encoding the DNA endonuclease and the gRNA. In some embodiments, the nucleic acid encoding the DNA endonuclease is an mRNA encoding the DNA endonuclease.

In some embodiments, according to any of the methods of treating a disease or condition associated with a POI (e.g., Hemophilia A where the POI is FVIII) described herein, the nucleic acid sequence encoding the POI or a functional derivative thereof (e.g., FVIII or a functional derivative thereof) is expressed under the control of the endogenous transferrin promoter.

In some embodiments, according to any of the methods of treating a disease or condition associated with a POI (e.g., Hemophilia A where the POI is FVIII) described herein, the nucleic acid sequence encoding the POI or a functional derivative thereof (e.g., FVIII or a functional derivative thereof) is expressed in the liver of the subject.

Implanting Cells into a Subject

In some embodiments, the ex vivo methods of the disclosure involve implanting the genome-edited cells into a subject who is in need of such method. This implanting step can be accomplished using any method of implantation known in the art. For example, the genetically modified cells can be injected directly in the subject's blood or otherwise administered to the subject.

In some embodiments, the methods disclosed herein include administering, which can be interchangeably used with "introducing" and "transplanting," genetically-modified, therapeutic cells into a subject, by a method or route that results in at least partial localization of the introduced cells at a desired site such that a desired effect(s) is produced. The therapeutic cells or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment.

When provided prophylactically, the therapeutic cells described herein can be administered to a subject in advance of any symptom of a disease or condition associated with a POI (e.g., Hemophilia A where the POI is FVIII). Accordingly, in some embodiments the prophylactic administration of a genetically modified hepatocyte cell population serves to prevent the occurrence of symptoms of the disease or condition.

When provided therapeutically in some embodiments, genetically modified hepatocyte cells are provided at (or after) the onset of a symptom or indication of a disease or condition associated with a POI (e.g., Hemophilia A where the POI is FVIII), e.g., upon the onset of disease or condition.

In some embodiments, a therapeutic hepatocyte cell population being administered according to the methods described herein has allogeneic hepatocyte cells obtained from one or more donors. "Allogeneic" refers to a hepatocyte cell or biological samples having hepatocyte cells obtained from one or more different donors of the same species, where the genes at one or more loci are not identical. For example, a hepatocyte cell population being administered to a subject can be derived from one more unrelated donor subjects, or from one or more non-identical siblings. In some embodiments, syngeneic hepatocyte cell populations can be used, such as those obtained from genetically identical animals, or from identical twins. In other embodiments, the hepatocyte cells are autologous cells; that is, the hepatocyte cells are obtained or isolated from a subject and administered to the same subject, i.e., the donor and recipient are the same.

In one embodiment, an effective amount refers to the amount of a population of therapeutic cells needed to prevent or alleviate at least one or more signs or symptoms of a disease or condition associated with a POI (e.g., Hemophilia A where the POI is FVIII), and relates to a sufficient amount of a composition to provide the desired effect, e.g., to treat a subject having the disease or condition. In embodiments, a therapeutically effective amount therefore refers to an amount of therapeutic cells or a composition having therapeutic cells that is sufficient to promote a particular effect when administered to a typical subject, such as one who has or is at risk for the disease or condition. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

For use in the various embodiments described herein, an effective amount of therapeutic cells, e.g., genome-edited hepatocyte cells, can be at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The therapeutic cells can be derived from one or more donors or can be obtained from an autologous source. In some embodiments described herein, the therapeutic cells are expanded in culture prior to administration to a subject in need thereof.

In some embodiments, modest and incremental increases in the levels of functional POI (e.g., FVIII) expressed in cells of subjects having a disease or condition associated with the POI (e.g., Hemophilia A) can be beneficial for ameliorating one or more symptoms of the disease or condition, for increasing long-term survival, and/or for reducing side effects associated with other treatments. Upon administration of such cells to human subjects, the presence of therapeutic cells that are producing increased levels of functional POI is beneficial. In some embodiments, effective treatment of a subject gives rise to at least about 1%, 3%, 5% or 7% functional POI relative to total POI in the treated subject. In some embodiments, functional POI is at least about 10% of total POI. In some embodiments, functional POI is at least, about or at most 20%, 30%, 40%, 50%, 60%, 70%, 80%, 90% or 100% of total POI. Similarly, the introduction of even relatively limited subpopulations of cells having significantly elevated levels of functional POI can be beneficial in various subjects because in some situations normalized cells will have a selective advantage relative to diseased cells. However, even modest levels of therapeutic cells with elevated levels of functional POI can be beneficial for ameliorating one or more aspects of the disease or condition in subjects. In some embodiments, about 10%, about 20%, about 30%, about 40%, about 50%, about 60%, about 70%, about 80%, about 90% or more of the therapeutic in subjects to whom such cells are administered are producing increased levels of functional POI.

In embodiments, the delivery of a therapeutic cell composition into a subject by a method or route results in at least partial localization of the cell composition at a desired site. A cell composition can be administered by any appropriate route that results in effective treatment in the subject, e.g., administration results in delivery to a desired location in the subject where at least a portion of the composition delivered, e.g., at least 1×10$^4$ cells, is delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous. For the delivery of cells, administration by injection or infusion can be made.

In one embodiment, the cells are administered systemically, in other words a population of therapeutic cells are administered other than directly into a target site, tissue, or organ, such that it enters, instead, the subject's circulatory system and, thus, is subject to metabolism and other like processes.

The efficacy of a treatment having a composition for the treatment of a disease or condition associated with a POI (e.g., Hemophilia A where the POI is FVIII) can be determined by the skilled clinician. However, a treatment is considered effective treatment if any one or all of the signs or symptoms of, as but one example, levels of functional POI are altered in a beneficial manner (e.g., increased by at least 10%), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

Composition

In one aspect, the present disclosure provides compositions for carrying out the methods disclosed herein. A composition can include one or more of the following: a genome-targeting nucleic acid (e.g., a gRNA); a site-directed polypeptide (e.g., a DNA endonuclease) or a nucleotide sequence encoding the site-directed polypeptide; and a polynucleotide to be inserted (e.g., a donor template) to effect the desired genetic modification of the methods disclosed herein.

In some embodiments, a composition has a nucleotide sequence encoding a genome-targeting nucleic acid (e.g., a gRNA).

In some embodiments, a composition has a site-directed polypeptide (e.g. DNA endonuclease). In some embodiments, a composition has a nucleotide sequence encoding the site-directed polypeptide.

In some embodiments, a composition has a polynucleotide (e.g., a donor template) to be inserted into a genome.

In some embodiments, a composition has (i) a nucleotide sequence encoding a genome-targeting nucleic acid (e.g., a gRNA) and (ii) a site-directed polypeptide (e.g., a DNA endonuclease) or a nucleotide sequence encoding the site-directed polypeptide.

In some embodiments, a composition has (i) a nucleotide sequence encoding a genome-targeting nucleic acid (e.g., a gRNA) and (ii) a polynucleotide (e.g., a donor template) to be inserted into a genome.

In some embodiments, a composition has (i) a site-directed polypeptide (e.g., a DNA endonuclease) or a nucleotide sequence encoding the site-directed polypeptide and (ii) a polynucleotide (e.g., a donor template) to be inserted into a genome.

In some embodiments, a composition has (i) a nucleotide sequence encoding a genome-targeting nucleic acid (e.g., a gRNA), (ii) a site-directed polypeptide (e.g., a DNA endonuclease) or a nucleotide sequence encoding the site-directed polypeptide and (iii) a polynucleotide (e.g., a donor template) to be inserted into a genome.

In some embodiments of any of the above compositions, the composition has a single-molecule guide genome-targeting nucleic acid. In some embodiments of any of the above compositions, the composition has a double-molecule genome-targeting nucleic acid. In some embodiments of any of the above compositions, the composition has two or more double-molecule guides or single-molecule guides. In some embodiments, the composition has a vector that encodes the nucleic acid targeting nucleic acid. In some embodiments, the genome-targeting nucleic acid is a DNA endonuclease, in particular, Cas9.

In some embodiments, a composition can contain composition that includes one or more gRNA that can be used for genome-edition, in particular, insertion of a sequence encoding a POI (e.g., FVIII) or derivative thereof into a genome of a cell. The gRNA for the composition can target a genomic site at, within, or near the endogenous transferrin gene. Therefore, in some embodiments, the gRNA can have a spacer sequence complementary to a genomic sequence at, within, or near the transferrin gene.

In some embodiments, a gRNA for a composition comprises a spacer sequence selected from those listed in Table 2 (e.g., a spacer sequence from any one of SEQ ID NOs: 1-188) and variants thereof having at least about 50%, about 55%, about 60%, about 65%, about 70%, about 75%, about 80%, about 85%, about 90% or about 95% identity or homology to any of those listed in Table 2. In some embodiments, the variants of gRNA for the kit have at least about 85% homology to any of those listed in Table 2.

In some embodiments, a gRNA for a composition has a spacer sequence that is complementary to a target site in the genome. In some embodiments, the spacer sequence is 15 bases to 20 bases in length. In some embodiments, a complementarity between the spacer sequence to the genomic sequence is at least 80%, at least 85%, at least 90%, at least 95%, at least 96%, at least 97%, at least 98%, at least 99% or at least 100%.

In some embodiments, a composition can have a DNA endonuclease or a nucleic acid encoding the DNA endonuclease and/or a donor template having a nucleic acid sequence encoding a POI (e.g., FVIII) or a functional derivative thereof. In some embodiments, the DNA endonuclease is Cas9. In some embodiments, the nucleic acid encoding the DNA endonuclease is DNA or RNA.

In some embodiments, one or more of any oligonucleotides or nucleic acid sequences for the kit can be encoded in an Adeno Associated Virus (AAV) vector. Therefore, in some embodiments, a gRNA can be encoded in an AAV vector. In some embodiments, a nucleic acid encoding a DNA endonuclease can be encoded in an AAV vector. In some embodiments, a donor template can be encoded in an AAV vector. In some embodiments, two or more oligonucleotides or nucleic acid sequences can be encoded in a single AAV vector. Thus, in some embodiments, a gRNA sequence and a DNA endonuclease-encoding nucleic acid can be encoded in a single AAV vector.

In some embodiments, a composition can have a liposome or a lipid nanoparticle. Therefore, in some embodiments, any compounds (e.g., a DNA endonuclease or a nucleic acid encoding thereof, gRNA and donor template) of the composition can be formulated in a liposome or lipid nanoparticle. In some embodiments, one or more such compounds are associated with a liposome or lipid nanoparticle via a covalent bond or non-covalent bond. In some embodiments, any of the compounds can be separately or together contained in a liposome or lipid nanoparticle. Therefore, in some embodiments, each of a DNA endonuclease or a nucleic acid encoding thereof, gRNA and donor template is separately formulated in a liposome or lipid nanoparticle. In some embodiments, a DNA endonuclease is formulated in a liposome or lipid nanoparticle with gRNA. In some embodiments, a DNA endonuclease or a nucleic acid encoding thereof, gRNA and donor template are formulated in a liposome or lipid nanoparticle together.

In some embodiments, a composition described above further has one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. In some embodiments, a composition can also include one or more components that can be used to facilitate or enhance the on-target binding or the cleavage of DNA by the endonuclease, or improve the specificity of targeting.

In some embodiments, any components of a composition are formulated with pharmaceutically acceptable excipients such as carriers, solvents, stabilizers, adjuvants, diluents, etc., depending upon the particular mode of administration and dosage form. In embodiments, guide RNA compositions are generally formulated to achieve a physiologically compatible pH, and range from a pH of about 3 to a pH of about 11, about pH 3 to about pH 7, depending on the formulation and route of administration. In some embodiments, the pH is adjusted to a range from about pH 5.0 to about pH 8. In some embodiments, the composition has a therapeutically effective amount of at least one compound as described herein, together with one or more pharmaceutically acceptable excipients. Optionally, the composition can have a combination of the compounds described herein, or can include a second active ingredient useful in the treatment or prevention of bacterial growth (for example and without limitation, anti-bacterial or anti-microbial agents), or can include a combination of reagents of the disclosure. In some embodiments, gRNAs are formulated with other one or more nucleic acids, e.g., nucleic acid encoding a DNA endonuclease and/or a donor template. Alternatively, a nucleic acid encoding a DNA endonuclease and a donor template, separately or in combination with other nucleic acids, are formulated with the method described above for gRNA formulation.

Suitable excipients can include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

In some embodiments, any compounds (e.g., a DNA endonuclease or a nucleic acid encoding thereof, gRNA and donor template) of a composition can be delivered via transfection such as electroporation. In some exemplary embodiments, a DNA endonuclease can be precomplexed with a gRNA, forming a Ribonucleoprotein (RNP) complex, prior to the provision to the cell and the RNP complex can be electroporated. In such embodiments, the donor template can be delivered via electroporation.

In some embodiments, a composition refers to a therapeutic composition having therapeutic cells that are used in an ex vivo treatment method.

In embodiments, therapeutic compositions contain a physiologically tolerable carrier together with the cell composition, and optionally at least one additional bioactive agent as described herein, dissolved or dispersed therein as an active ingredient. In some embodiments, the therapeutic composition is not substantially immunogenic when administered to a mammal or human subject for therapeutic purposes, unless so desired.

In general, the genetically-modified, therapeutic cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation having cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

In some embodiments, a cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition will depend on the nature of the disorder or condition, and can be determined by standard clinical techniques.

Kit

Some embodiments provide a kit that contains any of the above-described compositions, e.g., a composition for genome edition or a therapeutic cell composition, and one or more additional components.

In some embodiments, a kit can have one or more additional therapeutic agents that can be administered simultaneously or in sequence with the composition for a desired purpose, e.g., genome edition or cell therapy.

In some embodiments, a kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the Internet), can be provided. An example of this embodiment is a kit that includes a web address where the instructions can be viewed and/or from which the instructions can be downloaded. As with the instructions, this means for obtaining the instructions can be recorded on a suitable substrate.

Additional Therapeutic Approaches

Gene editing can be conducted using nucleases engineered to target specific sequences. To date there are four major types of nucleases: meganucleases and their derivatives, zinc finger nucleases (ZFNs), transcription activator like effector nucleases (TALENs), and CRISPR-Cas9 nuclease systems. The nuclease platforms vary in difficulty of design, targeting density and mode of action, particularly as the specificity of ZFNs and TALENs is through protein-DNA interactions, while RNA-DNA interactions primarily guide Cas9. Cas9 cleavage also requires an adjacent motif, the PAM, which differs between different CRISPR systems. Cas9 from *Streptococcus pyogenes* cleaves using a NRG PAM, CRISPR from *Neisseria meningitidis* can cleave at sites with PAMs including NNNNGATT, NNNNNGTTT, and NNNNGCTT. A number of other Cas9 orthologs target protospacer adjacent to alternative PAMs.

CRISPR endonucleases, such as Cas9, can be used in various embodiments of the methods of the disclosure. However, the teachings described herein, such as therapeutic target sites, could be applied to other forms of endonucleases, such as ZFNs, TALENs, HEs, or MegaTALs, or using combinations of nucleases. However, to apply the teachings of the present disclosure to such endonucleases, one would need to, among other things, engineer proteins directed to the specific target sites.

Additional binding domains can be fused to the Cas9 protein to increase specificity. The target sites of these constructs would map to the identified gRNA specified site, but would require additional binding motifs, such as for a zinc finger domain. In the case of Mega-TAL, a meganuclease can be fused to a TALE DNA-binding domain. The meganuclease domain can increase specificity and provide the cleavage. Similarly, inactivated or dead Cas9 (dCas9) can be fused to a cleavage domain and require the sgRNA/Cas9 target site and adjacent binding site for the fused DNA-binding domain. This likely would require some protein engineering of the dCas9, in addition to the catalytic inactivation, to decrease binding without the additional binding site.

In some embodiments, the compositions and methods of editing genome in accordance with the present disclosures (e.g., insertion of a FVIII-encoding sequence into the transferrin locus) can utilize or be done using any of the following approaches.

Zinc Finger Nucleases

Zinc finger nucleases (ZFNs) are modular proteins having an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN typically has 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will typically recognize a combined target sequence of 24-36 bp, not including the 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Natl Acad Sci USA 96 (6): 2758-63 (1999); Dreier B et al., J Mol Biol. 303 (4): 489-502 (2000); Liu Q et al., J Biol Chem. 277 (6): 3850-6 (2002); Dreier et al., J Biol Chem 280 (42): 35588-97 (2005); and Dreier et al., J Biol Chem. 276 (31): 29466-78 (2001).

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs have tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, *Science* 326 (5959): 1509-12 (2009); Mak et al., *Science* 335 (6069): 716-9 (2012); and Moscou et al., *Science* 326 (5959): 1501 (2009). The use of TALENs based on the "Golden Gate" platform, or cloning scheme, has been described by multiple groups; see, e.g., Cermak et al., *Nucleic Acids Res.* 39 (12): e82 (2011); Li et al., *Nucleic Acids Res.* 39 (14): 6315-25 (2011); Weber et al., *PLOS One.* 6 (2): e16765 (2011); Wang et al., *J Genet Genomics* 41 (6): 339-47, Epub 2014 Can 17 (2014); and Cermak T et al., *Methods Mol Biol.* 1239:133-59 (2015).

Homing Endonucleases

Homing endonucleases (HEs) are sequence-specific endonucleases that have long recognition sequences (14-44 base pairs) and cleave DNA with high specificity-often at sites unique in the genome. There are at least six known families of HEs as classified by their structure, including LAGLI-DADG, GIY-YIG, His-Cis box, H—N—H, PD-(D/E) xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., *Glycobiology* 24 (8): 663-80 (2014); Belfort and Bonocora, *Methods Mol Biol.* 1123:1-26 (2014); Hafez and Hausner, *Genome* 55 (8): 553-69 (2012); and references cited therein.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., *NAR* 42:2591-2601 (2014); Kleinstiver et al., G3 4:1155-65 (2014); and Boissel and Scharenberg, *Methods Mol. Biol.* 1239:171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., *NAR* 42, 8816-29 (2014). It is anticipated that other combinations of existing nuclease-based approaches will evolve and be useful in achieving the targeted genome modifications described herein.

dCas9-FokI or dCpf1-Fok1 and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 22 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function-retaining only the RNA-guided DNA binding function—and instead fusing a FokI domain to the deactivated Cas9; see, e.g., Tsai et al., *Nature Biotech* 32:569-76 (2014); and Guilinger et al., *Nature Biotech.* 32:577-82 (2014). Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Some embodiments of the disclosures provided herewith are further illustrated by the following non-limiting examples.

EXEMPLARY EMBODIMENTS

Embodiment 1

A system comprising: a deoxyribonucleic acid (DNA) endonuclease or nucleic acid encoding the DNA endonuclease; a guide RNA (gRNA) comprising a spacer sequence that is complementary to a genomic sequence within or near an endogenous transferrin locus in a cell, or nucleic acid encoding the gRNA; and a donor template comprising a nucleic acid sequence encoding a protein-of-interest (POI) or a functional derivative thereof.

Embodiment 2

The system of embodiment 1, wherein the gRNA comprises a spacer sequence that is complementary to a sequence within intron 1 of an endogenous transferrin gene in the cell.

Embodiment 3

The system of embodiment 1, wherein the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190.

Embodiment 4

The system of embodiment 3, wherein the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10.

Embodiment 5

The system of embodiment 3, wherein the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51.

Embodiment 6

The system of embodiment 3, wherein the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11.

Embodiment 7

The system of any one of embodiments 3-6, wherein the spacer sequence is 19 nucleotides in length and does not include the nucleotide at position 1 of the sequence from which it is selected.

Embodiment 8

The system of any one of embodiments 1-7, wherein the POI is selected from the group consisting of Factor VIII (FVIII), Factor IX, alpha-1-antitrypsin, FXIII, FVII, Factor X, a C1 esterase inhibitor, iduronate sulfatase, α-L-iduronidase, and Protein C.

Embodiment 9

The system of embodiment 8, wherein the POI is FVIII.

Embodiment 10

The system of any one of embodiments 1-9, wherein the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional derivative thereof.

Embodiment 11

The system of any one of embodiments 1-10, wherein the DNA endonuclease is Cas9.

Embodiment 12

The system of any one of embodiments 1-11, wherein the nucleic acid encoding the DNA endonuclease is codon-optimized for expression in a host cell.

Embodiment 13

The system of any one of embodiments 1-12, wherein the nucleic acid sequence encoding a POI or a functional derivative thereof is codon-optimized for expression in a host cell.

Embodiment 14

The system of any one of embodiments 1-13, wherein the nucleic acid sequence encoding a POI or a functional derivative thereof comprises a reduced content of CpG di-nucleotides than a nucleic acid sequence encoding the wild-type POI.

Embodiment 15

The system of any one of embodiments 1-13, wherein the nucleic acid sequence encoding a POI or a functional derivative thereof comprises about or less than 20 CpG di-nucleotides.

Embodiment 16

The system of embodiment 15, wherein the nucleic acid sequence encoding a POI or a functional derivative thereof comprises about or less than 10 CpG di-nucleotides.

Embodiment 17

The system of embodiment 16, wherein the nucleic acid sequence encoding a POI or a functional derivative thereof comprises about or less than 5 CpG di-nucleotides.

Embodiment 18

The system of embodiment 17, wherein the nucleic acid sequence encoding a POI or a functional derivative thereof does not comprise CpG di-nucleotides.

Embodiment 19

The system of any one of embodiments 1-18, wherein the nucleic acid encoding the DNA endonuclease is a deoxyribonucleic acid (DNA).

Embodiment 20

The system of any one of embodiments 1-18, wherein the nucleic acid encoding the DNA endonuclease is a ribonucleic acid (RNA).

Embodiment 21

The system of embodiment 20, wherein the RNA encoding the DNA endonuclease is an mRNA.

Embodiment 22

The system of any one of embodiments 1-21, wherein the donor template is encoded in an Adeno Associated Virus (AAV) vector.

Embodiment 23

The system of embodiment 22, wherein the donor template comprises a donor cassette comprising the nucleic acid sequence encoding a POI or a functional derivative thereof, and wherein the donor cassette is flanked on one or both sides by a gRNA target site.

Embodiment 24

The system of embodiment 23, wherein the donor cassette is flanked on both sides by a gRNA target site.

Embodiment 25

The system of embodiment 23 or 24, wherein the gRNA target site is a target site for a gRNA in the system.

Embodiment 26

The system of embodiment 25, wherein the gRNA target site of the donor template is the reverse complement of a genomic gRNA target site for a gRNA in the system.

Embodiment 27

The system of any one of embodiments 1-26, wherein the DNA endonuclease or nucleic acid encoding the DNA endonuclease is formulated in a liposome or lipid nanoparticle.

Embodiment 28

The system of embodiment 27, wherein the liposome or lipid nanoparticle also comprises the gRNA.

Embodiment 29

The system of any one of embodiments 1-28, comprising the DNA endonuclease precomplexed with the gRNA, forming a Ribonucleoprotein (RNP) complex.

Embodiment 30

A method of editing a genome in a cell, the method comprising providing the following to the cell: (a) a gRNA comprising a spacer sequence that is complementary to a genomic sequence within or near an endogenous transferrin locus in the cell, or nucleic acid encoding the gRNA; (b) a DNA endonuclease or nucleic acid encoding the DNA endonuclease; and (c) a donor template comprising a nucleic acid sequence encoding a POI or a functional derivative thereof.

Embodiment 31

The method of embodiment 30, wherein the gRNA comprises a spacer sequence that is complementary to a sequence within intron 1 of an endogenous transferrin gene in the cell.

Embodiment 32

The method of embodiment 30, wherein the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190.

Embodiment 33

The method of embodiment 32, wherein the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10.

Embodiment 34

The method of embodiment 32, wherein the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51.

Embodiment 35

The method of embodiment 32, wherein the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11.

Embodiment 36

The method of any one of embodiments 32-35, wherein the spacer sequence is 19 nucleotides in length and does not include the nucleotide at position 1 of the sequence from which it is selected.

Embodiment 37

The method of any one of embodiments 30-36, wherein the POI is selected from the group consisting of FVIII, Factor IX, alpha-1-antitrypsin, FXIII, FVII, Factor X, a C1 esterase inhibitor, iduronate sulfatase, α-L-iduronidase, and Protein C.

Embodiment 38

The method of embodiment 37, wherein the POI is FVIII.

Embodiment 39

The method of any one of embodiments 30-38, wherein the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; or a functional derivative thereof.

Embodiment 40

The method of any one of embodiments 30-39, wherein the DNA endonuclease is Cas9.

Embodiment 41

The method of any one of embodiments 30-40, wherein the nucleic acid encoding the DNA endonuclease is codon-optimized for expression in the cell.

Embodiment 42

The method of any one of embodiments 30-41, wherein the nucleic acid sequence encoding a POI or a functional derivative thereof is codon-optimized for expression in the cell.

Embodiment 43

The method of any one of embodiments 30-42, wherein the nucleic acid sequence encoding a POI or a functional derivative thereof comprises a reduced content of CpG di-nucleotides than a nucleic acid sequence encoding the wild-type POI.

Embodiment 44

The method of any one of embodiments 30-42, wherein the nucleic acid sequence encoding a POI or a functional derivative thereof comprises about or less than 20 CpG di-nucleotides.

Embodiment 45

The method of embodiment 44, wherein the nucleic acid sequence encoding a POI or a functional derivative thereof comprises about or less than 10 CpG di-nucleotides.

Embodiment 46

The method of embodiment 45, wherein the nucleic acid sequence encoding a POI or a functional derivative thereof comprises about or less than 5 CpG di-nucleotides.

Embodiment 47

The method of embodiment 46, wherein the nucleic acid sequence encoding a POI or a functional derivative thereof does not comprise CpG di-nucleotides.

Embodiment 48

The method of any one of embodiments 30-47, wherein the nucleic acid encoding the DNA endonuclease is a deoxyribonucleic acid (DNA).

Embodiment 49

The method of any one of embodiments 30-42, wherein the nucleic acid encoding the DNA endonuclease is a ribonucleic acid (RNA).

Embodiment 50

The method of embodiment 49, wherein the RNA encoding the DNA endonuclease is an mRNA.

Embodiment 51

The method of any one of embodiments 30-50, wherein the donor template is encoded in an Adeno Associated Virus (AAV) vector.

Embodiment 52

The method of any one of embodiments 30-51, wherein the donor template comprises a donor cassette comprising the nucleic acid sequence encoding a POI or a functional derivative thereof, and wherein the donor cassette is flanked on one or both sides by a gRNA target site.

Embodiment 53

The method of embodiment 52, wherein the donor cassette is flanked on both sides by a gRNA target site.

Embodiment 54

The method of embodiment 52 or 53, wherein the gRNA target site is a target site for the gRNA of (a).

Embodiment 55

The method of embodiment 54, wherein the gRNA target site of the donor template is the reverse complement of a gRNA target site in the cell genome for the gRNA of (a).

Embodiment 56

The method of any one of embodiments 30-55, wherein the DNA endonuclease or nucleic acid encoding the DNA endonuclease is formulated in a liposome or lipid nanoparticle.

Embodiment 57

The method of embodiment 56, wherein the liposome or lipid nanoparticle also comprises the gRNA.

Embodiment 58

The method of any one of embodiments 30-57, comprising providing to the cell the DNA endonuclease precomplexed with the gRNA, forming a Ribonucleoprotein (RNP) complex.

Embodiment 59

The method of any one of embodiments 30-58, wherein the gRNA of (a) and the DNA endonuclease or nucleic acid encoding the DNA endonuclease of (b) are provided to the cell more than 4 days after the donor template of (c) is provided to the cell.

Embodiment 60

The method of any one of embodiments 30-59, wherein the gRNA of (a) and the DNA endonuclease or nucleic acid encoding the DNA endonuclease of (b) are provided to the cell at least 14 days after (c) is provided to the cell.

Embodiment 61

The method of embodiment 59 or 60, wherein one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b).

Embodiment 62

The method of embodiment 61, wherein one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b) until a target level of targeted integration of the nucleic acid sequence encoding a POI or functional derivative and/or a target level of expression of the nucleic acid sequence encoding a POI or functional derivative is achieved.

Embodiment 63

The method of any one of embodiments 30-62, wherein the nucleic acid sequence encoding a POI or functional derivative is expressed under the control of the endogenous transferrin promoter.

Embodiment 64

The method of any one of embodiments 30-63, wherein the cell is a hepatocyte.

Embodiment 65

A genetically modified cell in which the genome of the cell is edited by the method of any one of embodiments 30-64.

Embodiment 66

The genetically modified cell of embodiment 65, wherein the nucleic acid sequence encoding a POI or functional derivative is expressed under the control of the endogenous transferrin promoter.

Embodiment 67

The genetically modified cell of embodiment 65 or 66, wherein the nucleic acid sequence encoding a POI or a functional derivative thereof is codon-optimized for expression in the cell.

Embodiment 68

The genetically modified cell of any one of embodiments 65-67, wherein the cell is a hepatocyte.

Embodiment 69

A method of treating a disease or condition associated with a POI in a subject, comprising providing the following to a cell in the subject: (a) a gRNA comprising a spacer sequence that is complementary to a genomic sequence within or near an endogenous transferrin locus in the cell, or nucleic acid encoding the gRNA; (b) a DNA endonuclease or nucleic acid encoding the DNA endonuclease; and (c) a donor template comprising a nucleic acid sequence encoding the POI or a functional derivative thereof.

Embodiment 70

The method of embodiment 69, wherein the gRNA comprises a spacer sequence that is complementary to a sequence within intron 1 of an endogenous transferrin gene in the cell.

Embodiment 71

The method of embodiment 69, wherein the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190.

Embodiment 72

The method of embodiment 71, wherein the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10.

Embodiment 73

The method of embodiment 71, wherein the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51.

Embodiment 74

The method of embodiment 71, wherein the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11.

Embodiment 75

The method of any one of embodiments 71-74, wherein the spacer sequence is 19 nucleotides in length and does not include the nucleotide at position 1 of the sequence from which it is selected.

Embodiment 76

The method of any one of embodiments 69-75, wherein the POI is i) FVIII and the disease or condition is Hemophilia A; ii) Factor IX and the disease or condition is Hemophilia B; iii) alpha-1-antitrypsin and the disease or condition is alpha-1-antitrypsin deficiency; iv) FXIII and the disease or condition is Factor XIII deficiency; v) FVII and the disease or condition is Factor VII deficiency; vi) Factor X and the disease or condition is Factor X deficiency; vii) a C1 esterase inhibitor, and the disease or condition is Hereditary Angioedema (HAE); viii) iduronate sulfatase, and the disease or condition is Hunter syndrome; ix) α-L-iduronidase, and the disease or condition is mucopolysaccharidosis type 1 (MPS 1); or x) Protein C and the disease or condition is Protein C deficiency.

Embodiment 77

The method of embodiment 76, wherein the POI is FVIII and the disease or condition is Hemophilia A.

Embodiment 78

The method of any one of embodiments 69-77, wherein the subject is a patient having or suspected of having the disease or condition.

Embodiment 79

The method of any one of embodiments 69-77, wherein the subject is diagnosed with a risk of the disease or condition.

Embodiment 80

The method of any one of embodiments 69-79, wherein the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; or a functional derivative thereof.

Embodiment 81

The method of any one of embodiments 69-80, wherein the DNA endonuclease is Cas9.

Embodiment 82

The method of any one of embodiments 69-81, wherein the nucleic acid encoding the DNA endonuclease is codon-optimized for expression in the cell.

Embodiment 83

The method of any one of embodiments 69-82, wherein the nucleic acid sequence encoding a POI or a functional derivative thereof is codon-optimized for expression in the cell.

Embodiment 84

The method of any one of embodiments 69-83, wherein the nucleic acid sequence encoding a POI or a functional derivative thereof comprises a reduced content of CpG di-nucleotides than a nucleic acid sequence encoding the wild-type POI.

Embodiment 85

The method of any one of embodiments 69-83, wherein the nucleic acid sequence encoding a POI or a functional derivative thereof comprises about or less than 20 CpG di-nucleotides.

Embodiment 86

The method of embodiment 85, wherein the nucleic acid sequence encoding a POI or a functional derivative thereof comprises about or less than 10 CpG di-nucleotides.

Embodiment 87

The method of embodiment 86, wherein the nucleic acid sequence encoding a POI or a functional derivative thereof comprises about or less than 5 CpG di-nucleotides.

Embodiment 88

The method of embodiment 87, wherein the nucleic acid sequence encoding a POI or a functional derivative thereof does not comprise CpG di-nucleotides.

Embodiment 89

The method of any one of embodiments 69-88, wherein the nucleic acid encoding the DNA endonuclease is a deoxyribonucleic acid (DNA).

Embodiment 90

The method of any one of embodiments 69-83, wherein the nucleic acid encoding the DNA endonuclease is a ribonucleic acid (RNA).

Embodiment 91

The method of embodiment 90, wherein the RNA encoding the DNA endonuclease is an mRNA.

Embodiment 92

The method of any one of embodiments 69-91, wherein one or more of the gRNA of (a), the DNA endonuclease or nucleic acid encoding the DNA endonuclease of (b), and the donor template of (c) are formulated in a liposome or lipid nanoparticle.

Embodiment 93

The method of any one of embodiments 69-92, wherein the donor template is encoded in an Adeno Associated Virus (AAV) vector.

Embodiment 94

The method of any one of embodiments 69-93, wherein the donor template comprises a donor cassette comprising the nucleic acid sequence encoding a POI or a functional derivative thereof, and wherein the donor cassette is flanked on one or both sides by a gRNA target site.

Embodiment 95

The method of embodiment 94, wherein the donor cassette is flanked on both sides by a gRNA target site.

Embodiment 96

The method of embodiment 94 or 95, wherein the gRNA target site is a target site for the gRNA of (a).

Embodiment 97

The method of embodiment 96, wherein the gRNA target site of the donor template is the reverse complement of the gRNA target site in the cell genome for the gRNA of (a).

Embodiment 98

The method of any one of embodiments 69-97, wherein providing the donor template to the cell comprises administering the donor template to the subject.

Embodiment 99

The method of embodiment 98, wherein the administration is via intravenous route.

Embodiment 100

The method of any one of embodiments 69-99, wherein the DNA endonuclease or nucleic acid encoding the DNA endonuclease is formulated in a liposome or lipid nanoparticle.

Embodiment 101

The method of embodiment 100, wherein the liposome or lipid nanoparticle also comprises the gRNA.

Embodiment 102

The method of embodiment 101, wherein providing the gRNA and the DNA endonuclease or nucleic acid encoding the DNA endonuclease to the cell comprises administering the liposome or lipid nanoparticle to the subject.

Embodiment 103

The method of embodiment 102, wherein the administration is via intravenous route.

Embodiment 104

The method of any one of embodiments 69-103, comprising providing to the cell the DNA endonuclease pre-complexed with the gRNA, forming a Ribonucleoprotein (RNP) complex.

Embodiment 105

The method of any one of embodiments 69-104, wherein the gRNA of (a) and the DNA endonuclease or nucleic acid encoding the DNA endonuclease of (b) are provided to the cell more than 4 days after the donor template of (c) is provided to the cell.

Embodiment 106

The method of any one of embodiments 69-105, wherein the gRNA of (a) and the DNA endonuclease or nucleic acid encoding the DNA endonuclease of (b) are provided to the cell at least 14 days after the donor template of (c) is provided to the cell.

Embodiment 107

The method of embodiment 105 or 106, wherein one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b).

Embodiment 108

The method of embodiment 107, wherein one or more additional doses of the gRNA of (a) and the DNA endonuclease or nucleic acid encoding the DNA endonuclease of (b) are provided to the cell following the first dose of the gRNA of (a) and the DNA endonuclease or nucleic acid encoding the DNA endonuclease of (b) until a target level of targeted integration of the nucleic acid sequence encoding a POI or functional derivative and/or a target level of expression of the nucleic acid sequence encoding a POI or functional derivative is achieved.

Embodiment 109

The method of any one of embodiments 105-108, wherein providing the gRNA of (a) and the DNA endonuclease or nucleic acid encoding the DNA endonuclease of (b) to the cell comprises administering to the subject a lipid nanoparticle comprising nucleic acid encoding the DNA endonuclease and the gRNA.

Embodiment 110

The method of any one of embodiments 105-109, wherein providing the donor template of (c) to the cell comprises administering to the subject the donor template encoded in an AAV vector.

Embodiment 111

The method of any one of embodiments 69-110, wherein the nucleic acid sequence encoding a POI or functional derivative is expressed under the control of the endogenous transferrin promoter.

Embodiment 112

The method of any one of embodiments 69-111, wherein the cell is a hepatocyte.

Embodiment 113

The method of any one of embodiments 69-112, wherein the nucleic acid sequence encoding a POI or functional derivative is expressed in the liver of the subject.

Embodiment 114

A method of treating a disease or condition associated with a POI in a subject comprising administering the genetically modified cell of any one of embodiments 65-68 to the subject.

Embodiment 115

The method of embodiment 114, wherein the genetically modified cell is autologous to the subject.

Embodiment 116

The method of embodiment 114 or 115, further comprising obtaining a biological sample from the subject, wherein the biological sample comprises a hepatocyte cell, and wherein the genetically modified cell is prepared from the hepatocyte.

Embodiment 117

A kit comprising one or more elements of the system of any one of embodiments 1-29, and further comprising instructions for use.

Embodiment 118

A gRNA comprising a spacer sequence that is complementary to a genomic sequence within or near an endogenous transferrin locus in a cell.

Embodiment 119

The gRNA of embodiment 118, wherein the gRNA comprises a spacer sequence that is complementary to a sequence within intron 1 of an endogenous transferrin gene in the cell.

Embodiment 120

The gRNA of embodiment 118, wherein the gRNA comprises a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190.

Embodiment 121

The gRNA of embodiment 120, wherein the gRNA comprises a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10.

Embodiment 122

The gRNA of embodiment 120, wherein the gRNA comprises a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51.

Embodiment 123

The gRNA of embodiment 120, wherein the gRNA comprises a spacer sequence from any one of SEQ ID NOs: 5, 6, 9, 8, and 11 or a variant thereof having no more than 3 mismatches compared to any one of SEQ ID NOs: 5, 6, 9, 8, and 11.

Embodiment 124

The gRNA of any one of embodiments 120-123, wherein the spacer sequence is 19 nucleotides in length and does not include the nucleotide at position 1 of the sequence from which it is selected.

Embodiment 125

A donor template comprising a nucleotide sequence encoding a protein-of-interest (POI) or a functional derivative thereof for targeted integration into intron 1 of a transferrin gene, wherein the donor template comprises, from 5' to 3', i) a first gRNA target site; ii) a splice acceptor; iii) the nucleotide sequence encoding a POI or a functional derivative thereof; and iv) a polyadenylation signal.

Embodiment 126

The donor template of embodiment 125, wherein the donor template further comprises a second gRNA target site downstream of the iv) polyadenylation signal.

Embodiment 127

The donor template of embodiment 126, wherein the first gRNA target site and the second gRNA target site are the same.

Embodiment 128

The donor template of any one of embodiments 125-127, wherein the donor template further comprises a sequence encoding the terminal portion of the transferrin signal peptide encoded on exon 2 of the transferrin gene or a variant thereof that retains at least some of the activity of the endogenous sequence between the ii) splice acceptor and iii) nucleotide sequence encoding a POI or a functional derivative thereof.

Embodiment 129

The donor template of any one of embodiments 125-128, wherein the donor template further comprises a polynucleotide spacer between the i) first gRNA target site and the ii) splice acceptor.

Embodiment 130

The donor template of embodiment 129, wherein the polynucleotide spacer is 18 nucleotides in length.

Embodiment 131

The donor template of any one of embodiments 125-130, wherein the donor template is flanked on one side by a first AAV ITR and/or flanked on the other side by a second AAV ITR.

Embodiment 132

The donor template of embodiment 131, wherein the first AAV ITR is an AAV2 ITR and/or the second AAV ITR is an AAV2 ITR.

Embodiment 133

The donor template of any one of embodiments 125-132, wherein the POI is selected from the group consisting of Factor VIII (FVIII), Factor IX, alpha-1-antitrypsin, FXIII, FVII, Factor X, a C1 esterase inhibitor, iduronate sulfatase, α-L-iduronidase, and Protein C.

Embodiment 134

The donor template of embodiment 133, wherein the POI is FVIII.

Embodiment 135

The donor template of embodiment 134, wherein the iii) nucleotide sequence encoding a POI or a functional derivative thereof encodes a mature human B-domain deleted FVIII.

EXAMPLES

Example 1: Identification of Guide RNA that Cleave the Genomic DNA Within Intron 1 of Human Transferrin To identify guide RNAs that efficiently target Cas9 cleavage within intron 1 of the human transferrin gene an in silico algorithm that is a based upon the CCTop algorithm (Stemmer M, Thumberger T, del Sol Keyer M, Wittbrodt J, Mateo J L (2015) CCTop: An Intuitive, Flexible and Reliable CRISPR/Cas9 Target Prediction Tool. PLOS ONE 10 (4): c0124633. doi.org/10.1371/journal.pone.0124633) was used to identify all possible gRNA target sites for spCas9 (NGG PAM) within the 1928 bp intron 1 of transferrin. The top scoring 188 guides from the in silico analysis were synthesized by in vitro transcription and evaluated by transfection into the human liver cell line HuH7 that was engineered to express the spCas9 nuclease. The cleavage efficiency at the on-target site for each guide RNA was measured using the TIDES protocol (Brinkman et al. 2104, *Nucleic Acids Research*, 42:168) in which PCR primers flanking the predicted cleavage site are used to amplify the genomic DNA from treated cells followed by Sanger sequencing of the PCR product. The sequencing chromatogram data is then analyzed using a computer algorithm that calculates the frequency of inserted or deleted bases at the predicted cleavage site. The frequency of inserted or deleted bases (INDELS) is used to calculate the overall cleavage frequency. The results from 2 independent transfections, Experiment 1 and Experiment 2, are shown in Table 2 where the guides are ranked according to the cutting efficiency obtained in Experiment 1. The cutting efficiency of the guides ranged from 0% to greater than 90%. About 20 guides exhibited cutting efficiencies in the range of 75% or greater. Fifty-five of the guide target sequences matched the transferrin gene sequence of non-human primate (*Macaca fascicularis* and *Macaca mulatta*) as shown in Table 2.

TABLE 2

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
|---|---|---|---|---|---|---|
| Transferrin_T12 | AAGGAAGCGGTGCCATCGAG (SEQ ID NO: 1) | | 133746909 | + | 62.6 | SQ |
| Transferrin_T168 | AACTTCTGCCTGCCATTCAT (SEQ ID NO: 2) | | 133747152 | + | 39.4 | SQ |
| Transferrin_T73 | AGCAAAGGGTTTTGATAACC (SEQ ID NO: 3) | Y | 133746758 | − | 39 | SQ |

TABLE 2-continued

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
|---|---|---|---|---|---|---|
| Transferrin_T99 | TTGCCTGGGAGGGTCAAATG (SEQ ID NO: 4) | | 133747013 | + | 28.3 | SQ |
| Transferrin_T26 | GGCTTGGCCAACGACAAGCA (SEQ ID NO: 5) | | 133747914 | + | DR | 93.4 |
| Transferrin_T111 | CCTTGTGGGCCACCACAGCA (SEQ ID NO: 6) | | 133747519 | − | 89.9 | 92.8 |
| Transferrin_T76 | GGGCCCACTCCCTATGCTGA (SEQ ID NO: 7) | | 133748369 | − | 80.9 | 88.9 |
| Transferrin_T128 | TCTGAGTCTGAGCCAATAGA (SEQ ID NO: 8) | | 133748241 | − | 90.2 | 88.6 |
| Transferrin_T188 | CCTGCCTCCAGAGTTCCCAT (SEQ ID NO: 9) | | 133747319 | − | 93.6 | 88.2 |
| Transferrin_T151 | ACAGCTCTCCAGGATGCATG (SEQ ID NO: 10) | | 133747445 | − | 82.2 | 86.7 |
| Transferrin_T67 | GGCCCATGGGAAATCCTAGG (SEQ ID NO: 11) | Y | 133747375 | − | 92.5 | 85.6 |
| Transferrin_T138 | AGGGTGGTCAGTAGGAAACT (SEQ ID NO: 12) | | 133748213 | + | 87.6 | 84.9 |
| Transferrin_T115 | CCTTGCTGTGGTGGCCCACA (SEQ ID NO: 13) | | 133747529 | + | 63.3 | 84.9 |
| Transferrin_T45 | GGTAGCAAGCCAATGTGTTG (SEQ ID NO: 14) | | 133748037 | + | SQ | 84.3 |
| Transferrin_T180 | GCAGATTGTCATCTCCAGCT (SEQ ID NO: 15) | | 133748154 | + | 92.2 | 84.2 |
| Transferrin_T148 | CCACAGCAAGGCTGACTCAC (SEQ ID NO: 16) | | 133747507 | − | 93.4 | 82.5 |
| Transferrin_T100 | ACTGAGGCTTATGTTCCATG (SEQ ID NO: 17) | Y | 133748082 | + | 84.9 | 82.5 |
| Transferrin_T66 | GGGCAAAAGCTCATGTGATA (SEQ ID NO: 18) | Y | 133747581 | + | 76.1 | 82.1 |
| Transferrin_T162 | ATACTGAGGCTTATGTTCCA (SEQ ID NO: 19) | | 133748080 | + | 81 | 81.3 |
| Transferrin_T175 | CCAGTGAGTCAGCCTTGCTG (SEQ ID NO: 20) | | 133747517 | + | 81.7 | 81.1 |
| Transferrin_T172 | GGATTTCCCATGGGCCAAGA (SEQ ID NO: 21) | | 133747392 | + | 80.7 | 79.3 |
| Transferrin_T104 | GGGTCAAATGAGGGTCAGCG (SEQ ID NO: 22) | | 133747023 | + | 16.3 | 78.1 |
| Transferrin_T19 | TCAACTATGGAAAACCAGCG (SEQ ID NO: 23) | | 133748004 | − | 72.6 | 77.4 |
| Transferrin_T77 | CATAAGCCTCAGTATGCACA (SEQ ID NO: 24) | | 133748062 | − | 62 | 77.1 |
| Transferrin_T62 | TATGTTCCATGGGGGGCCAG (SEQ ID NO: 25) | | 133748091 | + | 15.8 | 76.6 |
| Transferrin_T106 | AGGGCCCACTCCCTATGCTG (SEQ ID NO: 26) | | 133748370 | − | 76.5 | 76.4 |
| Transferrin_T163 | GCTGTGGGCCTCCTCTCCAC (SEQ ID NO: 27) | | 133747473 | + | 82 | 75.7 |
| Transferrin_T134 | ACAAATGCCCCATGAATGGC (SEQ ID NO: 28) | | 133747150 | − | 83.6 | 75.6 |

TABLE 2-continued

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
|---|---|---|---|---|---|---|
| Transferrin_T167 | GTGGCTGTCAAGGCCTTTCT (SEQ ID NO: 29) | Y | 133748341 | + | 72.2 | 75.2 |
| Transferrin_T61 | TCCTGTCCATGAACACTACA (SEQ ID NO: 30) | | 133748281 | - | 87.3 | 74.7 |
| Transferrin_T6 | AGACAGCATCGCCCCTAGAA (SEQ ID NO: 31) | | 133748344 | - | 72.6 | 74.5 |
| Transferrin_T44 | CCTTCTTGGCCAGTAGTTGA (SEQ ID NO: 32) | | 133747805 | - | 79.4 | 73.5 |
| Transferrin_T3 | AAGGTCACCCTGCTTGTCGT (SEQ ID NO: 33) | | 133747911 | - | DR | 73.2 |
| Transferrin_T68 | GAGGGAAAATGGGGGTCGCT (SEQ ID NO: 34) | | 133747410 | + | 63.8 | 72.5 |
| Transferrin_T103 | TAGGAGGCAACATAAGCCTG (SEQ ID NO: 35) | | 133747359 | - | 69.4 | 72.2 |
| Transferrin_T81 | AAAACGCCCTGTGCATACTG (SEQ ID NO: 36) | | 133748066 | + | 56.7 | 72.1 |
| Transferrin_T146 | GTGAGTCAGCCTTGCTGTGG (SEQ ID NO: 37) | | 133747520 | + | 65.9 | 72 |
| Transferrin_T63 | GGCTGTCAAGGCCTTTCTAG (SEQ ID NO: 38) | Y | 133748343 | + | 22.8 | 71.8 |
| Transferrin_T87 | AGGTAGCAAGCCAATGTGTT (SEQ ID NO: 39) | | 133748036 | + | 7.7 | 71.6 |
| Transferrin_T184 | GATTGTCATCTCCAGCTGGG (SEQ ID NO: 40) | | 133748157 | + | 80.2 | 70.7 |
| Transferrin_T116 | TCCTGGCCGGCTCCTCACCA (SEQ ID NO: 41) | | 133746972 | + | 82.6 | 69.8 |
| Transferrin_T24 | ATTCTCGCCTATGGGAACTC (SEQ ID NO: 42) | | 133747322 | + | 78.1 | 69.3 |
| Transferrin_T21 | TGGCTTGGCCAACGACAAGC (SEQ ID NO: 43) | | 133747913 | + | DR | 67.7 |
| Transferrin_T41 | TTGGCTTGCTACCTCAACTA (SEQ ID NO: 44) | | 133748017 | - | 50.2 | 67.6 |
| Transferrin_T55 | GAGGTAGCAAGCCAATGTGT (SEQ ID NO: 45) | | 133748035 | + | 77.5 | 67.1 |
| Transferrin_T90 | AGGAGACAAGGCGGATACAG (SEQ ID NO: 46) | | 133748130 | + | 82.7 | 66.7 |
| Transferrin_T101 | GACTCTGGGTCTGCTACTCA (SEQ ID NO: 47) | | 133747859 | - | 72.3 | 66.3 |
| Transferrin_T39 | CCGCTGGTTTTCCATAGTTG (SEQ ID NO: 48) | | 133748016 | + | 66.4 | 65.7 |
| Transferrin_T150 | CCTCAACTATGGAAAACCAG (SEQ ID NO: 49) | | 133748006 | - | 68.1 | 65.2 |
| Transferrin_T156 | TGGATTTTAATAGTTACCCA (SEQ ID NO: 50) | Y-Fasic | 133747624 | + | 73.5 | 64.6 |
| Transferrin_T40 | GGGGATAAAGGCAAGTAACG (SEQ ID NO: 51) | Y | 133747240 | - | 53.1 | 64.5 |
| Transferrin_T8 | CCGGGTTGCAGGGAACGCGC (SEQ ID NO: 52) | Y | 133746528 | - | 9.5 | 64.4 |
| Transferrin_T53 | CGCGCGGGCCAGCGACTCTG (SEQ ID NO: 53) | | 133746513 | - | 11 | 64.3 |

TABLE 2-continued

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
|---|---|---|---|---|---|---|
| Transferrin_T117 | CTGAGGCTTATGTTCCATGG (SEQ ID NO: 54) | Y | 133748083 | + | 70.9 | 63.8 |
| Transferrin_T49 | CGGAGTGCATGCAGGCTGCG (SEQ ID NO: 55) |  | 133746558 | - | 68.1 | 63.7 |
| Transferrin_T83 | ACAGGCTTATGTTGCCTCCT (SEQ ID NO: 56) |  | 133747371 | + | 55 | 63.7 |
| Transferrin_T64 | GGGCATTTGTCACACTGTTG (SEQ ID NO: 57) | Y | 133747173 | + | 12.9 | 63.7 |
| Transferrin_T120 | TGGCCCCTCCTCATGCATCC (SEQ ID NO: 58) |  | 133747447 | + | 51.5 | 62.6 |
| Transferrin_T161 | AAAATGGAGGGATAGTTCAG (SEQ ID NO: 59) |  | 133747691 | + | 82 | 62.5 |
| Transferrin_T183 | TGTGACAAATGCCCCATGAA (SEQ ID NO: 60) |  | 133747154 | - | 64.3 | 62.2 |
| Transferrin_T182 | GTGGTCAGTAGGAAACTGGG (SEQ ID NO: 61) |  | 133748216 | + | 86.6 | 61.1 |
| Transferrin_T119 | TGAGGCTTATGTTCCATGGG (SEQ ID NO: 62) |  | 133748084 | + | 67.6 | 61.1 |
| Transferrin_T18 | GGGATAAAGGCAAGTAACGT (SEQ ID NO: 63) | Y | 133747239 | 1 | 9.1 | 61.1 |
| Transferrin_T107 | AGGGCAAAAGCTCATGTGAT (SEQ ID NO: 64) | Y | 133747580 | + | 57.9 | 60 |
| Transferrin_T20 | GCCATCGAGCGGTCAGAGCA (SEQ ID NO: 65) |  | 133746920 | + | SQ | 59 |
| Transferrin_T80 | CCCTCAACTACTGGCCAAGA (SEQ ID NO: 66) |  | 133747815 | + | 45.6 | 58.4 |
| Transferrin_T133 | CCTCAACTACTGGCCAAGAA (SEQ ID NO: 67) |  | 133747816 | + | 60.3 | 58.3 |
| Transferrin_T84 | GAGGGTGGTCAGTAGGAAAC (SEQ ID NO: 68) |  | 133748212 | + | 70.9 | 57.7 |
| Transferrin_T85 | GTCGCTGGGGTGGCCATCCC (SEQ ID NO: 69) | Y | 133747424 | + | 59.3 | 56.6 |
| Transferrin_T143 | TGGGGAGAGAAAACTAAACG (SEQ ID NO: 70) |  | 133747189 | - | 57.1 | 56.6 |
| Transferrin_T15 | CCTGAGCGCGGAGTGCATGC (SEQ ID NO: 71) |  | 133746566 | - | 17.7 | 56.5 |
| Transferrin_T96 | GCGACCCCATTTTCCCTCT (SEQ ID NO: 72) |  | 133747396 | - | 60.7 | 56.3 |
| Transferrin_T118 | CTCAACTATGGAAAACCAGC (SEQ ID NO: 73) |  | 133748005 | - | 59.7 | 56 |
| Transferrin_T152 | GATCCACAAAGCCTGTGGAG (SEQ ID NO: 74) |  | 133747474 | - | 66.3 | 55.9 |
| Transferrin_T38 | CCCCGCACAGAGCACTTCAC (SEQ ID NO: 75) |  | 133747269 | + | 64.3 | 55.6 |
| Transferrin_T132 | TGCAAGGTAATGCTCCACTG (SEQ ID NO: 76) | Y | 133747295 | + | 84.1 | 55.5 |
| Transferrin_T149 | AGGGGACGTCAGCCTCTGAA (SEQ ID NO: 77) |  | 133746846 | - | 54 | 54.5 |
| Transferrin_T171 | AGGGAAAATGGGGGTCGCTG (SEQ ID NO: 78) |  | 133747411 | + | 64.6 | 54.1 |

TABLE 2-continued

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
|---|---|---|---|---|---|---|
| Transferrin_T30 | TGAGGACACATTCTCGCCTA (SEQ ID NO: 79) | Y | 133747313 | + | SQ | 53.8 |
| Transferrin_T71 | TGCCTCCTAGGATITCCCAT (SEQ ID NO: 80) | Y | 133747383 | + | 44.8 | 53.7 |
| Transferrin_T158 | CTTGGCCCATGGGAAATCCT (SEQ ID NO: 81) | Y | 133747378 | - | 66 | 53.6 |
| Transferrin_T36 | AGGAGTTCGGACTTGACAAG (SEQ ID NO: 82) | | 133746785 | - | 63.6 | 53.6 |
| Transferrin_T27 | ACATAAGCCTCAGTATGCAC (SEQ ID NO: 83) | | 133748063 | - | 30.4 | 52.5 |
| Transferrin_T130 | CAGGACATCTACAGCTCCCA (SEQ ID NO: 84) | | 133746874 | - | 48.5 | 52.3 |
| Transferrin_T124 | GGGCCCCACCTCAGGAGGTC (SEQ ID NO: 85) | Y | 133747107 | - | 27.9 | 52.3 |
| Transferrin_T185 | AACGACAAGCAGGGTGACCT (SEQ ID NO: 86) | | 133747923 | + | DR | 52.2 |
| Transferrin_T79 | GCAGGACATCTACAGCTCCC (SEQ ID NO: 87) | | 133746875 | - | 33.8 | 51.6 |
| Transferrin_T72 | CCTGTGAAGTGCTCTGTGCG (SEQ ID NO: 88) | | 133747259 | - | 62 | 50.4 |
| Transferrin_T179 | TGCCTGGGAGGGTCAAATGA (SEQ ID NO: 89) | | 133747014 | + | 68.4 | 49.8 |
| Transferrin_T170 | TGGCCATGCCTGCACCCCTC (SEQ ID NO: 90) | | 133748183 | + | 68.1 | 49.7 |
| Transferrin_T181 | GCCAGCAGAGGGTGGTCAGT (SEQ ID NO: 91) | | 133748205 | + | 73.1 | 49.2 |
| Transferrin_T42 | CTCCTGTCCATGAACACTAC (SEQ ID NO: 92) | | 133748282 | - | 68.8 | 49 |
| Transferrin_T114 | GGAGTGGGCCCTTCCACCTC (SEQ ID NO: 93) | | 133748391 | + | 51.5 | 48.8 |
| Transferrin_T23 | CAACTATGGAAAACCAGCGG (SEQ ID NO: 94) | | 133748003 | - | 71.2 | 48.7 |
| Transferrin_T144 | TACTGAGGCTTATGTTCCAT (SEQ ID NO: 95) | | 133748081 | + | 60.6 | 48.7 |
| Transferrin_T1 | CCCATGCTCTGACCGCTCGA (SEQ ID NO: 96) | Y | 133746911 | - | 69.7 | 48.5 |
| Transferrin_T186 | CTCCCCGACCTCCTGAGGTG (SEQ ID NO: 97) | Y | 133747114 | + | 54.1 | 48.3 |
| Transferrin_T58 | GGGGAATGGTCAGACCCGGG (SEQ ID NO: 98) | Y | 133746825 | - | 48.8 | 48.3 |
| Transferrin_T113 | CTTGTGCCCTGTAGTGTTCA (SEQ ID NO: 99) | | 133748285 | + | 47.1 | 46.5 |
| Transferrin_T29 | CCCGCGCGTTCCCTGCAACC (SEQ ID NO: 100) | | 133746538 | + | 38.1 | 45.8 |
| Transferrin_T2 | CCATCGAGCGGTCAGAGCAT (SEQ ID NO: 101) | Y | 133746921 | + | 43.3 | 45. |
| Transferrin_T48 | GCCCTGTAGTGTTCATGGAC (SEQ ID NO: 102) | | 133748290 | + | 63.4 | 45.2 |
| Transferrin_T17 | AAATCAGAGCACGTCTAACC (SEQ ID NO: 103) | | 133746750 | + | 51.2 | 45.1 |

TABLE 2-continued

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
|---|---|---|---|---|---|---|
| Transferrin_T153 | GCCTGTGAAGTGCTCTGTGC (SEQ ID NO: 104) | | 133747260 | − | 22.6 | 45 |
| Transferrin_T60 | CTCGCCTATGGGAACTCTGG (SEQ ID NO: 105) | | 133747325 | + | 71.1 | 44.5 |
| Transferrin_T164 | GGCCCCACCTCAGGAGGTCG (SEQ ID NO: 106) | Y | 133747106 | − | 53.7 | 44.4 |
| Transferrin_T47 | CCGCGCGTTCCCTGCAACCC (SEQ ID NO: 107) | | 133746539 | + | 16.3 | 44.3 |
| Transferrin_T110 | TGGCTGTCAAGGCCTTTCTA (SEQ ID NO: 108) | Y | 133748342 | + | 40 | 44.2 |
| Transferrin_T177 | TGGCAGATGCTGAGTACCAG (SEQ ID NO: 109) | | 133747046 | + | 59.4 | 43.8 |
| Transferrin_T13 | GTTAATTTACCCTCAACTAC (SEQ ID NO: 110) | | 133747806 | + | 46.3 | 42.8 |
| Transferrin_T7 | CCTGCATGCACTCCGCGCTC (SEQ ID NO: 111) | | 133746576 | + | 12 | 42.7 |
| Transferrin_T89 | GACCCTCATTTGACCCTCCC (SEQ ID NO: 112) | | 133747006 | − | 45.6 | 41.4 |
| Transferrin_T16 | CCATTAGGGCAACCTTCTAT (SEQ ID NO: 113) | | 133748239 | + | 61.4 | 41.2 |
| Transferrin_T155 | ATGCATGAGGAGGGGCCACC (SEQ ID NO: 114) | | 133747432 | − | 44 | 41 |
| Transferrin_T108 | GTCAGCCACTGCCCCATAGC (SEQ ID NO: 115) | | 133747075 | − | 37.4 | 40.9 |
| Transferrin_T160 | CCTATGGGAACTCTGGAGGC (SEQ ID NO: 116) | | 133747329 | + | 53.5 | 40.2 |
| Transferrin_T139 | ACTTCTGCCTGCCATTCATG (SEQ ID NO: 117) | | 133747153 | + | 60.5 | 40.1 |
| Transferrin_T11 | CGGTGGCCGCCCGGGTTGCA (SEQ ID NO: 118) | Y | 133746538 | − | 6.5 | 39.9 |
| Transferrin_T169 | GGGGACGTCAGCCTCTGAAA (SEQ ID NO: 119) | | 133746845 | − | 38.8 | 39.7 |
| Transferrin_T5 | GAGGACACATTCTCGCCTAT (SEQ ID NO: 120) | Y | 133747314 | + | 32.4 | 39.2 |
| Transferrin_T131 | GCATGGCATTCAAGGCCTCC (SEQ ID NO: 121) | | 133746820 | + | 35.5 | 38.9 |
| Transferrin_T22 | CATCGAGCGGTCAGAGCATG (SEQ ID NO: 122) | Y | 133746922 | + | 46.2 | 38.5 |
| Transferrin_T126 | CTCAACTACTGGCCAAGAAG (SEQ ID NO: 123) | | 133747817 | + | 60.3 | 38.3 |
| Transferrin_T145 | CTGTGGTGGCCCACAAGGAG (SEQ ID NO: 124) | | 133747534 | + | 62.4 | 37.9 |
| Transferrin_T187 | TCTGCTGGCCAGAGGGGTGC (SEQ ID NO: 125) | | 133748181 | − | 55 | 36.3 |
| Transferrin_T112 | AGGCGAGAATGTGTCCTCAG (SEQ ID NO: 126) | Y | 133747299 | − | SQ | 36.2 |
| Transferrin_T14 | GCTCGATGGCACCGCTTCCT (SEQ ID NO: 127) | | 133746897 | − | 50.9 | 36.2 |
| Transferrin_T70 | GTCCTGGCCGGCTCCTCACC (SEQ ID NO: 128) | | 133746971 | + | 48.2 | 36.2 |

TABLE 2-continued

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
| --- | --- | --- | --- | --- | --- | --- |
| Transferrin_T57 | TTTCAGCTACCCCAACACAT (SEQ ID NO: 129) | Y-Mulatta | 133748036 | - | 38.2 | 35.8 |
| Transferrin_T4 | GGGTAGCACCGCAGAGTCGC (SEQ ID NO: 130) | | 133746515 | + | 7.6 | 33.3 |
| Transferrin_T92 | CCCTTCTTGGCCAGTAGTTG (SEQ ID NO: 131) | Y-Fasic | 133747806 | - | 29 | 31.2 |
| Transferrin_T102 | AAAGGGGAATGGTCAGACCC (SEQ ID NO: 132) | | 133746828 | - | 46.1 | 31.1 |
| Transferrin_T159 | AGCTAGCAATTCCTTGAGAG (SEQ ID NO: 133) | Y | 133747224 | + | 49.3 | 30.4 |
| Transferrin_T10 | CATGCACTCCGCGCTCAGGC (SEQ ID NO: 134) | | 133746580 | + | 49.3 | 29.7 |
| Transferrin_T157 | TTGCCTCCTAGGATTTCCCA (SEQ ID NO: 135) | Y | 133747382 | + | 41.2 | 29 |
| Transferrin_T173 | CATCACAGCACTTGCCTGGG (SEQ ID NO: 136) | Y | 133747002 | + | 39.9 | 28.7 |
| Transferrin_T121 | TGATGACCCCCTCCCTGGTG (SEQ ID NO: 137) | | 133746974 | - | 26.1 | 28.7 |
| Transferrin_T137 | AGCAGATTGTCATCTCCAGC (SEQ ID NO: 138) | | 133748153 | + | 34.3 | 28.1 |
| Transferrin_T98 | TCAAATGAGGGTCAGCGAGG (SEQ ID NO: 139) | | 133747026 | + | 47.8 | 27.8 |
| Transferrin_T141 | TGGCCGGCTCCTCACCAGGG (SEQ ID NO: 140) | | 133746975 | + | 36.8 | 26.8 |
| Transferrin_T50 | GATGGCAATTCCTCCCCCGC (SEQ ID NO: 141) | | 133748000 | + | 31.8 | 25.4 |
| Transferrin_T94 | CAAGGAATTGCTAGCTTATG (SEQ ID NO: 142) | Y | 133747207 | - | 25.7 | 24.1 |
| Transferrin_T86 | TAACGTGGGGTCCTCTCTCA (SEQ ID NO: 143) | Y | 133747225 | - | 29.6 | 22.4 |
| Transferrin_T35 | AGTGCTCTGTGCGGGGATAA (SEQ ID NO: 144) | | 133747252 | - | 29 | 21.8 |
| Transferrin_T174 | CATTTTCCCTCTTGGCCCAT (SEQ ID NO: 145) | | 133747388 | - | 13.4 | 21 |
| Transferrin_T97 | TTCACTGCTGCAAGATTTAC (SEQ ID NO: 146) | | 133746710 | - | 3.9 | 20.9 |
| Transferrin_T127 | GTGAGGAGCCGGCCAGGACT (SEQ ID NO: 147) | | 133746957 | - | SQ | 20.2 |
| Transferrin_T56 | ATGTTGCACACATCCTGCTA (SEQ ID NO: 148) | Y | 133747072 | + | 18.2 | 20.1 |
| Transferrin_T65 | TCAAGGAATTGCTAGCTTAT (SEQ ID NO: 149) | Y | 133747208 | - | 35.8 | 19.3 |
| Transferrin_T123 | TCTTGGATCCAAGTCCTGGC (SEQ ID NO: 150) | | 133746959 | + | 41.7 | 19.1 |
| Transferrin_T59 | TTCTGAGTTACACCCCTTCT (SEQ ID NO: 151) | Y | 133747819 | - | 22.2 | 18.9 |
| Transferrin_T129 | TTCAGAGGCTGACGTCCCCT (SEQ ID NO: 152) | | 133746859 | + | 23.8 | 18.5 |
| Transferrin_T9 | CCAATAGAAGGTTGCCCTAA (SEQ ID NO: 153) | | 133748229 | - | 56.9 | 17.6 |

TABLE 2-continued

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
|---|---|---|---|---|---|---|
| Transferrin_T122 | CACTCCCCGACCTCCTGAGG (SEQ ID NO: 154) | Y | 133747112 | + | 30 | 15. |
| Transferrin_T31 | CGCGTTCCCTGCAACCCGGG (SEQ ID NO: 155) | Y | 133746542 | + | 24.3 | 13.6 |
| Transferrin_T28 | GATGGCACCGCTTCCTTGGC (SEQ ID NO: 156) | | 133746893 | − | 15.4 | 13.3 |
| Transferrin_T43 | TATGAAGGGGGCCCCACCTC (SEQ ID NO: 157) | | 133747115 | − | 25.4 | 12.9 |
| Transferrin_T125 | TGCTGTGATGACCCCCTCCC (SEQ ID NO: 158) | | 133746979 | − | 28.5 | 12.7 |
| Transferrin_T165 | CACATCCTGCTATGGGGCAG (SEQ ID NO: 159) | Y | 133747080 | + | 21.1 | 11.9 |
| Transferrin_T82 | AGGCTGCGCGGTGGCCGCCC (SEQ ID NO: 160) | Y | 133746546 | − | 37.6 | 11.3 |
| Transferrin_T109 | TGGGGCATTTGTCACACTGT (SEQ ID NO: 161) | Y | 133747171 | + | 38.6 | 11.2 |
| Transferrin_T52 | CTCAAGGAATTGCTAGCTTA (SEQ ID NO: 162) | Y | 133747209 | − | 27.8 | 10 |
| Transferrin_T34 | CTATGGAAAACCAGCGGGGG (SEQ ID NO: 163) | | 133748000 | − | 11.4 | 8.8 |
| Transferrin_T88 | TGTTGCACACATCCTGCTAT (SEQ ID NO: 164) | Y | 133747073 | + | 17.9 | 8.6 |
| Transferrin_T51 | AGAGGGAAAATGGGGTCGC (SEQ ID NO: 165) | | 133747409 | + | 6 | 7.7 |
| Transferrin_T46 | CTTATGTTCCATGGGGGCC (SEQ ID NO: 166) | | 133748089 | + | 32.4 | 7.2 |
| Transferrin_T178 | TCTGACCATTCCCCTTTCAG (SEQ ID NO: 167) | | 133746844 | + | 3.2 | 5.6 |
| Transferrin_T74 | GGGGCATTTGTCACACTGTT (SEQ ID NO: 168) | Y | 133747172 | + | SQ | 5.1 |
| Transferrin_T176 | CCGCGCTCAGGCTGGAAGCC (SEQ ID NO: 169) | | 133746588 | + | 2.9 | 4.3 |
| Transferrin_T54 | GCGGTGGCCGCCCGGGTTGC (SEQ ID NO: 170) | Y | 133746539 | − | 24.8 | 3.3 |
| Transferrin_T32 | TGCTTGTCGTTGGCCAAGCC (SEQ ID NO: 171) | | 133747901 | − | DR | 2.9 |
| Transferrin_T136 | TCCCTGGTGAGGAGCCGGCC (SEQ ID NO: 172) | | 133746963 | − | 1.3 | 2.8 |
| Transferrin_T78 | TTATGTTCCATGGGGGCCA (SEQ ID NO: 173) | | 133748090 | + | 51.1 | 2.4 |
| Transferrin_T154 | TITTAATAGTTACCCATGGC (SEQ ID NO: 174) | Y-Fasic | 133747628 | + | 2.3 | 2.4 |
| Transferrin_T140 | CCAGGCTTCCAGCCTGAGCG (SEQ ID NO: 175) | Y | 133746578 | − | 5.4 | 1.9 |
| Transferrin_T93 | CAGGCTGCGCGGTGGCCGCC (SEQ ID NO: 176) | Y | 133746547 | − | 9.2 | 1.6 |
| Transferrin_T95 | ATGTGTGCAACATCTGCCAC (SEQ ID NO: 177) | | 133747052 | − | 0.4 | 1.1 |
| Transferrin_T37 | AGTGCATGCAGGCTGCGCGG (SEQ ID NO: 178) | Y | 133746555 | − | 2.7 | 1 |

TABLE 2-continued

Cleavage efficiency of 188 guide RNAs targeting intron 1 of human transferrin

| Guide Name | Guide Sequence(20mer) | NHP match[1] | CutSite[2] | Strand[3] | Expt 1[4] | Expt 2[4] |
|---|---|---|---|---|---|---|
| Transferrin_T91 | ACTCCCCGACCTCCTGAGGT (SEQ ID NO: 179) | Y | 133747113 | + | 14.6 | 0.9 |
| Transferrin_T166 | GAAAGGGGAATGGTCAGACC (SEQ ID NO: 180) | | 133746829 | - | 0.5 | 0.9 |
| Transferrin_T105 | CGCGCTCAGGCTGGAAGCCT (SEQ ID NO: 181) | | 133746589 | + | 23.9 | 0.8 |
| Transferrin_T142 | GTGTCTAGAAGCCCAAGCAA (SEQ ID NO: 182) | | 133746645 | - | 3.8 | 0.8 |
| Transferrin_T25 | CCCGGGTTGCAGGGAACGCG (SEQ ID NO: 183) | | 133746529 | - | 3.2 | 0.8 |
| Transferrin_T135 | TITCAGAGGCTGACGTCCCC (SEQ ID NO: 184) | | 133746858 | + | 0.3 | 0.8 |
| Transferrin_T69 | GAGCTGTAGATGTCCTGCCA (SEQ ID NO: 185) | | 133746890 | + | 0 | 0.8 |
| Transferrin_T147 | GGGTCATCACAGCACTTGCC (SEQ ID NO: 186) | Y | 133746998 | + | 1.2 | 0.7 |
| Transferrin_T33 | GGATAAAGGCAAGTAACGTG (SEQ ID NO: 187) | Y | 133747238 | - | 0.5 | 0.7 |
| Transferrin_T75 | TCTCCCTCAGCATAGGGAGT (SEQ ID NO: 188) | | 133748376 | + | 1.8 | 0.5 |

[1]NHP = Non-human primate; Y = 100% match to gene sequence in both *Macaca fascicularis* and *Macaca mulatta*; Y-Fasic = 100% match to gene sequence of *Macaca fascicularis*; Y-Mulatta = 100% match to gene sequence of *Macaca mulatta*.
[2]Cut site is the location of the cleavage site in the human genome.
[3]+/- indicates if the gRNA is complementary to the + (top) or - (bottom) strand of the genomic DNA.
[4]SQ: poor sequence quality prevented assignment of a value; DR: Difficult region of sequence prevented assignment of a value. Note: gRNA T169, T149, T135, T129 were observed to contain single nucleotide polymorphisms (SNP).

Table 3 lists the cutting efficiencies in HuH7 cells for the 55 guides that matched to non-human primate.

TABLE 3

Subset of guides from Table 2 that have 100% identity to non-human primate gnomic sequence of transferrin intron 1

| Guide Name | Guide Sequence(20mer) | CutSite1 | Strand | Expt 1 | Expt 2 |
|---|---|---|---|---|---|
| Transferrin_T73 | AGCAAAGGGTTTTGATAACC (SEQ ID NO: 3) | 133746758 | - | 39 | SQ |
| Transferrin_T67 | GGCCCATGGGAAATCCTAGG (SEQ ID NO: 11) | 133747375 | - | 92.5 | 85.6 |
| Transferrin_T100 | ACTGAGGCTTATGTTCCATG (SEQ ID NO: 17) | 133748082 | + | 84.9 | 82.5 |
| Transferrin_T66 | GGGCAAAAGCTCATGTGATA (SEQ ID NO: 18) | 133747581 | + | 76.1 | 82.1 |
| Transferrin_T167 | GTGGCTGTCAAGGCCTTTCT (SEQ ID NO: 29) | 133748341 | + | 72.2 | 75.2 |
| Transferrin_T63 | GGCTGTCAAGGCCTTTCTAG (SEQ ID NO: 38) | 133748343 | + | 22.8 | 71.8 |
| Transferrin_T156 | TGGATTTTAATAGTTACCCA (SEQ ID NO: 50) | 133747624 | + | 73.5 | 64.6 |
| Transferrin_T40 | GGGGATAAAGGCAAGTAACG (SEQ ID NO: 51) | 133747240 | - | 53.1 | 64.5 |

TABLE 3-continued

Subset of guides from Table 2 that have 100% identity to non-human primate gnomic sequence of transferrin intron 1

| Guide Name | Guide Sequence(20mer) | CutSite1 | Strand | Expt 1 | Expt 2 |
|---|---|---|---|---|---|
| Transferrin_T8 | CCGGGTTGCAGGGAACGCGC (SEQ ID NO: 52) | 133746528 | - | 9.5 | 64.4 |
| Transferrin_T117 | CTGAGGCTTATGTTCCATGG (SEQ ID NO: 54) | 133748083 | + | 70.9 | 63.8 |
| Transferrin_T64 | GGGCATTTGTCACACTGTTG (SEQ ID NO: 57) | 133747173 | + | 12.9 | 63.7 |
| Transferrin_T18 | GGGATAAAGGCAAGTAACGT (SEQ ID NO: 63) | 133747239 | - | 9.1 | 61.1 |
| Transferrin_T107 | AGGGCAAAAGCTCATGTGAT (SEQ ID NO: 64) | 133747580 | + | 57.9 | 60 |
| Transferrin_T85 | GTCGCTGGGGTGGCCATCCC (SEQ ID NO: 69) | 133747424 | + | 59.3 | 56.6 |
| Transferrin_T132 | TGCAAGGTAATGCTCCACTG (SEQ ID NO: 76) | 133747295 | + | 84.1 | 55.5 |
| Transferrin_T30 | TGAGGACACATTCTCGCCTA (SEQ ID NO: 79) | 133747313 | + | SQ | 53.8 |
| Transferrin_T71 | TGCCTCCTAGGATITCCCAT (SEQ ID NO: 80) | 133747383 | + | 44.8 | 53.7 |
| Transferrin_T158 | CTTGGCCCATGGGAAATCCT (SEQ ID NO: 81) | 133747378 | - | 66 | 53.6 |
| Transferrin_T124 | GGGCCCCACCTCAGGAGGTC (SEQ ID NO: 85) | 133747107 | - | 27.9 | 52.3 |
| Transferrin_T1 | CCCATGCTCTGACCGCTCGA (SEQ ID NO: 96) | 133746911 | - | 69.7 | 48.5 |
| Transferrin_T186 | CTCCCCGACCTCCTGAGGTG (SEQ ID NO: 97) | 133747114 | + | 54.1 | 48.3 |
| Transferrin_T58 | GGGGAATGGTCAGACCCGGG (SEQ ID NO: 98) | 133746825 | - | 48.8 | 48.3 |
| Transferrin_T2 | CCATCGAGCGGTCAGAGCAT (SEQ ID NO: 101) | 133746921 | + | 43.3 | 45.7 |
| Transferrin_T164 | GGCCCCACCTCAGGAGGTCG (SEQ ID NO: 106) | 133747106 | - | 53.7 | 44.4 |
| Transferrin_T110 | TGGCTGTCAAGGCCTTTCTA (SEQ ID NO: 108) | 133748342 | + | 40 | 44.2 |
| Transferrin_T11 | CGGTGGCCGCCCGGGTTGCA (SEQ ID NO: 118) | 133746538 | - | 6.5 | 39.9 |
| Transferrin_T5 | GAGGACACATTCTCGCCTAT (SEQ ID NO: 120) | 133747314 | + | 32.4 | 39.2 |
| Transferrin_T22 | CATCGAGCGGTCAGAGCATG (SEQ ID NO: 122) | 133746922 | + | 46.2 | 38.5 |
| Transferrin_T112 | AGGCGAGAATGTGTCCTCAG (SEQ ID NO: 126) | 133747299 | - | SQ | 36.2 |
| Transferrin_T57 | TTTCAGCTACCCCAACACAT (SEQ ID NO: 129) | 133748036 | - | 38.2 | 35.8 |
| Transferrin_T92 | CCCTTCTTGGCCAGTAGTTG (SEQ ID NO: 131) | 133747806 | - | 29 | 31.2 |
| Transferrin_T159 | AGCTAGCAATTCCTTGAGAG (SEQ ID NO: 133) | 133747224 | + | 49.3 | 30.4 |
| Transferrin_T157 | TTGCCTCCTAGGATTTCCCA (SEQ ID NO: 135) | 133747382 | + | 41.2 | 29 |

TABLE 3-continued

Subset of guides from Table 2 that have 100% identity to non-human primate gnomic sequence of transferrin intron 1

| Guide Name | Guide Sequence(20mer) | CutSite1 | Strand | Expt 1 | Expt 2 |
|---|---|---|---|---|---|
| Transferrin_T173 | CATCACAGCACTTGCCTGGG (SEQ ID NO: 136) | 133747002 | + | 39.9 | 28.7 |
| Transferrin_T94 | CAAGGAATTGCTAGCTTATG (SEQ ID NO: 142) | 133747207 | - | 25.7 | 24.1 |
| Transferrin_T86 | TAACGTGGGGTCCTCTCTCA (SEQ ID NO: 143) | 133747225 | - | 29.6 | 22.4 |
| Transferrin_T56 | ATGTTGCACACATCCTGCTA (SEQ ID NO: 148) | 133747072 | + | 18.2 | 20.1 |
| Transferrin_T65 | TCAAGGAATTGCTAGCTTAT (SEQ ID NO: 149) | 133747208 | - | 35.8 | 19.3 |
| Transferrin_T59 | TTCTGAGTTACACCCCTTCT (SEQ ID NO: 151) | 133747819 | - | 22.2 | 18.9 |
| Transferrin_T122 | CACTCCCCGACCTCCTGAGG (SEQ ID NO: 154) | 133747112 | + | 30 | 15.7 |
| Transferrin_T31 | CGCGTTCCCTGCAACCCGGG (SEQ ID NO: 155) | 133746542 | + | 24.3 | 13.6 |
| Transferrin_T165 | CACATCCTGCTATGGGGCAG (SEQ ID NO: 159) | 133747080 | + | 21.1 | 11.9 |
| Transferrin_T82 | AGGCTGCGCGGTGGCCGCCC (SEQ ID NO: 160) | 133746546 | - | 37.6 | 11.3 |
| Transferrin_T109 | TGGGGCATTTGTCACACTGT (SEQ ID NO: 161) | 133747171 | + | 38.6 | 11.2 |
| Transferrin_T52 | CTCAAGGAATTGCTAGCTTA (SEQ ID NO: 162) | 133747209 | - | 27.8 | 10 |
| Transferrin_T88 | TGTTGCACACATCCTGCTAT (SEQ ID NO: 164) | 133747073 | + | 17.9 | 8.6 |
| Transferrin_T74 | GGGGCATTTGTCACACTGTT (SEQ ID NO: 168) | 133747172 | + | SQ | 5.1 |
| Transferrin_T54 | GCGGTGGCCGCCCGGGTTGC (SEQ ID NO: 170) | 133746539 | - | 24.8 | 3.3 |
| Transferrin_T154 | TTTTAATAGTTACCCATGGC (SEQ ID NO: 174) | 133747628 | + | 2.3 | 2.4 |
| Transferrin_T140 | CCAGGCTTCCAGCCTGAGCG (SEQ ID NO: 175) | 133746578 | - | 5.4 | 1.9 |
| Transferrin_T93 | CAGGCTGCGCGGTGGCCGCC (SEQ ID NO: 176) | 133746547 | - | 9.2 | 1.6 |
| Transferrin_T37 | AGTGCATGCAGGCTGCGCGG (SEQ ID NO: 178) | 133746555 | - | 2.7 | 1 |
| Transferrin_T91 | ACTCCCCGACCTCCTGAGGT (SEQ ID NO: 179) | 133747113 | + | 14.6 | 0.9 |
| Transferrin_T147 | GGGTCATCACAGCACTTGCC (SEQ ID NO: 186) | 133746998 | + | 1.2 | 0.7 |
| Transferrin_T33 | GGATAAAGGCAAGTAACGTG (SEQ ID NO: 187) | 133747238 | - | 0.5 | 0.7 |

SQ: poor sequence quality prevented assignment of a value

Guide RNA molecules that mediate better than average cutting efficiencies tended to be clustered together in certain regions of intron 1 as shown in FIG. 1. This may reflect the accessibility of the genomic DNA to the gRNA/Can9 complex. Much of the genome is condensed into heterochromatin that is bound by regulatory proteins. Thus, it is not a priori obvious or predictable which guide RNA target sequences within a defined region of the genome, such as an intron, will mediate efficient cutting by Cas9 nuclease.

Example 2: Validation of Top Cutting Human Transferrin Guides in HEPG2 Cells

The cutting efficiency of selected guides targeting intron 1 of transferrin was confirmed in an additional human liver derived cell line, HepG2, using chemically synthesized guide RNA. Guide RNA made by in vitro transcription may contain mixtures of full length and partial guide RNA molecules. Chemically synthesized guide RNA molecules are generally composed of >75% full length guide molecules and in addition contain chemically modified bases that make the guide RNA more resistant to cleavage by nucleases in the cell. Ten of the transferrin gRNA that have a 100% match to the cognate transferrin intron 1 sequence in non-human primates *M. fasciicularis* and/or *M. mulatta* were chemically synthesized and tested in HepG2 cells. Preference was given to guides with lower in silico scores (lower guide numbers) that are predicted to have less off-target sites. In addition, guides from different regions of the intron were selected. The results (Table 4) demonstrated that cutting efficiency ranged from 25% to 87%. The most effective guide RNA of the 10 tested as synthetic guides were T100 and T132 which both cut about 86% of the transferrin alleles in HepG2 cells. However, additional gRNA molecules identified from the initial screen in HuH7 cells are alternative options for selection.

TABLE 4

Cutting efficiency of 10 selected human transferrin chemically synthesized guide RNA in HepG2 cells

| Name | Sequence | % INDEL | Average % INDEL | $R^2$ |
|---|---|---|---|---|
| TF_T2 | CCATCGAGCGGTCAGAGCAT (SEQ ID NO: 101) | 38.5<br>30 | 34.3 | 0.99<br>0.99 |
| TF_T22 | CATCGAGCGGTCAGAGCATG (SEQ ID NO: 122) | 30<br>29 | 29.5 | 0.99<br>0.98 |
| TF_T1 | CCCATGCTCTGACCGCTCGA (SEQ ID NO: 96) | 57.5<br>77.7<br>32.2<br>33 | 50.1 | 0.77<br>0.97<br>0.96<br>0.98 |
| TF_T64 | GGGCATTTGTCACACTGTTG (SEQ ID NO: 57) | 37.5<br>77.5<br>15.6<br>20.7 | 37.8 | 0.98<br>0.87<br>0.99<br>0.99 |
| TF_T40 | GGGGATAAAGGCAAGTAACG (SEQ ID NO: 51) | 27.6<br>23.1 | 25.4 | 0.98<br>0.99 |
| TF_T132 | TGCAAGGTAATGCTCCACTG (SEQ ID NO: 76) | 78.3<br>93.9 | 86.1 | 0.96<br>0.98 |
| TF_T71 | TGCCTCCTAGGATTTCCCAT (SEQ ID NO: 80) | 28.7<br>59<br>21.4 | 36.4 | 0.98<br>0.97<br>0.97 |
| TF_T66 | GGGCAAAAGCTCATGTGATA (SEQ ID NO: 18) | 61.4<br>52.7 | 57.1 | 0.91<br>0.90 |
| TF_T100 | ACTGAGGCTTATGTTCCATG (SEQ ID NO: 17) | 79.6<br>94.9 | 87.3 | 0.96<br>0.97 |
| TF_T117 | CTGAGGCTTATGTTCCATGG (SEQ ID NO: 54) | 73.2<br>28<br>66.7 | 56 | 0.97<br>0.97<br>0.98 |

Transfection and INDEL analysis was performed 2 or 3 times for each gRNA and the average value calculated. The $R^2$ value is a measure of the quality of the TIDES analysis with higher values indicative of higher quality data. $R^2$ values above 0.95 are considered to be of high quality, and therefore gRNAs with high cutting efficiencies and $R^2$ values above 0.95 can be useful in protocols for cleavage of transferrin intron 1.

Example 3: Evaluation of Cleavage Efficiency of Transferrin GRNA In Vivo in Mice To deliver Cas9 and the gRNA molecules targeting intron 1 of human transferrin to the hepatocytes of mice, a lipid nanoparticle (LNP) delivery vehicle was used. The gRNA was chemically synthesized, incorporating chemically modified nucleotides to improve resistance to nucleases. The spCas9 mRNA was designed to encode the spCas9 protein fused to a nuclear localization domain (NLS), which is required to transport the spCas9 protein into the nuclear compartment where cleavage of genomic DNA can occur. Additional components of the Cas9 mRNA included a KOZAK sequence at the 5' end prior to the first codon to promote ribosome binding, and a polyA tail at the 3' end composed of a series of A residues. An examplary spCas9 mRNA with NLS sequences used in the studies described herein comprised the nucleotide sequence of SEQ ID NO: 223. The mRNA can be produced by different methods well known in the art. One of such methods used was in vitro transcription using T7 polymerase, in which the sequence of the mRNA was encoded in a plasmid that contained a T7 polymerase promoter. Briefly, upon incubation of the plasmid in an appropriate buffer containing T7 polymerase and ribonucleotides, an RNA molecule was produced that encodes the amino acid sequence of the desired protein. Either natural ribonucleotides or chemically modified ribonucleotides in the reaction mixture were used to generate mRNA molecules with either natural chemical structure or with modified chemical structures that may have advantages in terms of expression, stability or immunogenicity. In addition, the sequence of the spCas9 coding sequence were optimized for codon usage by utilizing the most frequently used codon for each amino acid. Additionally, the coding sequence were optimized to remove cryptic ribosome binding sites and upstream open reading frames to promote the most efficient translation of the mRNA into spCas9 protein.

A primary component of the LNP used in these studies is the lipid C12-200 (Love et al. (2010), PNAS vol. 107, 1864-1869). The C12-200 lipid forms a complex with the highly-charged RNA molecules. The C12-200 is combined with 1,2-Dioleoyl-sn-glycero-3-phosphoethanolamine (DOPE), DMPE-mPEG2000 and cholesterol. When mixed under controlled conditions, for example in a NanoAssemblr device (Precision NanoSystems) with nucleic acids such as gRNA and mRNA, a self-assembly of LNP occurred in which the nucleic acid was encapsulated inside the LNP. To assemble the gRNA and the Cas9 mRNA in the LNP, ethanol and lipid stocks were pipetted into glass vials as appropriate. The ratio of C12-200 to DOPE, DMPE-mPEG2000 and cholesterol was adjusted to optimize the formulation. A typical ratio was composed of C12-200, DOPE, cholesterol and mPEG2000-DMG at a molar ratio of 50:10:38.5:1.5. The gRNA and mRNA were diluted in 100 mM Na Acetate (pH 4.0) in RNase free tubes. The NanoAssemblr cartridge (Precision NanoSystems) was washed with ethanol on the lipid side and with buffer on the RNA side. The working stock of lipids were pulled into a syringe, air removed from the syringe and inserted in the cartridge. The same procedure was used for loading a syringe with the mixture of gRNA and Cas9 mRNA. The Nanoassemblr run was then performed under standard conditions as specified by the manufacturer of the instrument. The LNP suspension was then dialyzed using 10 k molecular weight cutoff (MWCO) dialysis cartridges in 4 liters of PBS for 2 h followed by overnight dialysis. It was then concentrated using centrifugation through 100 k MWCO spin cartridges (Amicon) including washing three times in PBS during centrifugation. Finally, the LNP suspension was sterile filtered through 0.2 µM syringe filter. Endotoxin levels were checked using commercial endotoxin kit (LAL assay) and particle size distribution was determined by dynamic light scattering to determine that the particle sizes lie within the expected range of 45 to 65 nanometers. The concentration of encapsulated RNA was determined using a ribogreen assay (Thermo Fisher). Alternatively, the gRNA and the Cas9 mRNA were formulated separately into LNPs and then mixed together prior to treatment of cells in culture or injection into animals. Using separately formulated gRNA and Cas9 mRNA allowed specific ratios of gRNA and Cas9 mRNA to be tested.

Alternative LNP formulations that utilize alternative cationic lipid molecules were also used for in vivo delivery of the gRNA and Cas9 mRNA. Freshly prepared LNP encapsulating the gRNA molecule and Cas9 mRNA were mixed at a 1:1 mass ratio of the RNA and injected into the tail vein (TV injection) of Hemophilia A mice. Alternatively, the LNP was dosed by retro orbital (RO) injection. The dose of LNP given to mice ranged from 0.5 to 2 mg of RNA per kg of body weight. Three days after injection of the LNP, the mice were sacrificed and a piece of the left and right lobes of the liver and a piece of the spleen were collected and genomic DNA was purified from each. The genomic DNA was then subjected to TIDES analysis to measure the cutting frequency and cleavage profile at the target site in transferrin intron 1.

Example 4a: Targeted Integration of a Therapeutic Gene of Interest at Mouse Transferrin Intron 1

An approach to express a therapeutic protein required to treat a disease is the targeted integration of the cDNA or coding sequence of the gene encoding that protein into the transferrin locus in the liver in vivo. Targeted integration is a process by which a donor DNA template is integrated into the genome of an organism at the site of a double-strand break, such integration occurring either by HDR or NHEJ. This approach uses the introduction into the cells of the organism a sequence-specific DNA nuclease and a donor DNA template encoding the therapeutic gene. To evaluate whether a CRISPR-Cas9 nuclease targeted to transferrin intron 1 is capable of promoting targeted integration of a donor DNA template, the donor DNA template is delivered in an AAV virus, preferably an AAV8 virus in the case of mice, which preferentially transduces the hepatocytes of the liver after intravenous injection. The sequence-specific gRNA targeting intron 1 of transferrin and the Cas9 mRNA are delivered to the hepatocytes of the liver of the same mice by intravenous or RO injection of an LNP formulation encapsulating the gRNA and Cas9 mRNA. In one case the AAV8-donor template is injected into the mice before the LNP since it is known that transduction of the hepatocytes by AAV takes several hours to days and the delivered donor DNA is stably maintained in the nuclei of the hepatocytes for weeks to months. In contrast the gRNA and mRNA delivered by an LNP will persist in the hepatocytes for only 1 to 4 days due to the inherent instability of RNA molecules. In another case the LNP is injected into the mice between 1 day and 28 days, or longer, after the AAV-donor template. The donor DNA template incorporates several design features with the goal of (i) maximizing integration and (ii) maximizing expression of the encoded therapeutic protein.

For integration to occur via HDR homology arms need to be included on either side of the therapeutic gene cassette. These homology arms are composed of the sequences on either side of the gRNA cut site in the mouse transferrin intron 1. While longer homology arms generally promote more efficient HDR the length of the homology arms can be limited by the packaging limit for the AAV virus of about 4.7 to 5.0 Kb. Thus, identifying the optimal length of homology arm requires testing. Integration can also occur via NHEJ mechanisms in which the free ends of a double-stranded DNA donor are joined to the ends of a double-strand break. In this case homology arms are not required. However, incorporating gRNA cut sites either side of the gene cassette can improve the efficiency of integration by generating linear double-strand fragments. By using gRNA cleavage sites in the reverse orientation, integration in the desired forward orientation can be favored. See, for example, Suzuki et al. (2016). Nature vol 540, p 144. Introduction of a mutation in the furin cleavage site of FVIII can generate FVIII that cannot be cleaved by furin during expression of the protein resulting in a one chain FVIII polypeptide that has been shown to have improved stability in the plasma while maintaining full functionality.

Figures 2, 3:
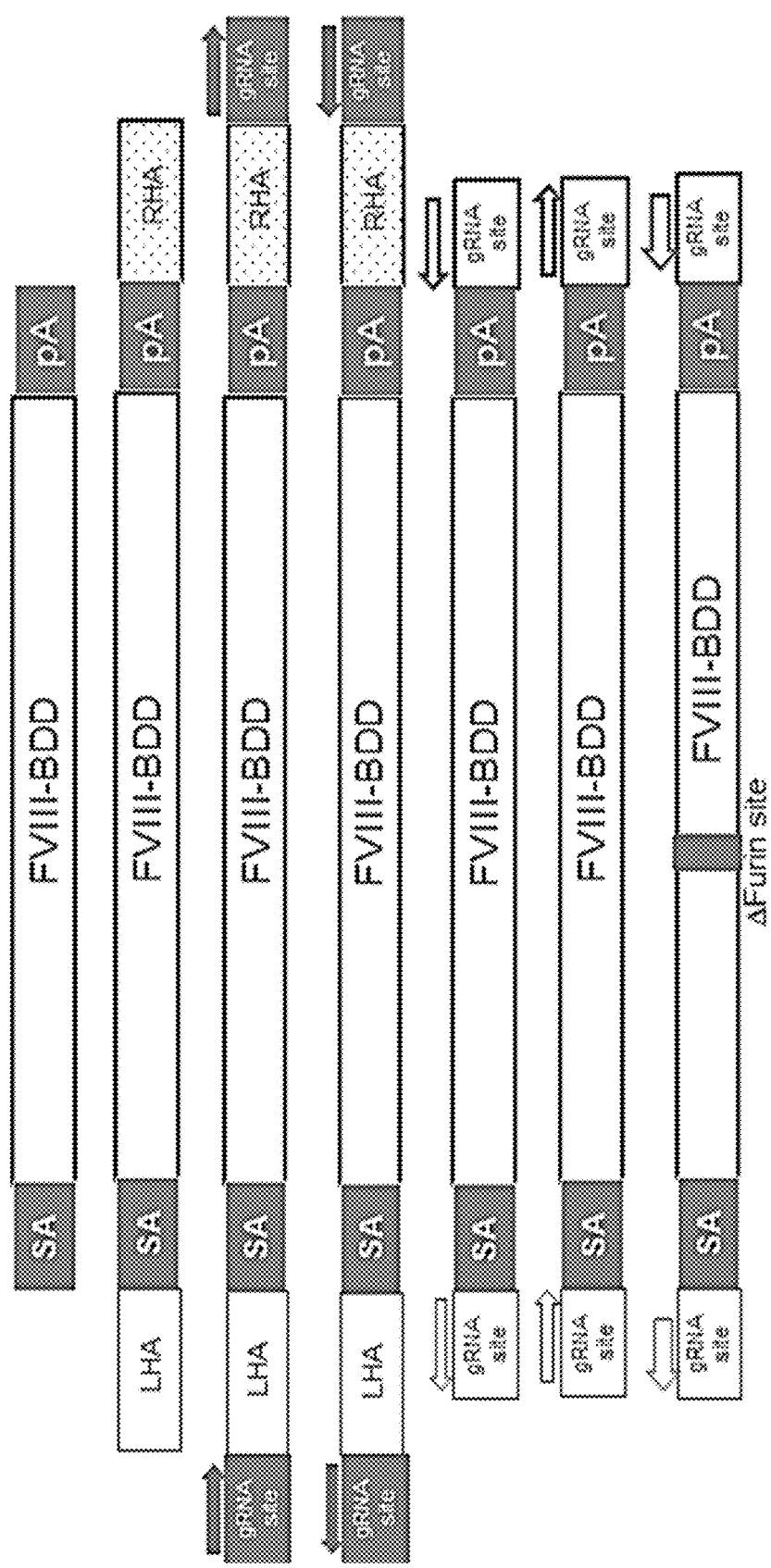
FIG. 2 shows designs of DNA donor templates for targeted integration into transferrin intron 1 used in Example 4A. SA: splice acceptor sequence; LHA: Left homology arm; RHA: right homology arm; pA: poly adenylation signal; gRNA site: target site for gRNA that mediates cutting by gRNA targeted Cas9 nuclease; delta furin: deletion of the furin site in FVIII; FVIII-BDD: coding sequence for human FVIII with B-domain deletion (BDD) in which the B-domain is replaced by the SQ link peptide.
FIG. 3 shows the design of pCB1009, a FVIII donor cassette for targeted integration into mouse transferrin intron 1 used in Example 4B. ITR: inverted terminal repeat of AAV2; gRNA mTF T2: target site for gRNA mTF-T2; 18:18 bp spacer; SA: splice acceptor sequence; TF SP: sequence encoding the last 4 amino acids of the signal peptide of mouse transferrin; s pA: poly adenylation signal; FVIII: coding sequence of mature human B-domain deleted FVIII.

Exemplary DNA donors designed to integrate a FVIII gene at transferrin intron 1 are shown in FIG. 2.

Production of AAV8 or other AAV serotype virus packaged with the FVIII donor DNA is accomplished using well established viral packaging methods. In one such method HEK293 cells are transfected with 3 plasmids, one encoding the AAV packaging proteins, the second encoding Adenovirus helper proteins, and the 3rd containing the FVIII donor DNA sequence flanked by AAV ITR sequences. The transfected cells give rise to AAV particles of the serotype specified by the composition of the AAV capsid proteins encoded on the first plasmid. These AAV particles are collected from the cell supernatant or the supernatant and the lysed cells and purified over a Cesium Chloride (CsCl) gradient or an Iodixanol gradient or by other methods as desired. The purified viral particles are quantified by measuring the number of genome copies of the donor DNA by quantitative PCR (Q-PCR).

In vivo delivery of the gRNA and the Cas9 mRNA are accomplished by various methods. In the first case, the gRNA and Cas9 protein are expressed from an AAV viral vector. In this case the transcription of the gRNA is driven off a U6 promoter and the Cas9 mRNA transcription is driven from either a ubiquitous promoter like EF1-alpha or preferably a liver specific promoter and enhancer such as the transthyretin promoter/enhancer. The size of the spCas9 gene (4.4 Kb) precludes inclusion of the spCas9 and the gRNA cassettes in a single AAV, thereby requiring separate AAV to deliver the gRNA and spCas9. In a second case, an AAV vector that has sequence elements that promote self-inactivation of the viral genome is used. In this case, including cleavage sites for the gRNA in the vector DNA results in cleavage of the vector DNA in vivo. By including cleavage sites in locations that block expression of the Cas9 when cleaved, Cas9 expression is limited to a shorter time period. In the third, alternative approach to deliver the gRNA and Cas9 to cells in vivo, a non-viral delivery method is used. In one example, lipid nanoparticles (LNP) are used as a non-viral delivery method. Several different ionizable cationic lipids are available for use in LNP. These include C12-200 (Love et al. (2010), PNAS vol. 107, 1864-1869), MC3, LN16, MD1 among others. In one type of LNP a GalNac moiety is attached to the outside of the LNP and acts as a ligand for uptake into the liver via the asialyloglycoprotein receptor. Any of these cationic lipids are used to formulate LNP for delivery of gRNA and Cas9 mRNA to the liver.

To evaluate targeted integration and expression of FVIII, Hemophilia A mice that lack mouse FVIII protein due to a genetic defect, are first injected intravenously with an AAV virus, preferentially an AAV8 virus, that encapsulates the FVIII donor DNA template. The dose of AAV ranges from $10^{10}$ vector genomes (VG) to $10^{12}$ VG per mouse, equivalent to $4 \times 10^{11}$ VG/kg to $4 \times 10^{13}$ VG/kg. The viral titer in genome copies per ml is determined by quantitative PCR based methods well known in the art. Between 1 h and 28 days after injection of the AAV-donor the same mice are given i.v. injections of an LNP encapsulating the gRNA and the Cas9 mRNA. The Cas9 mRNA and gRNA are encapsulated into separate LNP and then mixed prior to injection at an RNA mass ratio of 1:1. The dose of LNP given ranges from 0.25 mg to 2 mg of RNA per kg of body weight. The LNP is dosed by tail vein injection or by retroorbital injection. The impact of the time of LNP injection relative to AAV injection upon the efficiency of targeted integration and FVIII protein expression is evaluated by testing times of 1 hr, 24 h, 48 h, 72 h, 96 h, 120 h, 144 h, 168 h, 14 days, and 28 days after AAV dosing.

In another example, the donor DNA template is delivered in vivo using a non-viral delivery system which is an LNP. DNA molecules are encapsulated into similar LNP particles as those described above and delivered to the hepatocytes in the liver after i.v. injection. While escape of the DNA from the endosome to the cytoplasm occurs relatively efficiently, translocation of large charged DNA molecules into the nucleus is not efficient. In one case the way to improve the delivery of DNA to the nucleus is mimicing the AAV genome by incorporation of the AAV ITR into the donor DNA template. In this case, the ITR sequences stabilize the DNA or otherwise improve nuclear translocation. The removal of CG di-nucleotides (CpG sequences) form the donor DNA template sequence also improves nuclear delivery. DNA containing CG di-nucleotides is recognized by the innate immune system and eliminated. Removal of CpG sequences that are present in artificial DNA sequences improves the persistence of DNA delivered by non-viral and viral vectors. The process of codon optimization typically increases the content of CG di-nucleotides because the most frequent codons in many cases have a C residue in the 3rd position which increases the chance of creating a CG when the next codon starts with a G. A combination of LNP delivery of the donor DNA template followed 1 h to 5 days later with an LNP containing the gRNA and Cas9 mRNA is evaluated in Hemophilia A mice To evaluate the effectiveness of in vivo delivery of gRNA/Cas9 and donor DNA templates the injected Hemophilia mice are evaluated for FVIII levels in the blood at different times starting about 7 days after dosing the second component. Blood samples are collected by RO bleeding and the plasma is separated and assayed for FVIII activity using a chromogenic assay (Diapharma). FVIII protein standards are used to calibrate the assay and calculate the units per ml of FVIII activity in the blood.

The expression of FVIII mRNA is also measured in the livers of the mice at the end of the study. Total RNA extracted from the livers of the mice is assayed for the levels of transferrin mRNA and FVIII mRNA using Q-PCR. The ratio of FVIII mRNA to transferrin mRNA when compared to untreated mice is an indication of the % of transferrin transcripts that have been co-opted to produce a hybrid transferrin-FVIII mRNA.

The genomic DNA from the livers of treated mice is evaluated for targeted integration events at the target site of the gRNA, specifically in transferrin intron 1. PCR primer pairs are designed to amplify the junction fragments at either end of the predicted targeted integration. These primers are designed to detect integration in either the forward and reverse orientations. Sequencing of the PCR products confirms if the expected integration event has occurred. To quantify the percentage of transferrin alleles that have undergone targeted integration a standard is synthesized that corresponds to the expected junction fragments. When spiked into genomic DNA from untreated mice at different concentrations and then subjected to the same PCR reaction a standard curve is generated and used to calculate the copy number of alleles with integration events in the samples from treated mice. This can be performed using a real time PCR instrument which is well known in the art. Alternatively, droplet digital PCR can be used to quantify the targeted integration frequency without the need for a standard curve.

Example 4B: Targeted Integration of a Factor VIIII Donor Template into Transferrin Intron 1 Mediated by CRISPR/Cas9 Results in Expression of Therapeutic Levels of Human FVIII One approach to express a therapeutic protein required to treat a disease is the targeted integration of the cDNA or coding sequence of the gene encoding that protein into the transferrin gene locus in the cells of the liver in vivo. Targeted integration is a process by which a donor DNA template is integrated into the genome of an organism at the site of a double-strand break that is introduced at a specific genomic site, such integration occurring either by homology directed repair (HDR) or non-homologous end joining (NHEJ), both of which are natural processes mediated by the cellular machinery of a host cell (Auer, T. O., et al. (2014). *Genome research*, 24 (1), 142-153). In this case the desired target organ in which targeted integration should occur is the liver, and specifically the hepatocytes of the liver. Hepatocytes in vivo are mostly non-dividing and it is known that the dominant cellular mechanism that repairs double-strand breaks in the DNA of non-dividing cells is non-homologous end joining (NHEJ) (Mao, Z. et al. (2008). *Cell cycle*, 7 (18), 2902-2906). In the presence of a linear double-stranded DNA molecule (referred to as the donor) the donor DNA can be inserted at the double-strand break by the NHEJ machinery (Maresca, M., et al. (2013). *Genome research*, 23 (3), 539-546; Auer, T. O., et al. (2014). *Genome research*, 24 (1), 142-153). Alternatively, the ends of the double-strand break in the genome can be re-joined to each other by the same NHEJ machinery, an event that is typically more frequent than insertion of the donor template. Repair by NHEJ is an error prone process and this leads to the introduction of insertions or deletions at the site of the double-strand break. Targeted integration of a donor template delivered as a plasmid at a double-strand break in the genome has been shown to be enhanced by the inclusion of cut sites for the sequence-specific nuclease in the donor plasmid (Cristea, S., et al. (2013). *Biotechnology and bioengineering*, 110 (3), 871-880).

We evaluated whether a CRISPR-Cas9 nuclease targeted to transferrin intron 1 was capable of promoting targeted integration of a donor DNA template encoding a therapeutic gene of interest in mice and if this would result in the expression of the therapeutic gene. This was tested using a human FVIII gene as a candidate therapeutic gene, however, any gene of interest that encodes a protein whose therapeutic effect requires that it be secreted (e.g., secreted from a hepatocyte) could be expressed using this approach. The mouse transferrin coding sequence can be found in GenBank Acc #NM_133977) and the gene is located on chromosome 9 at NP_598738.1 in the NCBI genome sequence for *Mus Musculus*.

To identify guide RNA molecules that can direct cleavage by *Streptococcus pyogenes* Cas9 (spCas9) within intron 1 of the mouse transferrin gene an in silico analysis was performed on intron 1 of mouse transferrin using the publicly available CCTOP algorithm (Stemmer, M., et al. (2015). *PloS One*, 10 (4), e0124633) which identifies all potential guide RNA target sequences with a NGG PAM within the target DNA sequence and performs an in silico off-target prediction against the entire genome of the same organism. The output is a list of guide RNA sequences ranked in order of potential cleavage at sites other than the target site (off-target potential). Guides target sites located at the exon boundaries, or within the predicted poly-pyrimidine tract/branch point of the intron that might impair splicing were excluded. Based on this analysis we selected guide RNA mTF-T1 (target sequence excluding PAM: 5' TAACAAGCAAGACCCGTCGC 3', SEQ ID NO: 189), and mTF-T2 (target sequence excluding PAM: 5' GAGAACGCACCACTTTACGA 3', SEQ ID NO: 190). A list of the 10 top ranked sites in the mouse genome with similarity to the mTF-T1 and mTF-T2 guides are shown in Table 5. In this list the first row is the on-target site in the transferrin gene and the next 9 rows are the next closest matched sequences in the genome which therefore represent potential off-target sites for that gRNA. For both mTF-T1 and mTF-T2, the potential off-target sites with the closest matches to the guide contain 4 mismatches out of the 20 nucleotide guide target sequence. A "core" sequence located at nucleotides +4 to +7 upstream of PAM within the guide RNA has been identified that is particularly sensitive to target-mismatch (Zheng, T., Hou, Y., Zhang, P., Zhang, Z., Xu, Y., Zhang, L., . . . & Peng, W. (2017). Scientific reports, 7, 40638). All but one of the potential off-target sites identified for both guides contain mismatches within this core region.

TABLE 5

In silico analysis of the potential target sites in the mouse genome for gRNA mTF-1 and mTF-2. The first row is the on-target site in the mouse transferrin (Trf)

| Chromosome | strand | MM | Target sequence | alignment | position | gene name |
|---|---|---|---|---|---|---|
| Guide RNA mTF-T1 | | | | | | |
| chr9 | + | 0 | TAACAAGCAAGACCCGTCGC\|\|\|\|\|\|\|\|\|[\|\|\|\|\|\|\|\|\|\|\|PAM (SEQ ID NO: 189) | | Intronic | Trf |
| chr7 | + | 4 | TCACAAACAGGACACGTCGC\|-\|\|\|\|-\|[\|-\|\|\|-\|\|\|\|\|\|PAM (SEQ ID NO: 199) | | Intergenic | Ano1 |
| chr10 | + | 4 | TCACAGGCAAGACACATCGC\|-\|\|\|-\|[\|\|\|\|\|-\|-\|\|\|\|\|PAM (SEQ ID NO: 200) | | Intronic | Gm25613 |
| chr1 | + | 4 | TAACATCCAGGACCCGTTGC\|\|\|\|\|--\|[\|-\|\|\|\|\|\|\|\|-\|\|PAM (SEQ ID NO: 201) | | Intronic | Cnnm4 |
| chr17 | + | 3 | TAAGAAGCAAGACCTGGCGC\|\|\|-\|\|\|\|\|[\|\|\|\|\|-\|-\|\|\|PAM (SEQ ID NO: 202) | | Intergenic | 1700122O11Rik |
| chrX | - | 4 | AAACAAACAAGCCCCGTGGC-\|\|\|\|\|-\|[\|\|\|-\|\|\|\|\|-\|\|\|PAM (SEQ ID NO: 203) | | Intronic | Huwe1 |
| chr3 | + | 4 | CAACAAGAAAGACGCGGCGC-\|\|\|\|\|\|-[\|\|\|\|\|-\|\|-\|\|\|PAM (SEQ ID NO: 204) | | Intronic | Gm30382 |
| chr13 | + | 4 | CAGCAAGCAAGATCCGTCTC-\|-\|\|\|\|\|\|[\|\|\|\|-\|\|\|\|\|-\|PAM (SEQ ID NO: 205) | | Intergenic | Cplx2 |
| chr17 | - | 4 | TATCAATCAAGACACGTCAC\|\|-\|\|\|-\|[\|\|\|\|\|-\|\|\|\|-\|PAM (SEQ ID NO: 206) | | Intronic | Wdr27 |
| chr14 | + | 4 | TCAAAAGCAAGACCCATCAC\|-\|-\|\|\|\|[\|\|\|\|\|\|\|\|-\|-\|PAM (SEQ ID NO: 207) | | Intergenic | NA |
| Guide RNA mTF-T2 | | | | | | |
| chr9 | + | 0 | GAGAACGCACCACTTTACGA\|\|\|\|\|\|\|\|\|[\|\|\|\|\|\|\|\|\|\|\|PAM (SEQ ID NO: 190) | | Intronic | Trf |
| chr5 | - | 4 | ATGCACACACCACTTTACGA--\|-\|\|-\|[\|\|\|\|\|\|\|\|\|\|\|\|PAM (SEQ ID NO: 208) | | Intronic | Klhl5 |
| chr1 | + | 4 | GAGAAGAGAACACTTTACGA\|\|\|\|\|---[\|-\|\|\|\|\|\|\|\|\|\|\|PAM (SEQ ID NO: 209) | | Intronic | Iqca |
| chr7 | + | 4 | GTGAAGCCACCACTTTAAGA\|-\|\|\|--\|[\|\|\|\|\|\|\|\|\|\|-\|\|\|PAM (SEQ ID NO: 210) | | Intergenic | RP23-74K24.10 |

TABLE 5-continued

In silico analysis of the potential target sites in the mouse genome for gRNA mTF-1 and mTF-2. The first row is the on-target site in mouse transferrin (Trf)

| Chromosome | strand | MM | Target sequence alignment | position | gene name |
|---|---|---|---|---|---|
| chr10 | - | 4 | GTGAAAGCCCCACTTTAAGA\|-\|\|\|-\|\|[-\|\|\|\|\|\|\|\|-\|\|]PAM (SEQ ID NO: 211) | Intronic | Pcdh15 |
| chr8 | - | 4 | CAGCACTCACCACTTTACAA-\|\|-\|\|-\|[\|\|\|\|\|\|\|\|\|\|-\|]PAM (SEQ ID NO: 212) | Intronic | Gm2366 |
| chr5 | + | 4 | GAAGACACACCACTTTACCA\|\|--\|\|-\|[\|\|\|\|\|\|\|\|\|\|-\|]PAM (SEQ ID NO: 213) | Intronic | Fam193a |
| chr3 | + | 4 | CTGAACGCACTACTTTACCA--\|\|\|\|\|\|[\|\|-\|\|\|\|\|\|\|-\|]PAM (SEQ ID NO: 214) | Intronic | Hs2st1 |
| chr6 | - | 4 | CAGAACCCACCACCTTACCA-\|\|\|\|\|-\|[\|\|\|\|\|\|-\|\|\|\|-\|]PAM (SEQ ID NO: 215) | IntergenicErc1 | |
| chr9 | | 4 | GACAGCGCACCACTTTCTGA\|\|-\|-\|\|\|[\|\|\|\|\|\|\|\|\|-\|\|\|]PAM (SEQ ID NO: 216) | Intronic | Gm37611 |

The ability of the mTF-T1 and mTF-T2 guides to direct cleavage by spCas9 of the mouse genome at the on-target site in transferrin was tested in the mouse liver cell line Hepa1-6. Hepa1-6 cells were cultured in DMEM+10% FBS in a 5% $CO_2$ incubator. A ribonuclear-protein complex (RNP) composed of the gRNA bound to *Streptococcus pyogenes* Cas9 (spCas9) protein was pre-formed by mixing 2.4 µl of spCas9 (0.8 µg/µl) and 3 µl of the synthetic gRNA (20 µMolar) and 7 µl of PBS (1:5 spCas9: gRNA ratio) and incubated at room temperature for 10 minutes. For nucleofection the entire vial of SF supplement reagent (Lonza) was added to the SF Nucleofector reagent (Lonza) to prepare the complete nucleofection reagent. For each nucleofection $1 \times 10^5$ Hepa1-6 cells were re-suspended in 20 µl of the complete nucleofection reagent, added to the RNP then transferred to a nucleofection cuvette (16 well strip) that was placed in the 4D nucleofection device (Lonza) and nucleofected using program EH-100. After allowing the cells to rest for 10 mins they were transferred to an appropriately sized plate with fresh complete media. Forty-eight hours post nucleofection the cells were collected genomic DNA was extracted and purified using the Qiagen DNeasy kit (cat 69506).

To evaluate the frequency of spCas9/gRNA mediated cutting at the target site in transferrin intron 1, a pair of primers flanking the target site were used in a polymerase chain reaction (PCR) to amplify a short region from the genomic DNA that encompasses the predicted cut site. The resulting PCR product was purified using the Qiagen PCR Purification Kit (Cat no. 28106) and sequenced directly using Sanger sequencing with primers designated as TIDE primers located at either end of the PCR product. Because the mTF-T1 and mTF-T2 guide RNA target sites are at different locations within transferrin intron 1, separate sets of primers were needed for each guide RNA. The sequences of the PCR primers are shown in Table 6. The PCR prrimers were also used as primers to sequence the PCR products.

TABLE 6

PCR and sequencing primers used in TIDE analysis of mouse transferrin T1 and T2 guides on-target cleavage

| gRNA | Primer name | Primer Sequence (5' to 3') | Amplicon size |
|---|---|---|---|
| mTF-T1 | Trf Primer F1 | CAGTATAGTCCAAACAGCATGGTG (SEQ ID NO: 217) | 744 bp |
| | Trf Primer R1 | CACTGAAATCCACACGATGGAGA (SEQ ID NO: 218) | |
| mTF-T2 | Trf Primer F2 | GCCTTTCCTAGAGTTGGTGTCTAG (SEQ ID NO: 219) | 602 bp |
| | Trf Primer R2 | CAAGTGAGTCAAACCAGAGGC (SEQ ID NO: 220) | |

The sequence chromatograms were analyzed by a Tracking of Indels by Decomposition (TIDES) algorithm that determined the frequency of insertions and deletions (IN-DELS) present at the predicted cut site for the gRNA/Cas9 complex (Brinkman, E. K., Chen, T., Amendola, M., & van Steensel, B. (2014). *Nucleic acids research*, 42 (22), e168-e168). The overall frequency of INDEL generation for gRNA mTF-T1 was between and 80 and 89% when tested in 2 independent experiments indicating efficient cutting by the gRNA/spCas9 in the genome of these cells. The overall frequency of INDEL generation for gRNA mTF-T2 was between 85 and 94% when tested in 2 independent experiments indicating efficient cutting by the gRNA/spCas9 in the genome of these cells.

To confirm that mTF-T1 and mTF-T2 could target cleavage by spCas9 to the predicted on-target sites in vivo in the livers of mice, spCas9 mRNA and the guide RNA were delivered to the hepatocytes of mice using a lipid nanoparticle (LNP) delivery vehicle. The sgRNA was chemically synthesized incorporating chemically modified nucleotides to improve resistance to nucleases. The gRNA for mTF1 was composed of the following structure: 5' UsAsAs-CAAGCAAGACCCGUCGCGUUUUAGAgcua-GAAAuagcAAGUUAAAAUAAGGC UAGUCCGUUAU- CaacuuGAAAaaguggcaccgagucggugcusususU-3' (SEQ ID NO: 221), where "A, G, U, C" are native RNA nucleotides, "a, g, u, c" are 2'-O-methyl nucleotides, and "s" represents a phosphorothioate backbone. The gRNA for mTF2 was composed of the following structure: 5' GsAsGsAACGCACCACUUUACGAGUUUUAGAgcua-GAAAuagcAAGUUAAAAUAAGGC UAGUCCGUUAU-CaacuuGAAAaaguggcaccgagucggugcusususU-3' (SEQ ID NO: 222), where "A, G, U, C" are native RNA nucleotides, "a, g, u, c" are 2'-O-methyl nucleotides, and "s" represents a phosphorothioate backbone. The mouse transferrin targeting sequence of the gRNA is underlined, the remainder of the gRNA sequence is the common scaffold sequence. The spCas9 mRNA was designed to encode the spCas9 protein fused to a nuclear localization domain (NLS) which is required to transport the spCas9 protein into the nuclear compartment where cleavage of genomic DNA can occur. Additional components of the Cas9 mRNA are a KOZAK sequence at the 5' end prior to the first codon to promote ribosome binding, and a polyA tail at the 3' end composed of a series of A residues. An example of the sequence of a spCas9 mRNA with NLS sequences is shown in SEQ ID NO: 223. The mRNA can be produced by different methods well known in the art. One of such methods used herein is in vitro transcription using T7 polymerase in which the sequence of the mRNA is encoded in a plasmid that contains a T7 polymerase promoter. Briefly, upon incubation of the plasmid in an appropriate buffer containing T7 polymerase and ribonucleotides an RNA molecule was produced that encodes the amino acid sequence of the desired protein. Either natural ribonucleotides or chemically modified ribonucleotides in the reaction mixture was used to generate mRNA molecules with either natural chemical structure or with modified chemical structures that may have advantages in terms of expression, stability or immunogenicity. In addition, the sequence of the spCas9 coding sequence was optimized for codon usage by utilizing the most frequently used codon for each amino acid. Additionally, the coding sequence was optimized to remove cryptic ribosome binding sites and upstream open reading frames in order to promote the most efficient translation of the mRNA into spCas9 protein.

A primary component of the LNP used in these studies is the lipid C12-200 (Love, K. T., Mahon, K. P., Levins, C. G., Whitehead, K. A., Querbes, W., Dorkin, J. R., . . . & Frank-Kamenetsky, M. (2010). *Proceedings of the National Academy of Sciences*, 107 (5), 1864-1869). The C12-200 lipid forms a complex with the highly-charged RNA molecules. The C12-200 was combined with 1,2-Dioleoyl-sn-glycero-3-phosphoethanolamine (DOPE), DMPE-mPEG2000 and cholesterol. When mixed under controlled conditions for example in a NanoAssemblr device (Precision NanoSystems) with nucleic acids such as gRNA and mRNA, a self-assembly of LNP occurred in which the nucleic acid was encapsulated inside the LNP. To assemble the gRNA and the Cas9 mRNA in the LNP, ethanol and lipid stocks were pipetted into glass vials as appropriate. The ratio of C12-200 to DOPE, DMPE-mPEG2000 and cholesterol was adjusted to optimize the formulation. A typical ratio was composed of C12-200, DOPE, cholesterol and mPEG2000-DMG at a molar ratio of 50:10:38.5:1.5. The gRNA and mRNA were diluted in 100 mM Na citrate in RNase free tubes. The NanoAssemblr® cartridge (Precision NanoSystems) was washed with ethanol on the lipid side and with buffer on the RNA side. The working stock of lipids were pulled into a syringe, air removed from the syringe and inserted in the cartridge. The same procedure was used for loading a syringe with the mixture of gRNA and Cas9 mRNA. The NanoAssemblr run was then performed under standard conditions. The LNP suspension was then dialyzed using a 10 k MWCO dialysis cartridges in 4 liters of PBS for 4 h and then concentrated using centrifugation through 100 k MWCO spin cartridges (Amicon) including washing three times in PBS during centrifugation. Finally, the LNP suspension was sterile filtered through 0.2 µM syringe filter. Endotoxin levels were checked using commercial endotoxin kit (LAL assay) and particle size distribution was determined by dynamic light scattering. The concentration of encapsulated RNA was determined using a RiboGreen® assay (Thermo Fisher). Alternatively, the gRNA and the Cas9 mRNA were formulated separately into LNP and then mixed together prior to treatment of cells in culture or injection into animals. Using separately formulated gRNA and Cas9 mRNA allowed specific ratios of gRNA and Cas9 mRNA to be tested.

Alternative LNP formulations that utilize alternative cationic lipid molecules may also be used for in vivo delivery of the gRNA and Cas9 mRNA. Freshly prepared LNP encapsulating the mTF-T1 gRNA and Cas9 mRNA or mTF-T2 gRNA and Cas9 mRNA were mixed at a 1:1 mass ratio of the RNA and injected into the tail vein (TV injection) of Hemophilia A mice (n=5 per group) at a dose of 2 mg of RNA per kg of body weight. Three days after injection of the LNP the mice were sacrificed and the whole livers were collected, and genomic DNA was purified from each. The genomic DNA was then subjected to TIDES analysis to measure the cutting frequency and cleavage profile at the target site in mouse transferrin intron. The cutting efficiency with gRNA mTF-T1 was between 5% and 10% of the alleles and sequencing of the target site in the genome of the mice identified a single nucleotide polymorphism (SNP) within the target site that likely reduced the efficiency by which the mTF-T1 guide recognized its target. The cutting efficiency with gRNA mTF-T2 was on average 55% (+/−3%) in 5 mice demonstrating robust on-target cutting directed by the mTF-T2 guide RNA.

Hemophilia A is an extensively studied disease (Coppola et al., J Blood Med. 2010; 1:183-195) in which subjects have mutations in the Factor VIII gene that results in low levels of functional Factor VIII protein in their blood. Factor VIII is a critical component of the coagulation cascade and in the absence of sufficient amounts of FVIII the blood fails to form a stable clot at sites of injury resulting in excessive bleeding. Hemophilia A subjects that are not effectively treated experience bleeding into joints resulting in joint destruction. Intracranial bleeding can also occur and can sometimes be fatal.

A human FVIII donor cassette was constructed with structure shown in FIG. 3 and the DNA sequence in SEQ ID NO: 224. The sequence elements in order from 5' to 3' are composed of the inverted terminal repeat of AAV2 (ITR), the target site for gRNA mTF-T2, a 18 bp spacer, a splice acceptor, a sequence (ggctgtgtctggct, SEQ ID NO: 225) that encodes the last 4 amino acids of the signal peptide of mouse transferrin, the coding sequence of mature human B-domain deleted FVIII, a polyadenylation signal (s pA), the target site for gRNA mTF-T2 and the inverted terminal repeat of AAV2 (ITR). The sequence of the target site for gRNA mTF-T2 was the reverse complement of the target sequence in the mouse genome which may favor integration in the forward orientation. The polyadenylation signal is a short 49 bp sequence shown to effectively direct polyadenylation (Levitt et al., 1989; GENES & DEVELOPMENT 3:1019-1025). The FVIII coding sequence encoded a variant FVIII protein containing the amino acid sequence SFSQNATNVSNNSNTSNDSNVSPPVLKRHQR (SEQ ID NO: 226) in place of the B-domain, which includes a heterologous 17 amino acid sequence (represented in bold) replacing most of the B-domain. This sequence contains 6 tripeptides that correspond to potential N-linked glycosylation sites (consensus sequence NXS/T, where X is any amino acid) and have been shown to improve the expression of FVIII (McIntosh, J., Lenting, P. J., Rosales, C., Lee, D., Rabbanian, S., Raj, D., . . . & Waddington, S. (2013). *Blood*, blood-2012).

Packaging of the pCB1009 FVIII donor DNA into AAV8 was accomplished using well established viral packaging methods in HEK293 cells that are transfected with 3 plasmids, one encoding the AAV packaging proteins, the second encoding Adenovirus helper proteins and the 3rd containing the FVIII donor DNA sequence flanked by AAV ITR sequences. The transfected cells give rise to AAV particles of the serotype specified by the composition of the AAV capsid proteins encoded on the first plasmid. These AAV particles were collected from the cell supernatant or the supernatant and the lysed cells and purified over a CsCl gradient. The purified viral particles were quantified by measuring the number of genome copies of the donor DNA by digital droplet PCR (DD-PCR).

To evaluate if this gene editing strategy could be used to treat Hemophilia A we used a mouse model in which the mouse FVIII gene is inactivated. These Hemophilia A mice have no detectable FVIII in their blood which makes it possible to measure exogenously supplied FVIII. A cohort of 5 hemophilia A mice were injected intravenously (i.v.) into the tail vein with AAV8-pCB1009 at a dose of 2e12 vg/kg body weight. The AAV8 virus preferentially transduces the hepatocytes of the liver after intravenous injection. Four weeks later the same mice were injected i.v. with a 1:1 mixture of two LNP, one encapsulating spCas9 mRNA and one encapsulating the guide RNA mTF-T2 at a total RNA dose of 2 mg/kg of body weight. The LNP is taken up primarily by hepatocytes. At 10 days after dosing of the LNP, blood samples were taken by retroorbital bleeds into capillary tubes containing sodium citrate (1:9 ratio of sodium citrate to blood) and the plasma was collected by centrifugation. The plasma samples were then assayed for FVIII activity using a FVIII activity assay (Diapharma, Chromogenix Coatest® SP Factor FVIII, cat #K824086kit). As standards in this assay we used Kogenate™ (Bayer), a recombinant human FVIII used in the treatment of hemophilia patients. The results of the assay are reported as percentage of normal human FVIII activity (normal FVIII activity is defined as 1 IU/ml). FVIII activity averaged 954% (+/−251%) of normal human FVIII levels (FIG. 4), equivalent to 9.54 IU/ml or 9.5-fold greater than average levels in humans without hemophilia. Naïve hemophilia A mice had undetectable FVIII activity (<0.5% of normal). These data demonstrate that targeting integration of a FVIII gene into intron 1 of transferrin can be achieved using spCas9 and an appropriate gRNA specific to transferrin intron 1 delivered in an LNP and an appropriate donor template and that this results in the expression of high levels of active FVIII protein.

Targeted integration of a FVIII donor into transferrin intron 1 was also tested in the immune deficient NSG strain of mice (NOD.Cg-Prkde$^{scid}$/Il2rg$^{tm1Wjl}$/SzJ) obtained from Jackson labs (Bar Harbor, Maine). These mice lack both B cells and T cells and thus are unable to mount an immune response to foreign proteins. Because human FVIII is a foreign protein in mice an immune response against human FVIII may be generated, and this can be avoided if NSG mice are used. A cohort of 5 NSG mice were injected i.v. with AAV8-pCB1009 at a dose of 2e12 vg/kg body weight. The AAV8 virus preferentially transduces the hepatocytes of the liver after intravenous injection. Four weeks later the same mice were injected i.v. with a 1:1 mixture of two LNP, one encapsulating spCas9 mRNA and one encapsulating the guide RNA mTF-T2 at a total RNA dose of 2 mg/kg of body weight. The LNP is taken up primarily by hepatocytes. At 10 days after dosing of the LNP, blood samples were taken by retroorbital bleeds into capillary tubes containing sodium citrate (1:9 ratio of sodium citrate to blood) and the plasma was collected by centrifugation. Because NSG mice express mouse FVIII, the activity from the exogenously delivered human FVIII gene cannot be distinguished using a standard FVIII activity assay. Therefore, the plasma samples were assayed for FVIII activity using a capture-activity assay, also referred to as a capture-CoA test, in which the plasma is first incubated on a plate coated with a mixture of antibodies that specifically bind human FVIII but do not recognize mouse FVIII. This type of assay has been described and used to measure FVIII levels in wild type mice (McIntosh, J., et al. (2013). *Blood* 121:3335-44). Briefly, 96 well plates were coated with 100 μl of a mixture of 1 μg/mL of each anti-FVIII antibody (Antibody 8023 and antibody 8024, from Green Mountain Antibodies, Burlington, VT) diluted in 0.05 M carbonate buffer and incubated overnight at 4° C. Wells were washed three times with 0.05% Tween20 in PBS (5 min each), then blocked with 5% Bovine Serum Albumin (BSA) in 0.05% Tween20 in PBS for 1 hour at 37° C. Following removal of blocking buffer, wells were washed 3× with 0.05% Tween20 in PBS (5 minutes each). The plasma samples were diluted to 1% plasma in Coatest buffer (supplied in the chromogenic assay kit) then 100 μl was added to the appropriate wells. The standards were prepared by mixing purified recombinant human FVIII (Kogenate) into naïve Hemophilia A mouse plasma to achieve FVIII concentrations of 1 to 10 IU/mL and then diluted to 1% plasma in Coatest buffer to prepare the top standard. This top standard was serially diluted in 1% hemophilia A mouse plasma and 100 μl was added to each well of the plate. After incubation for 2 hours at 37° C. the wells were washed three times with 0.05% Tween20 in PBS (5 minutes each). The FVIII bound in each well was then assayed using the commercial FVIII activity assay (Diapharma, Chromogenix Coatest SP Factor FVIII, cat #K824086kit). A direct comparison of this capture Coatest and the Chromogenix Coatest SP Factor FVIII assay on the same Hemophilia A mouse plasma samples demonstrated no differences in the FVIII activity levels that were measured indicating that the capture-CoA test accurately determines human FVIII levels in mice with endogenous mouse FVIII. The results of the assay are reported as percentage of normal human FVIII activity (normal FVIII activity is defined as 1 IU/ml). FVIII activity averaged 476% (+/−124%) of normal, representing 4.76 IU/ml (FIG. 5). These data demonstrate that targeting a FVIII donor template into transferrin intron 1 using CRISPR/cas9 can generate high levels of active FVIII protein in NSG mice.

Example 5: Detection of Targeted Integration into Mouse Transferrin Intron 1

The Hemophilia A mice described in Example 4B (FIG. 4) that expressed human FVIII levels between 500% and 1100% of normal on day 10 after LNP dosing were sacrificed on either day 10 after LNP dosing (1 mouse) or day 26 after LNP dosing (4 mice), and the whole liver of each mouse was homogenized, and genomic DNA was extracted from an aliquot of the homogenate. The purified genomic DNA was evaluated for targeted integration events at the target site of the TF-T2 gRNA in transferrin intron 1. A pair of PCR primers were designed to amplify the junction fragment at the 5' end of the predicted integration of the FVIII donor in the forward orientation. Trf primer F2 (GCCTTTCCTAGAGTTGGTGTCTAG, SEQ ID NO: 219) is complementary to a sequence in the mouse transferrin intron 1 and the F8primerR1 primer (CAATGTTGAACAGGTGGTCAGTG, SEQ ID NO: 227) is complementary to the 5' end of the FVIII coding sequence in the donor template as shown in FIG. 6 where the arrows indicate the direction in which the primers will prime DNA synthesis in a PCR reaction. In the event that the FVIII donor template was to integrate into the on-target site in transferrin intron 1 in the reverse orientation (the orientation in which the 3' end of the FVIII coding sequence is proximal to transferrin exon 1) this can be detected using PCR with primers F8primerR1 (CAATGTTGAACAGGTGGTCAGTG, SEQ ID NO: 227) and Trf Primer R2 (CAAGTGAGTCAAACCAGAGGC, SEQ ID NO: 220) as shown in FIG. 6.

Figure 7A:
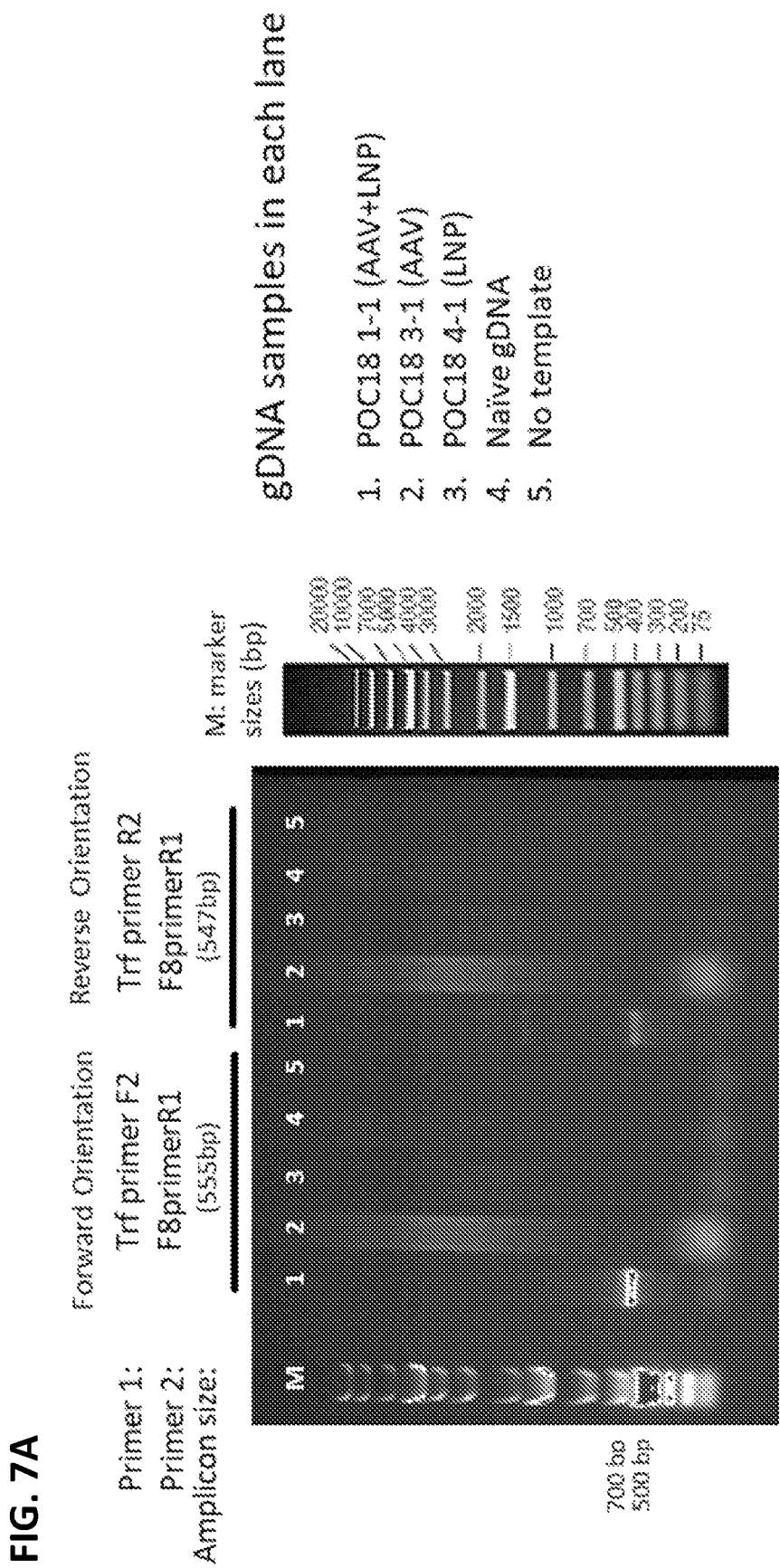
FIGS. 7A and 7B show PCR analysis of the genomic DNA from the liver of mice that received either no treatment (Naïve gDNA), AAV8-pCB1009 alone (AAV), LNP encapsulating spCas9 mRNA and mTF-T2 gRNA alone (LNP), or AAV8-pCB1009 followed by LNP encapsulating spCas9 mRNA and mTF-T2 gRNA (AAV+LNP).

Both sets of primers were used in PCR amplification reactions containing either no genomic DNA (negative control), genomic DNA from a naïve Hemophilia A mouse (negative control), genomic DNA from a mouse that had been injected with AAV8-pCB1009 followed 4 weeks later by an LNP encapsulating the spCas9 mRNA and TF-T2 gRNA (and was expressing human FVIII) and sacrificed 10 days after injection with the LNP, or a mouse that was injected only with AAV8-pCB1009 or a mouse that was injected only with LNP encapsulating the spCas9 mRNA and TF-T2 gRNA. Equal amounts of genomic DNA were used in each PCR reaction. The PCR products were run on a 1% agarose gel, stained with ethidium bromide and visualized under U.V. light. FIG. 7A shows that only the genomic DNA from the mouse that had been injected with AAV8-pCB1009 followed 4 weeks later by an LNP encapsulating the spCas9 mRNA and TF-T2 gRNA (animal number 1-1) gave rise to a band. The size of this band corresponded to the expected size (555 bp) of the PCR product predicted for the integration of the FVIII donor cassette in the forward orientation into intron 1. These data support that the FVIII donor was integrated into the on-target site in transferrin intron 1 in the forward orientation when both the AAV donor and LNP had been injected into the mice. No PCR product was generated when the mouse had been injected only with AAV8-pCB1009 demonstrating that integration did not occur at this site in transferrin in the absence of the gRNA and spCas9 nuclease. While this PCR analysis is not quantitative, the observation of a weaker PCR product using primers F8primerR1 and Trf Primer R2 which detect integration of the FVIII cassette in the reverse orientation, suggests lower levels of integration of the FVIII donor in the reverse orientation compared to the forward orientation.

Figure 7B:
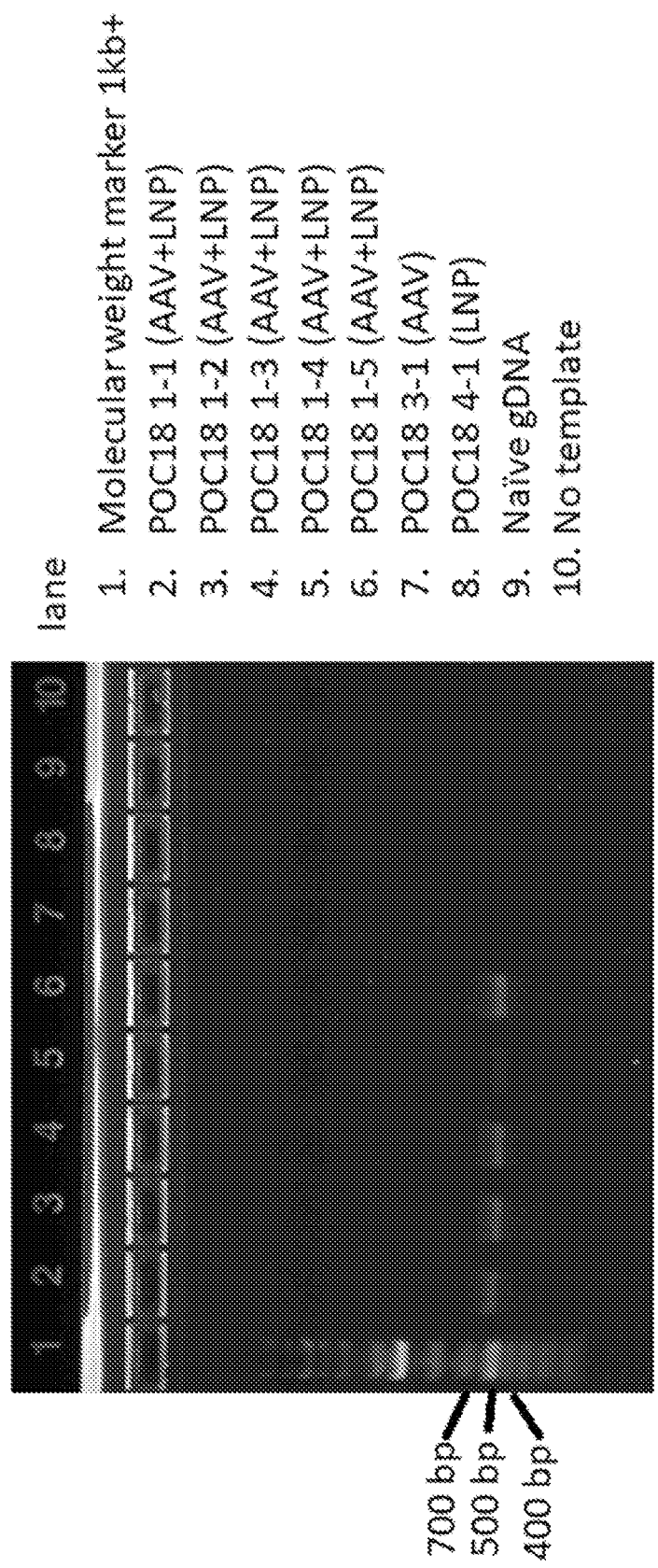

An additional 4 mice that had been injected with AAV8-pCB1009 followed 4 weeks later by an LNP encapsulating the spCas9 mRNA and TF-T2 gRNA and then sacrificed 26 days after the LNP injection (animal numbers 1-2, 1-3, 1-4, 1-5) were analyzed using the in-out PCR assay with primers Trf primer 2 and F8primerR1 which detects the forward orientation of the 5' end of the integration event. The results shown in FIG. 7B demonstrate that the expected 555 bp PCR product was detected in all 4 of these additional mice as well as the previously assayed mouse (animal 1-1) that had been injected with both pAAV8-pCB1009 and the LNP. The controls of genomic DNA from the livers of mice injected with pAAV8-pCB1009 alone or LNP alone or a naïve mouse did not generate a PCR product. These data demonstrate that targeted integration into transferrin intron 1 occurred only when both the FVIII donor template and the spCas9/gRNA were injected and not when either component alone was injected The 555 bp PCR product generated by the amplification of the genomic DNA from mouse 1-1 with Trf primer F2 and F8primerR1 was cloned into a plasmid vector using T/A TOPO cloning and a number of clones were sequenced to determine if the expected junction sequence between transferrin intron 1 and the FVIII donor cassette was present. TABLE. 7 shows the predicted sequence of the expected integration event from joining of the ends of the donor template after cleavage by CRISPR/Cas9 to the ends of the mouse genome in transferrin intron 1 after cleavage by CRISPR/Cas9 without any inserted or deleted nucleotides and the actual sequence reads of 7 clones of the 5' junction (Trf primer F2/F8primerR1 PCR product). A separate PCR reaction between primer Trf primer R2 and a primer at the 3' end of the FVIII cassette was used to amplify the 3' junction of the forward integration orientation, and 3 clones of this 3' junction (Trf primer R2/F8primerF2 PCR product) were also sequenced and these data are presented in Table 8. In Table 7 and Table 8, the bold text in the predicted sequence is the FVIII donor cassette, and the transferrin intronic sequence is in non-bold text. In the sequences from the individual clone's nucleotides in bold are insertions relative to the predicted sequence and "-" indicates a deleted nucleotide relative to the predicted sequence.

TABLE 7

Sequences of the 5' end junction between mouse transferrin intron 1 and the FVIII donor cassette.
5' Trf-F8 Junction Sequence (5'->3')

Predicted GGGATGAGAGGAGGGTGGAACAGAGGAGAGGTGGCCATTAAGACCCTTCGCGAAGGCGGTA
Sequence: CTCCTCAAAGCGTACTAAAGAATTATTCTTTTACATTTC (SEQ ID NO: 228)

Clone #

1    GGGATGAGAGGAGGGTGGAACAGAGGAGAGGTGGCCATTAAGACCCTTCGACGAAGGCGGT
ACTCCTCAAAGCGTACTAAAGAATTATTCTTTTACATTTC (SEQ ID NO: 229)

2    GGGATGAGAGGAGGGTGGAACAGAGGAGAGGTGGCCATTAAGACCCTTCGTCGAAGGCGGT
ACTCCTCAAAGCGTACTAAAGAATTATTCTTTTACATTTC (SEQ ID NO: 230)

TABLE 7-continued

Sequences of the 5' end junction between mouse transferrin intron 1 and the FVIII donor cassette.
5' Trf-F8 Junction Sequence (5'->3')

| | |
|---|---|
| 3 | GGGATGAGAGGAGGGTGGAACAGAGGAGAGGTGGCCATTAAGACCCTTCGCGAAGGCGGTA<br>CTCCTCAAAGCGTACTAAAGAATTATTCTTTTACATTTC (SEQ ID NO: 228) |
| 4 | GGGATGAGAGGAGGGTGGAACAGAGGAGAGGTGGCCATTAAGACCCTTCGTCGAAGGCGGT<br>ACTCCTCAAAGCGTACTAAAGAATTATTCTTTTACATTTC (SEQ ID NO: 230) |
| 5 | GGGATGAGAGGAGGGTGGAACAGAGGAGAGGTGGCCATTAAGACCCTTCGCGAAGGCGGTA<br>CTCCTCAAAGCGTACTAAAGAATTATTCTTTTACATTTC (SEQ ID NO: 228) |
| 6 | GGGATGAGAGGAGGGTGGAACAGAGGAGAGGTGGCCATTAAGACCCTTCGTCGAAGGCGGT<br>ACTCCTCAAAGCGTACTAAAGAATTATTCTTTTACATTTC (SEQ ID NO: 230) |
| 7 | GGGATGAGAGGAGGGTGGAACAGAGGAGAGGTGGCCATTAAGACCCTCG---<br>AAGGCGGTACTCCTCAAAGCGTACTAAAGAATTATTCTTTTACATTTC (SEQ ID NO: 231) |

TABLE 8

Sequences of the 3' end junction between mouse transferrin intron 1 and the FVIII donor cassette
3' F8-Trf Junction Sequence (5'->3')

Predicted Sequence: TTTCATTAGATCTGTGTGTTGGTTTTTTGTGTGGAGAACGCACCACTTTATAAAGTGGTGCGTT CTCTCCCCAGGCACGGGGAGCGGGTCCTTTATGCCT (SEQ ID NO: 232)

Clone #

| | |
|---|---|
| 1 | TTTCATTAGATCTGTGTGTTGGTTTTTTGTGTGGAGAACGCACCACTTTATAAAGTGGTGCGTTC<br>TCTCCCCAGGCACGGGGAGCGGGTCCTTTATGCCT (SEQ ID NO: 232) |
| 2 | TTTCATTAGATCTGTGTGTTGGTTTTTTGTGTGGAGAACGCACCACT----<br>AAAGTGGTGCGTTCTCTCCCCAGGCACGGGGAGCGGGTCCTTTATGCCT (SEQ ID NO: 233) |
| 3 | TTTCATTAGATCTGTGTGTTGGTTTTTTGTGTGGAGAACGCACCACTG---<br>TAAAGTGGTGCGTTCTCTCCCCAGGCACGGGGAGCGGGTCCTTTATGCCT<br>(SEQ ID NO: 234) |

Seven clones of the 5' junction were sequenced, and 3 clones at the 3' junction were sequenced. The sequence data confirm that the FVIII donor cassette was integrated at the on-target site in intron 1 of transferrin. After cleavage by CRISPR/Cas9, nucleotides may be added or deleted during the NHEJ repair process. At the 5' junction there was either no addition or deletion of nucleotides (2 clones), a 1 bp insertion (4 clones) or a 3 bp deletion (1 clone). At the 3' junction 1 clone had no inserted or deleted bases while 1 clone had a 4 bp deletion and 1 clone had a 3 bp deletion and a 1 bp insertion. These data show that the integration of the FVIII donor cassette at the predicted site in transferrin intron 1 occurred precisely without large insertions or deletions of either the genomic DNA or of the donor template DNA.

Example 6: Quantitative Measurement of the Frequency of Targeted Integration of a FVIII Donor into Mouse Transferrin Intron 1

Figure 8:
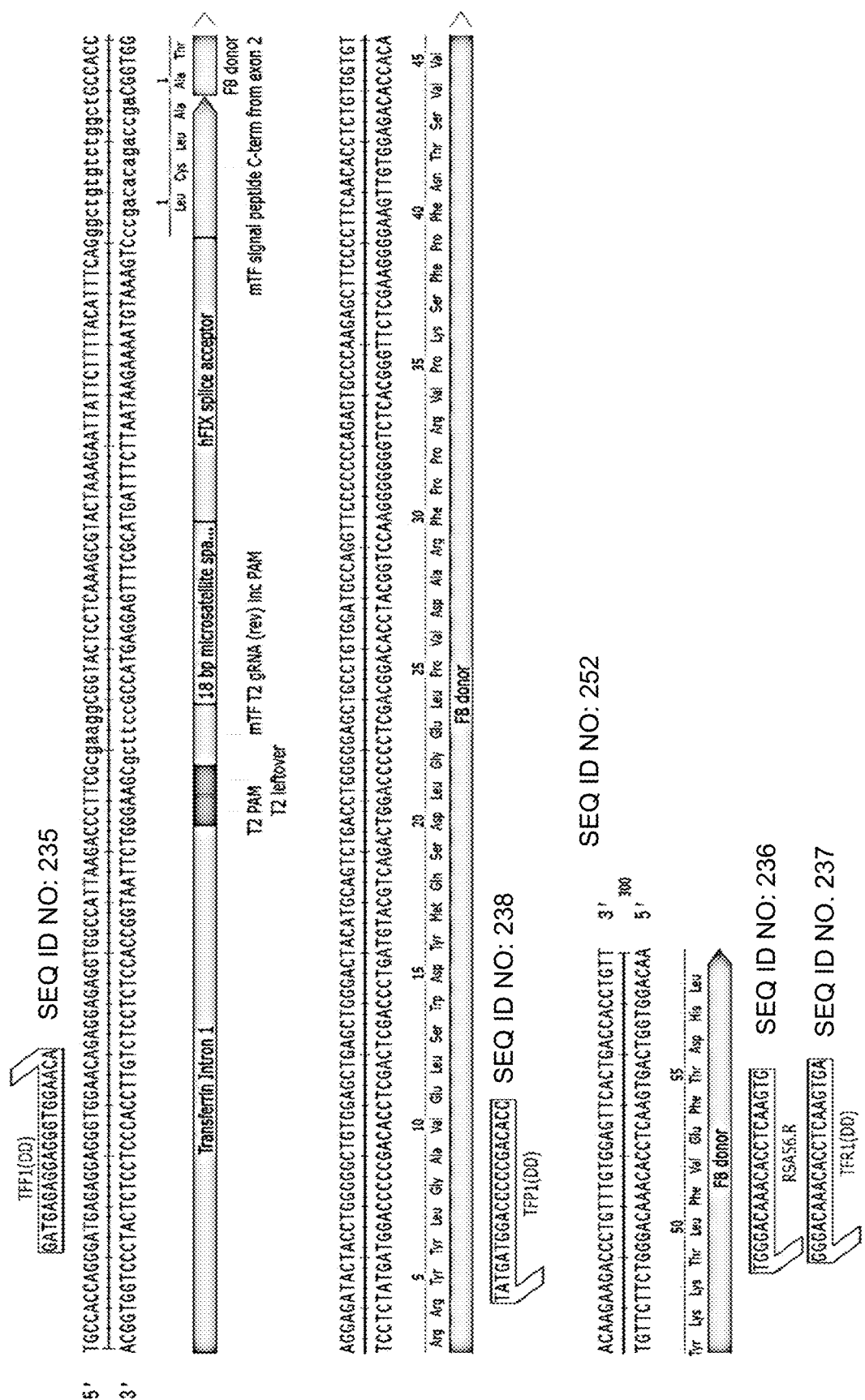
FIG. 8 shows the sequence of the predicted 5' end of the insertion of the FVIII donor cassette pCB1009 into the cut site for mTF-T2 gRNA in mouse transferrin intron 1 and the locations of primers and probes used for DD-PCR.

To quantify the percentage of transferrin alleles in the liver that have undergone targeted integration in the forward orientation (the orientation that is capable of producing FVIII protein wherein the 5' end of the FVIII gene is closest to exon 1 of transferrin), a digital droplet PCR assay was used. Digital droplet (DD)-PCR is a method for accurate quantitation of the absolute copy numbers of a specific nucleic acid sequence in a sample (Quan, P. L., et al. (2018). Sensors, 18 (4), 1271). To quantify integration of the FVIII donor in the forward orientation at the mTF2 gRNA target site, an in-out PCR amplicon was designed in which the binding site for the forward primer, TFF1 (DD), is located on the 5' side of the mTF-T2 gRNA target site in mouse transferrin intron 1, and the binding sites for two reverse primers, RSA56.R and TFR1 (DD), are located within the 5' end of the FVIII donor cassette. The sequences of the primers and probes are shown in Table 9 and their location within the predicted integration event is shown in FIG. 8. The probe was labeled with the florescent dye FAM. Two primer sets were used; primer set 1 consisted of TFF1 (DD) and RSA56.R; primer set 2 consisted of TFF1 (DD) and TFR1 (DD). The same probe was used with both primer sets. A reference PCR amplicon was designed against the mouse Albumin gene to determine the copy number of mouse genomic DNA used in each reaction. The reference assay is run in the same reaction mix as the assay for the transferrin/FVIII junction. The reference probe was labeled with fluorescent dye HEX.

TABLE 9

Sequences of PCR primers and probes used in
DD-PCR quantitation of targeted integration of the
FVIII donor cassette into mouse transferrin intron 1

| Oligonucleotide name | Type | Sequence (5' to 3') | Location |
|---|---|---|---|
| TFF1(DD) | Forward primer | GATGAGAGGAGGGTGGAACA (SEQ ID NO: 235) | Mouse transferrin intron 1 |
| RSA56.R | Reverse primer | GTGAACTCCACAAACAGGGT (SEQ ID NO: 236) | FVIII donor |
| TFR1(DD) | Reverse primer | AGTGAACTCCACAAACAGGG (SEQ ID NO: 237) | FVIII donor |
| TFP1(DD) | Probe | CCACAGCCCCAGGTAGTAT (SEQ ID NO: 238) | FVIII donor |
| AlbF(DD) | Forward primer | TCTAGTAATGGAAGCCTGGT (SEQ ID NO: 239) | Mouse albumin, intron 1 |
| AlbR(DD) | Reverse primer | AGGCCCTATGAGACCGTAAT (SEQ ID NO: 240) | Mouse albumin, intron 1 |
| AlbP(DD) | Probe | TGCATCTGAGAACCCTTAGGTG (SEQ ID NO: 241) | Mouse albumin, intron 1 |

At the time of sacrifice of the mice the whole liver was homogenized using a bead-based homogenizer and total genomic DNA was extracted from an aliquot of the homogenate using the Qiagen DNA/RNA Mini Kit (cat #80204). The concentration of the purified genomic DNA was determined by absorbance at 260 nm and equal amounts from each sample were assayed by DD-PCR using both of the target primer/probe sets and the reference primer/probe. The copy number determined for the target sequence (transferrin/FVIII) was divided by the copy number of the reference sequence (albumin) to calculate the number of copies of the target sequence per copy of albumin. Because the albumin gene is a single copy gene in the mouse genome the number of copies of the target sequence per copy of albumin represents the copy number of the target sequence per haploid genome. This value was multiplied by 100 to determine the integration frequency as a percentage per haploid genome and these results are in Table 10. A mouse that was injected with only the AAV8 virus pAAV8-pCB1009 which encodes the donor template had no detectable targeted integration into the mTF-T2 target site in transferrin intron 1, demonstrating that as expected there is no targeted integration in the absence of the delivery of spCas9 mRNA and mTF-T2 gRNA. Similarly, a mouse that was injected with only the LNP encapsulating spCas9 mRNA and mTF-T2 gRNA had no detectable targeted integration. No targeted integration was measured in naïve mice. These controls also demonstrate that this DD-PCR assay for targeted integration does not give a signal in a mouse that was injected with the pAAV8-pCB1009 virus and therefore contained episomal copies of the FVIII donor template. The five mice that were injected with both the pAAV8-pCB1009 virus and the LNP encapsulating spCas9 mRNA and mTF-T2 gRNA had targeted integration frequencies of between 0.33% and 2.8% per haploid genome. One mouse (animal 1-4) had a lower integration frequency of 0.33% while the other 4 mice had relatively similar targeted integration frequencies between 1.9% and 2.8%.

TABLE 10

Frequency of targeted integration of FVIII donor cassette in the forward
orientation into mouse transferrin intron 1 at the mTF-T2 gRNA cut site measured by
droplet-digital PCR

| Mouse number | Termination date (days after LNP) | Injected with AAV8-pCB1009 | Injected with LNP encapsulating spCas9 and mTF-T2 gRNA | Targeted integration frequency (% per haploid genome) | | |
|---|---|---|---|---|---|---|
| | | | | DD-PCR Primer Set 1 | DD-PCR Primer Set 2 | Average of 2 primer sets |
| POC18 1-1 | Day 10 | + | + | 2.52 | 3.21 | 2.87 |
| POC18 1-2 | Day 26 | + | + | 2.42 | 2.39 | 2.40 |
| POC18 1-3 | Day 26 | + | + | 2.82 | 2.83 | 2.82 |
| POC18 1-4 | Day 26 | + | + | 0.33 | 0.29 | 0.31 |
| POC18 1-5 | Day 26 | + | + | 1.87 | 1.78 | 1.82 |
| POC18 3-1 | Day 28[#] | + | − | 0.00 | 0.03 | 0.02 |
| POC18 4-1 | Day 3[%] | − | + | 0.00 | 0.01 | 0.00 |
| Naïve mouse | — | − | − | 0.00 | 0.00 | 0.00 |

[#]28 days after AAV dosing
[%]3 days after LNP

If it is assumed that the majority of cells in the liver are diploid, then integration may occur in one copy (mono-allelic) or both copies (bi-allelic) of the transferrin gene in a modified cell. If the majority of cells with an integration event contain a mono-allelic integration event, then the frequency of cells with an integration event will be higher than the measured integration frequency per haploid genome.

These results demonstrate that integration into a small percentage (0.33 to 2.8%) of the transferrin alleles in the liver, representing a low percentage of the cells is sufficient to generate levels of FVIII in the blood in the range of 500% to 1100% of normal human FVIII levels (see FIG. 4 for FVIII levels in these mice at day 10 post LNP).

Example 7: Measurement of the Levels of FVIII mRNA in the Livers of Mice After Crispr/Cas9 Mediated Targeted Integration into Transferrin Intron 1

The expression of FVIII mRNA is measured in the livers of the mice at the end of the study. Total RNA extracted from the livers of the mice is assayed for the levels of transferrin mRNA and FVIII mRNA using Q-PCR or DD-PCR. The ratio of FVIII mRNA to transferrin mRNA when compared to untreated mice is an indication of the percentage of transferrin transcripts that have been co-opted to produce a hybrid transferrin-FVIII mRNA.

Example 8: Targeted Integration into Primate Transferrin Intron 1

The same methodologies described in Example 4 for the mouse are applied to primate species using a gRNA that targets transferrin intron 1 of the primate. Either AAV8 or an LNP is used to first deliver the donor DNA template by i.v. injection. The doses used are based upon those found to be successful in the mouse. Subsequently the same primates are given i.v. injections of LNP encapsulating the gRNA and Cas9 mRNA. The same LNP formulation and doses found to be effective in the mice are used. Because a Hemophilia model of primates does not exist, FVIII protein needs to be measured using a human FVIII specific ELISA assay or a human FVIII specific capture-CoA test assay. The same molecular analyses of targeted integration and FVIII mRNA levels described in Example 4 are performed in the primate. The primate is a good pre-clinical model to enable translation to clinical evaluation.

Example 9: Evaluation of on-Target Cleavage by GRNA/Cas9

Primary human hepatocytes are one of the most relevant cell types for evaluation of potency and off-target cleavage of a gRNA/Cas9 that will be delivered to the liver of subjects. These cells are grown in culture as adherent monolayers for a limited duration. Methods have been established for transfection of adherent cells with mRNA, for example MessengerMax™ (Invitrogen). After transfection with a mixture of Cas9 mRNA and gRNA the on-target cleavage efficiency is measured using TIDES analysis.

Figures 9, 10:
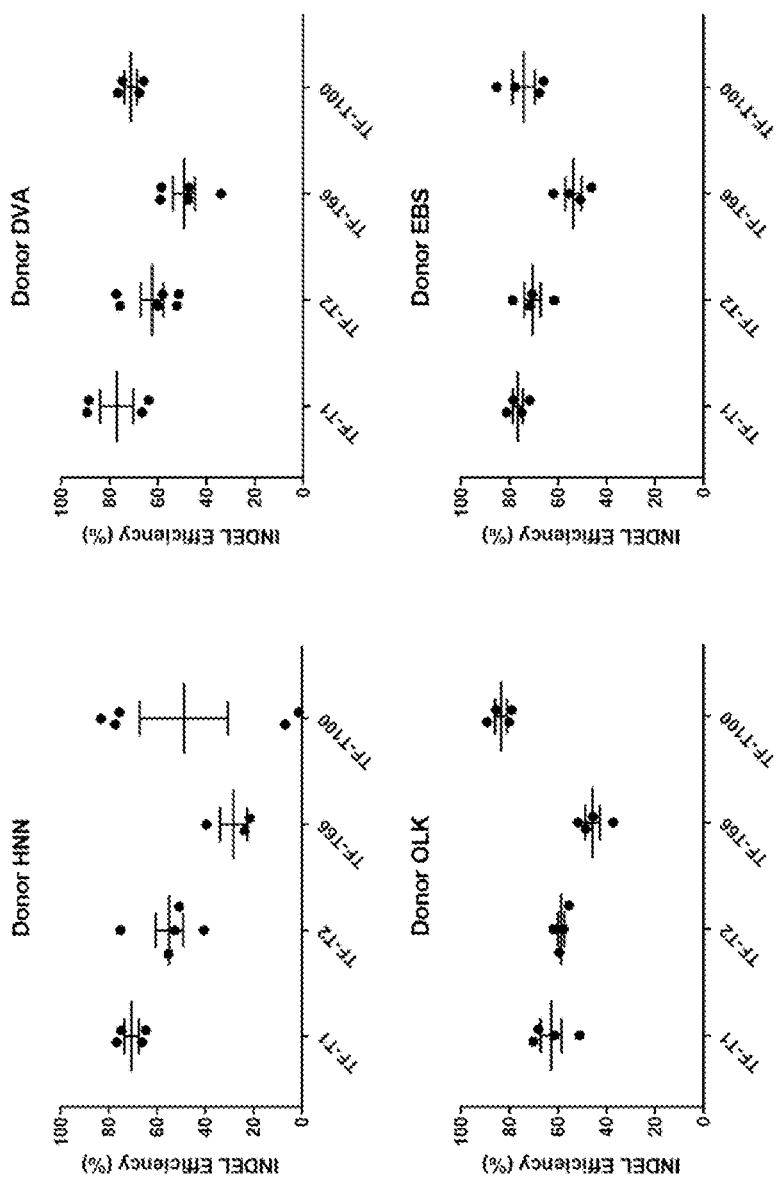
FIG. 9 shows the results for cutting efficiency of guide RNAs TF-T1, TF-T2, TF-T66, and TF-T100 (targeting human transferrin intron 1) in primary human hepatocytes from 4 donors.
FIG. 10 shows the design of pCB099, a FVIII donor cassette for targeted integration into mouse albumin intron 1 used in Example 12. ITR: inverted terminal repeat of AAV2; gRNA T1: target site for gRNA mAlbT1; 18:18 bp spacer; SA: splice acceptor sequence; TG: TG di-nucleotide completing the last amino acid partially encoded on albumin exon 1; spA: poly adenylation signal; mature FVIII: coding sequence of mature human B-domain deleted FVIII.

While human liver cell lines derived from tumors are convenient cell culture models for evaluating different gRNA molecules, these cells contain numerous genetic changes compared to normal hepatocytes. While the gene expression profile of liver cancer cell lines such as HuH7 and HepG2 generally reflect those of normal hepatocytes there are numerous differences. In particular differences in the chromatin organization of cancer cell lines compared to normal tissues is to be expected and may influence the accessibility of Cas9 to genomic targets. In order to select gRNA sequences to be used in humans a normal human cell representative of the cell type being targeted may be used where possible. In the case of the gene editing strategy described herein, the most relevant cells are normal hepatocytes obtained from humans. Such cells are referred to as primary human hepatocytes and are obtained from individuals who have died. Cryopreserved human hepatocytes from 4 different donors (EBS, OLK, HNN, and DVA) were plated on tissue culture plates in optimized media and transfected the same day with a mixture of 0.6 µg Cas9 mRNA and 0.2 µg of synthetic gRNA using the MessengerMax™ reagent (Invitrogen). Genomic DNA was extracted from the cells 48 h later and the on-target cutting frequency was measured by determining the INDEL frequency using TIDES analysis. As shown in FIG. 9, the cutting efficiency of selected guides targeting transferrin intron 1 ranged from 20% to 84% in hepatocytes from the 4 donors. Additional guide RNAs targeting human transferrin intron 1 can be selected from Table 2 for evaluation in primary human hepatocytes. Using this approach optimal cutting guides can be identified that are candidates for gene editing at the transferrin gene in subjects in vivo, or ex vivo in cells isolated from subjects.

Example 10A: Evaluation of Off-Target Cleavage of Selected Guide RNA Molecules

An additional criterion for the selection of a gRNA for therapeutic use is determination of off-target sites and frequencies. While in silico prediction algorithms can be helpful in narrowing down potential gRNA molecules, data generated in a relevant cell will be more meaningful. In the case of the gene editing strategies described herein, relevant cell systems for evaluation of off-target cleavage include HepG2 cells and primary human hepatocytes. HepG2 cells can be nucleofected with the selected gRNA and Cas9 protein in a ribonucleoprotein (RNP) complex, resulting in on-target cleavage. One approach for identifying off-target sites is GUIDE-seq (Tsai et al., Nat Biotechnol 2015 February; 33 (2): 187-197), in which a double-stranded oligonucleotide is co-nucleofected into the HepG2 cells together with the gRNA and Cas9 RNP. Other methods include deep sequencing, whole genome Sequencing, ChIP-seq (Nature Biotechnology 32, 677-683 2014), BLESS (2013 Crosetto et al. doi: 10.1038/nmeth.2408), high-throughput, genome-wide, translocation sequencing (HTGTS) as described in 2015 Frock et al. doi: 10.1038/nbt.3101, Digenome-seq (2015 Kim et al. doi: 10.1038/nmeth.3284), and IDLV (2014 Wang et al. doi: 10.1038/nbt.3127).

At between 2 and 3 days after transfection, genomic DNA is isolated from the cells and on-target cleavage is measured using the same TIDES based methodology described above. The same genomic DNA is subjected to the GuideSeq analysis approach (described in Tsai et al. (2015), Nature Biotech 33, 187-197; doi: 10.1038/nbt.3117). This method relies on the integration of the double-stranded oligonucleotide at sites of double-strand breaks. After random shearing of the genomic DNA and ligation of linkers, PCR using primers complementary to the linker and the integrated oligonucleotide is used to amplify the integration sites which are then sequenced. Once the sites of double-strand breaks at off-target sites are identified, whole genome sequencing can be performed to determine the frequency of off-target cleavage at each of these sites.

Example 10B: Analysis of Off-Target Sites for Transferrin Intron 1 Targeted Guides in Human Cells Off-target sites for human transferrin gRNAs T1, T2, T66 and T100 were evaluated in the human liver cell line HepG2 using the GUIDE-seq method. GUIDE-seq (Tsai et al. 2015) is an empirical method to find off-target cleavage sites. GUIDE-seq relies on the spontaneous capture of an oligonucleotide at the site of a double-strand break in chromosomal DNA. In brief, following transfection of relevant cells with the gRNA/Cas9 RNP complex and double-stranded oligonucleotide genomic DNA is purified from the cells, sonicated and a series of adapter ligations performed to create a library. The oligonucleotide-containing libraries are subjected to high-throughput DNA sequencing and the output processed with the default GUIDE-seq software to identify site of oligonucleotide capture.

In detail, the double-stranded GUIDE-seq oligo was generated by annealing two complementary single-stranded oligonucleotides by heating to 89° C. then cooling slowly to room temperature. RNP were prepared by mixing 240 pmol of guide RNA (Synthego Corp, Menlo Park, CA) and 48 pmol of 20 μMolar Cas9 TrueCut V2 (ThermoFisher Scientific) in a final volume of 4.8 μl. In a separate tube 4 μl of the 10 μMolar GUIDeseq double-stranded oligonucleotide was mixed with 1.2 μl of the RNP mix then added to a Nucleofection cassette (Lonza). To this was added 16.4 μl of Nucleofector SF solution (Lonza) and 3.6 μl of Supplement (Lonza). HepG2 cells grown as adherent cultures were treated with trypsin to release them from the plate then after deactivation of the trypsin, cells were pelleted and resuspended at 12.5 e6 cells/ml in Nucleofector solution and 20 μl (2.5 e5 cells) added to each nucleofection cuvette. Nucleofection was performed with the EH-100 cell program in the 4-D Nucleofector Unit (Lonza). After incubation at room temperature for 10 minutes 80 μl of complete HepG2 media was added and the cell suspension placed in a well of a 48 well plate and incubated at 37° C. in 5% $CO_2$ for 48 hours. The cells were released with trypsin, pelleted by centrifugation (300 g 10 mins), then genomic DNA was extracted using the DNeasy Blood and Tissue Kit (Qiagen). The human transferrin intron 1 region was PCR amplified using pairs of primers shown in Table 11 that flank the location of the on-target site for each of the 4 gRNA.

TABLE 11

PCR and sequencing primers used for TIDE analysis of human transferrin intron 1 guides TF-T1, TF-T2, TF-T66 and TF-T100

| gRNA | PCR/Sequencing Primer | Primer Sequence |
|---|---|---|
| TFT1/ TFT2 | hTF1,2 PCR Primer F | TTCCATTGCCTCTCTACGCC (SEQ ID NO: 242) |
| | hTF1,2 PCR Primer R | CTGAAGCCAGCCATGGGTAA (SEQ ID NO: 243) |
| | hTF1,2 Sequencing Primer F | GCACGTCTAACCAGGTTATC (SEQ ID NO: 244) |
| TFT66 | hTF66 PCR Primer F | CTATGGGAACTCTGGAGGCAG (SEQ ID NO: 245) |
| | hTF66 PCR Primer R | CCCCATGGAACATAAGCCTCA (SEQ ID NO: 246) |
| | hTF66 Sequencing Primer F | CTCATGCATCCTGGAGAGCT (SEQ ID NO: 247) |
| TFT100 | hTF100 PCR Primer F | GGCATCATTCTCTGAGTCT-CACTC (SEQ ID NO: 248) |
| | hTF100 PCR Primer R | GCCCTGATGCAATCAAGGTAGG (SEQ ID NO: 249) |
| | hTF100 Sequencing Primer F | GAGTCTCACTCCCTCTTCTC (SEQ ID NO: 250) |

The PCR reactions were performed using Platinum PCR SuperMix High Fidelity (Invitrogen) using 35 cycles of PCR and an annealing temperature of 55° C. PCR products were first analyzed by agarose gel electrophoresis to confirm that the right sized products had been generated then directly sequenced using primers located at either end of the PCR product. Sequence data was then analyzed using Tsunami, a modified version of the TIDES algorithm (Brinkman et al. (2104); Nucleic Acids Research, 2014, 1). This determines the frequency of insertions and deletions (INDELS) present at the predicted cut site for the gRNA/Cas9 complex. Compared to the protocol described by Tsai et al. we performed GUIDE-seq with 40 pmol (~1.67 μM) capture oligonucleotide to increase the sensitivity of off-target cleavage site identification. The TIDE analysis demonstrated that in HepG2 cells the capture of the GUIDE-seq oligonucleotide at the on-target sites is shown in Table 12. Guide RNTA TF-T1, TF-T2 and TF-T100 exhibited high frequencies of total INDELS (>94%) and ds GUIDE-seq oligo integration rates between 12% and 80%. Guide RNA TF-T66 exhibited low total INDELS and essentially undetectable integration of the ds GuideSeq oligo.

TABLE 12

Frequency of total INDEL and capture of the GUIDE-seq oligonucleotide at the on-target site for human transferrin guides TF-1, TF-2, TF-66 and TF-100 in HepG2 cells

| gRNA | Replicate | Total INDEL efficiency (%) | $R^2$ of TIDE analysis | dsODN[1] capture (%) |
|---|---|---|---|---|
| TF-T1 | 1 | 96 | 0.9776 | 14.3 |
| | 2 | 94.7 | 0.9796 | 13.4 |
| | 3 | 94.3 | 0.9745 | 16.4 |
| TF-T2 | 1 | 97.8 | 0.9873 | 80.3 |
| | 2 | 97.9 | 0.9847 | 80.9 |
| | 3 | 96.7 | 0.9775 | 79.5 |
| TF-T66 | 1 | 2.3 | 0.9899 | 0 |
| | 2 | 1.5 | 0.9918 | 0.1 |
| | 3 | 0.4 | 0.9944 | 0.1 |

TABLE 12-continued

Frequency of total INDEL and capture of the GUIDE-seq oligonucleotide at the on-target site for human transferrin guides TF-1, TF-2, TF-66 and TF-100 in HepG2 cells

| gRNA | Replicate | Total INDEL efficiency (%) | $R^2$ of TIDE analysis | dsODN[1] capture (%) |
|---|---|---|---|---|
| TF-T100 | 1 | 96.6 | 0.9661 | 14.4 |
|  | 2 | 94.2 | 0.9531 | 11.8 |
|  | 3 | 95.2 | 0.9518 | 15.2 |

[1]Double-stranded (ds) oligodeoxynucleotide (ODN)

In order to achieve a sensitivity of approximately 0.01% (able to detect 1 integration event per 10,000 genomes) we defined a minimum of 10,000 unique on-target sequence reads per transfection with a minimum of 50% on-target cleavage. Samples without transfection of RNP of spCas9 and the sgRNA were processed in parallel. Sites (+/−1 kb) found in both RNP-containing and RNP-naive samples are excluded from further analysis.

GUIDE-seq was performed in the human hepatoma cell line HepG2. The Y-adapter was prepared by annealing the Common Adapter to each of the sample barcode adapters (A01-A16) that contain the 8-mer molecular index. Genomic DNA extracted from the HepG2 cells that had been nucleofected with RNP and the GUIDE-seq oligo were quantified using Qubit and all samples normalized to 400 ng in 120 µl volume TE Buffer. The genomic DNA was sheared to an average length of 200 bp according to the standard operating procedure for the Covaris S220 sonicator. To confirm average fragment length, 1 µl of the sample was analyzed on a TapeStation according to manufacturer protocol. Samples of sheared DNA were cleaned up using AMPure XP SPRI beads according to manufacturer protocol and eluted in 17 µl of TE Buffer. The end repair reaction was performed on the genomic DNA by mixing 1.2 µl of dNTP mix (5 mM each dNTP), 3 µl of 10×T4 DNA Ligase Buffer, 2.4 µl of End-Repair Mix, 2.4 µl of 10× Platinum Taq Buffer (Mg2+ free), and 0.6 µl of Taq Polymerase (non-hotstart) and 14 µl sheared DNA sample (from previous step) for a total volume of 22.5 µl per tube and incubated in a thermocycler (12° C. 15 min; 37° C. 15 min; 72° C. 15 min; 4° C. hold). To this was added 1 µl annealed Y Adapter (10 µM), 2 µl T4 DNA Ligase and the mixture incubated in a thermocycler (16° C., 30 min; 22° C., 30 min; 4° C. hold). The sample was cleaned up using a AMPure XP SPRI beads according to manufacturer protocol and eluted in 23 µl of TE Buffer. 1 µl of sample was run on a TapeStation according to manufacturer protocol to confirm ligation of adapters to fragments. To prepare the GUIDE-seq library a reaction was prepared containing 14 µl nuclease-free $H_2O$, 3.6 µl 10× Platinum Taq Buffer, 0.7 µl dNTP mix (10 mM each), 1.4 µl $MgCl_2$, 50 mM, 0.36 µl Platinum Taq Polymerase, 1.2 µl sense or antisense gene specific primer (10 µM), 1.8 µl TMAC (0.5M), 0.6 µl P5_1 (10 µM) and 10 µl of the sample from the previous step. This mix was incubated in a thermocycler (95° C. 5 min, then 15 cycles of 95° C. 30 sec, 70° C. (minus 1° C. per cycle) for 2 min, 72° C. 30 sec, followed by 10 cycles of 95° C. 30 sec, 55° C. 1 min, 72° C. 30 sec, followed by 72° C. 5 mins). The PCR reaction was cleaned up using AMPure XP SPRI beads according to manufacturer protocol and eluted in 15 µl of TE Buffer. 1 µl of sample was checked on TapeStation according to manufacturer protocol to track sample progress. A second PCR was performed by mixing 6.5 µl Nuclease-free $H_2O$, 3.6 µl 10× Platinum Taq Buffer (Mg2+ free), 0.7 µl dNTP mix (10 mM each), 1.4 µl $MgCl_2$ (50 mM), 0.4 µl Platinum Taq Polymerase, 1.2 µl of Gene Specific Primer (GSP) 2 (sense; + or antisense; −), 1.8 µl TMAC (0.5M), 0.6 µl P5_2 (10 µM) and 15 µl of the PCR product from the previous step. If GSP1+ was used in the first PCR then GSP2+ was used in PCR2. If GSP1-primer was used in the first PCR reaction then GSP2-primer was used in this second PCR reaction. After adding 1.5 µl of P7 (10 µM) the reaction was incubated in a thermocycler with the following program: 95° C. 5 min, then 15 cycles of 95° C. 30 sec, 70° C. (minus 1° C. per cycle) for 2 min, 72° C. 30 sec, followed by 10 cycles of 95° C. 30 sec, 55° C. 1 min, 72° C. 30 sec, followed by 72° C. 5 mins. The PCR reaction was cleaned up using AMPure XP SPRI beads according to manufacturer protocol and eluted in 30 µl of TE Buffer and 1 µl analyzed on a TapeStation according to manufacturer protocol to confirm amplification. The library of PCR products was quantitated using Kapa Biosystems kit for Illumina Library Quantification, according to manufacturer supplied protocol and subjected to next generation sequencing on the Illumina system to determine the sites at which the oligonucleotide had become integrated.

GUIDE-seq was completed on 3 independent cell sample replicates (from 3 independent transfections) for each guide and the results are listed in Tables 13 and 14. The GUIDE-seq approach resulted in a 12% to 81% frequency of oligo capture in HepG2 cells for guides TF-T1, TF-T2 and TF-T100, indicating that this method is appropriate in this cell type. On-target read counts met the pre-set criteria of a minimum of 10,000 on-target reads for guides TF-T1, TF-T2 and TF-TF-T100, but not for TF-T66. The low on-target INDEL frequency for TF-T66 determined by TIDES (Table 12) is consistent with the low frequency of on-target reads.

In order for an off-target site to be considered as genuine it needs to be reproducible in cell sample replicates. We considered off-target sites that were detected in at least 2 of the 3 cell sample replicates to be genuine events.

GUIDE-seq with the TF-T1 guide RNA detected a total of 18 off-target sites but only 2 of these sites were present in at least 2 of the replicate cell transfection samples (Table 11). For TF-T2 a total of 28 off-target sites were detected but only 7 were present in at least 2 replicates. For TF-T66 a total of 26 off-target sites were detected but only 2 were present in at least 2 replicates. For TF-T100 a total of 28 off-target sites were detected but only 11 were present in at least 2 replicates.

TABLE 13

Summary of GUIDE-seq results for guide RNA TF-T1, TF-T2, TF-T66 and TF-100 in HepG2 cells

| Guide Name | GUIDE-seq Off-Targets | Present in Multiple Replicates | On-Target Read Count |
|---|---|---|---|
| TF_T1 | 18 | 2 | 27802 |
| TF_T2 | 28 | 7 | 66427 |
| TF_T66 | 26 | 2 | 275 |
| TF_T100 | 28 | 11 | 48732 |

TABLE 14

Details of the off-target sites detected by GUIDE-seq in at least 2 of the cell sample replicates. Position refers to the genomic location in Genome Reference Consortium Human Build 38 (hg38). The NCBI Genome Data Viewer was used to annotate each position (www.ncbi.nlm.nih.gov/genome/gdv)

| Chromosome | Position | Location Type | Mis-matches | Gene Name | Off-Target/On-Target |
|---|---|---|---|---|---|
| gRNA TF-T1 | | | | | |
| chr15 | 67164903 | Exonic | 7 | SMAD3 (SMAD Family member 3) | 0.09% |
| chr3 | 93470521 | Intergenic | 11 | | 0.05% |
| gRNA TF-T2 | | | | | |
| chr15 | 58491290 | Intronic | 2 | LIPC (lipase C hepatic type) | 52.42% |
| chr6 | 79778437 | Intergenic | NA | | 2.72% |
| chr5 | 12807248 | ncRNA | 3 | Uncharacterized non-coding RNA | 0.23% |
| chr4 | 139515920 | Intronic | 4 | SETD7 (SET domain containing lysine methyltransferase 7) | 0.19% |
| chr13 | 70697776 | Intergenic | 7 | | 0.19% |
| chr18 | 41928748 | Intergenic | 4 | | 0.11% |
| gRNA TF-T66 | | | | | |
| chr22 | 35383115 | Exonic | 5 | HMOX1 (heme oxygenase 1) | 54.90% |
| chr10 | 12043063 | Exonic | 2 | UPF2 (regulator of nonsense mediated RNA decay) | 4.36% |
| gRNA TF-T100 | | | | | |
| chr6 | 1199653 | Intergenic | 2 | | 26.80% |
| chr3 | 40781749 | ncRNA | 2 | uncharacterized | 11.84% |
| chr9 | 133062007 | Exonic | 4 | CEL (carboxyl ester lipase) | 6.04% |
| chr9 | 133082565 | Exonic | 3 | CELP (carboxyl ester lipase pseudogene) | 3.00% |
| chr1 | 7950696 | Intergenic | 3 | | 1.31% |
| chr | 26162603 | Intronic | 1 | NFEL2L3 (nuclear factor, erythroid 2 like 3) | 1.20% |
| chr3 | 133746922 | Intronic | NA | TF (transferrin) | 0.40% |
| chr4 | 13257702 | complement RNA | 2 | | 0.15% |
| chrX | 71096529 | Exonic | 3 | FOX04 (forkhead box04) | 0.13% |
| chr4 | 58165963 | Intergenic | 4 | | 0.03% |

Comparison of the read counts for each off-target site compared to the on-target site in GUIDE-seq provides an estimate of the off-target frequency of the genuine off-target sites for each gRNA and is summarized in Table 14 (Off-Target/On-Target) along with information on the genomic site and whether the cut site lies within the coding region of a gene. The algorithm used for the GUIDE-seq analysis also provides the number of mis-matched nucleotides between the predicted off-target site in the genome and the guide RNA. Off-target sites with small numbers of mis-matches in the range of 1 to 3 mis-matches are more likely to be recognized efficiently than those having larger numbers of mis-matches in the range of 4 or more mis-matches. In some case an alignment to the gRNA was not identified (NA in Table 14). The two off-target sites detected for gRNA TF-T1 were detected at 0.09% and 0.05% of the on-target read count and had 5 and 9 mis-matches to the gRNA. One of these sites lies within an exon of the SMAD3 gene and the other site is in an intergenic region.

The TF-T2 gRNA exhibited a high frequency off-target site within an intron of the hepatic lipase C gene with a read count frequency that was 54.9% of the on-target read count and 2 mis-matches to the gRNA. The other 5 off-target sites had read counts less than 3% of the on-target site. These results demonstrate that in contrast to the TF-T1 gRNA, the TF-T2 gRNA can direct spCas9 to cleave the genome at an off-target site at a significant frequency. The TF-T1 and TF-T2 gRNA were ranked similarly by the in silico analysis of off-target sites. The GuideSeq results demonstrate that target specificity of a given gRNA cannot be predicted by in silico analysis alone.

The value of the GUIDE-seq results for the TF-T66 guide are limited due to the low on-target cleavage.

GUIDE-seq detected 4 off-target sites for the TF-T100 guide RNA with read counts that were more than 2% of the on-target read count. One of these sites had a read count that was 28% of the on-target read count and 2 mismatches to the gRNA. This off-target site is located in a intergenic region where the risk of a deleterious effect on the cell is less likely. The other 3 most frequent sites lie within an exon of the carboxyl ester lipase gene, a pseudo gene of carboxyl ester lipase and within a non-coding RNA.

Overall, the results from the GUIDE-seq analysis in HepG2 cells demonstrate that selection of a gRNA with high specificity for the on-target site cannot be predicted by in silico analysis alone. Of the 4 gRNA that were profiled by GuideSeq, the TF-T1 gRNA has the most favorable off-target profile with only 2 off-target sites identified that were cleaved in-frequently with read counts less than 0.1% of the on-target read count. Screening of additional gRNA with target sites in human transferrin intron 1 for the existence of off-target cleavage sites in the human genome using the GuideSeq methodology described herein is envisaged as an approach to identify additional gRNA that could be used to target integration of donor templates containing therapeutic genes into transferrin intron 1 for the purpose of expressing the encoded therapeutic protein.

Example 11: Additional Modes of Delivery

In another example, the donor DNA template is delivered in vivo using a non-viral delivery system which is an LNP. DNA molecules are encapsulated into similar LNP particles as those described above and delivered to the hepatocytes in the liver after i.v. injection. While escape of the DNA from the endosome to the cytoplasm occurs relatively efficiently, translocation of large charged DNA molecules into the nucleus is not efficient. In one case, the delivery of DNA to the nucleus is improved by mimicking the AAV genome by incorporation of AAV ITR sequences into the donor DNA template. In this case, the ITR sequences stabilize the DNA or otherwise improve nuclear translocation. The removal of CG di-nucleotides (CpG sequences) form the donor DNA template sequence also improves nuclear delivery. DNA containing CG di-nucleotides is recognized by the innate immune system and eliminated. Removal of CpG sequences that are present in artificial DNA sequences improves the persistence of DNA delivered by non-viral and viral vectors. The process of codon optimization typically increases the content of CG di-nucleotides because the most frequent codons in many cases have a C residue in the 3rd position, which increases the chance of creating a CG when the next codon starts with a G. A combination of LNP delivery of the donor DNA template followed 1 h to 5 days later with an LNP containing the gRNA and Cas9 mRNA is evaluated in Hemophilia A mice.

In vivo delivery of the gRNA and the Cas9 mRNA is accomplished by various methods. In one case, the gRNA and Cas9 protein are expressed from an AAV viral vector. In this case the transcription of the gRNA is driven by a U6 promoter and the Cas9 mRNA transcription is driven by either a ubiquitous promoter, e.g., EF1-alpha, or a liver-specific promoter/enhancer, such as the transthyretin promoter/enhancer. The size of the spCas9 gene (4.4 Kb) precludes inclusion of the spCas9 and the gRNA cassettes in a single AAV, thereby requiring separate AAV to deliver the gRNA and spCas9. In a second case, an AAV vector that has sequence elements that promote self-inactivation of the viral genome is used. In this case, including cleavage sites for the gRNA in the vector DNA results in cleavage of the vector DNA in vivo. By including cleavage sites in locations that blocks expression of the Cas9 when cleaved, Cas9 expression is limited to a shorter time period. In the third, alternative approach to deliver the gRNA and Cas9 to cells in vivo, a non-viral delivery method is used. In one example, lipid nanoparticles (LNP) are used as a non-viral delivery method. Several different ionizable cationic lipids are available for use in LNP. These include C12-200 (Love et al. (2010), PNAS vol. 107, 1864-1869), MC3, LN16, MD1 among others. In one type of LNP a GalNac moiety is attached to the outside of the LNP and acts as a ligand for uptake into the liver via the asialyloglycoprotein receptor. Any of these cationic lipids are used to formulate LNP for delivery of gRNA and Cas9 mRNA to the liver.

Example 12: Comparison of the Relative Expression Levels of FVIII after Integration into the Transferrin Locus and the Albumin Locus The serum albumin gene is the most highly expressed gene in the liver of mammals as evidenced by the fact that serum albumin is the most abundant protein in the blood of mammals. In humans the serum albumin protein level is between 35 grams per liter and 55 grams per liter (Levitt Int J Gen Med 9, 229-255). By comparison the level of transferrin protein in humans is between 2 and 3 grams per liter (*Normal Reference Range Table*. Interactive Case Study Companion to Pathlogical Basis of Disease. The University of Texas Southwestern Medical Center at Dallas. Archived from the original on 2011 Dec. 25. *Retrieved* 2008 Oct. 25. Kumar V, Hagler H K (1999). Interactive Case Study Companion to Robbins Pathologic Basis of Disease (6th Edition (CD-ROM for Windows & Macintosh, Individual) ed.). W B Saunders Co. *ISBN* 0-7216-8462-9). The levels of the mRNA transcripts for human serum albumin and human transferrin as determined by the RNAseq method and available at the NCBI Genome browser (www.ncbi.nlm.nih.gov) are 41,385 and 1,622, respectively indicating that the transcript for serum albumin is approximately 25-fold more abundant than that of transferrin. In mice albumin protein levels in the blood of wild type mice are about 20 grams per liter (Zaias et al., J American Association for Laboratory Animal Science, 48, 387-390) compared to about 1 gram per liter for transferrin protein (Lyoumi ey al, 2007 Blood 109, 811-818).

The relative levels of the RNA for Albumin and transferrin in mouse liver can be found in various online databases for example the Expression Atlas (www.ebi.ac.uk/gxa/home) wherein the relative levels in the CD-1 strain of mice was 11230 for albumin RNA and 177 for transferrin RNA, indicating an approximately 60-fold higher RNA level for albumin than transferrin. Relative RNA values for another common strain of mice, C57B16 which is the background strain for hemophilia A mice, were 9346 for albumin and 150 for transferrin (//www.ebi.ac.uk/gxa/home), again indicative of about a 60-fold higher level of albumin RNA in the liver as compared to transferrin. These data demonstrate that the endogenous transferrin locus is expressed at a significantly lower level than the endogenous albumin locus in mice and in humans.

Targeted integration of a human FVIII coding sequence into intron 1 of mouse albumin using C12-200-based LNPs containing spCas9 mRNA and a gRNA (mALbT1) targeted to mouse albumin intron 1 was performed as follows. Hemophilia A mice were injected with 2 e12 vg/kg of AAV8-pCB099, an AAV8 virus packaged with donor cassette pCB099 (SEQ ID NO: 251) as shown in FIG. 10. pCB099 contains the identical DNA sequence encoding the mature FVIII protein coding sequence present in AAV8-pCB1009 flanked by the same splice acceptor and polyadenylation sequence as present in AAV8-pCB1009, and further flanked by target sites (CCTGTAACGATCGG-GAACTGGCA, SEQ ID NO: 252) for the mALbT1 gRNA. Mouse albumin exon 1 encodes the signal peptide and the pro-peptide followed by 7 bp encoding the N-terminus of the mature albumin protein (encoding Glu-Ala plus 1 bp (C)). At the 5' end of the mature FVIII coding sequence in AAV8-pCB099, a TG di-nucleotide was added, such that after integration into albumin intron 1, RNA splicing between albumin exon 1 and the splice acceptor in the integrated donor generates an mRNA in which the signal peptide and pro-peptide of albumin plus 3 amino acids (Glu-Ala-Leu) is fused in frame to the N-terminus of the FVIII protein. Four weeks after injection of AAV8-pCB099 the mice were injected with LNP encapsulating spCas9 mRNA and the mAlbT1 gRNA at a dose of 2 mg of RNA per kg. The FVIII activity in the blood was measured 10 days after dosing of the LNP. The mice were then sacrificed and the frequency of targeted integration of the FVIII cassette in the forward orientation at the on-target site in albumin intron 1 was measured using a DD-PCR assay essentially as described in Example 6 but with primers and probes specific for the mouse albumin locus and the AAV8-pCB099 donor cassette. The results are summarized in Table 15 together with the same data set for mice with targeted integration into transferrin intron 1 that are described in Example 4b and Example 6. The targeted integration frequencies for the two genomic loci were similar with a mean of 2.45% for albumin and 2.47% for transferrin (excluding the mouse 1-4 that had significantly lower targeted integration) and were not statistically different (p=0.53) using the students T-test. The mean FVIII activity in the mice where the FVIII cassette was integrated into albumin intron 1 was 25.6% while for mice with the FVIII cassette integrated into transferrin intron 1 the mean FVIII activity was 954%, and this difference in FVIII activity was statistically significant (P<0.001 using students T-test). Dividing the FVIII activity level by the targeted integration frequency normalizes the FVIII levels to the number of integrated copies of the cassette. The mean ratio of FVIII divided by integration frequency was 10.3 for albumin targeted mice and 403 for transferrin targeted mice (excluding mouse 1-4 that had significantly lower targeted integration and thus a much higher value for the normalized FVIII activity), and this difference was statistically significant (P<0.001 using the students T-test). These data demonstrate that integration of the FVIII cassette into transferrin intron 1 results in approximately 40-fold higher levels of FVIII expression than integration into albumin intron 1 when normalized for integration frequency. This result would not have been predicted or expected given that the albumin gene is more transcriptionally active than the transferrin gene as evidenced by the higher transcripts determined by GuideSeq and the about 25-fold higher levels of albumin protein as compared to transferrin protein.

These results demonstrate that the transferrin locus and specifically integration into intron 1 of transferrin is a superior approach for expression of FVIII as compared to albumin, a result that is un-expected given the well documented higher transcriptional activity of the albumin locus as compared to transferrin. Thus, the transferrin locus and specifically integration into intron 1 of the transferrin gene, using the approach described herein is a preferred method for expressing FVIII or other thereapeutically relevant proteins.

TABLE 15

Comparison of FVIII activity levels and targeted integration frequencies in Hemophilia A mice in which the FVIII donor cassette was targeted into albumin intron 1 or transferrin intron 1

| Locus | Mouse ID | FVIII activity in blood (% of normal) | Targeted integration frequency (% per haploid genome) | FVIII activity divided by integration frequency |
|---|---|---|---|---|
| Albumin | 3-1 | 34.5 | 2.95 | 11.7 |
|  | 3-2 | 24.7 | 2.58 | 9.6 |
|  | 3-3 | 14.0 | 1.33 | 10.5 |
|  | 3-4 | 18.3 | 2.54 | 7.2 |
|  | 3-5 | 36.4 | 2.89 | 12.6 |
| Transferrin | 1-1 | 1144 | 2.87 | 418 |
|  | 1-2 | 1060 | 2.40 | 422 |
|  | 1-3 | 1089 | 2.82 | 386 |
|  | 1-4 | 957 | 0.31 | 3087 |
|  | 1-5 | 521 | 1.82 | 387 |

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

SEQUENCE LISTING

In addition to sequences disclosed elsewhere in the present disclosures, the following sequences are provided as they are mentioned or used in various exemplary embodiments of the disclosures, which are provided for the purpose of illustration.

| SEQ ID NO | Sequence | Description |
|---|---|---|
| 1 | AAGGAAGCGGTGCCATCGAG | Transferrin_T12 gRNA spacer |
| 2 | AACTTCTGCCTGCCATTCAT | Transferrin_T168 gRNA spacer |
| 3 | AGCAAAGGGTTTTGATAACC | Transferrin_T73 gRNA spacer |
| 4 | TTGCCTGGGAGGGTCAAATG | Transferrin_T99 gRNA spacer |
| 5 | GGCTTGGCCAACGACAAGCA | Transferrin_T26 gRNA spacer |

-continued

| SEQ ID NO | Sequence | Description |
|---|---|---|
| 6 | CCTTGTGGGCCACCACAGCA | Transferrin_T111 gRNA spacer |
| 7 | GGGCCCACTCCCTATGCTGA | Transferrin_T76 gRNA spacer |
| 8 | TCTGAGTCTGAGCCAATAGA | Transferrin_T128 gRNA spacer |
| 9 | CCTGCCTCCAGAGTTCCCAT | Transferrin_T188 gRNA spacer |
| 10 | ACAGCTCTCCAGGATGCATG | Transferrin_T151 gRNA spacer |
| 11 | GGCCCATGGGAAATCCTAGG | Transferrin_T67 gRNA spacer |
| 12 | AGGGTGGTCAGTAGGAAACT | Transferrin_T138 gRNA spacer |
| 13 | CCTTGCTGTGGTGGCCCACA | Transferrin_T115 gRNA spacer |
| 14 | GGTAGCAAGCCAATGTGTTG | Transferrin_T45 gRNA spacer |
| 15 | GCAGATTGTCATCTCCAGCT | Transferrin_T180 gRNA spacer |
| 16 | CCACAGCAAGGCTGACTCAC | Transferrin_T148 gRNA spacer |
| 17 | ACTGAGGCTTATGTTCCATG | Transferrin_T100 gRNA spacer |
| 18 | GGGCAAAAGCTCATGTGATA | Transferrin_T66 gRNA spacer |
| 19 | ATACTGAGGCTTATGTTCCA | Transferrin_T162 gRNA spacer |
| 20 | CCAGTGAGTCAGCCTTGCTG | Transferrin_T175 gRNA spacer |
| 21 | GGATTTCCCATGGGCCAAGA | Transferrin_T172 gRNA spacer |
| 22 | GGGTCAAATGAGGGTCAGCG | Transferrin_T104 gRNA spacer |
| 23 | TCAACTATGGAAAACCAGCG | Transferrin_T19 gRNA spacer |
| 24 | CATAAGCCTCAGTATGCACA | Transferrin_T77 gRNA spacer |
| 25 | TATGTTCCATGGGGGGCCAG | Transferrin_T62 gRNA spacer |
| 26 | AGGGCCCACTCCCTATGCTG | Transferrin_T106 gRNA spacer |
| 27 | GCTGTGGGCCTCCTCTCCAC | Transferrin_T163 gRNA spacer |
| 28 | ACAAATGCCCCATGAATGGC | Transferrin_T134 gRNA spacer |
| 29 | GTGGCTGTCAAGGCCTTTCT | Transferrin_T167 gRNA spacer |
| 30 | TCCTGTCCATGAACACTACA | Transferrin_T61 gRNA spacer |

-continued

| SEQ ID NO | Sequence | Description |
|---|---|---|
| 31 | AGACAGCATCGCCCCTAGAA | Transferrin_T6 gRNA spacer |
| 32 | CCTTCTTGGCCAGTAGTTGA | Transferrin_T44 gRNA spacer |
| 33 | AAGGTCACCCTGCTTGTCGT | Transferrin_T3 gRNA spacer |
| 34 | GAGGGAAAATGGGGGTCGCT | Transferrin_T68 gRNA spacer |
| 35 | TAGGAGGCAACATAAGCCTG | Transferrin_T103 gRNA spacer |
| 36 | AAAACGCCCTGTGCATACTG | Transferrin_T81 gRNA spacer |
| 37 | GTGAGTCAGCCTTGCTGTGG | Transferrin_T146 gRNA spacer |
| 38 | GGCTGTCAAGGCCTTTCTAG | Transferrin_T63 gRNA spacer |
| 39 | AGGTAGCAAGCCAATGTGTT | Transferrin_T87 gRNA spacer |
| 40 | GATTGTCATCTCCAGCTGGG | Transferrin_T184 gRNA spacer |
| 41 | TCCTGGCCGGCTCCTCACCA | Transferrin_T116 gRNA spacer |
| 42 | ATTCTCGCCTATGGGAACTC | Transferrin_T24 gRNA spacer |
| 43 | TGGCTTGGCCAACGACAAGC | Transferrin_T21 gRNA spacer |
| 44 | TTGGCTTGCTACCTCAACTA | Transferrin_T41 gRNA spacer |
| 45 | GAGGTAGCAAGCCAATGTGT | Transferrin_T55 gRNA spacer |
| 46 | AGGAGACAAGGCGGATACAG | Transferrin_T90 gRNA spacer |
| 47 | GACTCTGGGTCTGCTACTCA | Transferrin_T101 gRNA spacer |
| 48 | CCGCTGGTTTTCCATAGTTG | Transferrin_T39 gRNA spacer |
| 49 | CCTCAACTATGGAAAACCAG | Transferrin_T150 gRNA spacer |
| 50 | TGGATTTTAATAGTTACCCA | Transferrin_T156 gRNA spacer |
| 51 | GGGGATAAAGGCAAGTAACG | Transferrin_T40 gRNA spacer |
| 52 | CCGGGTTGCAGGGAACGCGC | Transferrin_T8 gRNA spacer |
| 53 | CGCGCGGGCCAGCGACTCTG | Transferrin_T53 gRNA spacer |
| 54 | CTGAGGCTTATGTTCCATGG | Transferrin_T117 gRNA spacer |
| 55 | CGGAGTGCATGCAGGCTGCG | Transferrin_T49 gRNA spacer |

| SEQ ID NO | Sequence | Description |
|---|---|---|
| 56 | ACAGGCTTATGTTGCCTCCT | Transferrin_T83 gRNA spacer |
| 57 | GGGCATTTGTCACACTGTTG | Transferrin_T64 gRNA spacer |
| 58 | TGGCCCCTCCTCATGCATCC | Transferrin_T120 gRNA spacer |
| 59 | AAAATGGAGGGATAGTTCAG | Transferrin_T161 gRNA spacer |
| 60 | TGTGACAAATGCCCCATGAA | Transferrin_T183 gRNA spacer |
| 61 | GTGGTCAGTAGGAAACTGGG | Transferrin_T182 gRNA spacer |
| 62 | TGAGGCTTATGTTCCATGGG | Transferrin_T119 gRNA spacer |
| 63 | GGGATAAAGGCAAGTAACGT | Transferrin_T18 gRNA spacer |
| 64 | AGGGCAAAAGCTCATGTGAT | Transferrin_T107 gRNA spacer |
| 65 | GCCATCGAGCGGTCAGAGCA | Transferrin_T20 gRNA spacer |
| 66 | CCCTCAACTACTGGCCAAGA | Transferrin_T80 gRNA spacer |
| 67 | CCTCAACTACTGGCCAAGAA | Transferrin_T133 gRNA spacer |
| 68 | GAGGGTGGTCAGTAGGAAAC | Transferrin_T84 gRNA spacer |
| 69 | GTCGCTGGGGTGGCCATCCC | Transferrin_T85 gRNA spacer |
| 70 | TGGGGAGAGAAAACTAAACG | Transferrin_T143 gRNA spacer |
| 71 | CCTGAGCGCGGAGTGCATGC | Transferrin_T15 gRNA spacer |
| 72 | GCGACCCCATTTTCCCTCT | Transferrin_T96 gRNA spacer |
| 73 | CTCAACTATGGAAAACCAGC | Transferrin_T118 gRNA spacer |
| 74 | GATCCACAAAGCCTGTGGAG | Transferrin_T152 gRNA spacer |
| 75 | CCCCGCACAGAGCACTTCAC | Transferrin_T38 gRNA spacer |
| 76 | TGCAAGGTAATGCTCCACTG | Transferrin_T132 gRNA spacer |
| 77 | AGGGGACGTCAGCCTCTGAA | Transferrin_T149 gRNA spacer |
| 78 | AGGGAAAATGGGGTCGCTG | Transferrin_T171 gRNA spacer |
| 79 | TGAGGACACATTCTCGCCTA | Transferrin_T30 gRNA spacer |
| 80 | TGCCTCCTAGGATTTCCCAT | Transferrin_T71 gRNA spacer |

-continued

| SEQ ID NO | Sequence | Description |
|---|---|---|
| 81 | CTTGGCCCATGGGAAATCCT | Transferrin_T158 gRNA spacer |
| 82 | AGGAGTTCGGACTTGACAAG | Transferrin_T36 gRNA spacer |
| 83 | ACATAAGCCTCAGTATGCAC | Transferrin_T27 gRNA spacer |
| 84 | CAGGACATCTACAGCTCCCA | Transferrin_T130 gRNA spacer |
| 85 | GGGCCCCACCTCAGGAGGTC | Transferrin_T124 gRNA spacer |
| 86 | AACGACAAGCAGGGTGACCT | Transferrin_T185 gRNA spacer |
| 87 | GCAGGACATCTACAGCTCCC | Transferrin_T79 gRNA spacer |
| 88 | CCTGTGAAGTGCTCTGTGCG | Transferrin_T72 gRNA spacer |
| 89 | TGCCTGGGAGGGTCAAATGA | Transferrin_T179 gRNA spacer |
| 90 | TGGCCATGCCTGCACCCCTC | Transferrin_T170 gRNA spacer |
| 91 | GCCAGCAGAGGGTGGTCAGT | Transferrin_T181 gRNA spacer |
| 92 | CTCCTGTCCATGAACACTAC | Transferrin_T42 gRNA spacer |
| 93 | GGAGTGGGCCCTTCCACCTC | Transferrin_T114 gRNA spacer |
| 94 | CAACTATGGAAAACCAGCGG | Transferrin_T23 gRNA spacer |
| 95 | TACTGAGGCTTATGTTCCAT | Transferrin_T144 gRNA spacer |
| 96 | CCCATGCTCTGACCGCTCGA | Transferrin_T1 gRNA spacer |
| 97 | CTCCCCGACCTCCTGAGGTG | Transferrin_T186 gRNA spacer |
| 98 | GGGGAATGGTCAGACCCGGG | Transferrin_T58 gRNA spacer |
| 99 | CTTGTGCCCTGTAGTGTTCA | Transferrin_T113 gRNA spacer |
| 100 | CCCGCGCGTTCCCTGCAACC | Transferrin_T29 gRNA spacer |
| 101 | CCATCGAGCGGTCAGAGCAT | Transferrin_T2 gRNA spacer |
| 102 | GCCCTGTAGTGTTCATGGAC | Transferrin_T48 gRNA spacer |
| 103 | AAATCAGAGCACGTCTAACC | Transferrin_T17 gRNA spacer |
| 104 | GCCTGTGAAGTGCTCTGTGC | Transferrin_T153 gRNA spacer |
| 105 | CTCGCCTATGGGAACTCTGG | Transferrin_T60 gRNA spacer |

| SEQ ID NO | Sequence | Description |
|---|---|---|
| 106 | GGCCCCACCTCAGGAGGTCG | Transferrin_T164 gRNA spacer |
| 107 | CCGCGCGTTCCCTGCAACCC | Transferrin_T47 gRNA spacer |
| 108 | TGGCTGTCAAGGCCTTTCTA | Transferrin_T110 gRNA spacer |
| 109 | TGGCAGATGCTGAGTACCAG | Transferrin_T177 gRNA spacer |
| 110 | GTTAATTTACCCTCAACTAC | Transferrin_T13 gRNA spacer |
| 111 | CCTGCATGCACTCCGCGCTC | Transferrin_T7 gRNA spacer |
| 112 | GACCCTCATTTGACCCTCCC | Transferrin_T89 gRNA spacer |
| 113 | CCATTAGGGCAACCTTCTAT | Transferrin_T16 gRNA spacer |
| 114 | ATGCATGAGGAGGGGCCACC | Transferrin_T155 gRNA spacer |
| 115 | GTCAGCCACTGCCCCATAGC | Transferrin_T108 gRNA spacer |
| 116 | CCTATGGGAACTCTGGAGGC | Transferrin_T160 gRNA spacer |
| 117 | ACTTCTGCCTGCCATTCATG | Transferrin_T139 gRNA spacer |
| 118 | CGGTGGCCGCCCGGGTTGCA | Transferrin_T11 gRNA spacer |
| 119 | GGGGACGTCAGCCTCTGAAA | Transferrin_T169 gRNA spacer |
| 120 | GAGGACACATTCTCGCCTAT | Transferrin_T5 gRNA spacer |
| 121 | GCATGGCATTCAAGGCCTCC | Transferrin_T131 gRNA spacer |
| 122 | CATCGAGCGGTCAGAGCATG | Transferrin_T22 gRNA spacer |
| 123 | CTCAACTACTGGCCAAGAAG | Transferrin_T126 gRNA spacer |
| 124 | CTGTGGTGGCCCACAAGGAG | Transferrin_T145 gRNA spacer |
| 125 | TCTGCTGGCCAGAGGGGTGC | Transferrin_T187 gRNA spacer |
| 126 | AGGCGAGAATGTGTCCTCAG | Transferrin_T112 gRNA spacer |
| 127 | GCTCGATGGCACCGCTTCCT | Transferrin_T14 gRNA spacer |
| 128 | GTCCTGGCCGGCTCCTCACC | Transferrin_T70 gRNA spacer |
| 129 | TTTCAGCTACCCCAACACAT | Transferrin_T57 gRNA spacer |
| 130 | GGGTAGCACCGCAGAGTCGC | Transferrin_T4 gRNA spacer |

-continued

| SEQ ID NO | Sequence | Description |
|---|---|---|
| 131 | CCCTTCTTGGCCAGTAGTTG | Transferrin_T92 gRNA spacer |
| 132 | AAAGGGGAATGGTCAGACCC | Transferrin_T102 gRNA spacer |
| 133 | AGCTAGCAATTCCTTGAGAG | Transferrin_T159 gRNA spacer |
| 134 | CATGCACTCCGCGCTCAGGC | Transferrin_T10 gRNA spacer |
| 135 | TTGCCTCCTAGGATTTCCCA | Transferrin_T157 gRNA spacer |
| 136 | CATCACAGCACTTGCCTGGG | Transferrin_T173 gRNA spacer |
| 137 | TGATGACCCCTCCCTGGTG | Transferrin_T121 gRNA spacer |
| 138 | AGCAGATTGTCATCTCCAGC | Transferrin_T137 gRNA spacer |
| 139 | TCAAATGAGGGTCAGCGAGG | Transferrin_T98 gRNA spacer |
| 140 | TGGCCGGCTCCTCACCAGGG | Transferrin_T141 gRNA spacer |
| 141 | GATGGCAATTCCTCCCCCGC | Transferrin_T50 gRNA spacer |
| 142 | CAAGGAATTGCTAGCTTATG | Transferrin_T94 gRNA spacer |
| 143 | TAACGTGGGGTCCTCTCTCA | Transferrin_T86 gRNA spacer |
| 144 | AGTGCTCTGTGCGGGGATAA | Transferrin_T35 gRNA spacer |
| 145 | CATTTTCCCTCTTGGCCCAT | Transferrin_T174 gRNA spacer |
| 146 | TTCACTGCTGCAAGATTTAC | Transferrin_T97 gRNA spacer |
| 147 | GTGAGGAGCCGGCCAGGACT | Transferrin_T127 gRNA spacer |
| 148 | ATGTTGCACACATCCTGCTA | Transferrin_T56 gRNA spacer |
| 149 | TCAAGGAATTGCTAGCTTAT | Transferrin_T65 gRNA spacer |
| 150 | TCTTGGATCCAAGTCCTGGC | Transferrin_T123 gRNA spacer |
| 151 | TTCTGAGTTACACCCCTTCT | Transferrin_T59 gRNA spacer |
| 152 | TTCAGAGGCTGACGTCCCCT | Transferrin_T129 gRNA spacer |
| 153 | CCAATAGAAGGTTGCCCTAA | Transferrin_T9 gRNA spacer |
| 154 | CACTCCCCGACCTCCTGAGG | Transferrin_T122 gRNA spacer |
| 155 | CGCGTTCCCTGCAACCCGGG | Transferrin_T31 gRNA spacer |

| SEQ ID NO | Sequence | Description |
|---|---|---|
| 156 | GATGGCACCGCTTCCTTGGC | Transferrin_T28 gRNA spacer |
| 157 | TATGAAGGGGGCCCCACCTC | Transferrin_T43 gRNA spacer |
| 158 | TGCTGTGATGACCCCCTCCC | Transferrin_T125 gRNA spacer |
| 159 | CACATCCTGCTATGGGCAG | Transferrin_T165 gRNA spacer |
| 160 | AGGCTGCGCGGTGGCCGCCC | Transferrin_T82 gRNA spacer |
| 161 | TGGGGCATTTGTCACACTGT | Transferrin_T109 gRNA spacer |
| 162 | CTCAAGGAATTGCTAGCTTA | Transferrin_T52 gRNA spacer |
| 163 | CTATGGAAAACCAGCGGGGG | Transferrin_T34 gRNA spacer |
| 164 | TGTTGCACACATCCTGCTAT | Transferrin_T88 gRNA spacer |
| 165 | AGAGGGAAAATGGGGGTCGC | Transferrin_T51 gRNA spacer |
| 166 | CTTATGTTCCATGGGGGCC | Transferrin_T46 gRNA spacer |
| 167 | TCTGACCATTCCCCTTTCAG | Transferrin_T178 gRNA spacer |
| 168 | GGGGCATTTGTCACACTGTT | Transferrin_T74 gRNA spacer |
| 169 | CCGCGCTCAGGCTGGAAGCC | Transferrin_T176 gRNA spacer |
| 170 | GCGGTGGCCGCCCGGGTTGC | Transferrin_T54 gRNA spacer |
| 171 | TGCTTGTCGTTGGCCAAGCC | Transferrin_T32 gRNA spacer |
| 172 | TCCCTGGTGAGGAGCCGGCC | Transferrin_T136 gRNA spacer |
| 173 | TTATGTTCCATGGGGGCCA | Transferrin_T78 gRNA spacer |
| 174 | TITTAATAGTTACCCATGGC | Transferrin_T154 gRNA spacer |
| 175 | CCAGGCTTCCAGCCTGAGCG | Transferrin_T140 gRNA spacer |
| 176 | CAGGCTGCGCGGTGGCCGCC | Transferrin_T93 gRNA spacer |
| 177 | ATGTGTGCAACATCTGCCAC | Transferrin_T95 gRNA spacer |
| 178 | AGTGCATGCAGGCTGCGCGG | Transferrin_T37 gRNA spacer |
| 179 | ACTCCCCGACCTCCTGAGGT | Transferrin_T91 gRNA spacer |
| 180 | GAAAGGGGAATGGTCAGACC | Transferrin_T166 gRNA spacer |

| SEQ ID NO | Sequence | Description |
|---|---|---|
| 181 | CGCGCTCAGGCTGGAAGCCT | Transferrin_T105 gRNA spacer |
| 182 | GTGTCTAGAAGCCCAAGCAA | Transferrin_T142 gRNA spacer |
| 183 | CCCGGGTTGCAGGGAACGCG | Transferrin_T25 gRNA spacer |
| 184 | TTTCAGAGGCTGACGTCCCC | Transferrin_T135 gRNA spacer |
| 185 | GAGCTGTAGATGTCCTGCCA | Transferrin_T69 gRNA spacer |
| 186 | GGGTCATCACAGCACTTGCC | Transferrin_T147 gRNA spacer |
| 187 | GGATAAAGGCAAGTAACGTG | Transferrin_T33 gRNA spacer |
| 188 | TCTCCCTCAGCATAGGGAGT | Transferrin_T75 gRNA spacer |
| 189 | TAACAAGCAAGACCCGTCGC | mTF-T1 gRNA spacer |
| 190 | GAGAACGCACCACTTTACGA | mTF-T2 gRNA spacer |
| 191 | NNNNNNNNNNNNNNNNNNNNRG<br>N is any nucleotide, R is G or A | Exemplary target nucleic acid sequence |
| 192 | SFSQNPPVLKRHQR | SQ link |
| 193 | CTGACCTCTTCTCTTCCTCCCACAG | synthetic splice acceptor |
| 194 | ggagtgggcccttccacctctggcctctctcccccag | native splice acceptor sequence from the Transferrin gene intron 1/exon 2 boundary of human |
| 195 | AAUAAA | polyadentylation signal |
| 196 | AATAAAGATCTTTATTTTCATTAGATCTGTGTGTTGGTTTTTTGTGTG | consensus synthetic poly A signal sequence |
| 197 | CTGTGCCTTCTAGTTGCCAGCCATCTGTTGTTTGCCCCTCCCCCGTGCCTTCCTTGACCCTGGAAG GTGCCACTCCCACTGTCCTTTCCTAATAAAATGAGGAAATTGCATCGCATTGTCTGAGTAGGTGT CATTCTATTCTGGGGGGGGGTGGGCAGGACAGCAAGGGGGAGGATTGGGAAGACAATAG CAGGCATGCTGGGGATGCGGTGGGCTCTATGG | bovine growth hormone polyA signal sequence |
| 198 | TAAGATACATTGATGAGTTTGGACAAACCACAACTAGAATGCAGTGAAAAAAATGCTTTATTTGT GAAATTTGTGATGCTATTGCTTTATTTGTAACCATTATAAGCTGCAATAAACAAGTT | SV40 polyadenylation signal sequence |
| 199 | TCACAAACAGGACACGTCGC | Guide RNA mTF-T1 potential off-target site 1 |
| 200 | TCACAGGCAAGACACATCGC | Guide RNA mTF-T1 potential off-target site 2 |

| SEQ ID NO | Sequence | Description |
|---|---|---|
| 201 | TAACATCCAGGACCCGTTGC | Guide RNA mTF-T1 potential off-target site 3 |
| 202 | TAAGAAGCAAGACCTGGCGC | Guide RNA mTF-T1 potential off-target site 4 |
| 203 | AAACAAACAAGCCCCGTGGC | Guide RNA mTF-T1 potential off-target site 5 |
| 204 | CAACAAGAAAGACGCGGCGC | Guide RNA mTF-T1 potential off-target site 6 |
| 205 | CAGCAAGCAAGATCCGTCTC | Guide RNA mTF-T1 potential off-target site 7 |
| 206 | TATCAATCAAGACACGTCAC | Guide RNA mTF-T1 potential off-target site 8 |
| 207 | TCAAAAGCAAGACCCATCAC | Guide RNA mTF-T1 potential off-target site 9 |
| 208 | ATGCACACACCACTTTACGA | Guide RNA mTF-T2 potential off-target site 1 |
| 209 | GAGAAGAGAACACTTTACGA | Guide RNA mTF-T2 potential off-target site 2 |
| 210 | GTGAAGCCACCACTTTAAGA | Guide RNA mTF-T2 potential off-target site 3 |
| 211 | GTGAAAGCCCCACTTTAAGA | Guide RNA mTF-T2 potential off-target site 4 |
| 212 | CAGCACTCACCACTTTACAA | Guide RNA mTF-T2 potential off-target site 5 |
| 213 | GAAGACACACCACTTTACCA | Guide RNA mTF-T2 potential off-target site 6 |
| 214 | CTGAACGCACTACTTTACCA | Guide RNA mTF-T2 potential off-target site 7 |
| 215 | CAGAACCCACCACCTTACCA | Guide RNA mTF-T2 potential off-target site 8 |
| 216 | GACAGCGCACCACTTTCTGA | Guide RNA mTF-T2 potential off-target site 9 |
| 217 | CAGTATAGTCCAAACAGCATGGTG | Trf Primer F1 |
| 218 | CACTGAAATCCACACGATGGAGA | Trf Primer R1 |
| 219 | GCCTTTCCTAGAGTTGGTGTCTAG | Trf Primer F2 |
| 220 | CAAGTGAGTCAAACCAGAGGC | Trf Primer R2 |

| SEQ ID NO | Sequence | Description |
|---|---|---|
| 221 | UsAsAsCAAGCAAGACCCGUCGCGUUUUAGAgcuaGAAAuagcAAGUUAAAAUAAGGCUAGUC<br>CGUUAUCaacuuGAAAaaguggcaccgagucggugcusususU<br>"A, G, U, C" are native RNA nucleotides, "a, g, u, c" are 2'-O-<br>methyl nucleotides, and "s" represents a phosphorothioate backbone | gRNA mTF1 |
| 222 | GsAsGsAACGCACCACUUUACGAGUUUUAGAgcuaGAAAuagcAAGUUAAAAUAAGGCUAGUC<br>CGUUAUCaacuuGAAAaaguggcaccgagucggugcusususU<br>"A, G, U, C" are native RNA nucleotides, "a, g, u, c" are 2'-O-<br>methyl nucleotides, and "s" represents a phosphorothioate backbone | gRNA mTF2 |
| 223 | GGAAATAAGAGAGAAAAGAAGAGTAAGAAGAAATATAAGAGCCACCATGGCCCCAAAGAAGA<br>AGCGGAAGGTCGGTATCCACGGAGTCCCAGCAGCCGACAAGAAGTACAGCATCGGCCTGGACA<br>TCGGCACCAACTCTGTGGGCTGGGCCGTGATCACCGACGAGTACAAGGTGCCCAGCAGAAAT<br>TCAAGGTGCTGGGCAACACCGACCGGCACAGCATCAAGAAGAACCTGATCGGAGCCCTGCTGT<br>TCGACAGCGGCGAAACAGCCGAGGCCACCCGGCTGAAGAGAACCGCCAGAAGAAGATACACC<br>AGACGGAAGAACCGGATCTGCTATCTGCAAGAGATCTTCAGCAACGAGATGGCCAAGGTGGAC<br>GACAGCTTCTTCCACAGACTGGAAGAGTCCTTCCTGGTGGAAGAGGACAAGAAGCACGAGAGA<br>CACCCCATCTTCGGCAACATCGTGGACGAGGTGGCCTACCACGAGAAGTACCCCACCATCTACC<br>ACCTGAGAAAGAAACTGGTGGACAGCACCGACAAGGCCGACCTGAGACTGATCTACCTGGCCC<br>TGGCCCACATGATCAAGTTCAGAGGCCACTTCCTGATCGAGGGCGACCTGAACCCCGACAACAG<br>CGACGTGGACAAGCTGTTCATCCAGCTGGTGCAGACCTACAACCAGCTGTTCGAGGAAAACCCC<br>ATCAACGCCAGCGGCGTGGACGCCAAGGCTATCCTGTCTGCCAGACTGAGCAAGAGCAGAAGG<br>CTGGAAAATCTGATCGCCCAGCTGCCCGGCGAGAAGAAGAACGGCCTGTTCGGCAACCTGATT<br>GCCCTGAGCCTGGGCCTGACCCCCAACTTCAAGAGCAACTTCGACCTGGCCGAGGATGCCAAAC<br>TGCAGCTGAGCAAGGACACCTACGACGACGACCTGGACAACCTGCTGGCCCAGATCGGCGACC<br>AGTACGCCGACCTGTTCCTGGCCGCCAAGAACCTGTCTGACGCCATCCTGCTGAGCGACATCCT<br>GAGAGTGAACACCGAGATCACCAAGGCCCCCCTGAGCGCCTCTATGATCAAGAGATACGACGA<br>GCACCACCAGGACCTGACCCTGCTGAAAGCTCTCGTGCGGCAGCAGCTGCCTGAGAAGTACAAA<br>GAAATCTTCTTCGACCAGAGCAAGAACGGCTACGCCGGCTACATCGATGGCGGCGCTAGCCAG<br>GAAGAGTTCTACAAGTTCATCAAGCCCATCCTGGAAAAGATGGACGGCACCGAGGAACTGCTC<br>GTGAAGCTGAACAGAGAGGACCTGCTGAGAAAGCAGAGAACCTTCGACAACGGCAGCATCCCC<br>CACCAGATCCACCTGGGAGAGCTGCACGCTATCCTGAGAAGGCAGGAAGATTTTTACCCATTCC<br>TGAAGGACAACCGGGAAAAGATCGAGAAGATCCTGACCTTCAGGATCCCCTACTACGTGGGCC<br>CCCTGGCCAGAGGCAACAGCAGATTCGCCTGGATGACCAGAAAGAGCGAGGAAACCATCACCC<br>CCTGGAACTTCGAGGAAGTGGTGGACAAGGGCGCCAGCGCCCAGAGCTTCATCGAGAGAATGA<br>CAAACTTCGATAAGAACCTGCCCAACGAGAAGGTGCTGCCCAAGCACAGCCTGCTGTACGAGTA<br>CTTCACCGTGTACAACGAGCTGACCAAAGTGAAATACGTGACCGAGGGAATGAGAAAGCCCGC<br>CTTCCTGAGCGGCGAGCAGAAAAAGGCCATCGTGGACCTGCTGTTCAAGACCAACAGAAAAGT<br>GACCGTGAAGCAGCTGAAAGAGGACTACTTCAAGAAAATCGAGTGCTTCGACTCCGTGGAAAT<br>CTCCGGCGTGGAAGATAGATTCAACGCCTCCCTGGGCACATACCACGATCTGCTGAAAATTATC<br>AAGGACAAGGACTTCCTGGATAACGAAGAGAACGAGGACATTCTGGAAGATATCGTGCTGACC<br>CTGACACTGTTTGAGGACCGCGAGATGATCGAGGAAAAGCTGAAAACCTACGCTCACCTGTTCG<br>ACGACAAAGTGATGAAGCAGCTGAAGAGAAGGCGGTACACCGGCTGGGGCAGGCTGAGCAGA<br>AAGCTGATCAACGGCATCAGAGACAAGCAGAGCGGCAAGACAATCCTGGATTTCCTGAAGTCC<br>GACGGCTTCGCCAACCGGAACTTCATGCAGCTGATCCACGACGACAGCCTGACATTCAAAGAGG<br>ACATCCAGAAAGCCCAGGTGTCCGGCCAGGGCGACTCTCTGCACGAGCATATCGCTAACCTGC<br>CGGCAGCCCCGCTATCAAGAAGGGCATCCTGCAGACAGTGAAGGTGGTGGACGAGCTCGTGAA<br>AGTGATGGGCAGACACAAGCCCGAGAACATCGTGATCGAGATGGCTAGAGAGAACCAGACCAC<br>CCAGAAGGGACAGAAGAACTCCCGCGAGAGGATGAAGAGAATCGAAGAGGGCATCAAAGAGC<br>TGGGCAGCCAGATCCTGAAAGAACACCCCGTGGAAAACACCCAGCTGCAGAACGAGAAGCTGT<br>ACCTGTACTACCTGCAGAATGGCCGGGATATGTACGTGGACCAGGAACTGGACATCAACAGACT<br>GTCCGACTACGATGTGGACCATATCGTGCCTCAGAGCTTTCTGAAGGACGACTCCATCGATAAC<br>AAAGTGCTGACTCGGAGCGACAAGAACAGAGGCAAGAGCGACAACGTGCCCTCCGAAGAGGT<br>CGTGAAGAAGATGAAGAACTACTGGCGACAGCTGCTGAACGCCAAGCTGATTACCCAGAGGAA<br>GTTCGATAACCTGACCAAGGCCGAGAGGCGGCCTGAGCGAGCTGGATAAGGCCGGCTTCAT<br>CAAGAGGCAGCTGGTGGAAACCAGACAGATCACAAAGCACGTGGCACAGATCCTGGACTCCCG<br>GATGAACACTAAGTACGACGAAAACGATAAGCTGATCCGGGAAGTGAAAGTGATCACCCTGAA<br>GTCCAAGCTGGTGTCCGATTTCCGGAAGGATTTCCAGTTTTACAAAGTGCGCGAGATCAACAAC<br>TACCACCACGCCCACGACGCCTACCTGAACGCCGTCGTGGGAACCGCCCTGATCAAAAAGTACC<br>CTAAGCTGGAAAGCGAGTTCGTGTACGGCGACTACAAGGTGTACGACGTGCGGAAGATGATCG<br>CCAAGAGCGAGCAGGAAATCGGCAAGGCTACCGCCAAGTACTTCTTCTACAGCAACATCATGAA<br>CTTTTTCAAGACCGAAATCACCCTGGCCAACGGCGAGATCAGAAAGCGCCCTCTGATCGAGACA<br>AACGGCGAAACCGGGGAGATCGTGTGGGATAAGGGCAGAGACTTCGCCACAGTGCGAAAGGT<br>GCTGAGCATGCCCCAAGTGAATATCGTGAAAAAGACCGAGGTGCAGACAGGCGGCTTCAGCAA<br>AGAGTCTATCCTGCCCAAGAGGAACAGCGACAAGCTGATCGCCAGAAAGAAGGACTGGGACCC<br>CAAGAAGTACGGCGGCTTCGACAGCCCTACCGTGGCCTACTCTGTGCTGGTGGTGGCTAAGGTG<br>GAAAAGGGCAAGTCCAAGAAACTGAAGAGTGTGAAAGAGCTGCTGGGGATCACCATCATGGA<br>AAGAAGCAGCTTTGAGAAGAACCCTATCGACTTTCTGGAAGCCAAGGGCTACAAAGAAGTGAA<br>AAAGGACCTGATCATCAAGCTGCCTAAGTACTCCCTGTTCGAGCTGGAAAACGGCAGAAAGAG<br>AATGCTGGCCTCTGCCGGCGAACTGCAGAAGGGAAACGAGCTGGCCCTGCCTAGCAAATATGT<br>\|GAACTTCCTGTACCTGGCCTCCCACTATGAGAAGCTGAAGGGCAGCCCTGAGGACAACGAACAG<br>AAACAGCTGTTTGTGGAACAGCATAAGCACTACCTGGACGAGATCATCGAGCAGATCAGCGAG<br>TTCTCCAAGAGAGTGATCCTGGCCGACGCCAATCTGGACAAGGTGCTGTCTGCCTACAACAAGC<br>ACAGGGACAAGCCTATCAGAGAGCAGGCCGAGAATATCATCCACCTGTTCACCCTGACAAACCT | spCas9 mRNA<br>with NLS<br>sequences |

| SEQ ID NO | Sequence | Description |
|---|---|---|
| | GGGCGCTCCTGCCGCCTTCAAGTACTTTGACACCACCATCGACCGGAAGAGGTACACCAGCACC<br>AAAGAGGTGCTGGACGCCACCCTGATCCACCAGAGCATCACCGGCCTGTACGAGACAAGAATC<br>GACCTGTCTCAGCTGGGAGGCGACAAGAGACCTGCCGCCACTAAGAAGGCCGGACAGGCCAAA<br>AAGAAGAAGTGAGCGGCCGCTTAATTAAGCTGCCTTCTGCGGGGCTTGCCTTCTGGCCATGCCC<br>TTCTTCTCTCCCTTGCACCTGTACCTCTTGGTCTTTGAATAAAGCCTGAGTAGGAAGAAAAAAA<br>AAAAAAAAAAAAAAAAAAAAAAAAAAAAAAAAAAAAAAAAAAAAAAAAAAAAAAAAAAAAAAA<br>AAAAAAAAA | |
| 224 | cctgcaggcagctgcgcgctcgctcgctcactgaggccgcccgggcaaagcccgggcgtcgggcg<br>accttggtcgcccggcctcagtgagcgagcgagcgcgcagagagggagtggccaactccatcac<br>taggggttcctgcggcccGCGGgagaacgcaccacttttacgaaggCGGTACTCC<br>TCAAAGCGTACTAAAGAATTATTCTTTTACATTTCAGggctgtgtctggct<br>GCCACCAGGAGATACTACCTGGGGGCTGTGGAGCTGAGCTGGGACTACATGCAGTCTGACCTG<br>GGGGAGCTGCCTGTGGATGCCAGGTTCCCCCCCAGAGTGCCCAAGAGCTTCCCCTTCAACACCT<br>CTGTGGTGTACAAGAAGACCCTGTTTGTGGAGTTCACTGACCACCTGTTCAACATTGCCAAGCCC<br>AGGCCCCCCTGGATGGGCCTGCTGGGCCCCACCATCCAGGCTGAGGTGTATGACACTGTGGTG<br>ATCACCCTGAAGAACATGGCCAGCCACCCTGTGAGCCTGCATGCTGTGGGGGTGAGCTACTGG<br>AAGGCCTCTGAGGGGGCTGAGTATGATGACCAGACCAGCCAGGAGGGAGAAGGAGGATGACAA<br>GGTGTTCCCTGGGGGCAGCCACACCTATGTGTGGCAGGTGCTGAAGGAGAATGGCCCCCATGGC<br>CTCTGACCCCCTGTGCCTGACCTACAGCTACCTGAGCCATGTGGACCTGGTGAAGGACCTGAAC<br>TCTGGCCTGATTGGGGCCCTGCTGGTGTGCAGGGAGGGCAGCCTGGCCAAGGAGAAGACCCA<br>GACCCTGCACAAGTTCATCCTGCTGTTTGCTGTGTTTGATGAGGGCAAGAGCTGGCACTCTGAA<br>ACCAAGAACAGCCTGATGCAGGACAGGGATGCTGCCTCTGCCAGGGCCTGGCCAAGATGCAC<br>ACTGTGAATGGCTATGTGAACAGGAGCCTGCCTGGCCTGATTGGCTGCCACAGGAAGTCTGTGT<br>ACTGGCATGTGATTGGCATGGGCACCACCCCTGAGGTGCACAGCATCTTCCTGGAGGGCCACAC<br>CTTCCTGGTCAGGAACCACAGGCAGGCCAGCCTGGAGATCAGCCCCATCACCTTCCTGACTGCC<br>CAGACCCTGCTGATGGACCTGGGCCAGTTCCTGCTGTTCTGCCACATCAGCAGCCACCAGCATG<br>ATGGCATGGAGGCCTATGTGAAGGTGGACAGCTGCCCTGAGGAGCCCCAGCTGAGGATGAAG<br>AACAATGAGGAGGCTGAGGACTATGATGATGACCTGACTGACTCTGAGATGGATGTGGTGAGG<br>TTTGATGATGACAACAGCCCCAGCTTCATCCAGATCAGGTCTGTGGCCAAGAAGCACCCCAAGA<br>CCTGGGTGCACTACATTGCTGCTGAGGAGGAGGACTGGGACTATGCCCCCCTGGTGCTGGCCCC<br>TGATGACAGGAGCTACAAGAGCCAGTACCTGAACAATGGCCCCCAGAGGATTGGCAGGAAGTA<br>CAAGAAGGTCAGGTTCATGGCCTACACTGATGAAACCTTCAAGACCAGGGAGGCCATCCAGCAT<br>GAGTCTGGCATCCTGGGCCCCCTGCTGTATGGGGAGGTGGGGGACACCCTGCTGATCATCTTCA<br>AGAACCAGGCCAGCAGGCCCTACAACATCTACCCCCCATGGCATCACTGATGTGAGGCCCCTGTA<br>CAGCAGGAGGCTGCCCAAGGGGGTGAAGCACCTGAAGGACTTCCCCATCCTGCCTGGGGAGAT<br>CTTCAAGTACAAGTGGACTGTGACTGTGGAGGATGGCCCCACCAAGTCTGACCCCAGGTGCCTG<br>ACCAGATACTACAGCAGCTTTGTGAACATGGAGAGGGACCTGGCCTCTGGCCTGATTGGCCCCC<br>TGCTGATCTGCTACAAGGAGTCTGTGGACCAGAGGGGCAACCAGATCATGTCTGACAAGAGGA<br>ATGTGATCCTGTTCTCTGTGTTTGATGAGAACAGGAGCTGGTACCTGACTGAGAACATCCAGAG<br>GTTCCTGCCCAACCCTGCTGGGGTGCAGCTGGAGGACCCTGAGTTCCAGGCCAGCAACATCATG<br>CACAGCATCAATGGCTATGTGTTTGACAGCCTGCAGCTGTCTGTGTGCCTGCATGAGGTGGCCT<br>ACTGGTACATCCTGAGCATTGGGGCCCAGACTGACTTCCTGTCTGTGTTCTTCTCTGGCTACACCT<br>TCAAGCACAAGATGGTGTATGAGGACACCCTGACCCTGTTCCCCTTCTCTGGGGAGACTGTGTTC<br>ATGAGCATGGAGAACCCTGGCCTGTGGATTCTGGGCTGCCACAACTCTGACTTCAGGAACAGG<br>GGCATGACTGCCCTGCTGAAAGTCTCCAGCTGTGACAAGAACACTGGGGACTACTATGAGGACA<br>GCTATGAGGACATCTCTGCCTACCTGCTGAGCAAGAACAATGCCATTGAGCCCAGGAGCTTCAG<br>CCAGAATGCCACTAATGTGTCTAACAACAGCAACACCAGCAATGACAGCAATGTGTCTCCCCCA<br>GTGCTGAAGAGGCACCAGAGGGAGATCACCAGGACCACCCTGCAGTCTGACCAGGAGGAGATT<br>GACTATGATGACACCATCTCTGTGGAGATGAAGAAGGAGGACTTTGACATCTACGACGAGGAC<br>GAGAACCAGAGCCCCAGGAGCTTCCAGAAGAAGACCAGGCACTACTTCATTGCTGCTGTGGAGA<br>AGGCTGTGGGACTATGGCATGAGCAGCAGCCCCCATGTGCTGAGGAACAGGGCCCAGTCTGGC<br>TCTGTGCCCCAGTTCAAGAAGGTGGTGTTCCAGGAGTTCACTGATGGCAGCTTCACCCAGCCCCT<br>GTACAGAGGGGAGCTGAATGAGCACCTGGGCCTGCTGGGCCCCTACATCAGGGCTGAGGTGG<br>AGGACAACATCATGGTGACCTTCAGGAACCAGGCCAGCAGGCCCTACAGCTTCTACAGCAGCCT<br>GATCAGCTATGAGGAGGACCAGAGGCAGGGGCTGAGCCCAGGAAGAACTTTGTGAAGCCCA<br>ATGAAACCAAGACCTACTTCTGGAAGGTGCAGCACCACATGGCCCCCACCAAGGATGAGTTTGA<br>CTGCAAGGCCTGGGCCTACTTCTCTGATGTGGACCTGGAGAAGGATGTGCACTCTGGCCTGATT<br>GGCCCCCTGCTGGTGTGCCACACCAACACCCTGAACCCTGCCCATGGCAGGCAGGTGACTGTGC<br>AGGAGTTTGCCCTGTTCTTCACCATCTTTGATGAAACCAAGAGCTGGTACTTCACTGAGAACATG<br>GAGAGGAACTGCAGGGCCCCCTGCAACATCCAGATGGAGGACCCCACCTTCAAGGAGAACTAC<br>AGGTTCCATGCCATCAATGGCTACATCATGGACACCCTGCCTGGCCTGGTGATGGCCCAGGACC<br>AGAGGATCAGGTGGTACCTGCTGAGCATGGGCAGCAATGAGAACATCCACAGCATCCACTTCTC<br>TGGCCATGTGTTCACTGTGAGGAAGAAGGAGGAGTACAAGATGGCCCTGTACAACCTGTACCCT<br>GGGGTGTTTGAGACTGTGGAGATGCTGCCCAGCAAGGCTGGCATCTGGAGGGTGGAGTGCCTG<br>ATTGGGGAGCACCTGCATGCTGGCATGAGCACCCTGTTCCTGGTGTACAGCAACAAGTGCCAGA<br>CCCCCCTGGGCATGGCCTCTGGCCACATCAGGGACTTCCAGATCACTGCCTCTGGCCAGTATGG<br>CCAGTGGGCCCCCAAGCTGGCCAGGCTGCACTACTCTGGCAGCATCAATGCCTGGAGCACCAAG<br>GAGCCCTTCAGCTGGATCAAGGTGGACCTGCTGGCCCCCATGATCATCCATGGCATCAAGACC<br>AGGGGGCCAGGCAGAAGTTCAGCAGCCTGTACATCAGCCAGTTCATCATCATGTACAGCCTGGA<br>TGGCAAGAAGTGGCAGACCTACAGGGGCAACAGCACTGGCACCCTGATGGTGTTCTTTGGCAA<br>TGTGGACAGCTCTGGCATCAAGCACAACATCTTCAACCCCCCCATCATTGCCAGATACATCAGGC<br>TGCACCCCACCCACTACAGCATCAGGAGCACCCTGAGGATGGAGCTGATGGGCTGTGACCTGAA<br>CAGCTGCAGCATGCCCCTGGGCATGGAGAGCAAGGCCATCTCTGATGCCCAGATCACTGCCAGC<br>AGCTACTTCACCAACATGTTTGCCACCTGGAGCCCCAGCAAGGCCAGGCTGCACCTGCAGGGCA | pCB1009 (FVIII donor for integration intro Transferrin intron 1) |

| SEQ ID NO | Sequence | Description |
|---|---|---|
| | GGAGCAATGCCTGGAGGCCCCAGGTCAACAACCCCAAGGAGTGGCTGCAGGTGGACTTCCAGA<br>AGACCATGAAGGTGACTGGGGTGACCACCCAGGGGGTGAAGAGCCTGCTGACCAGCATGTATG<br>TGAAGGAGTTCCTGATCAGCAGCAGCCAGGATGGCCACCAGTGGACCCTGTTCTTCCAGAATGG<br>CAAGGTGAAGGTGTTCCAGGGCAACCAGGACAGCTTCACCCCTGTGGTGAACAGCCTGGACCC<br>CCCCCTGCTGACCAGATACCTGAGGATTCACCCCCAGAGCTGGGTGCACCAGATTGCCCTGAGG<br>ATGGAGGTGCTGGGCTGTGAGGCCCAGGACCTGTACTGAtcgcgaataaaagatctttattttc<br>attagatctgtgtgttggttttttgtgtggagaacgcaccactttacgaaggcAATTgccttag<br>gccgcaggaaccccagtgatggagttggccactccctctgcgcgctcgctcgctcactgagg<br>ccgggcgaccaaaggtcgcccgacgcccgggctttgcccgggcggcctcagtgagcgagcgagcg<br>cgcagctgcctgcagg | |
| 225 | ggctgtgtctggct | Terminal portion of sequence encoding signal peptide from Transferrin Exon 2 |
| 226 | SFSQNATNVSNNSNTSNDSNVSPPVLKRHQR | Variant FVIII B-domain |
| 227 | CAATGTTGAACAGGTGGTCAGTG | F8primerR1 primer |
| 228 | GGGATGAGAGGAGGGTGGAACAGAGGAGAGGTGGCCATTAA-<br>GACCCTTCGCGAAGGCGGTACTCCTCAAAGCGTACTAAA-GAATTATTCTTTTACATTTC | Predicted sequence for 5' Trf-F8 Junction |
| 229 | GGGATGAGAGGAGGGTGGAACAGAGGAGAGGTGGCCATTAAGACCCTTCGAC-<br>GAAGGCGGTACTCCTCAAAGCGTACTAAAGAATTATTCTTTTACATTTC | Clone 1 5' Trf-F8 Junction |
| 230 | GGGATGAGAGGAGGGTGGAACAGAGGAGAGGTGGCCATTAA-<br>GACCCTTCGTCGAAGGCGGTACTCCTCAAAGCGTACTAAAGAATTATTCTTTTACATTTC | Clone 2/4/6 5' Trf-F8 Junction |
| 231 | GGGATGAGAGGAGGGTGGAACAGAGGAGAGGTGGCCATTAAGACCCTCGAAGGCGGTACTCC<br>TCAAAGCGTACTAAAGAATTATTCTTTTACATTTC | Clone 7 5' Trf-F8 Junction |
| 232 | TTTCATTAGATCTGTGTGTTGGTTTTTTGTGTGGAGAACGCACCAC-<br>TTTATAAAGTGGTGCGTTCTCTCCCCAGGCACGGGGAGCGGGTCCTTTATGCCT | Predicted sequence for 3' F8-Trf Junction |
| 233 | TTTCATTAGATCTGTGTGTTGGTTTTTTGTGTGGAGAACGCACCACTAAAGTGGTGCGTTCTCTCC<br>CCAGGCACGGGGAGCGGGTCCTTTATGCCT | Clone 2 3' F8-Trf Junction |
| 234 | TTTCATTAGATCTGTGTGTTGGTTTTTTGTGTGGAGAACGCACCACTGTAAAGTGGTGCGTTCTC<br>TCCCCAGGCACGGGGAGCGGGTCCTTTATGCCT | Clone 3 3' F8-Trf Junction |
| 235 | GATGAGAGGAGGGTGGAACA | TFF1(DD) primer |
| 236 | GTGAACTCCACAAACAGGGT | RSA56.R primer |
| 237 | AGTGAACTCCACAAACAGGG | TFR1(DD) primer |
| 238 | CCACAGCCCCCAGGTAGTAT | TFP1(DD) probe |
| 239 | TCTAGTAATGGAAGCCTGGT | AlbF(DD) primer |
| 240 | AGGCCCTATGAGACCGTAAT | AlbR(DD) primer |
| 241 | TGCATCTGAGAACCCTTAGGTG | AlbP(DD) probe |
| 242 | TTCCATTGCCTCTCTACGCC | hTF1,2 PCR Primer F |
| 243 | CTGAAGCCAGCCATGGGTAA | hTF1,2 PCR Primer R |
| 244 | GCACGTCTAACCAGGTTATC | hTF1,2 Sequencing Primer F |
| 245 | CTATGGGAACTCTGGAGGCAG | hTF66 PCR Primer F |

| SEQ ID NO | Sequence | Description |
|---|---|---|
| 246 | CCCCATGGAACATAAGCCTCA | hTF66 PCR Primer R |
| 247 | CTCATGCATCCTGGAGAGCT | hTF66 Sequencing Primer F |
| 248 | GGCATCATTCTCTGAGTCTCACTC | hTF100 PCR Primer F |
| 249 | GCCCTGATGCAATCAAGGTAGG | hTF100 PCR Primer R |
| 250 | GAGTCTCACTCCCTCTTCTC | hTF100 Sequencing Primer F |
| 251 | cctgcaggcagctgcgcgctcgctcgctcactgaggccgcccgggcaaagcccgggcgtc gggcgacctttggtcgcccggcctcagtgagcgagcgagcgcgcagagagggagtgg ccaactccatcactaggggttcctgcggcctaaggcAATTGCCTGTAACGATCGGGAA CTGGCAGATCcacacaaaaaaccaacacacacagatctaatgaaaataaagatctttttattcgc gaTCAGTACAGGTCCTGGGCCTCACAGCCCAGCACCTCCATCCTCAGGGCAATCTGGTGCACCCA GCTCTGGGGGTGAATCCTCAGGTATCTGGTCAGCAGGGGGGGTCCAGGCTGTTCACCACAGG GGTGAAGCTGTCCTGGTTGCCCTGGAACACCTTCACCTTGCCATTCTGGAAGAACAGGGTCCAC TGGTGGCCATCCTGGCTGCTGCTGATCAGGAACTCCTTCACATACATGCTGGTCAGCAGGCTCTT CACCCCCTGGGTGGTCACCCCAGTCACCTTCATGGTCTTCTGGAAGTCCACCTGCAGCCACTCCT TGGGGTTGTTGACCTGGGGCCTCCAGGCATTGCTCCTGCCCTGCAGGTGCAGCCTGGCCTTGCT GGGGCTCCAGGTGGCAAACATGTTGGTGAAGTAGCTGCTGGCAGTGATCTGGGCATCAGAGAT GGCCTTGCTCTCCATGCCCAGGGGCATGCTGCAGCTGTTCAGGTCACAGCCCATCAGCTCCATCC TCAGGGTGCTCCTGATGCTGTAGTGGGTGGGGTGCAGCCTGATGTATCTGGCAATGATGGGGG GGTTGAAGATGTTGTGCTTGATGCCAGAGCTGTCCACATTGCCAAAGAACACCATCAGGGTGCC AGTGCTGTTGCCCCTGTAGGTCTGCCACTTCTTGCCATCCAGGCTGTACATGATGATGAACTGGC TGATGTACAGGCTGCTGAACTTCTGCCTGGCCCCCTGGGTCTTGATGCCATGGATGATCATGGG GGCCAGCAGGTCCACCTTGATCCAGCTGAAGGGCTCCTTGGTGCTCCAGGCATTGATGCTGCCA GAGTAGTGCAGCCTGGCCAGCTTGGGGGCCCACTGGCCATACTGGCCAGAGGCAGTGATCTGG AAGTCCCTGATGTGGCCAGAGGCCATGCCCAGGGGGGTCTGGCACTTGTTGCTGTACACCAGG AACAGGGTGCTCATGCCAGCATGCAGGTGCTCCCCAATCAGGCACTCCACCCTCCAGATGCCAG CCTTGCTGGGCAGCATCTCCACAGTCTCAAACACCCCAGGGTACAGGTTGTACAGGGCCATCTT GTACTCCTCCTTCTTCCTCACAGTGAACACATGGCCAGAGAAGTGGATGCTGTGGATGTTCTCAT TGCTGCCCATGCTCAGCAGGTACCACCTGATCCTCTGGTCCTGGGCCATCACCAGGCCAGGCAG GGTGTCCATGATGTAGCCATTGATGGCATGGAACCTGTAGTTCTCCTTGAAGGTGGGGTCCTCC ATCTGGATGTTGCAGGGGGCCCTGCAGTTCCTCTCCATGTTCTCAGTGAAGTACCAGCTCTTGGT TTCATCAAAGATGGTGAAGAACAGGGCAAACTCCTGCACAGTCACCTGCCTGCCATGGGCAGG GTTCAGGGTGTTGGTGTGGCACACCAGCAGGGGGCCAATCAGGCCAGAGTGCACATCCTTCTCC AGGTCCACATCAGAGAAGTAGGCCCAGGCCTTGCAGTCAAACTCATCCTTGGTGGGGCCATGT GGTGCTGCACCTTCCAGAAGTAGGTCTTGGTTTCATTGGGCTTCACAAAGTTCTTCCTGGGCTCA GCCCCCTGCCTCTGGTCCTCCTCATAGCTGATCAGGCTGCTGTAGAAGCTGTAGGGCCTGCTGGC CTGGTTCCTGAAGGTCACCATGATGTTGTCCTCCACCTCAGCCCTGATGGGGCCCAGCAGG CCCAGGTGCTCATTCAGCTCCCCTCTGTACAGGGGCTGGGTGAAGCTGCCATCAGTGAACTCCT GGAACACCACCTTCTTGAACTGGGGCACAGAGCCAGACTGGGCCCTGTTCCTCAGCACCATGGGG GCTGCTGCTCATGCCATAGTCCCACAGCCTCTCCACAGCAGCAATGAAGTAGTGCCTGGTCTTCT TCTGGAAGCTCCTGGGGCTCTGGTTCTCGTCCTCGTCGTAGATGTCAAAGTCCTCCTTCTTCATCT CCACAGAGATGGTGTCATCATAGTCAATCCTCCTGGTCAGACTGCAGGGTGGTCCTGGTGAT CTCCCTCTGGTGCCTCTTCAGCACTGGGGGAGACACATTGCTGCTCATTGCTGGTGTTGCTGTTGT TAGACACATTAGTGGCATTCTGGCTGAAGCTCCTGGGCTCAATGGCATTGTTCTTGCTCAGCAGG TAGGCAGAGATGTCCTCATAGCTGTCCTCATAGTAGTCCCCAGTGTTCTTGTCACAGCTGGAGAC TTTCAGCAGGGCAGTCATGCCCCTGTTCCTGAAGTCAGAGTTGTGGCAGCCCAGAATCCACAGG CCAGGGTTCTCCATGCTCATGAACACAGTCTCCCCAGAGAAGGGGAACAGGGTCAGGGTCCT CATACACCATCTTGTGCTTGAAGGTGTAGCCAGAGAAGAACACAGACAGGAAGTCAGTCTGGG CCCCAATGCTCAGGATGTACCAGTAGGCCACCTCATGCAGGCACACAGACAGCTGCAGGCTGTC AAACACATAGCCATTGATGCTGTGCATGATGTTGCTGGCCTGGAACTCAGGGTCCTCCAGCTGC ACCCCAGCAGGGTTGGGCAGGAACCTCTGGATGTTCTCAGTCAGGTACCAGCTCCTGTTCTCATC AAACACAGAGAACAGGATCACATTCCTCTTGTCAGACATGATCTGGTTGCCCCTCTGGTCCACAG ACTCCTTGTAGCAGATCAGCAGGGGGCCAATCAGGCCAGAGGCCAGGTCCCTCTCCATGTTCAC AAAGCTGCTGTAGTATCTGGTCAGGCACCTGGGGTCAGACTTGGTGGGGCCATCCTCCACAGTC ACAGTCCACTTGTACTTGAAGATCTCCCCAGGCAGGATGGGGAAGTCCTTCAGGTGCTTCACCC CCTTGGGCAGCCTCCTGCTGTACAGGGGCCTCACATCAGTGATGCCATGGGGTAGATGTTGTA GGGCTGCTGGCCTGGTTCTTGAAGATGATCAGGGTGTCCCCACCTCCCCATACAGCAGG GGGCCCAGGATGCCAGACTCATGCTGGATGGCCTCCCTGGTCTTGAAGGTTTCATCAGTGTAGG CCATGAACCTGACCTTCTTGTACTTCCTGCCAATCCTCTGGGGGCCATTGTTCAGGTACTGGCTCT TGTAGCTCCTGTCATCAGGGGCCAGCACCAGGGGGGCATAGTCCCAGTCCTCCTCCTCAGCAGC AATGTAGTGCACCCAGGTCTTGGGGTGCTTCTTGGCCACAGACCTGATCTGGATGAAGCTGGGG CTGTTGTCATCATCAAACCTCACCACATCCATCTCAGAGTCAGTCAGGTCATCATCATAGTCCTCA GCCTCCTCATTGTTCTTCATCCTCAGCTGGGGCTCCTCAGGGCAGCTGTCCACCTTCACATAGGCC | pCB099 (FVIII donor for integration into albumin intron 1) |

| SEQ ID NO | Sequence | Description |
|---|---|---|
| | TCCATGCCATCATGCTGGTGGCTGCTGATGTGGCAGAACAGCAGGAACTGGCCCAGGTCCATCA GCAGGGTCTGGGCAGTCAGGAAGGTGATGGGGCTGATCTCCAGGCTGGCCTGCCTGTGGTTCC TGACCAGGAAGGTGTGGCCCTCCAGGAAGATGCTGTGCACCTCAGGGGTGGTGCCCATGCCAA TCACATGCCAGTACACAGACTTCCTGTGGCAGCCAATCAGGCCAGGCAGGCTCCTGTTCACATA GCCATTCACAGTGTGCATCTTGGGCCAGGCCCTGGCAGAGGCAGCATCCCTGTCCTGCATCAGG CTGTTCTTGGTTTCAGAGTGCCAGCTCTTGCCCTCATCAAACACAGCAAACAGCAGGATGAACTT GTGCAGGGTCTGGGTCTTCTCCTTGGCCAGGCTGCCCTCCCTGCACACCAGCAGGGCCCCAATC AGGCCAGAGTTCAGGTCCTTCACCAGGTCCACATGGCTCAGGTAGCTGTAGGTCAGGCACAGG GGGTCAGAGGGCATGGGGCATTCTCCTTCAGCACCTGCCACACATAGGTGTGGCTGCCCCCAG GGAACACCTTGTCATCCTCCTTCTCCCTCTGGCTGGTCTGGTCATCATACTCAGCCCCCTCAGAGG CCTTCCAGTAGCTCACCCCCACAGCATGCAGGCTCACAGGGTGGCTGGCCATGTTCTTCAGGGT GATCACCACAGTGTCATACACCTCAGCCTGGATGGTGGGGCCCAGCAGGCCCATCCAGGGGGG CCTGGGCTTGGCAATGTTGAACAGGTGGTCAGTGAACTCCACAAACAGGGTCTTCTTGTACACC ACAGAGGTGTTGAAGGGGAAGCTCTTGGGCACTCTGGGGGGGAACCTGGCATCCACAGGCAG CTCCCCCAGGTCAGACTGCATGTAGTCCCAGCTCAGCTCCACAGCCCCCAGGTAGTATCTCCTGG TGGCCACTGAAATGTAAAAGAATAATTCTTTAGTACGCTTTGAGGAGTACCGCCTGTAACGATC GGGAACTGGCACCGCgggccgcaggaaccccctagtgatggagttggccactccctctctgcgcgc tcgctcgctcactgaggccgggcgaccaaaggtcgcccgacgcccgggctttgcccgggcggcct cagtgagcgagcgagcgcgcagctgcctgcagg | |
| 252 | TGCCACCAGGGATGAGAGGAGGGTGGAACAGAGGAGAGGTGGCCATTAAGACCCTTCGcgaag gCGGTACTCCTCAAAGCGTACTAAAGAATTATTCTTTTACAT-TTCAGggctgtgtctggctGCCACCAG GAGATACTACCTGGGGGCTGTGGAGCTGAGCTGGGACTACATGCAGTCTGACCTGGGGGAGCT GCCTGTGGATGCCAGGTTCCCCCCCAGAGTGCCCAAGAGCTTCCCCTTCAACACCTCTGTGGTGT ACAAGAAGACCCTGTTTGTGGAGTTCACTGACCACCTGTT | Predicted sequence for 5' Trf-F8 Junction |

---

What is claimed is:

1. A system comprising:
   a deoxyribonucleic acid (DNA) endonuclease or nucleic acid encoding the DNA endonuclease;
   a guide RNA (gRNA) comprising a spacer sequence that is complementary to a sequence within intron 1 of an endogenous transferrin gene in a cell; and
   a donor template comprising a nucleic acid sequence encoding a protein-of-interest (POI), wherein the POI is Factor VIII (FVIII).

2. The system of claim 1, wherein the gRNA comprises:
   i) a spacer sequence from any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190 or a variant thereof having no more than 3 mismatches compared to any one of SEQ ID NOs: 96, 5, 6, 9, 8, 11, 15, 16, 12, 7, 10, 17, 18, 29, 76, 50, 54, 81, 64, 51, 1-4, 13, 14, 19-28, 30-49, 52, 53, 55-63, 65-75, 77-80, 82-95, and 97-190;
   ii) a spacer sequence from any one of SEQ ID NOs: 5, 6, 9, 8, 11, 15, 16, 12, 7, and 10 or a variant thereof having no more than 3 mismatches compared to any one of SEQ ID NOs: 5, 6, 9, 8, 11, 15, 16, 12, 7, and 10;
   iii) a spacer sequence from any one of SEQ ID NOs: 17, 18, 29, 76, 50, 54, 81, 96, 64, and 51 or a variant thereof having no more than 3 mismatches compared to any one of SEQ ID NOs: 17, 18, 29, 76, 50, 54, 81, 96, 64, and 51; or
   iv) a spacer sequence from any one of SEQ ID NOs: 5, 6, 9, 8, and 11 or a variant thereof having no more than 3 mismatches compared to any one of SEQ ID NOs: 5, 6, 9, 8, and 11.

3. The system of claim 2, wherein the spacer sequence is 19 nucleotides in length and does not include the nucleotide at position 1 of the sequence from which it is selected.

4. The system of claim 1, wherein the DNA endonuclease is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional derivative thereof.

5. The system of claim 1, wherein the DNA endonuclease is Cas9.

6. The system of claim 1, wherein I) the nucleic acid encoding the DNA endonuclease is codon-optimized for expression in a host cell; II) the nucleic acid sequence encoding the POI is codon-optimized for expression in a host cell; and/or III) the nucleic acid sequence encoding the POI comprises a reduced content of CpG di-nucleotides than a nucleic acid sequence encoding the wild-type POI.

7. The system of claim 1, wherein the nucleic acid sequence encoding the POI:
   A) comprises about or less than 20 CpG di-nucleotides;
   B) comprises about or less than 10 CpG di-nucleotides;
   C) comprises about or less than 5 CpG di-nucleotides; or
   D) does not comprise CpG di-nucleotides.

8. The system of claim 1, wherein the nucleic acid encoding the DNA endonuclease is a ribonucleic acid (RNA).

9. The system of claim 1, wherein the donor template is encoded in an Adeno Associated Virus (AAV) vector.

10. The system of claim 1, wherein the donor template comprises a donor cassette comprising the nucleic acid sequence encoding the POI, and wherein the donor cassette is flanked on one or both sides by a gRNA target site.

11. The system of claim 10, wherein the gRNA target site is a target site for a gRNA in the system.

12. The system of claim 11, wherein the gRNA target site of the donor template is the reverse complement of a genomic gRNA target site for a gRNA in the system.

13. The system of claim 1, wherein the DNA endonuclease or nucleic acid encoding the DNA endonuclease is formulated in a liposome or lipid nanoparticle.

14. The system of claim 13, wherein the liposome or lipid nanoparticle also comprises the gRNA.

15. The system of claim 1, comprising the DNA endonuclease precomplexed with the gRNA, forming a Ribonucleoprotein (RNP) complex.

* * * * *

SEQUENCE LISTING

<160> NUMBER OF SEQ ID NOS: 252

<210> SEQ ID NO 1
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T12 gRNA spacer

<400> SEQUENCE: 1
aaggaagcgg tgccatcgag                                           20

<210> SEQ ID NO 2
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T168 gRNA spacer

<400> SEQUENCE: 2
aacttctgcc tgccattcat                                           20

<210> SEQ ID NO 3
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T73 gRNA spacer

```
<400> SEQUENCE: 3
agcaaagggt tttgataacc                                               20

<210> SEQ ID NO 4
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T99 gRNA spacer

<400> SEQUENCE: 4
ttgcctggga gggtcaaatg                                               20

<210> SEQ ID NO 5
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T26 gRNA spacer

<400> SEQUENCE: 5
ggcttggcca acgacaagca                                               20

<210> SEQ ID NO 6
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T111 gRNA spacer

<400> SEQUENCE: 6
ccttgtgggc caccacagca                                               20

<210> SEQ ID NO 7
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T76 gRNA spacer

<400> SEQUENCE: 7
gggcccactc cctatgctga                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T128 gRNA spacer

<400> SEQUENCE: 8
tctgagtctg agccaataga                                               20
```

<210> SEQ ID NO 9
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T188 gRNA spacer

<400> SEQUENCE: 9
cctgcctcca gagttcccat                                          20

<210> SEQ ID NO 10
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T151 gRNA spacer

<400> SEQUENCE: 10
acagctctcc aggatgcatg                                          20

<210> SEQ ID NO 11
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T67 gRNA spacer

<400> SEQUENCE: 11
ggcccatggg aaatcctagg                                          20

<210> SEQ ID NO 12
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T138 gRNA spacer

<400> SEQUENCE: 12
agggtggtca gtaggaaact                                          20

<210> SEQ ID NO 13
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T115 gRNA spacer

<400> SEQUENCE: 13
ccttgctgtg gtggcccaca                                          20

<210> SEQ ID NO 14
<211> LENGTH: 20
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T45 gRNA spacer

<400> SEQUENCE: 14
ggtagcaagc caatgtgttg                                                    20

<210> SEQ ID NO 15
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T180 gRNA spacer

<400> SEQUENCE: 15
gcagattgtc atctccagct                                                    20

<210> SEQ ID NO 16
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T148 gRNA spacer

<400> SEQUENCE: 16
ccacagcaag gctgactcac                                                    20

<210> SEQ ID NO 17
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T100 gRNA spacer

<400> SEQUENCE: 17
actgaggctt atgttccatg                                                    20

<210> SEQ ID NO 18
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T66 gRNA spacer

<400> SEQUENCE: 18
gggcaaaagc tcatgtgata                                                    20

<210> SEQ ID NO 19
<211> LENGTH: 20
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: Transferrin_T162 gRNA spacer

<400> SEQUENCE: 19
atactgaggc ttatgttcca                                                    20

<210> SEQ ID NO 20
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T175 gRNA spacer

<400> SEQUENCE: 20
ccagtgagtc agccttgctg                                                    20

<210> SEQ ID NO 21
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T172 gRNA spacer

<400> SEQUENCE: 21
ggatttccca tgggccaaga                                                    20

<210> SEQ ID NO 22
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T104 gRNA spacer

<400> SEQUENCE: 22
gggtcaaatg agggtcagcg                                                    20

<210> SEQ ID NO 23
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T19 gRNA spacer

<400> SEQUENCE: 23
tcaactatgg aaaaccagcg                                                    20

<210> SEQ ID NO 24
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T77 gRNA spacer

<400> SEQUENCE: 24
```
cataagcctc agtatgcaca                                           20

<210> SEQ ID NO 25
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T62 gRNA spacer

<400> SEQUENCE: 25
tatgttccat gggggggccag                                          20

<210> SEQ ID NO 26
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T106 gRNA spacer

<400> SEQUENCE: 26
agggcccact ccctatgctg                                           20

<210> SEQ ID NO 27
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T163 gRNA spacer

<400> SEQUENCE: 27
gctgtgggcc tcctctccac                                           20

<210> SEQ ID NO 28
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T134 gRNA spacer

<400> SEQUENCE: 28
acaaatgccc catgaatggc                                           20

<210> SEQ ID NO 29
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T167 gRNA spacer

<400> SEQUENCE: 29
gtggctgtca aggcctttct                                           20

```
<210> SEQ ID NO 30
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T61 gRNA spacer

<400> SEQUENCE: 30
tcctgtccat gaacactaca                                               20

<210> SEQ ID NO 31
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T6 gRNA spacer

<400> SEQUENCE: 31
agacagcatc gcccctagaa                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T44 gRNA spacer

<400> SEQUENCE: 32
ccttcttggc cagtagttga                                               20

<210> SEQ ID NO 33
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T3 gRNA spacer

<400> SEQUENCE: 33
aaggtcaccc tgcttgtcgt                                               20

<210> SEQ ID NO 34
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T68 gRNA spacer

<400> SEQUENCE: 34
gagggaaaat gggggtcgct                                               20

<210> SEQ ID NO 35
<211> LENGTH: 20
<212> TYPE: DNA
<213> ORGANISM: Artificial sequence
```

-continued

```
<220> FEATURE:
<223> OTHER INFORMATION: Synthetic polynucleotide
<220> FEATURE:
<221> NAME/KEY: misc_feature
<223> OTHER INFORMATION: Transferrin_T103 gRNA spacer

<400> SEQUENCE: 35
taggaggcaa cataagcctg                                                    20

<210> SEQ ID NO 36
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T81 gRNA spacer

<400> SEQUENCE: 36
aaaacgccct gtgcatactg                                                    20

<210> SEQ ID NO 37
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T146 gRNA spacer

<400> SEQUENCE: 37
gtgagtcagc cttgctgtgg                                                    20

<210> SEQ ID NO 38
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T63 gRNA spacer

<400> SEQUENCE: 38
ggctgtcaag gcctttctag                                                    20

<210> SEQ ID NO 39
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T87 gRNA spacer

<400> SEQUENCE: 39
aggtagcaag ccaatgtgtt                                                    20

<210> SEQ ID NO 40
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

<223> OTHER INFORMATION: Transferrin_T184 gRNA spacer

<400> SEQUENCE: 40
gattgtcatc tccagctggg					20

<210> SEQ ID NO 41
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T116 gRNA spacer

<400> SEQUENCE: 41
tcctggccgg ctcctcacca					20

<210> SEQ ID NO 42
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T24 gRNA spacer

<400> SEQUENCE: 42
attctcgcct atgggaactc					20

<210> SEQ ID NO 43
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T21 gRNA spacer

<400> SEQUENCE: 43
tggcttggcc aacgacaagc					20

<210> SEQ ID NO 44
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T41 gRNA spacer

<400> SEQUENCE: 44
ttggcttgct acctcaacta					20

<210> SEQ ID NO 45
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T55 gRNA spacer

<400> SEQUENCE: 45
gaggtagcaa gccaatgtgt                                               20

<210> SEQ ID NO 46
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T90 gRNA spacer

<400> SEQUENCE: 46
aggagacaag gcggatacag                                               20

<210> SEQ ID NO 47
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T101 gRNA spacer

<400> SEQUENCE: 47
gactctgggt ctgctactca                                               20

<210> SEQ ID NO 48
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T39 gRNA spacer

<400> SEQUENCE: 48
ccgctggttt tccatagttg                                               20

<210> SEQ ID NO 49
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T150 gRNA spacer

<400> SEQUENCE: 49
cctcaactat ggaaaaccag                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T156 gRNA spacer

<400> SEQUENCE: 50
tggattttaa tagttaccca                                               20

<210> SEQ ID NO 51

```
<210> SEQ ID NO 51
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T40 gRNA spacer

<400> SEQUENCE: 51
ggggataaag gcaagtaacg                                         20

<210> SEQ ID NO 52
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T8 gRNA spacer

<400> SEQUENCE: 52
ccgggttgca gggaacgcgc                                         20

<210> SEQ ID NO 53
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T53 gRNA spacer

<400> SEQUENCE: 53
cgcgcgggcc agcgactctg                                         20

<210> SEQ ID NO 54
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T117 gRNA spacer

<400> SEQUENCE: 54
ctgaggctta tgttccatgg                                         20

<210> SEQ ID NO 55
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T49 gRNA spacer

<400> SEQUENCE: 55
cggagtgcat gcaggctgcg                                         20

<210> SEQ ID NO 56
<211> LENGTH: 20
<212> TYPE: DNA
<213> ORGANISM: Artificial sequence
<220> FEATURE:
```

```
<223> OTHER INFORMATION: Synthetic polynucleotide
<220> FEATURE:
<221> NAME/KEY: misc_feature
<223> OTHER INFORMATION: Transferrin_T83 gRNA spacer

<400> SEQUENCE: 56
acaggcttat gttgcctcct                                                    20

<210> SEQ ID NO 57
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T64 gRNA spacer

<400> SEQUENCE: 57
gggcatttgt cacactgttg                                                    20

<210> SEQ ID NO 58
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T120 gRNA spacer

<400> SEQUENCE: 58
tggcccctcc tcatgcatcc                                                    20

<210> SEQ ID NO 59
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T161 gRNA spacer

<400> SEQUENCE: 59
aaaatggagg gatagttcag                                                    20

<210> SEQ ID NO 60
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T183 gRNA spacer

<400> SEQUENCE: 60
tgtgacaaat gccccatgaa                                                    20

<210> SEQ ID NO 61
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T182 gRNA spacer
```

```
<400> SEQUENCE: 61
gtggtcagta ggaaactggg                                              20

<210> SEQ ID NO 62
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T119 gRNA spacer

<400> SEQUENCE: 62
tgaggcttat gttccatggg                                              20

<210> SEQ ID NO 63
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T18 gRNA spacer

<400> SEQUENCE: 63
gggataaagg caagtaacgt                                              20

<210> SEQ ID NO 64
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T107 gRNA spacer

<400> SEQUENCE: 64
agggcaaaag ctcatgtgat                                              20

<210> SEQ ID NO 65
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T20 gRNA spacer

<400> SEQUENCE: 65
gccatcgagc ggtcagagca                                              20

<210> SEQ ID NO 66
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T80 gRNA spacer

<400> SEQUENCE: 66
ccctcaacta ctggccaaga                                              20
```

```
<210> SEQ ID NO 67
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T133 gRNA spacer

<400> SEQUENCE: 67
cctcaactac tggccaagaa                                               20

<210> SEQ ID NO 68
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T84 gRNA spacer

<400> SEQUENCE: 68
gagggtggtc agtaggaaac                                               20

<210> SEQ ID NO 69
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T85 gRNA spacer

<400> SEQUENCE: 69
gtcgctgggg tggccatccc                                               20

<210> SEQ ID NO 70
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T143 gRNA spacer

<400> SEQUENCE: 70
tggggagaga aaactaaacg                                               20

<210> SEQ ID NO 71
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T15 gRNA spacer

<400> SEQUENCE: 71
cctgagcgcg gagtgcatgc                                               20

<210> SEQ ID NO 72
<211> LENGTH: 20
```

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T96 gRNA spacer

<400> SEQUENCE: 72
gcgaccccca ttttccctct                                                    20

<210> SEQ ID NO 73
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T118 gRNA spacer

<400> SEQUENCE: 73
ctcaactatg gaaaaccagc                                                    20

<210> SEQ ID NO 74
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T152 gRNA spacer

<400> SEQUENCE: 74
gatccacaaa gcctgtggag                                                    20

<210> SEQ ID NO 75
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T38 gRNA spacer

<400> SEQUENCE: 75
ccccgcacag agcacttcac                                                    20

<210> SEQ ID NO 76
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T132 gRNA spacer

<400> SEQUENCE: 76
tgcaaggtaa tgctccactg                                                    20

<210> SEQ ID NO 77
<211> LENGTH: 20
<212> TYPE: DNA
<213> ORGANISM: Artificial sequence
<220> FEATURE:
<223> OTHER INFORMATION: Synthetic polynucleotide
```

```
<220> FEATURE:
<221> NAME/KEY: misc_feature
<223> OTHER INFORMATION: Transferrin_T149 gRNA spacer

<400> SEQUENCE: 77
aggggacgtc agcctctgaa                                                    20

<210> SEQ ID NO 78
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T171 gRNA spacer

<400> SEQUENCE: 78
agggaaaatg ggggtcgctg                                                    20

<210> SEQ ID NO 79
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T30 gRNA spacer

<400> SEQUENCE: 79
tgaggacaca ttctcgccta                                                    20

<210> SEQ ID NO 80
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T71 gRNA spacer

<400> SEQUENCE: 80
tgcctcctag gatttcccat                                                    20

<210> SEQ ID NO 81
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T158 gRNA spacer

<400> SEQUENCE: 81
cttggcccat gggaaatcct                                                    20

<210> SEQ ID NO 82
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T36 gRNA spacer
```

```
<400> SEQUENCE: 82
aggagttcgg acttgacaag                                              20

<210> SEQ ID NO 83
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T27 gRNA spacer

<400> SEQUENCE: 83
acataagcct cagtatgcac                                              20

<210> SEQ ID NO 84
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T130 gRNA spacer

<400> SEQUENCE: 84
caggacatct acagctccca                                              20

<210> SEQ ID NO 85
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T124 gRNA spacer

<400> SEQUENCE: 85
gggccccacc tcaggaggtc                                              20

<210> SEQ ID NO 86
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T185 gRNA spacer

<400> SEQUENCE: 86
aacgacaagc agggtgacct                                              20

<210> SEQ ID NO 87
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T79 gRNA spacer

<400> SEQUENCE: 87
gcaggacatc tacagctccc                                              20
```

<210> SEQ ID NO 88
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T72 gRNA spacer

<400> SEQUENCE: 88
cctgtgaagt gctctgtgcg                                               20

<210> SEQ ID NO 89
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T179 gRNA spacer

<400> SEQUENCE: 89
tgcctgggag ggtcaaatga                                               20

<210> SEQ ID NO 90
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T170 gRNA spacer

<400> SEQUENCE: 90
tggccatgcc tgcacccctc                                               20

<210> SEQ ID NO 91
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T181 gRNA spacer

<400> SEQUENCE: 91
gccagcagag ggtggtcagt                                               20

<210> SEQ ID NO 92
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T42 gRNA spacer

<400> SEQUENCE: 92
ctcctgtcca tgaacactac                                               20

<210> SEQ ID NO 93
<211> LENGTH: 20
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T114 gRNA spacer

<400> SEQUENCE: 93
ggagtgggcc cttccacctc                                              20

<210> SEQ ID NO 94
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T23 gRNA spacer

<400> SEQUENCE: 94
caactatgga aaaccagcgg                                              20

<210> SEQ ID NO 95
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T144 gRNA spacer

<400> SEQUENCE: 95
tactgaggct tatgttccat                                              20

<210> SEQ ID NO 96
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T1 gRNA spacer

<400> SEQUENCE: 96
cccatgctct gaccgctcga                                              20

<210> SEQ ID NO 97
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T186 gRNA spacer

<400> SEQUENCE: 97
ctccccgacc tcctgaggtg                                              20

<210> SEQ ID NO 98
<211> LENGTH: 20
<212> TYPE: DNA
<213> ORGANISM: Artificial sequence
<220> FEATURE:
<223> OTHER INFORMATION: Synthetic polynucleotide
<220> FEATURE:
```

<221> NAME/KEY: misc_feature
<223> OTHER INFORMATION: Transferrin_T58 gRNA spacer

<400> SEQUENCE: 98
ggggaatggt cagacccggg                                            20

<210> SEQ ID NO 99
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T113 gRNA spacer

<400> SEQUENCE: 99
cttgtgccct gtagtgttca                                            20

<210> SEQ ID NO 100
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T29 gRNA spacer

<400> SEQUENCE: 100
cccgcgcgtt ccctgcaacc                                            20

<210> SEQ ID NO 101
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T2 gRNA spacer

<400> SEQUENCE: 101
ccatcgagcg gtcagagcat                                            20

<210> SEQ ID NO 102
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T48 gRNA spacer

<400> SEQUENCE: 102
gccctgtagt gttcatggac                                            20

<210> SEQ ID NO 103
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T17 gRNA spacer

<400> SEQUENCE: 103
aaatcagagc acgtctaacc                                                20

<210> SEQ ID NO 104
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T153 gRNA spacer

<400> SEQUENCE: 104
gcctgtgaag tgctctgtgc                                                20

<210> SEQ ID NO 105
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T60 gRNA spacer

<400> SEQUENCE: 105
ctcgcctatg ggaactctgg                                                20

<210> SEQ ID NO 106
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T164 gRNA spacer

<400> SEQUENCE: 106
ggccccacct caggaggtcg                                                20

<210> SEQ ID NO 107
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T47 gRNA spacer

<400> SEQUENCE: 107
ccgcgcgttc cctgcaaccc                                                20

<210> SEQ ID NO 108
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T110 gRNA spacer

<400> SEQUENCE: 108
tggctgtcaa ggcctttcta                                                20

```
<210> SEQ ID NO 109
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T177 gRNA spacer

<400> SEQUENCE: 109
tggcagatgc tgagtaccag                                             20

<210> SEQ ID NO 110
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T13 gRNA spacer

<400> SEQUENCE: 110
gttaatttac cctcaactac                                             20

<210> SEQ ID NO 111
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T7 gRNA spacer

<400> SEQUENCE: 111
cctgcatgca ctccgcgctc                                             20

<210> SEQ ID NO 112
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T89 gRNA spacer

<400> SEQUENCE: 112
gaccctcatt tgaccctccc                                             20

<210> SEQ ID NO 113
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T16 gRNA spacer

<400> SEQUENCE: 113
ccattagggc aaccttctat                                             20

<210> SEQ ID NO 114
<211> LENGTH: 20
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<223> OTHER INFORMATION: Transferrin_T155 gRNA spacer

<400> SEQUENCE: 114
atgcatgagg aggggccacc                                               20

<210> SEQ ID NO 115
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T108 gRNA spacer

<400> SEQUENCE: 115
gtcagccact gccccatagc                                               20

<210> SEQ ID NO 116
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T160 gRNA spacer

<400> SEQUENCE: 116
cctatgggaa ctctggaggc                                               20

<210> SEQ ID NO 117
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T139 gRNA spacer

<400> SEQUENCE: 117
acttctgcct gccattcatg                                               20

<210> SEQ ID NO 118
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T11 gRNA spacer

<400> SEQUENCE: 118
cggtggccgc ccgggttgca                                               20

<210> SEQ ID NO 119
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

```
<223> OTHER INFORMATION: Transferrin_T169 gRNA spacer

<400> SEQUENCE: 119
ggggacgtca gcctctgaaa                                               20

<210> SEQ ID NO 120
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T5 gRNA spacer

<400> SEQUENCE: 120
gaggacacat tctcgcctat                                               20

<210> SEQ ID NO 121
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T131 gRNA spacer

<400> SEQUENCE: 121
gcatggcatt caaggcctcc                                               20

<210> SEQ ID NO 122
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T22 gRNA spacer

<400> SEQUENCE: 122
catcgagcgg tcagagcatg                                               20

<210> SEQ ID NO 123
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T126 gRNA spacer

<400> SEQUENCE: 123
ctcaactact ggccaagaag                                               20

<210> SEQ ID NO 124
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T145 gRNA spacer

<400> SEQUENCE: 124
```

```
ctgtggtggc ccacaaggag                                              20

<210> SEQ ID NO 125
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T187 gRNA spacer

<400> SEQUENCE: 125
tctgctggcc agagggtgc                                               20

<210> SEQ ID NO 126
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T112 gRNA spacer

<400> SEQUENCE: 126
aggcgagaat gtgtcctcag                                              20

<210> SEQ ID NO 127
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T14 gRNA spacer

<400> SEQUENCE: 127
gctcgatggc accgcttcct                                              20

<210> SEQ ID NO 128
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T70 gRNA spacer

<400> SEQUENCE: 128
gtcctggccg gctcctcacc                                              20

<210> SEQ ID NO 129
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T57 gRNA spacer

<400> SEQUENCE: 129
tttcagctac cccaacacat                                              20

<210> SEQ ID NO 130
```

```
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T4 gRNA spacer

<400> SEQUENCE: 130
gggtagcacc gcagagtcgc                                               20

<210> SEQ ID NO 131
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T92 gRNA spacer

<400> SEQUENCE: 131
cccttcttgg ccagtagttg                                               20

<210> SEQ ID NO 132
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T102 gRNA spacer

<400> SEQUENCE: 132
aaaggggaat ggtcagaccc                                               20

<210> SEQ ID NO 133
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T159 gRNA spacer

<400> SEQUENCE: 133
agctagcaat tccttgagag                                               20

<210> SEQ ID NO 134
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T10 gRNA spacer

<400> SEQUENCE: 134
catgcactcc gcgctcaggc                                               20

<210> SEQ ID NO 135
<211> LENGTH: 20
<212> TYPE: DNA
<213> ORGANISM: Artificial sequence
<220> FEATURE:
```

<223> OTHER INFORMATION: Synthetic polynucleotide
<220> FEATURE:
<221> NAME/KEY: misc_feature
<223> OTHER INFORMATION: Transferrin_T157 gRNA spacer

<400> SEQUENCE: 135
ttgcctccta ggatttccca                                              20

<210> SEQ ID NO 136
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T173 gRNA spacer

<400> SEQUENCE: 136
catcacagca cttgcctggg                                              20

<210> SEQ ID NO 137
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T121 gRNA spacer

<400> SEQUENCE: 137
tgatgacccc ctccctggtg                                              20

<210> SEQ ID NO 138
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T137 gRNA spacer

<400> SEQUENCE: 138
agcagattgt catctccagc                                              20

<210> SEQ ID NO 139
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T98 gRNA spacer

<400> SEQUENCE: 139
tcaaatgagg gtcagcgagg                                              20

<210> SEQ ID NO 140
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T141 gRNA spacer

```
<400> SEQUENCE: 140
tggccggctc ctcaccaggg                                               20

<210> SEQ ID NO 141
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T50 gRNA spacer

<400> SEQUENCE: 141
gatggcaatt cctcccccgc                                               20

<210> SEQ ID NO 142
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T94 gRNA spacer

<400> SEQUENCE: 142
caaggaattg ctagcttatg                                               20

<210> SEQ ID NO 143
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T86 gRNA spacer

<400> SEQUENCE: 143
taacgtgggg tcctctctca                                               20

<210> SEQ ID NO 144
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T35 gRNA spacer

<400> SEQUENCE: 144
agtgctctgt gcggggataa                                               20

<210> SEQ ID NO 145
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T174 gRNA spacer

<400> SEQUENCE: 145
cattttccct cttggcccat                                               20
```

```
<210> SEQ ID NO 146
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T97 gRNA spacer

<400> SEQUENCE: 146
ttcactgctg caagatttac                                                20

<210> SEQ ID NO 147
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T127 gRNA spacer

<400> SEQUENCE: 147
gtgaggagcc ggccaggact                                                20

<210> SEQ ID NO 148
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T56 gRNA spacer

<400> SEQUENCE: 148
atgttgcaca catcctgcta                                                20

<210> SEQ ID NO 149
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T65 gRNA spacer

<400> SEQUENCE: 149
tcaaggaatt gctagcttat                                                20

<210> SEQ ID NO 150
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T123 gRNA spacer

<400> SEQUENCE: 150
tcttggatcc aagtcctggc                                                20

<210> SEQ ID NO 151
<211> LENGTH: 20
```

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T59 gRNA spacer

<400> SEQUENCE: 151
ttctgagtta cacccttct                                              20

<210> SEQ ID NO 152
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T129 gRNA spacer

<400> SEQUENCE: 152
ttcagaggct gacgtcccct                                             20

<210> SEQ ID NO 153
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T9 gRNA spacer

<400> SEQUENCE: 153
ccaatagaag gttgccctaa                                             20

<210> SEQ ID NO 154
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T122 gRNA spacer

<400> SEQUENCE: 154
cactccccga cctcctgagg                                             20

<210> SEQ ID NO 155
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T31 gRNA spacer

<400> SEQUENCE: 155
cgcgttccct gcaacccggg                                             20

<210> SEQ ID NO 156
<211> LENGTH: 20
<212> TYPE: DNA
<213> ORGANISM: Artificial sequence
<220> FEATURE:
<223> OTHER INFORMATION: Synthetic polynucleotide
```

```
<220> FEATURE:
<221> NAME/KEY: misc_feature
<223> OTHER INFORMATION: Transferrin_T28 gRNA spacer

<400> SEQUENCE: 156
gatggcaccg cttccttggc                                                      20

<210> SEQ ID NO 157
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T43 gRNA spacer

<400> SEQUENCE: 157
tatgaagggg gccccacctc                                                      20

<210> SEQ ID NO 158
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T125 gRNA spacer

<400> SEQUENCE: 158
tgctgtgatg accccctccc                                                      20

<210> SEQ ID NO 159
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T165 gRNA spacer

<400> SEQUENCE: 159
cacatcctgc tatggggcag                                                      20

<210> SEQ ID NO 160
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T82 gRNA spacer

<400> SEQUENCE: 160
aggctgcgcg gtggccgccc                                                      20

<210> SEQ ID NO 161
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T109 gRNA spacer
```

```
<400> SEQUENCE: 161
tggggcattt gtcacactgt                                             20

<210> SEQ ID NO 162
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T52 gRNA spacer

<400> SEQUENCE: 162
ctcaaggaat tgctagctta                                             20

<210> SEQ ID NO 163
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T34 gRNA spacer

<400> SEQUENCE: 163
ctatggaaaa ccagcggggg                                             20

<210> SEQ ID NO 164
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T88 gRNA spacer

<400> SEQUENCE: 164
tgttgcacac atcctgctat                                             20

<210> SEQ ID NO 165
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T51 gRNA spacer

<400> SEQUENCE: 165
agagggaaaa tgggggtcgc                                             20

<210> SEQ ID NO 166
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T46 gRNA spacer

<400> SEQUENCE: 166
cttatgttcc atgggggggcc                                            20
```

<210> SEQ ID NO 167
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T178 gRNA spacer

<400> SEQUENCE: 167
tctgaccatt cccctttcag                                        20

<210> SEQ ID NO 168
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T74 gRNA spacer

<400> SEQUENCE: 168
ggggcatttg tcacactgtt                                        20

<210> SEQ ID NO 169
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T176 gRNA spacer

<400> SEQUENCE: 169
ccgcgctcag gctggaagcc                                        20

<210> SEQ ID NO 170
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T54 gRNA spacer

<400> SEQUENCE: 170
gcggtggccg cccgggttgc                                        20

<210> SEQ ID NO 171
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T32 gRNA spacer

<400> SEQUENCE: 171
tgcttgtcgt tggccaagcc                                        20

<210> SEQ ID NO 172
<211> LENGTH: 20
<212> TYPE: DNA

```
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T136 gRNA spacer

<400> SEQUENCE: 172
tccctggtga ggagccggcc                                               20

<210> SEQ ID NO 173
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T78 gRNA spacer

<400> SEQUENCE: 173
ttatgttcca tgggggccca                                               20

<210> SEQ ID NO 174
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T154 gRNA spacer

<400> SEQUENCE: 174
ttttaatagt tacccatggc                                               20

<210> SEQ ID NO 175
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T140 gRNA spacer

<400> SEQUENCE: 175
ccaggcttcc agcctgagcg                                               20

<210> SEQ ID NO 176
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T93 gRNA spacer

<400> SEQUENCE: 176
caggctgcgc ggtggccgcc                                               20

<210> SEQ ID NO 177
<211> LENGTH: 20
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: Transferrin_T95 gRNA spacer

<400> SEQUENCE: 177
atgtgtgcaa catctgccac                                               20

<210> SEQ ID NO 178
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T37 gRNA spacer

<400> SEQUENCE: 178
agtgcatgca ggctgcgcgg                                               20

<210> SEQ ID NO 179
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T91 gRNA spacer

<400> SEQUENCE: 179
actccccgac ctcctgaggt                                               20

<210> SEQ ID NO 180
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T166 gRNA spacer

<400> SEQUENCE: 180
gaaaggggaa tggtcagacc                                               20

<210> SEQ ID NO 181
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T105 gRNA spacer

<400> SEQUENCE: 181
cgcgctcagg ctggaagcct                                               20

<210> SEQ ID NO 182
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T142 gRNA spacer

<400> SEQUENCE: 182
```

```
gtgtctagaa gcccaagcaa                                                 20

<210> SEQ ID NO 183
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T25 gRNA spacer

<400> SEQUENCE: 183 cccggggttgc agggaacgcg                                                20

<210> SEQ ID NO 184
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T135 gRNA spacer

<400> SEQUENCE: 184
tttcagaggc tgacgtcccc                                                 20

<210> SEQ ID NO 185
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T69 gRNA spacer

<400> SEQUENCE: 185
gagctgtaga tgtcctgcca                                                 20

<210> SEQ ID NO 186
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T147 gRNA spacer

<400> SEQUENCE: 186
gggtcatcac agcacttgcc                                                 20

<210> SEQ ID NO 187
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T33 gRNA spacer

<400> SEQUENCE: 187
ggataaaggc aagtaacgtg                                                 20
```

```
<210> SEQ ID NO 188
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Transferrin_T75 gRNA spacer

<400> SEQUENCE: 188
tctccctcag catagggagt                                              20

<210> SEQ ID NO 189
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: mTF-T1 gRNA spacer

<400> SEQUENCE: 189
taacaagcaa gacccgtcgc                                              20

<210> SEQ ID NO 190
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: mTF-T2 gRNA spacer

<400> SEQUENCE: 190
gagaacgcac cactttacga                                              20

<210> SEQ ID NO 191
<211> LENGTH: 23
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Exemplary target nucleic acid sequence
<220> FEATURE:
<221> NAME/KEY: misc_feature
<222> LOCATION: (1)..(21)
<223> OTHER INFORMATION: N is any nucleotide
<220> FEATURE:
<221> NAME/KEY: misc_feature
<222> LOCATION: (22)..(22)
<223> OTHER INFORMATION: R is G or A

<400> SEQUENCE: 191
nnnnnnnnnn nnnnnnnnnn nrg                                          23

<210> SEQ ID NO 192
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: SQ link

<400> SEQUENCE: 192
```

Ser Phe Ser Gln Asn Pro Pro Val Leu Lys Arg His Gln Arg
1               5                   10

<210> SEQ ID NO 193
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: synthetic splice acceptor

<400> SEQUENCE: 193
ctgacctctt ctcttcctcc cacag                                            25

<210> SEQ ID NO 194
<211> LENGTH: 37
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: native splice acceptor sequence from the
      Transferrin gene intron 1/exon 2 boundary of human

<400> SEQUENCE: 194
ggagtgggcc cttccacctc tggcctctct cccccag                               37

<210> SEQ ID NO 195
<211> LENGTH: 6
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: polyadentylation signal

<400> SEQUENCE: 195 aauaaa                                                                  6

<210> SEQ ID NO 196
<211> LENGTH: 49
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: consensus synthetic poly A signal sequence

<400> SEQUENCE: 196
aataaaagat ctttattttc attagatctg tgtgttggtt ttttgtgtg                   49

<210> SEQ ID NO 197
<211> LENGTH: 225
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: bovine growth hormone polyA signal sequence

<400> SEQUENCE: 197
ctgtgccttc tagttgccag ccatctgttg tttgcccctc ccccgtgcct tccttgaccc       60

```
tggaaggtgc cactcccact gtcctttcct aataaaatga ggaaattgca tcgcattgtc    120
tgagtaggtg tcattctatt ctgggggtg gggtggggca ggacagcaag ggggaggatt    180
gggaagacaa tagcaggcat gctggggatg cggtgggctc tatgg                   225

<210> SEQ ID NO 198
<211> LENGTH: 122
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SV40 polyadenylation signal sequence

<400> SEQUENCE: 198
taagatacat tgatgagttt ggacaaacca caactagaat gcagtgaaaa aaatgcttta    60
tttgtgaaat ttgtgatgct attgctttat ttgtaaccat tataagctgc aataaacaag    120
tt                                                                   122

<210> SEQ ID NO 199
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T1 potential off-target site 1

<400> SEQUENCE: 199
tcacaaacag gacacgtcgc                                                20

<210> SEQ ID NO 200
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T1 potential off-target site 2

<400> SEQUENCE: 200
tcacaggcaa gacacatcgc                                                20

<210> SEQ ID NO 201
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T1 potential off-target site 3

<400> SEQUENCE: 201
taacatccag gacccgttgc                                                20

<210> SEQ ID NO 202
<211> LENGTH: 20
<212> TYPE: DNA
<213> ORGANISM: Artificial sequence
<220> FEATURE:
<223> OTHER INFORMATION: Synthetic polynucleotide
<220> FEATURE:
```

```
<221> NAME/KEY: misc_feature
<223> OTHER INFORMATION: Guide RNA mTF-T1 potential off-target site 4

<400> SEQUENCE: 202
taagaagcaa gacctggcgc                                          20

<210> SEQ ID NO 203
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T1 potential off-target site 5

<400> SEQUENCE: 203
aaacaaacaa gccccgtggc                                          20

<210> SEQ ID NO 204
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T1 potential off-target site 6

<400> SEQUENCE: 204
caacaagaaa gacgcggcgc                                          20

<210> SEQ ID NO 205
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T1 potential off-target site 7

<400> SEQUENCE: 205
cagcaagcaa gatccgtctc                                          20

<210> SEQ ID NO 206
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T1 potential off-target site 8

<400> SEQUENCE: 206
tatcaatcaa gacacgtcac                                          20

<210> SEQ ID NO 207
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T1 potential off-target site 9

<400> SEQUENCE: 207
```
tcaaaagcaa gacccatcac                                          20

<210> SEQ ID NO 208
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 1

<400> SEQUENCE: 208
atgcacacac cactttacga                                          20

<210> SEQ ID NO 209
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 2

<400> SEQUENCE: 209
gagaagagaa cactttacga                                          20

<210> SEQ ID NO 210
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 3

<400> SEQUENCE: 210
gtgaagccac cactttaaga                                          20

<210> SEQ ID NO 211
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 4

<400> SEQUENCE: 211
gtgaaagccc cactttaaga                                          20

<210> SEQ ID NO 212
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 5

<400> SEQUENCE: 212
cagcactcac cactttacaa                                          20

```
<210> SEQ ID NO 213
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 6

<400> SEQUENCE: 213
gaagacacac cactttacca                                              20

<210> SEQ ID NO 214
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 7

<400> SEQUENCE: 214
ctgaacgcac tactttacca                                              20

<210> SEQ ID NO 215
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 8

<400> SEQUENCE: 215
cagaacccac caccttacca                                              20

<210> SEQ ID NO 216
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Guide RNA mTF-T2 potential off-target site 9

<400> SEQUENCE: 216
gacagcgcac cactttctga                                              20

<210> SEQ ID NO 217
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Trf Primer F1

<400> SEQUENCE: 217
cagtatagtc caaacagcat ggtg                                         24

<210> SEQ ID NO 218
<211> LENGTH: 23
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<223> OTHER INFORMATION: Trf Primer R1

<400> SEQUENCE: 218
cactgaaatc cacacgatgg aga                                              23

<210> SEQ ID NO 219
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Trf Primer F2

<400> SEQUENCE: 219
gcctttccta gagttggtgt ctag                                             24

<210> SEQ ID NO 220
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Trf Primer R2

<400> SEQUENCE: 220
caagtgagtc aaaccagagg c                                                21

<210> SEQ ID NO 221
<211> LENGTH: 100
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: gRNA mTF1
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (2)..(3)
<223> OTHER INFORMATION: phosphorothioate backbone
<220> FEATURE:
<221> NAME/KEY: misc_feature
<222> LOCATION: (3)..(4)
<223> OTHER INFORMATION: phosphorothioate backbone
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: 2'-O-methyladenosine
<220> FEATURE:
```

```
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: 2'-O-methyladenosine
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: 2'-O-methyladenosine
<220> FEATURE:
<221> NAME/KEY: modified_base
<222> LOCATION: (70)..(70)
<223> OTHER INFORMATION: cm
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (77)..(78)
<223> OTHER INFORMATION: 2'-O-methyladenosine
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: 2'-O-methyladenosine
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: 2'-O-methyladenosine
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
```

-continued

```
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: misc_feature
<222> LOCATION: (97)..(98)
<223> OTHER INFORMATION: phosphorothioate backbone
<220> FEATURE:
<221> NAME/KEY: modified_base
<222> LOCATION: (97)..(100)
<223> OTHER INFORMATION: um
<220> FEATURE:
<221> NAME/KEY: misc_feature
<222> LOCATION: (98)..(99)
<223> OTHER INFORMATION: phosphorothioate backbone
<220> FEATURE:
<221> NAME/KEY: misc_feature
<222> LOCATION: (99)..(100)
<223> OTHER INFORMATION: phosphorothioate backbone

<400> SEQUENCE: 221
uaacaagcaa gacccgucgc guuuuagagc uagaaauagc aaguuaaaau aaggcuaguc      60
cguuaucaac uugaaaaagu ggcaccgagu cggugcuuuu                           100

<210> SEQ ID NO 222
<211> LENGTH: 100
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: gRNA mTF2
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (2)..(3)
<223> OTHER INFORMATION: phosphorothioate backbone
<220> FEATURE:
<221> NAME/KEY: misc_feature
<222> LOCATION: (3)..(4)
<223> OTHER INFORMATION: phosphorothioate backbone
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: 2'-O-methyladenosine
<220> FEATURE:
<221> NAME/KEY: modified_base
<222> LOCATION: (37)..(37)
<223> OTHER INFORMATION: um
<220> FEATURE:
<221> NAME/KEY: modified_base
```

```
<222> LOCATION: (38)..(38)
<223> OTHER INFORMATION: 2'-O-methyladenosine
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: 2'-O-methyladenosine
<220> FEATURE:
<221> NAME/KEY: modified_base
<222> LOCATION: (70)..(70)
<223> OTHER INFORMATION: cm
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (77)..(78)
<223> OTHER INFORMATION: 2'-O-methyladenosine
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: 2'-O-methyladenosine
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: 2'-O-methyladenosine
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
```

```
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: misc_feature
<222> LOCATION: (97)..(98)
<223> OTHER INFORMATION: phosphorothioate backbone
<220> FEATURE:
<221> NAME/KEY: modified_base
<222> LOCATION: (97)..(100)
<223> OTHER INFORMATION: um
<220> FEATURE:
<221> NAME/KEY: misc_feature
<222> LOCATION: (98)..(99)
<223> OTHER INFORMATION: phosphorothioate backbone
<220> FEATURE:
<221> NAME/KEY: misc_feature
<222> LOCATION: (99)..(100)
<223> OTHER INFORMATION: phosphorothioate backbone

<400> SEQUENCE: 222
gagaacgcac cacuuuacga guuuuagagc uagaaauagc aaguuaaaau aaggcuaguc    60
cguuaucaac uugaaaaagu ggcaccgagu cggugcuuuu                         100

<210> SEQ ID NO 223
<211> LENGTH: 4438
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: spCas9 mRNA with NLS sequences

<400> SEQUENCE: 223
ggaaataaga gagaaaagaa gagtaagaag aaatataaga gccaccatgg ccccaaagaa    60
gaagcggaag gtcggtatcc acggagtccc agcagccgac aagaagtaca gcatcggcct   120
ggacatcggc accaactctg tgggctgggc cgtgatcacc gacgagtaca aggtgcccag   180
caagaaattc aaggtgctgg gcaacaccga ccggcacagc atcaagaaga acctgatcgg   240
agccctgctg ttcgacagcg gcgaaacagc cgaggccacc cggctgaaga gaaccgccag   300
aagaagatac accagacgga gaaccggat ctgctatctg caagagatct tcagcaacga   360
gatggccaag gtggacgaca gcttcttcca cagactggaa gagtccttcc tggtggaaga   420
ggacaagaag cacgagagac accccatctt cggcaacatc gtggacgagg tggcctacca   480
cgagaagtac cccaccatct accacctgag aaagaaactg gtggacagca ccgacaaggc   540
cgacctgaga ctgatctacc tggccctggc ccacatgatc aagttcagag gccacttcct   600
gatcgagggc gacctgaacc ccgacaacag cgacgtggac aagctgttca tccagctggt   660
gcagacctac aaccagctgt tcgaggaaaa ccccatcaac gccagcggcg tggacgccaa   720
ggctatcctg tctgccagac tgagcaagag cagaaggctg gaaaatctga tcgcccagct   780
gcccggcgag aagaagaacg gcctgttcgg caacctgatt gccctgagcc tgggcctgac   840
ccccaacttc aagagcaact tcgacctggc cgaggatgcc aaactgcagc tgagcaagga   900
cacctacgac gacgacctgg acaacctgct ggcccagatc ggcgaccagt acgccgacct   960
gttcctggcc gccaagaacc tgtctgacgc catcctgctg agcgacatcc tgagagtgaa  1020
caccgagatc accaaggccc ccctgagcgc ctctatgatc aagagatacg acgagcacca  1080
```

```
ccaggacctg accctgctga agctctcgt gcggcagcag ctgcctgaga agtacaaaga   1140
aatcttcttc gaccagagca agaacggcta cgccggctac atcgatggcg gcgctagcca   1200
ggaagagttc tacaagttca tcaagcccat cctggaaaag atggacggca ccgaggaact   1260
gctcgtgaag ctgaacagag aggacctgct gagaaagcag agaaccttcg acaacggcag   1320
catcccccac cagatccacc tgggagagct gcacgctatc ctgagaaggc aggaagattt   1380
ttacccattc ctgaaggaca accgggaaaa gatcgagaag atcctgacct tcaggatccc   1440
ctactacgtg ggcccctgg ccagaggcaa cagcagattc gcctggatga ccagaaagag   1500
cgaggaaacc atcacccct ggaacttcga ggaagtggtg acaagggcg ccagcgccca   1560
gagcttcatc gagagaatga caaacttcga taagaacctg cccaacgaga aggtgctgcc   1620
caagcacagc ctgctgtacg agtacttcac cgtgtacaac gagctgacca aagtgaaata   1680
cgtgaccgag ggaatgagaa agcccgcctt cctgagcggc gagcagaaaa aggccatcgt   1740
ggacctgctg ttcaagacca acagaaaagt gaccgtgaag cagctgaaag aggactactt   1800
caagaaaatc gagtgcttcg actccgtgga aatctccggc gtggaagata gattcaacgc   1860
ctccctgggc acataccacg atctgctgaa aattatcaag gacaaggact tcctggataa   1920
cgaagagaac gaggacattc tggaagatat cgtgctgacc ctgacactgt ttgaggaccg   1980
cgagatgatc gaggaaaggc tgaaaaccta cgctcacctg ttcgacgaca aagtgatgaa   2040
gcagctgaag agaaggcggt acaccggctg ggcaggctg agcagaaagc tgatcaacgg   2100
catcagagac aagcagagcg gcaagacaat cctggatttc ctgaagtccg acggcttcgc   2160
caaccggaac ttcatgcagc tgatccacga cgacagcctg acattcaaag aggacatcca   2220
gaaagcccag gtgtccggcc agggcgactc tctgcacgag catatcgcta acctggccgg   2280
cagccccgct atcaagaagg gcatcctgca gacagtgaag gtggtggacg agctcgtgaa   2340
agtgatgggc agacacaagc ccgagaacat cgtgatcgag atggctagag agaaccagac   2400
cacccagaag ggacagaaga actcccgcga ggaggatgaag agaatcgaag agggcatcaa   2460
agagctgggc agccagatcc tgaaagaaca ccccgtggaa aacacccagc tgcagaacga   2520
gaagctgtac ctgtactacc tgcagaatgg ccgggatatg tacgtggacc aggaactgga   2580
catcaacaga ctgtccgact acgatgtgga ccatatcgtg cctcagagct ttctgaagga   2640
cgactccatc gataacaaag tgctgactcg gagcgacaag aacagaggca gagcgacaa   2700
cgtgccctcc gaagaggtcg tgaagaagat gaagaactac tggcgacagc tgctgaacgc   2760
caagctgatt acccagagga gttcgataa cctgaccaag gccgagagag cggcctgag   2820
cgagctggat aaggccggct tcatcaagag gcagctggtg gaaaccagac agatcacaaa   2880
gcacgtggca cagatcctgg actcccggat gaacactaag tacgacgaaa cgataagct   2940
gatccgggaa gtgaaagtga tcaccctgaa gtccaagctg gtgtccgatt ccggaagga   3000
tttccagtt tacaaagtgc gcgagatcaa caactaccac cacgcccacg acgcctacct   3060
gaacgccgtc gtgggaaccg ccctgatcaa aaagtaccct aagctggaaa gcgagttcgt   3120
gtacggcgac tacaaggtgt acgacgtgcg gaagatgatc gccaagagcg agcaggaaat   3180
cggcaaggct accgccaagt acttcttcta cagcaacatc atgaactttt tcaagaccga   3240
aatcaccctg gccaacggcg agatcagaaa gcgccctctg atcgagacaa acggcgaaac   3300
cggggagatc gtgtgggata gggcagaga cttcgccaca gtgcgaaagg tgctgagcat   3360
gccccaagtg aatatcgtga aaagaccga ggtgcagaca ggcggcttca gcaaagagtc   3420
tatcctgccc aagaggaaca gcgacaagct gatcgccaga aagaaggact gggacccaa   3480
```

```
gaagtacggc ggcttcgaca gccctaccgt ggcctactct gtgctggtgg tggctaaggt    3540
ggaaaagggc aagtccaaga aactgaagag tgtgaaagag ctgctgggga tcaccatcat    3600 ggaagaagc agctttgaga agaaccctat cgactttctg aagccaagg gctacaaaga     3660 agtgaaaaag gacctgatca tcaagctgcc taagtactcc ctgttcgagc tggaaaacgg    3720
cagaaagaga atgctggcct ctgccggcga actgcagaag ggaaacgagc tggccctgcc    3780
tagcaaatat gtgaacttcc tgtacctggc ctcccactat gagaagctga agggcagccc    3840
tgaggacaac gaacagaaac agctgtttgt ggaacagcat aagcactacc tggacgagat    3900
catcgagcag atcagcgagt tctccaagag agtgatcctg ccgacgcca atctggacaa     3960 ggtgctgtct gcctacaaca agcacaggga caagcctatc agagagcagg ccgagaatat    4020
catccacctg ttcaccctga caaacctggg cgctcctgcc gccttcaagt actttgacac    4080
caccatcgac cggaagaggt acaccagcac caaagaggtg ctggacgcca ccctgatcca    4140
ccagagcatc accggcctgt acgagacaag aatcgacctg tctcagctgg aggcgacaa     4200 gagacctgcc gccactaaga aggccggaca ggccaaaaag aagaagtgag cggccgctta    4260
attaagctgc cttctgcggg gcttgccttc tggccatgcc cttcttctct cccttgcacc    4320
tgtacctctt ggtctttgaa taaagcctga gtaggaagaa aaaaaaaaaa aaaaaaaaa    4380 aaaaaaaaaa aaaaaaaaaa aaaaaaaaaa aaaaaaaaaa aaaaaaaaaa aaaaaaa     4438

<210> SEQ ID NO 224
<211> LENGTH: 4838
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCB1009 (FVIII donor for integration intro
      Transferrin intron 1)

<400> SEQUENCE: 224
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggcccgc gggagaacgc accactttac gaaggcggta    180
ctcctcaaag cgtactaaag aattattctt ttacatttca gggctgtgtc tggctgccac    240
caggagatac tacctggggg ctgtggagct gagctgggac tacatgcagt ctgacctggg    300
ggagctgcct gtggatgcca ggttcccccc cagagtgccc aagagcttcc ccttcaacac    360
ctctgtggtg tacaagaaga ccctgttttgt ggagttcact gaccaccctgt tcaacattgc    420 caagcccagg cccccctgga tgggcctgct gggcccccacc atccaggctg aggtgtatga    480
cactgtggtg atcaccctga gaacatggc cagccaccct gtgagcctgc atgctgtggg    540
ggtgagctac tggaaggcct ctgaggggc tgagtatgat gaccagacca gccagaggga    600
gaaggaggat gacaaggtgt tccctggggg cagccacacc tatgtgtggc aggtgctgaa    660
ggagaatggc cccatggcct ctgaccccct gtgcctgacc tacagctacc tgagccatgt    720
ggacctggtg aaggacctga actctggcct gattggggcc ctgctggtgt gcaggagggg    780
cagcctggcc aaggagaaga cccagaccct gcacaagttc atcctgctgt ttgctgtgtt    840
tgatgaggga aagagctggc actctgaaac caagaacagc ctgatgcagg acagggatgc    900
tgcctctgcc agggcctggc ccaagatgca cactgtgaat ggctatgtga acaggagcct    960
```

```
gcctggcctg attggctgcc acaggaagtc tgtgtactgg catgtgattg gcatgggcac      1020 caccectgag gtgcacagca tcttcctgga gggccacacc ttcctggtca ggaaccacag      1080
gcaggccagc ctggagatca gccccatcac cttcctgact gcccagaccc tgctgatgga      1140
cctgggccag ttcctgctgt tctgccacat cagcagccac cagcatgatg gcatggaggc      1200
ctatgtgaag gtggacagct gccctgagga gccccagctg aggatgaaga caatgagga       1260 ggctgaggac tatgatgatg acctgactga ctctgagatg gatgtggtga ggtttgatga     1320
tgacaacagc cccagcttca tccagatcag gtctgtggcc aagaagcacc ccaagacctg      1380
ggtgcactac attgctgctg aggaggagga ctgggactat gcccccctgg tgctggcccc      1440
tgatgacagg agctacaaga gccagtacct gaacaatggc cccagagga ttggcaggaa      1500 gtacaagaag gtcaggttca tggcctacac tgatgaaacc ttcaagacca gggaggccat      1560
ccagcatgag tctggcatcc tgggcccct gctgtatggg gaggtggggg acaccctgct      1620
gatcatcttc aagaaccagg ccagcaggcc ctacaacatc tacccccatg gcatcactga      1680
tgtgaggccc ctgtacagca ggaggctgcc caagggggtg aagcacctga aggacttccc      1740
catcctgcct ggggagatct tcaagtacaa gtggactgtg actgtggagg atggccccac      1800
caagtctgac cccaggtgcc tgaccagata ctacagcagc tttgtgaaca tggagaggga      1860
cctggcctct ggcctgattg ccccctgct gatctgctac aaggagtctg tggaccagag      1920
gggcaaccag atcatgtctg acaagaggaa tgtgatcctg ttctctgtgt ttgatgagaa      1980
caggagctgg tacctgactg agaacatcca gaggttcctg cccaaccctg ctggggtgca      2040
gctggaggac cctgagttcc aggccagcaa catcatgcac agcatcaatg ctatgtgtt      2100 tgacagcctg cagctgtctg tgtgcctgca tgaggtggcc tactggtaca tcctgagcat      2160
tggggcccag actgacttcc tgtctgtgtt cttctctggc tacaccttca gcacaagat      2220 ggtgtatgag gacaccctga ccctgttccc cttctctggg gagactgtgt tcatgagcat      2280
ggagaaccct ggcctgtgga ttctgggctg ccacaactct gacttcagga caggggcat     2340 gactgccctg ctgaaagtct ccagctgtga caagaacact ggggactact atgaggacag      2400
ctatgaggac atctctgcct acctgctgag caagaacaat gccattgagc ccaggagctt     2460
cagccagaat gccactaatg tgtctaacaa cagcaacacc agcaatgaca gcaatgtgtc      2520 tccccccagtg ctgaagaggc accagaggga gatcaccagg accaccctgc agtctgacca      2580
ggaggagatt gactatgatg acaccatctc tgtggagatg aagaaggagg actttgacat      2640
ctacgacgag gacgagaacc agagcccag gagcttccag aagaagacca ggcactactt      2700
cattgctgct gtggagaggc tgtgggacta tggcatgagc agcagccccc atgtgctgag     2760
gaacagggcc cagtctggct ctgtgcccca gttcaagaag gtggtgttcc aggagttcac      2820
tgatggcagc ttcacccagc ccctgtacag agggagctg aatgagcacc tgggcctgct      2880
gggcccctac atcagggctg aggtggagga caacatcatg gtgaccttca ggaaccaggc      2940
cagcaggccc tacagcttct acagcagcct gatcagctat gaggaggacc agaggcaggg      3000
ggctgagccc aggaagaact tgtgaagcc caatgaaacc aagacctact tctggaaggt      3060
gcagcaccac atggccccca ccaaggatga gtttgactgc aaggcctggg cctacttctc      3120
tgatgtggac ctggagaagg atgtgcactc tggcctgatt ggcccctgc tggtgtgcca      3180 caccaacacc ctgaaccctg cccatggcag gcaggtgact gtgcaggagt ttgccctgtt      3240
cttcaccatc tttgatgaaa ccaagagctg gtacttcact gagaacatgg agaggaactg      3300
cagggccccc tgcaacatcc agatggagga ccccaccttc aaggagaact acaggttcca      3360
```

```
tgccatcaat ggctacatca tggacaccct gcctggcctg gtgatggccc aggaccagag   3420
gatcaggtgg tacctgctga gcatgggcag caatgagaac atccacagca tccacttctc   3480
tggccatgtg ttcactgtga ggaagaagga ggagtacaag atggccctgt acaacctgta   3540
ccctggggtg tttgagactg tggagatgct gcccagcaag gctggcatct ggagggtgga   3600
gtgcctgatt ggggagcacc tgcatgctgg catgagcacc ctgttcctgg tgtacagcaa   3660
caagtgccag accccctgg gcatggcctc tggccacatc agggacttcc agatcactgc   3720
ctctggccag tatggccagt gggcccccaa gctggccagg ctgcactact ctggcagcat   3780
caatgcctgg agcaccaagg agcccttcag ctggatcaag gtggacctgc tggcccccat   3840
gatcatccat ggcatcaaga cccagggggc caggcagaag ttcagcagcc tgtacatcag   3900
ccagttcatc atcatgtaca gcctggatgg caagaagtgg cagacctaca ggggcaacag   3960
cactggcacc ctgatggtgt tctttggcaa tgtggacagc tctggcatca agcacaacat   4020
cttcaacccc cccatcattg ccagatacat caggctgcac cccacccact acagcatcag   4080
gagcaccctg aggatggagc tgatgggctg tgacctgaac agctgcagca tgccccctgg   4140
catggagagc aaggccatct ctgatgccca gatcactgcc agcagctact tcaccaacat   4200
gtttgccacc tggagcccca gcaaggccag gctgcacctg cagggcagga gcaatgcctg   4260
gaggccccag gtcaacaacc ccaaggagtg gctgcaggtg gacttccaga agaccatgaa   4320
ggtgactggg gtgaccaccc aggggggtgaa gagcctgctg accagcatgt atgtgaagga   4380
gttcctgatc agcagcagcc aggatggcca ccagtggacc ctgttcttcc agaatggcaa   4440
ggtgaaggtg ttccagggca accaggacag cttcacccct gtggtgaaca gcctggaccc   4500 cccccctgctg accagatacc tgaggattca ccccccagagc tgggtgcacc agattgccct   4560
gaggatggag gtgctgggct gtgaggccca ggacctgtac tgatcgcgaa taaaagatct   4620 ttatttcat tagatctgtg tgttggtttt ttgtgtggag aacgcaccac tttacgaagg   4680
caattgcctt aggccgcagg aacccctagt gatggagttg gccactccct ctctgcgcgc   4740
tcgctcgctc actgaggccg ggcgaccaaa ggtcgcccga cgcccgggct ttgcccgggc   4800
ggcctcagtg agcgagcgag cgcgcagctg cctgcagg                            4838
```

<210> SEQ ID NO 225
<211> LENGTH: 14
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Terminal portion of sequence encoding signal
      peptide from Transferrin Exon 2

<400> SEQUENCE: 225
ggctgtgtct ggct                                                      14

<210> SEQ ID NO 226
<211> LENGTH: 31
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Variant FVIII B-domain

<400> SEQUENCE: 226

Ser Phe Ser Gln Asn Ala Thr Asn Val Ser Asn Asn Ser Asn Thr Ser
1               5                   10                  15

Asn Asp Ser Asn Val Ser Pro Pro Val Leu Lys Arg His Gln Arg
            20                  25                  30

<210> SEQ ID NO 227
<211> LENGTH: 23
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: F8primerR1 primer

<400> SEQUENCE: 227
caatgttgaa caggtggtca gtg                                              23

<210> SEQ ID NO 228
<211> LENGTH: 100
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Predicted sequence for 5' Trf-F8 Junction

<400> SEQUENCE: 228
gggatgagag gagggtggaa cagaggagag gtggccatta agacccttcg cgaaggcggt      60
actcctcaaa gcgtactaaa gaattattct tttacatttc                           100

<210> SEQ ID NO 229
<211> LENGTH: 101
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Clone 1 5' Trf-F8 Junction

<400> SEQUENCE: 229
gggatgagag gagggtggaa cagaggagag gtggccatta agacccttcg acgaaggcgg      60
tactcctcaa agcgtactaa agaattattc ttttacattt c                         101

<210> SEQ ID NO 230
<211> LENGTH: 101
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Clone 2/4/6 5' Trf-F8 Junction

<400> SEQUENCE: 230
gggatgagag gagggtggaa cagaggagag gtggccatta agacccttcg tcgaaggcgg      60
tactcctcaa agcgtactaa agaattattc ttttacattt c                         101

<210> SEQ ID NO 231
<211> LENGTH: 97
<212> TYPE: DNA
<213> ORGANISM: Artificial sequence
<220> FEATURE:

```
<223> OTHER INFORMATION: Synthetic polynucleotide
<220> FEATURE:
<221> NAME/KEY: misc_feature
<223> OTHER INFORMATION: Clone 7 5' Trf-F8 Junction

<400> SEQUENCE: 231
gggatgagag gagggtggaa cagaggagag gtgccatta agaccctcga aggcggtact      60
cctcaaagcg tactaaagaa ttattctttt acatttc                             97

<210> SEQ ID NO 232
<211> LENGTH: 100
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Predicted sequence for 3' F8-Trf Junction

<400> SEQUENCE: 232
tttcattaga tctgtgtgtt ggttttttgt gtggagaacg caccacttta taaagtggtg    60
cgttctctcc ccaggcacgg ggagcgggtc ctttatgcct                         100

<210> SEQ ID NO 233
<211> LENGTH: 96
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Clone 2 3' F8-Trf Junction

<400> SEQUENCE: 233
tttcattaga tctgtgtgtt ggttttttgt gtggagaacg caccactaaa gtggtgcgtt    60
ctctccccag gcacggggag cgggtccttt atgcct                              96

<210> SEQ ID NO 234
<211> LENGTH: 98
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Clone 3 3' F8-Trf Junction

<400> SEQUENCE: 234
tttcattaga tctgtgtgtt ggttttttgt gtggagaacg caccactgta aagtggtgcg    60
ttctctcccc aggcacgggg agcgggtcct ttatgcct                            98

<210> SEQ ID NO 235
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: TFF1(DD) primer

<400> SEQUENCE: 235
gatgagagga gggtggaaca                                                20

<210> SEQ ID NO 236
```

```
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: RSA56.R primer

<400> SEQUENCE: 236
gtgaactcca caaacagggt                                              20

<210> SEQ ID NO 237
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: TFR1(DD) primer

<400> SEQUENCE: 237
agtgaactcc acaaacaggg                                              20

<210> SEQ ID NO 238
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: TFP1(DD) probe

<400> SEQUENCE: 238
ccacagcccc caggtagtat                                              20

<210> SEQ ID NO 239
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: AlbF(DD) primer

<400> SEQUENCE: 239
tctagtaatg gaagcctggt                                              20

<210> SEQ ID NO 240
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: AlbR(DD) primer

<400> SEQUENCE: 240
aggccctatg agaccgtaat                                              20

<210> SEQ ID NO 241
<211> LENGTH: 22
<212> TYPE: DNA
<213> ORGANISM: Artificial sequence
<220> FEATURE:
```

<223> OTHER INFORMATION: Synthetic polynucleotide
<220> FEATURE:
<221> NAME/KEY: misc_feature
<223> OTHER INFORMATION: AlbP(DD) probe

<400> SEQUENCE: 241
tgcatctgag aacccttagg tg                                              22

<210> SEQ ID NO 242
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF1,2 PCR Primer F

<400> SEQUENCE: 242
ttccattgcc tctctacgcc                                                 20

<210> SEQ ID NO 243
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF1,2 PCR Primer R

<400> SEQUENCE: 243
ctgaagccag ccatgggtaa                                                 20

<210> SEQ ID NO 244
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF1,2 Sequencing Primer F

<400> SEQUENCE: 244
gcacgtctaa ccaggttatc                                                 20

<210> SEQ ID NO 245
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF66 PCR Primer F

<400> SEQUENCE: 245
ctatgggaac tctggaggca g                                               21

<210> SEQ ID NO 246
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF66 PCR Primer R

<400> SEQUENCE: 246
ccccatggaa cataagcctc a                                              21

<210> SEQ ID NO 247
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF66 Sequencing Primer F

<400> SEQUENCE: 247
ctcatgcatc ctggagagct                                                20

<210> SEQ ID NO 248
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF100 PCR Primer F

<400> SEQUENCE: 248
ggcatcattc tctgagtctc actc                                           24

<210> SEQ ID NO 249
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF100 PCR Primer R

<400> SEQUENCE: 249
gccctgatgc aatcaaggta gg                                             22

<210> SEQ ID NO 250
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: hTF100 Sequencing Primer F

<400> SEQUENCE: 250
gagtctcact ccctcttctc                                                20

<210> SEQ ID NO 251
<211> LENGTH: 4830
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: pCB099 (FVIII donor for integration into
      albumin intron 1)

<400> SEQUENCE: 251

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc tgcggcctaa ggcaattgcc tgtaacgatc gggaactggc   180
```
(Note: corrections below reflect the image)
```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc tgcggcctaa ggcaattgcc tgtaacgatc gggaactggc   180
agatccacac aaaaaaccaa cacacagatc taatgaaaat aaagatcttt tattcgcgat   240
cagtacaggt cctgggcctc acagcccagc acctccatcc tcagggcaat ctggtgcacc   300
cagctctggg ggtgaatcct caggtatctg gtcagcaggg gggggtccag gctgttcacc   360
acaggggtga agctgtcctg gttgccctgg aacaccttca ccttgccatt ctggaagaac   420
agggtccact ggtggccatc ctggctgctg ctgatcagga actccttcac atacatgctg   480
gtcagcaggc tcttcacccc ctgggtggtc accccagtca ccttcatggt cttctggaag   540
tccacctgca gccactcctt ggggttgttg acctggggcc tccaggcatt gctcctgccc   600
tgcaggtgca gcctggcctt gctggggctc caggtggcaa acatgttggt gaagtagctg   660
ctggcagtga tctgggcatc agagatggcc ttgctctcca tgcccagggg catgctgcag   720
ctgttcaggt cacagcccat cagctccatc ctcagggtgc tcctgatgct gtagtgggtg   780
gggtgcagcc tgatgtatct ggcaatgatg gggggttga agatgttgtg cttgatgcca   840
gagctgtcca cattgccaaa gaacaccatc agggtgccag tgctgttgcc cctgtaggtc   900
tgccacttct tgccatccag gctgtacatg atgatgaact ggctgatgta caggctgctg   960
aacttctgcc tggccccctg ggtcttgatg ccatggatga tcatgggggc cagcaggtcc  1020
accttgatcc agctgaaggg ctccttggtg ctccaggcat tgatgctgcc agagtagtgc  1080
agcctggcca gcttggggggc ccactggcca tactggccag aggcagtgat ctggaagtcc  1140
ctgatgtggc cagaggccat gcccagggg gtctggcact tgttgctgta caccaggaac  1200
agggtgctca tgccagcatg caggtgctcc ccaatcaggc actccaccct ccagatgcca  1260
gccttgctgg gcagcatctc cacagtctca aacacccag ggtacaggtt gtacagggcc   1320
atcttgtact cctccttctt cctcacagtg aacacatggc cagagaagtg gatgctgtgg  1380
atgttctcat gctgcccat gctcagcagg taccacctga tcctctggtc ctgggccatc   1440
accaggccag gcagggtgtc catgatgtag ccattgatgg catggaacct gtagttctcc  1500
ttgaaggtgg ggtcctccat ctggatgttg caggggggccc tgcagttcct ctccatgttc  1560
tcagtgaagt accagctctt ggttttcatca aagatggtga agaacagggc aaactcctgc  1620
acagtcacct gcctgccatg ggcagggttc agggtgttgg tgtggcacac cagcagggggg  1680 ccaatcaggc cagagtgcac atccttctcc aggtccacat cagagaagta ggcccaggcc  1740
ttgcagtcaa actcatcctt ggtgggggcc atgtggtgct gcaccttcca gaagtaggtc  1800
ttggtttcat tgggcttcac aaagttcttc ctgggctcag cccctgcct ctggtcctcc   1860 tcatagctga tcaggctgct gtagaagctg tagggcctgc tggcctggtt cctgaaggtc  1920
accatgatgt tgtcctccac ctcagccctg atgtagggggc ccagcaggcc caggtgctca  1980
ttcagctccc ctctgtacag gggctgggtg aagctgccat cagtgaactc ctggaacacc  2040
accttcttga actggggcac agagccagac tgggccctgt tcctcagcac atggggggctg  2100 ctgctcatgc catagtccca cagcctctcc acagcagcaa tgaagtagtg cctggtcttc  2160
ttctggaagc tcctgggggct ctggttctcg tcctcgtcgt agatgtcaaa gtcctccttc  2220
ttcatctcca cagagatggt gtcatcatag tcaatctcct cctggtcaga ctgcagggtg  2280
gtcctggtga tctccctctg gtgcctcttc agcactgggg gagacacatt gctgtcattg  2340
ctggtgttgc tgttgttaga cacattagtg gcattctggc tgaagctcct gggctcaatg  2400
```

```
gcattgttct tgctcagcag gtaggcagag atgtcctcat agctgtcctc atagtagtcc    2460
ccagtgttct tgtcacagct ggagactttc agcagggcag tcatgcccct gttcctgaag    2520
tcagagttgt ggcagcccag aatccacagg ccagggttct ccatgctcat gaacacagtc    2580
tccccagaga aggggaacag ggtcaggtg tcctcataca ccatcttgtg cttgaaggtg     2640
tagccagaga agaacacaga caggaagtca gtctgggccc caatgctcag gatgtaccag    2700
taggccacct catgcaggca cacagacagc tgcaggctgt caaacacata gccattgatg    2760
ctgtgcatga tgttgctggc ctggaactca gggtcctcca gctgcacccc agcagggttg    2820
ggcaggaacc tctggatgtt ctcagtcagg taccagctcc tgttctcatc aaacacagag    2880
aacaggatca cattcctctt gtcagacatg atctggttgc ccctctggtc cacagactcc    2940
ttgtagcaga tcagcagggg gccaatcagg ccagaggcca ggtccctctc catgttcaca    3000
aagctgctgt agtatctggt caggcacctg ggtcagact tggtggggcc atcctccaca     3060
gtcacagtcc acttgtactt gaagatctcc ccaggcagga tggggaagtc cttcaggtgc    3120
ttcaccccct tgggcagcct cctgctgtac aggggcctca catcagtgat gccatggggg    3180
tagatgttgt agggcctgct ggcctggttc ttgaagatga tcagcagggt gtcccccacc    3240
tccccataca gcaggggcc caggatgcca gactcatgct ggatggcctc cctggtcttg     3300
aaggtttcat cagtgtaggc catgaacctg accttcttgt acttcctgcc aatcctctgg    3360
gggccattgt tcaggtactg gctcttgtag ctcctgtcat caggggccag caccagggg    3420 gcatagtccc agtcctcctc ctcagcagca atgtagtgca cccaggtctt ggggtgcttc    3480
ttggccacag acctgatctg gatgaagctg ggctgttgt catcatcaaa cctcaccaca     3540
tccatctcag agtcagtcag gtcatcatca tagtcctcag cctcctcatt gttcttcatc    3600
ctcagctggg gctcctcagg gcagctgtcc accttcacat aggcctccat gccatcatgc    3660
tggtggctgc tgatgtggca gaacagcagg aactggccca ggtccatcag cagggtctgg    3720
gcagtcagga aggtgatggg gctgatctcc aggctggcct gcctgtggtt cctgaccagg    3780
aaggtgtggc cctccaggaa gatgctgtgc acctcagggg tggtgcccat gccaatcaca    3840
tgccagtaca cagacttcct gtggcagcca atcaggccag gcaggctcct gttcacatag    3900
ccattcacag tgtgcatctt gggccaggcc ctggcagagg cagcatccct gtcctgcatc    3960
aggctgttct tggtttcaga gtgccagctc ttgccctcat caaacacagc aaacagcagg    4020
atgaacttgt gcagggtctg ggtcttctcc ttggccaggc tgccctccct gcacaccagc    4080
agggccccaa tcaggccaga gttcaggtcc ttcaccaggt ccacatggct caggtagctg    4140
taggtcaggc acaggggtc agaggccatg gggccattct ccttcagcac ctgccacaca    4200
taggtgtggc tgccccagg gaacaccttg tcatcctcct tctccctctg gctggtctgg     4260
tcatcatact cagccccctc agaggccttc cagtagctca cccccacagc atgcaggctc    4320
acagggtggc tggccatgtt cttcagggtg atcaccacag tgtcatacac ctcagcctgg    4380 atggtgggc ccagcaggcc catccagggg ggcctgggct ggcaatgtt gaacaggtgg      4440 tcagtgaact ccacaaacag ggtcttcttg tacaccacag aggtgttgaa ggggaagctc    4500
ttgggcactc tggggggaa cctggcatcc acaggcagct ccccaggtc agactgcatg      4560 tagtcccagc tcagctccac agccccagg tagtatctcc tggtggccac tgaaatgtaa     4620
aagaataatt ctttagtacg ctttgaggag taccgcctgt aacgatcggg aactggcacc    4680
gcgggccgca ggaaccccta gtgatggagt tggccactcc ctctctgcgc gctcgctcgc    4740
```

```
tcactgaggc cgggcgacca aaggtcgccc gacgcccggg ctttgcccgg gcggcctcag    4800
tgagcgagcg agcgcgcagc tgcctgcagg                                     4830

<210> SEQ ID NO 252
<211> LENGTH: 300
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Predicted sequence for 5' Trf-F8 Junction

<400> SEQUENCE: 252
tgccaccagg gatgagagga gggtggaaca gaggagaggt ggccattaag acccttcgcg      60
aaggcggtac tcctcaaagc gtactaaaga attattcttt tacatttcag ggctgtgtct    120
ggctgccacc aggagatact acctgggggc tgtggagctg agctgggact acatgcagtc    180
tgacctgggg gagctgcctg tggatgccag gttcccccccc agagtgccca agagcttccc    240
cttcaacacc tctgtggtgt acaagaagac cctgtttgtg gagttcactg accacctgtt    300
```